United States Patent
Hirasawa et al.

(10) Patent No.: US 9,458,092 B2
(45) Date of Patent: Oct. 4, 2016

(54) α-SUBSTITUTED GLYCINAMIDE DERIVATIVE

(71) Applicant: KISSEI PHARMACEUTICAL CO., LTD., Matsumoto-shi, Nagano (JP)

(72) Inventors: Hideaki Hirasawa, Azumino (JP); Naohiro Kawamura, Joetsu (JP); Junichi Kobayashi, Azumino (JP)

(73) Assignee: KISSEI PHARMACEUTICAL CO., LTD., Matsumoto-shi (JP)

( * ) Notice: Subject to any disclaimer, the term of this patent is extended or adjusted under 35 U.S.C. 154(b) by 0 days.

(21) Appl. No.: 14/889,475

(22) PCT Filed: May 7, 2014

(86) PCT No.: PCT/JP2014/062218
§ 371 (c)(1),
(2) Date: Nov. 6, 2015

(87) PCT Pub. No.: WO2014/181788
PCT Pub. Date: Nov. 13, 2014

(65) Prior Publication Data
US 2016/0115119 A1    Apr. 28, 2016

(30) Foreign Application Priority Data

May 8, 2013   (JP) ................... 2013-098835

(51) Int. Cl.
| | |
|---|---|
| A61K 31/167 | (2006.01) |
| C07C 233/81 | (2006.01) |
| C07C 255/60 | (2006.01) |
| C07D 213/81 | (2006.01) |
| C07D 213/82 | (2006.01) |
| C07D 213/84 | (2006.01) |
| C07C 271/22 | (2006.01) |

(Continued)

(52) U.S. Cl.
CPC .......... *C07C 233/81* (2013.01); *C07C 237/22* (2013.01); *C07C 237/36* (2013.01); *C07C 255/60* (2013.01); *C07C 271/22* (2013.01); *C07D 213/56* (2013.01); *C07D 213/81* (2013.01); *C07D 213/82* (2013.01); *C07D 213/84* (2013.01); *C07D 215/54* (2013.01); *C07D 217/26* (2013.01); *C07D 221/04* (2013.01); *C07D 231/14* (2013.01); *C07D 233/90* (2013.01); *C07D 237/08* (2013.01); *C07D 237/24* (2013.01); *C07D 239/26* (2013.01); *C07D 239/28* (2013.01); *C07D 241/12* (2013.01); *C07D 241/24* (2013.01); *C07D 261/18* (2013.01); *C07D 263/34* (2013.01); *C07D 271/08* (2013.01); *C07D 275/02* (2013.01); *C07D 277/20* (2013.01); *C07D 277/30* (2013.01); *C07D 277/56* (2013.01); *C07D 307/78* (2013.01); *C07D 307/82* (2013.01); *C07D 317/62* (2013.01); *C07D 333/38* (2013.01); *C07D 333/70* (2013.01); *C07D 405/12* (2013.01); *C07D 409/12* (2013.01); *C07D 417/12* (2013.01); *C07D 471/04* (2013.01); *C07D 487/04* (2013.01); *C07C 2101/02* (2013.01); *C07C 2101/14* (2013.01); *C07C 2102/08* (2013.01); *C07C 2102/10* (2013.01)

(58) Field of Classification Search
USPC .............................. 514/255.06, 252.06, 280
See application file for complete search history.

(56) References Cited

U.S. PATENT DOCUMENTS

| | | |
|---|---|---|
| 5,296,591 A | 3/1994 | Hemmi et al. |
| 5,861,380 A | 1/1999 | Gyorkos et al. |

(Continued)

FOREIGN PATENT DOCUMENTS

| | | |
|---|---|---|
| WO | 2012/101244 A1 | 8/2012 |
| WO | 2012/124825 A1 | 9/2012 |

OTHER PUBLICATIONS

International Search Report for PCT/JP2014/062218 dated Jul. 22, 2014 [PCT/ISA/210].

*Primary Examiner* — Pancham Bakshi
(74) *Attorney, Agent, or Firm* — Sughrue Mion, PLLC

(57) ABSTRACT

The present invention is to provide a novel α-substituted glycinamide derivative, or a pharmaceutically acceptable salt thereof, a pharmaceutical composition comprising the same, and a pharmaceutical use thereof.

The present invention provides a compound represented by the general formula (I), which has TRPM8 inhibitory effects:

[Chem.]

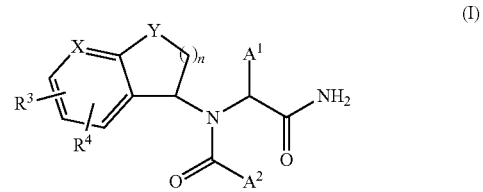

(I)

[wherein $A^1$ represents a $C_{6-10}$ aryl and the like, $A^2$ represents a $C_{6-10}$ aryl and the like, X represents CH and the like, Y represents —$CR^1R^2$— and the like, $R^1$ and $R^2$ independently represent a hydrogen atom and the like, $R^3$ and $R^4$ independently represent a halogen atom and the like, n is 1 or 2], or a pharmaceutically acceptable salt thereof. Furthermore, the compound (I) of the present invention can be used as an agent for treating or preventing diseases or symptoms caused by hyperexcitability or disorder of afferent neurons.

14 Claims, No Drawings

(51) Int. Cl.

| | | |
|---|---|---|
| *C07D 215/54* | (2006.01) | |
| *C07D 217/26* | (2006.01) | |
| *C07D 221/04* | (2006.01) | |
| *C07D 317/62* | (2006.01) | |
| *C07D 231/14* | (2006.01) | |
| *C07D 333/38* | (2006.01) | |
| *C07D 333/70* | (2006.01) | |
| *C07D 233/90* | (2006.01) | |
| *C07D 237/08* | (2006.01) | |
| *C07D 237/24* | (2006.01) | |
| *C07D 239/26* | (2006.01) | |
| *C07D 239/28* | (2006.01) | |
| *C07D 405/12* | (2006.01) | |
| *C07D 409/12* | (2006.01) | |
| *C07D 241/12* | (2006.01) | |
| *C07D 241/24* | (2006.01) | |
| *C07D 417/12* | (2006.01) | |
| *C07D 471/04* | (2006.01) | |
| *C07D 261/18* | (2006.01) | |
| *C07D 487/04* | (2006.01) | |
| *C07D 263/34* | (2006.01) | |
| *C07C 237/22* | (2006.01) | |
| *C07C 237/36* | (2006.01) | |
| *C07D 271/08* | (2006.01) | |
| *C07D 275/02* | (2006.01) | |
| *C07D 277/20* | (2006.01) | |
| *C07D 277/30* | (2006.01) | |
| *C07D 277/56* | (2006.01) | |
| *C07D 213/56* | (2006.01) | |
| *C07D 307/78* | (2006.01) | |
| *C07D 307/82* | (2006.01) | |

(56) References Cited

U.S. PATENT DOCUMENTS

| | | | |
|---|---|---|---|
| 2006/0167261 A1* | 7/2006 | Buchstaller | C07D 213/65 546/272.1 |
| 2007/0203139 A1* | 8/2007 | Bernstein | C07C 237/20 514/237.8 |
| 2012/0149699 A1 | 6/2012 | Macielag et al. | |

* cited by examiner

α-SUBSTITUTED GLYCINAMIDE DERIVATIVE

CROSS REFERENCE TO RELATED APPLICATIONS

This application is a National Stage of International Application No. PCT/JP2014/062218, filed on May 7, 2014, which claims priority from Japanese Patent Application No. 2013-098835, filed on May 8, 2013, the contents of all of which are incorporated herein by reference in their entirety.

TECHNICAL FIELD

The present invention relates to an α-substituted glycinamide derivative which is useful as a pharmaceutical, or a pharmaceutically acceptable salt thereof, a pharmaceutical composition comprising the same, and a pharmaceutical use thereof.

BACKGROUND ART

Transient Receptor Potential (TRP) channels are non-selective cation channels activated by various stimuli such as temperature, chemical compounds, etc., and divided into TRPM, TRPA, TRPV, TRPC, TRPP, TRPML, and TRPN families. Further, the TRPM family includes TRPM1, TRPM2, TRPM3, TRPM4a, TRPM4b, TRPM5, TRPM6, TRPM7 and TRPM8 channels (See, for example, Non-patent literature 1).

TRPM8, also known as CMR1 (cold and menthol sensitive receptor-1), is the eighth member of the TRPM family cloned in 2002 (See, for example, Non-patent literature 2), and is activated by cold temperature (8° C.-28° C.) or chemical compounds which evoke cold sensation such as menthol or icilin (See, for example, Non-patent literature 1 and 2). In addition to the primary afferent nerve (A-delta and C-fibers) and the trigeminal nerve, TRPM8 expression is also reported in taste papillae, vascular endothelium, the aorta, pulmonary arteries, the prostate, the male genital tract (See, for example, Non-patent literature 3), nerve fibers scattered in the human suburothelium (See, for example, Non-patent literature 4), prostate cancer (See, for example, Non-patent literature 5) and oral squamous carcinoma (See, for example, Non-patent literature 6).

In TRPM8 knockout mice, both lack of cold perception and deficiency in hypersensitivity to cold stimulation after nerve injury or inflammation are observed (See, for example, Non-patent literature 3).

In nervous system disorders, increase of TRPM8 expression and involvement in the hypersensitivity to cold in rats with sciatic nerve injury was reported (See, for example, Non-patent literature 7). It is reported that peripheral nerve injury evoked by oxaliplatin increases TRPM8 expression in mice and rats, and that TRPM8 is involved in the cold hypersensitivity evoked by oxaliplatin (See, for example, Non-patent literature 8 and 9). From the fact that patients taking oxaliplatin have increased reactivity to menthol compared with healthy volunteers, TRPM8 is considered to be involved in peripheral neuropathic pain evoked by oxaliplatin in humans as well as in rodents (See, for example, Non-patent literature 10).

In regards to the urinary tract diseases, TRPM8 is reported to be involved in the frequent urination symptoms evoked by cold temperature in rats (See, for example, Non-patent literature 11). Because of the expression in neurons projecting dichotomizing axons into both the skin and the bladder of rats, TRPM8 is considered to be involved in the urinary urgency evoked by cold (See, for example, Non-patent literature 12). In cats and patients with upper central nervous disorders such as stroke and spinal cord injury, infusion of a small amount of cold water into the bladder evokes micturition reflex that is not observed in normal volunteers, and this reflex is increased by the addition of menthol (See, for example, Non-patent literature 13 and 14). In cats, this reflex is decreased according to desensitization of C-fibers, so menthol-sensitive C-fibers are considered to be involved in the reflex (See, for example, Non-patent literature 13).

In patients with idiopathic detrusor overactivity or painful bladder syndrome, it is reported that TRPM8 expression is increased in nerve fibers in the suburothelium, and that TRPM8 expression correlates with the frequency of urination and pain scores (See, for example, Non-patent literature 15). Therefore, it is likely that TRPM8 plays an important role in the bladder afferent pathway during the bladder filling.

Accordingly, treatment or prevention of diseases or symptoms caused by the activation of TRPM8 are expected by inhibiting TRPM8.

In the meantime, as a compound of inhibiting TRPM8, N-(3-aminopropyl)-2-{[(3-methylphenyl)methyl]oxy}-N-(2-thienylmethyl)benzamide hydrochloride (hereinafter sometimes referred to as AMTB) is known.

[Chem. 1]

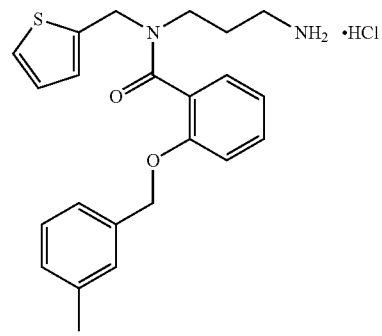

In anesthetized rats, AMTB suppresses the frequency of rhythmic bladder contractions and nociceptive reflex responses to bladder distension. However, after a high dose of AMTB administration, the decrease of the average blood pressure is observed, so there are still problems (See, for example, Non-patent literature 16).

AMTB has been also disclosed as Examples of a compound represented by the general formula (A) (see Patent literature 1, Example 24).

[Chem. 2]

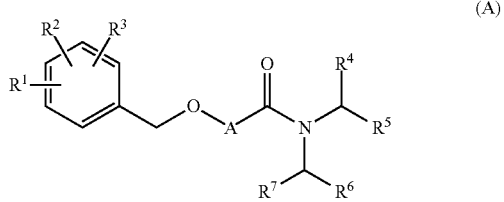

(A)

[wherein, $R^1$, $R^2$, $R^3$, $R^4$, $R^5$, $R^6$, $R^7$ and A have the same meanings as defined in Patent literature 1.]

However, general formula (A) has a different structure from the compounds of the present invention. Further, anything is neither described nor suggested about the compounds of the present invention in Patent literature 1.

In the meantime, a compound represented by the general formula (B) has been described as a α-substituted glycinamide derivative (see Patent literature 2).

[Chem. 3]

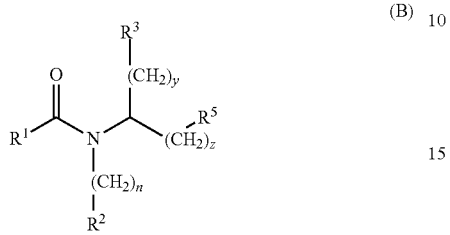

(B)

[wherein, $R^1$, $R^2$, $R^3$, $R^5$, n, y and z have the same meanings as defined in Patent literature 2.]

However, the compounds described in Patent literature 2 have a different structure from the compounds of the present invention. Further, the compounds of the present invention are different in the point that they are TRPM8 inhibitors relative to that the compound described in Patent literature 2 are oxytocin inhibitors.

CITATION LIST

Patent Literature

[Patent literature 1] International publication No. WO2007/017093
[Patent literature 2] International publication No. WO2004/020414

Non-Patent Literature

[Non-patent literature 1] Makoto Tominaga, "Folia Pharmacologica Japonica," 2004, Vol. 124, p. 219-227
[Non-patent literature 2] McKemy D D. et al., "Nature" 2002, Vol. 416, p. 52-58
[Non-patent literature 3] Broad L M. et al., "Expert Opin Ther Targets", 2009, Vol. 13, p. 69-81
[Non-patent literature 4] Andersson K E. et al., "BJU Int", 2010, Vol. 106, p. 1114-1127
[Non-patent literature 5] Zhang L. et al., "Endocr Relat Cancer", 2006, Vol. 13, p. 27-38
[Non-patent literature 6] Okamono Y. et al., "Int J Oncol", 2012, Vol. 40, p. 1431-1440
[Non-patent literature 7] Su L. et al., "BMC Neurosci", 2011, Vol. 12, p. 120
[Non-patent literature 8] Kawashiri T. et al., "Mol Pain", 2012, Vol. 8, p. 7
[Non-patent literature 9] Gauchan P. et al., "Neurosci Lett", 2009, Vol. 458, p. 93-95
[Non-patent literature 10] Kono T. et al., "Brain Behav", 2012, Vol. 2, 68-73
[Non-patent literature 11] Lei Z. et al., "Neurourol Urodyn", 2012, doi:10.1002/nau.22325
[Non-patent literature 12] Shibata Y. et al., "Neuroreport", 2011, Vol. 22, p. 61-67
[Non-patent literature 13] Lindstrom S. et al., "Acta Physiol Scand", 1991, Vol. 141, p. 1-10
[Non-patent literature 14] Geirsson G. et al., "J Urol", 1993, Vol. 150, 427-430
[Non-patent literature 15] Mukerji G. et al., "BMC Urol", 2006, Vol. 6, p. 6
[Non-patent literature 16] Lashinger E S. et al., "Am J Physiol Renal Physiol", 2008, Vol. 295, p. F803-F810

SUMMARY OF THE INVENTION

Objects to be Solved by the Invention

The present invention is to provide a novel α-substituted glycinamide derivative, or a pharmaceutically acceptable salt thereof, a pharmaceutical composition comprising the same, and a pharmaceutical use thereof.

Means for Solving the Objects

The present inventors have conducted extensive studies to find α-substituted glycinamide derivatives, and as a result found that compound (I) of the present invention or a pharmaceutically acceptable salt thereof have a potent TRPM8 inhibition, thereby completing the present invention.

That is, the means for solving the above-described objects are as shown below.

[1] A compound represented by the general formula (I) or a pharmaceutically acceptable salt thereof:

[Chem. 4]

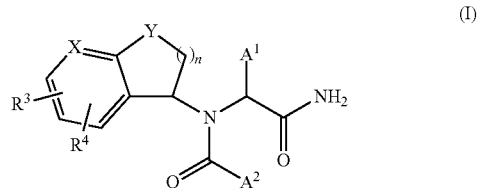

(I)

wherein
$A^1$ is a group selected from the group consisting of the following a) to c):
  a) $C_{6-10}$ aryl, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$alkyl, halo-$C_{1-6}$ alkoxy, $C_{1-6}$ alkoxycarbonyl, cyano, hydroxy-$C_{1-6}$ alkyl, carbamoyl, nitro, amino, $C_{1-6}$ alkoxycarbonylamino-$C_{1-6}$ alkyl, mono(di)$C_{1-6}$ alkylamino, ($C_{1-6}$ alkyl)carbonylamino, $C_{1-6}$ alkylsulfonylamino and $C_{1-6}$ alkylsulfonyl,
  b) 5-membered heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, cyano and halo-$C_{1-6}$ alkoxy, and
  c) 6-membered heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, cyano and halo-$C_{1-6}$ alkoxy;

$A^2$ is a group selected from the group consisting of the following d) to f):
  d) $C_{6-10}$ aryl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano, amino, nitro, carboxy, ($C_{1-6}$ alkyl)carbonylamino, ($C_{1-6}$ alkyl)carbonyloxy, ($C_{1-6}$ alkyl)carbonyl and ($C_{7-10}$ aralkyloxy)carbonyl,
  e) heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, cyano, mono(di)$C_{1-6}$ alkylamino, $C_{1-6}$ alkylsulfanyl, amino, (C$_{7-10}$ aralkyloxy)carbonyl, hydroxy-C$_{1-6}$ alkyl, hydroxy-C$_{1-6}$ alkoxy, C$_{2-6}$ alkenyl, morpholino and (C$_{1-6}$ alkyl)carbonyl, and f) C$_{3-6}$ cycloalkyl;
X is CH or N;
Y is —CR$^1$R$^2$— or an oxygen atom;
R$^1$ and R$^2$ independently represent a hydrogen atom, a halogen atom or C$_{1-6}$ alkyl;
R$^3$ and R$^4$ independently represent a hydrogen atom, a halogen atom, C$_{1-6}$ alkyl, C$_{1-6}$ alkoxy, halo-C$_{1-6}$ alkyl, halo-C$_{1-6}$ alkoxy, hydroxy-C$_{1-6}$ alkoxy, C$_{3-6}$ cycloalkyl, C$_{3-6}$ cycloalkoxy, C$_{2-6}$ alkenyl or cyano with the proviso that when X is CH, and R$^1$ and R$^2$ are hydrogen atoms, R$^3$ and R$^4$ are not hydrogen atoms at the same time; and
n is 1 or 2.

[2] The compound according to [1] or a pharmaceutically acceptable salt thereof, wherein X is CH; and n is 1.

[3] The compound according to [2] or a pharmaceutically acceptable salt thereof, wherein a group represented by the general formula:

[Chem. 5]

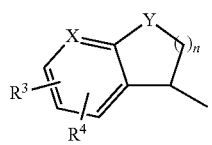
(II)

is a group represented by the following general formula:

[Chem. 6]

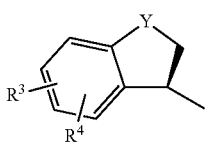
(III)

(wherein R$^3$ and R$^4$ independently represent a hydrogen atom, a halogen atom, C$_{1-6}$ alkyl, C$_{1-6}$ alkoxy, halo-C$_{1-6}$ alkyl, halo-C$_{1-6}$ alkoxy, hydroxy-C$_{1-6}$ alkoxy, C$_{3-6}$ cycloalkyl, C$_{3-6}$ cycloalkoxy, C$_{2-6}$ alkenyl or cyano with the proviso that R$^3$ and R$^4$ are not hydrogen atoms at the same time).

[4] The compound according to [3] or a pharmaceutically acceptable salt thereof, wherein Y is —CR$^1$R$^2$—.

[5] The compound according to [4] or a pharmaceutically acceptable salt thereof, wherein a group represented by the general formula:

[Chem. 7]

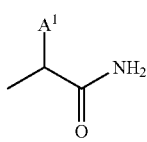
(IV)

is a group represented by the following general formula:

[Chem. 8]

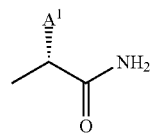
(V)

(wherein A$^1$ is a group selected from the group consisting of the following a1), b) and c):

a1) phenyl, wherein the ring is unsubstituted or substituted with 1 to 2 substituents independently selected from the group consisting of the following: a halogen atom, hydroxy, C$_{1-6}$ alkyl, C$_{1-6}$ alkoxy, halo-C$_{1-6}$ alkyl, halo-C$_{1-6}$ alkoxy, C$_{1-6}$ alkoxycarbonyl, cyano, hydroxy-C$_{1-6}$ alkyl, carbamoyl, nitro, amino, C$_{1-6}$ alkoxycarbonylamino-C$_{1-6}$ alkyl, mono(di)C$_{1-6}$ alkylamino, (C$_{1-6}$ alkyl)carbonylamino, C$_{1-6}$ alkylsulfonylamino and C$_{1-6}$ alkylsulfonyl, b) 5-membered heterocycle, wherein the ring is unsubstituted or substituted with 1 to 2 substituents independently selected from the group consisting of the following: a halogen atom, hydroxy, C$_{1-6}$ alkyl, C$_{1-6}$ alkoxy, halo-C$_{1-6}$ alkyl, cyano and halo-C$_{1-6}$ alkoxy, and c) 6-membered heterocycle, wherein the ring is unsubstituted or substituted with 1 to 2 substituents independently selected from the group consisting of the following: a halogen atom, hydroxy, C$_{1-6}$ alkyl, C$_{1-6}$ alkoxy, halo-C$_{1-6}$ alkyl, cyano and halo-C$_{1-6}$ alkoxy).

[6] The compound according to [5] or a pharmaceutically acceptable salt thereof, wherein a group represented by the general formula:

[Chem. 9]

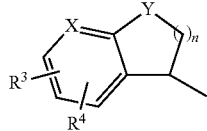
(II)

is a group represented by the following general formula:

[Chem. 10]

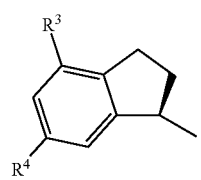
(VI)

(wherein R$^3$ and R$^4$ independently represent a hydrogen atom, a halogen atom, C$_{1-6}$ alkyl, C$_{1-6}$ alkoxy, halo-C$_{1-6}$ alkyl, halo-C$_{1-6}$ alkoxy, hydroxy-C$_{1-6}$ alkoxy, C$_{3-6}$ cycloalkyl, C$_{2-6}$ alkenyl or cyano with the proviso that R$^3$ and R$^4$ are not hydrogen atoms at the same time).

[7] The compound according to [6] or a pharmaceutically acceptable salt thereof, wherein A$^2$ is a group selected from the group consisting of the following d1) and e):

d1) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$alkyl, halo-$C_{1-6}$alkyl, halo-$C_{1-6}$alkoxy, cyano, amino, nitro, carboxy, ($C_{1-6}$alkyl)carbonylamino, ($C_{1-6}$alkyl)carbonyloxy, ($C_{1-6}$ alkyl)carbonyl and ($C_{7-10}$ aralkyloxy)carbonyl, and e) heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, cyano, mono(di)$C_{1-6}$ alkylamino, $C_{1-6}$ alkylsulfanyl, amino, ($C_{7-10}$ aralkyloxy)carbonyl, hydroxy-$C_{1-6}$ alkyl, hydroxy-$C_{1-6}$ alkoxy, $C_{2-6}$ alkenyl, morpholino and ($C_{1-6}$ alkyl)carbonyl.

[8] The compound according to [7] or a pharmaceutically acceptable salt thereof, wherein $A^1$ is a group selected from the group consisting of the following a2), b1) and c1):

a2) phenyl, wherein the ring is unsubstituted or substituted with 1 to 2 substituents independently selected from the group consisting of the following: a halogen atom, hydroxy, hydroxy-$C_{1-6}$ alkyl, cyano, amino, mono(di)$C_{1-6}$ alkylamino and $C_{1-6}$ alkoxy, b1) thiazolyl, and c1) a group selected from the group consisting of pyridyl, pyrimidinyl or pyrazinyl, wherein the each ring is unsubstituted or substituted with 1 to 2 substituents independently selected from the group consisting of the following: a halogen atom, $C_{1-6}$ alkyl, $C_{1-6}$ alkoxy and cyano;

$A^2$ is a group selected from the group consisting of the following d2) and e1):

d2) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano, ($C_{1-6}$ alkyl)carbonyloxy and amino, and e1) heterocycle, wherein the ring is unsubstituted or substituted with 1 to 2 substituents independently selected from the group consisting of the following: a halogen atom, $C_{1-6}$ alkyl, $C_{1-6}$ alkoxy, cyano, mono(di)$C_{1-6}$ alkylamino, $C_{1-6}$ alkylsulfanyl, amino, hydroxy-$C_{1-6}$ alkyl and $C_{2-6}$ alkenyl; and $R^3$ and $R^4$ independently represent a hydrogen atom, a halogen atom, $C_{1-6}$ alkyl, $C_{1-6}$ alkoxy, halo-$C_{1-6}$ alkyl, halo-$C_{1-6}$ alkoxy, $C_{3-6}$ cycloalkyl or cyano with the proviso that $R^3$ and $R^4$ are not hydrogen atoms at the same time.

[9] The compound according to [8] or a pharmaceutically acceptable salt thereof, wherein $A^2$ is a group selected from the group consisting of the following d2) and e2):

d2) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano, ($C_{1-6}$ alkyl)carbonyloxy and amino, and e2) a group selected from the group consisting of pyridyl, pyrimidinyl, pyrazinyl, thienyl, thiazolyl, isothiazolyl, 2,3-dihydrobenzofuranyl, pyrazolyl, imidazolyl, isoxazolyl, oxazolyl, furazanyl and benzo[1,3]dioxolyl, wherein the each ring is unsubstituted or substituted with 1 to 2 substituents independently selected from the group consisting of the following: a halogen atom, $C_{1-6}$ alkyl, $C_{1-6}$ alkoxy, cyano, mono(di)$C_{1-6}$ alkylamino, $C_{1-6}$ alkylsulfanyl, amino, hydroxy-$C_{1-6}$ alkyl and $C_{2-6}$ alkenyl.

[10] The compound according to [9] or a pharmaceutically acceptable salt thereof, wherein $A^1$ is phenyl, pyridyl or pyrazinyl, in which the each ring is unsubstituted or substituted with selected from the group consisting of the following: a halogen atom, amino, mono(di)$C_{1-6}$ alkylamino or hydroxy;

$A^2$ is a group selected from the group consisting of the following d3) and e3):

d3) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy and amino, and e3) a group selected from the group consisting of pyridyl, pyrimidinyl, pyrazinyl, thiazolyl, 2,3-dihydrobenzofuranyl, pyrazolyl, isoxazolyl and benzo[1,3]dioxolyl, wherein the each ring is unsubstituted or substituted with 1 to 2 substituents independently selected from the group consisting of the following: a halogen atom, $C_{1-6}$ alkyl, $C_{1-6}$ alkoxy, mono(di)$C_{1-6}$ alkylamino, $C_{1-6}$ alkylsulfanyl, and amino, and $R^3$ and $R^4$ independently represent a hydrogen atom, a halogen atom, $C_{1-6}$ alkyl, $C_{1-6}$ alkoxy, halo-$C_{1-6}$ alkoxy, $C_{3-6}$ cycloalkyl or cyano with the proviso that $R^3$ and $R^4$ are not hydrogen atoms at the same time.

[11] The compound according to [9] or a pharmaceutically acceptable salt thereof, wherein $A^1$ is phenyl, pyridyl or pyrazinyl, in which the each ring is unsubstituted or substituted with selected from the group consisting of the following: a halogen atom or hydroxy;

$A^2$ is a group selected from the group consisting of the following d4) and e3):

d4) phenyl, wherein the ring is unsubstituted or substituted with 1 to 2 substituents independently selected from the group consisting of the following: a halogen atom, hydroxy, $C_{1-6}$ alkoxy and amino, and e3) a group selected from the group consisting of pyridyl, pyrimidinyl, pyrazinyl, thiazolyl, 2,3-dihydrobenzofuranyl, pyrazolyl, isoxazolyl and benzo[1,3]dioxolyl, wherein the each ring is unsubstituted or substituted with 1 to 2 substituents independently selected from the group consisting of the following: a halogen atom, $C_{1-6}$ alkyl, $C_{1-6}$ alkoxy, mono(di)$C_{1-6}$ alkylamino, $C_{1-6}$ alkylsulfanyl, and amino, and $R^3$ and $R^4$ independently represent a hydrogen atom, a halogen atom, $C_{1-6}$ alkyl, $C_{1-6}$ alkoxy, halo-$C_{1-6}$ alkoxy, $C_{3-6}$ cycloalkyl or cyano with the proviso that $R^3$ and $R^4$ are not hydrogen atoms at the same time.

[12] The compound according to [1] selected from the following group or a pharmaceutically acceptable salt thereof:

N-[(R)-carbamoylphenylmethyl]-N-[(R)-4,6-difluoroindan-1-yl]nicotinamide (Example 1-1);

N-[(R)-carbamoylphenylmethyl]-N-[(R)-6-methoxyindan-1-yl]nicotinamide (Example 1-6);

N-[(R)-carbamoylphenylmethyl]-N-[(R)-6-chloroindan-1-yl]benzamide (Example 2-2LP);

N-[(R)-carbamoylphenylmethyl]-N-[(R)-6-methoxyindan-1-yl]benzamide (Example 2-4LP);

N-[(R)-carbamoylphenylmethyl]-N-[(R)-6-cyclopropylindan-1-yl]benzamide (Example 2-5LP);

N-[(R)-carbamoylphenylmethyl]-N-[(R)-6-difluoromethoxyindan-1-yl]benzamide (Example 2-11LP);

N-[(R)-carbamoylphenylmethyl]-N-[(R)-6-difluoromethoxyindan-1-yl]nicotinamide (Example 2-26LP);

2-amino-N-[(R)-carbamoylphenylmethyl]-N-[(R)-6-difluoromethoxyindan-1-yl]nicotinamide (Example 2-27LP);

N-[(R)-carbamoylphenylmethyl]-N-[(R)-6-chloroindan-1-yl]nicotinamide (Example 2-31LP);

2-amino-N-[(R)-carbamoylphenylmethyl]-N-[(R)-6-chloroindan-1-yl]nicotinamide (Example 2-33LP);

N-[(R)-carbamoylphenylmethyl]-N-[(R)-4-fluoro-6-methoxyindan-1-yl]nicotinamide (Example 2-39LP);
N-[(R)-carbamoylphenylmethyl]-N-[(R)-4-fluoro-6-methylindan-1-yl]nicotinamide (Example 2-40LP);
N-[(R)-carbamoylphenylmethyl]-N-[(R)-4-fluoroindan-1-yl]nicotinamide (Example 2-56LP);
N-[(R)-carbamoylpyridin-3-ylmethyl]-N-[(R)-6-chloro-4-fluoroindan-1-yl]benzamide (Example 2-66LP);
N-[(R)-carbamoylphenylmethyl]-N-[(R)-6-chloroindan-1-yl]thiazole-5-carboxamide (Example 2-71LP);
N-[(R)-carbamoylpyridin-3-ylmethyl]-N-[(R)-4,6-difluoroindan-1-yl]benzamide (Example 2-76LP);
N-[(R)-carbamoylphenylmethyl]-N-[(R)-6-chloro-4-fluoroindan-1-yl]-5-fluoronicotinamide (Example 2-86LP);
N-[(R)-carbamoylphenylmethyl]-N-[(R)-4,6-difluoroindan-1-yl]benzamide (Example 2-221LP);
N-[(R)-carbamoylphenylmethyl]-N-[(R)-6-cyanoindan-1-yl]-2-hydroxybenzamide (Example 3-2);
N-[(R)-carbamoylphenylmethyl]-N-[(S)-5-chloro-2,3-dihydrobenzofuran-3-yl]-2-hydroxybenzamide (Example 4-2);
2-amino-N-[(R)-carbamoylphenylmethyl]-N-[(R)-4,6-difluoroindan-1-yl]benzamide (Example 6-1);
N-[(R)-carbamoylpyridin-3-ylmethyl]-N-[(R)-6-chloro-4-fluoroindan-1-yl]-2-methylnicotinamide (Example 12);
2-amino-N-[(R)-carbamoylphenylmethyl]-N-[(R)-4,6-difluoroindan-1-yl]nicotinamide (Example 1-3);
N-[(R)-carbamoylphenylmethyl]-N-[(R)-6-chloro-4-fluoroindan-1-yl]benzamide (Example 2-6LP);
N-[(R)-carbamoylphenylmethyl]-N-[(R)-6-chloro-4-fluoroindan-1-yl]nicotinamide (Example 2-23LP);
N-[(R)-carbamoylphenylmethyl]-N-[(R)-4,6-difluoroindan-1-yl]-2-methoxynicotinamide (Example 2-36LP);
N-[(R)-carbamoylphenylmethyl]-N-[(R)-6-chloroindan-1-yl]-2-methoxynicotinamide (Example 2-46LP);
N-[(R)-carbamoylpyridin-3-ylmethyl]-N-[(R)-6-chloroindan-1-yl]benzamide (Example 2-87LP);
N-[(R)-carbamoylphenylmethyl]-N-[(R)-6-chloroindan-1-yl]-4-methylthiazole-5-carboxamide (Example 2-88LP);
N-[(R)-carbamoylphenylmethyl]-N-[(R)-6-chloro-4-fluoroindan-1-yl]-2-methoxybenzamide (Example 2-89LP);
N-[(R)-carbamoylphenylmethyl]-2-chloro-N-[(R)-6-chloro-4-fluoroindan-1-yl]nicotinamide (Example 2-93LP);
N-[(R)-carbamoylpyridin-3-ylmethyl]-2-chloro-N-[(R)-6-chloro-4-fluoroindan-1-yl]benzamide (Example 2-97LP);
N-[(R)-carbamoylphenylmethyl]-N-[(R)-6-chloro-4-fluoroindan-1-yl]-4-methylnicotinamide (Example 2-100LP);
N-[(R)-carbamoylphenylmethyl]-N-[(R)-6-chloro-4-fluoroindan-1-yl]-2-(methylamino)nicotinamide (Example 2-107LP);
N-[(R)-carbamoylphenylmethyl]-N-[(R)-6-chloro-4-fluoroindan-1-yl]-2,3-dihydrobenzofuran-7-carboxamide (Example 2-111LP);
N-[(R)-carbamoylpyridin-3-ylmethyl]-N-[(R)-6-chloro-4-fluoroindan-1-yl]-2-methoxybenzamide (Example 2-118LP);
N-[(R)-carbamoylphenylmethyl]-N-[(R)-6-chloroindan-1-yl]-2-(methylsulfanyl)nicotinamide (Example 2-125LP);
N-[(R)-carbamoylphenylmethyl]-N-[(R)-6-chloro-4-fluoroindan-1-yl]-2-(methylsulfanyl)nicotinamide (Example 2-128LP);
N-[(R)-carbamoylphenylmethyl]-N-[(R)-4,6-difluoroindan-1-yl]-2-methylnicotinamide (Example 2-131LP);
N-[(R)-carbamoylphenylmethyl]-N-[(R)-4,6-difluoroindan-1-yl]-4-methylthiazole-5-carboxamide (Example 2-132LP);
N-[(R)-carbamoylphenylmethyl]-N-[(R)-6-chloro-4-fluoroindan-1-yl]-2-methyl-2H-pyrazole-3-carboxamide (Example 2-133LP);
N-[(R)-carbamoylphenylmethyl]-N-[(R)-6-chloroindan-1-yl]-2-methylnicotinamide (Example 2-137LP);
N-[(R)-carbamoylphenylmethyl]-N-[(R)-6-chloro-4-fluoroindan-1-yl]-5-methylthiazole-4-carboxamide (Example 2-147LP);
N-[(R)-carbamoylphenylmethyl]-N-[(R)-6-chloro-4-fluoroindan-1-yl]-4-methylisoxazole-5-carboxamide (Example 2-150LP);
N-[(R)-carbamoylphenylmethyl]-N-[(R)-6-chloro-4-fluoroindan-1-yl]-3-methylpyridine-2-carboxamide (Example 2-152LP);
N-[(R)-carbamoylphenylmethyl]-N-[(R)-6-chloro-4-fluoroindan-1-yl]-4-methylpyrimidine-5-carboxamide (Example 2-154LP);
N-[(R)-carbamoyl-(3-fluorophenyl)methyl]-N-[(R)-6-chloro-4-fluoroindan-1-yl]-2-methylnicotinamide (Example 2-161LP);
N-[(R)-carbamoylphenylmethyl]-N-[(R)-6-chloro-4-fluoroindan-1-yl]-3-methylisonicotinamide (Example 2-167LP);
N-[(R)-carbamoyl-(3-hydroxyphenyl)methyl]-N-[(R)-6-chloro-4-fluoroindan-1-yl]-2-methylnicotinamide (Example 2-168LP);
N-[(R)-carbamoylpyridin-3-ylmethyl]-N-[(R)-6-chloro-4-fluoroindan-1-yl]benzo[1,3]dioxole-4-carboxamide (Example 2-172LP);
N-[(R)-carbamoylphenylmethyl]-N-[(R)-6-chloro-4-fluoroindan-1-yl]benzo[1,3]dioxole-4-carboxamide (Example 2-173LP);
N-[(R)-carbamoylphenylmethyl]-N-[(R)-6-chloro-4-fluoroindan-1-yl]-3-methylpyrazine-2-carboxamide (Example 2-175LP);
N-[(R)-carbamoylphenylmethyl]-N-[(R)-6-chloro-4-fluoroindan-1-yl]pyrazine-2-carboxamide (Example 2-179LP);
N-[(R)-carbamoylpyridin-3-ylmethyl]-N-[(R)-6-chloro-4-fluoroindan-1-yl]-2-methoxynicotinamide (Example 2-180LP);
N-[(RS)-carbamoylphenylmethyl]-N-[(SR)-5-chloro-7-fluoro-2,3-dihydrobenzofuran-3-yl]benzamide (Example 2-252M);
N-[(R)-carbamoylpyridin-3-ylmethyl]-N-[(R)-6-chloro-4-fluoroindan-1-yl]-2-hydroxybenzamide (Example 4-5, 19-1LP);
N-[(R)-carbamoylpyrazin-2-ylmethyl]-N-[(R)-6-chloro-4-fluoroindan-1-yl]-2-hydroxybenzamide (Example 4-8);
N-[(R)-carbamoylphenylmethyl]-N-[(R)-6-chloro-4-fluoroindan-1-yl]-2-hydroxy-3-methylbenzamide (Example 4-9);
N-[(R)-carbamoylphenylmethyl]-N-[(R)-6-chloro-4-fluoroindan-1-yl]-2-methoxynicotinamide (Example 11);
2-amino-N-[(R)-carbamoylphenylmethyl]-N-[(R)-6-chloro-4-fluoroindan-1-yl]nicotinamide (Example 13);
N-[(R)-carbamoylphenylmethyl]-N-[(R)-6-chloro-4-fluoroindan-1-yl]-2-methylnicotinamide (Example 14LP);
N-[(R)-carbamoylphenylmethyl]-N-[(R)-6-chloro-4-fluoroindan-1-yl]-4-methylthiazole-5-carboxamide (Example 15LP);
N-[(R)-carbamoyl-(3-dimethylaminophenyl)methyl]-N-[(R)-6-chloro-4-fluoroindan-1-yl]-2-methylnicotinamide (Example 18-13LP);
N-[(R)-carbamoyl-(3-dimethylaminophenyl)methyl]-N-[(R)-6-chloro-4-fluoroindan-1-yl]-2-hydroxybenzamide (Example 19-6LP);

N-[(R)-carbamoylpyridin-3-ylmethyl]-N-[(R)-6-chloro-4-fluoroindan-1-yl]-2-hydroxy-4-methylbenzamide (Example 19-12LP);

N-[(R)-carbamoylpyridin-3-ylmethyl]-N-[(R)-6-chloro-4-fluoroindan-1-yl]-2-fluoro-6-hydroxybenzamide (Example 19-15LP);

N-[(R)-carbamoylpyridin-3-ylmethyl]-N-[(R)-6-chloro-4-fluoroindan-1-yl]-4-fluoro-2-hydroxybenzamide (Example 19-16LP);

N-[(R)-carbamoylpyridin-3-ylmethyl]-4-chloro-N-[(R)-6-chloro-4-fluoroindan-1-yl]-2-hydroxybenzamide (Example 19-17LP);

N-[(R)-carbamoylpyridin-3-ylmethyl]-N-[(R)-6-chloro-4-fluoroindan-1-yl]-3-fluoro-2-hydroxybenzamide (Example 19-25LP);

N-[(R)-(3-aminophenyl)carbamoylmethyl]-N-[(R)-6-chloro-4-fluoroindan-1-yl]-2-methylnicotinamide (Example 21-1);

N-[(R)-(3-aminophenyl)carbamoylmethyl]-N-[(R)-6-chloro-4-fluoroindan-1-yl]-2-hydroxybenzamide (Example 21-2);

N-[(R)-carbamoyl(5-fluoropyridin-3-yl)methyl]-N-[(R)-6-chloro-4-fluoroindan-1-yl]-2-hydroxybenzamide (Example 19-31LP); and N-[(R)-carbamoylpyridin-3-ylmethyl]-N-[(R)-6-chloro-4-fluoroindan-1-yl]-2-hydroxy-3-methylbenzamide (Example 19-41LP).

[13] A pharmaceutical composition comprising the compound according to any one of [1] to [12] or a pharmaceutically acceptable salt thereof.

[14] The pharmaceutical composition according to [13], which is an agent for the treatment or prevention of a disease or a symptom caused by hyperexcitability or a disorder of afferent neurons.

[15] A method for preventing or treating a disease or a symptom caused by hyperexcitability or a disorder of afferent neurons, comprising administering an effective amount of the compound according to any one of [1] to [12] or a pharmaceutically acceptable salt thereof.

[16] Use of the compound according to any one of [1] to [12] or a pharmaceutically acceptable salt thereof for the manufacture of a pharmaceutical composition for preventing or treating a disease or a symptom caused by hyperexcitability or a disorder of afferent neurons.

As another embodiment,

[17] A compound represented by the general formula (I) or a pharmaceutically acceptable salt thereof:

[Chem. 11]

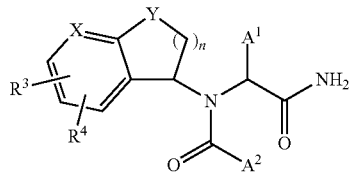

(I)

(wherein $A^1$ is a group selected from the group consisting of the following aa) to cc):

aa) $C_{6-10}$ aryl, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, $C_{1-6}$ alkoxycarbonyl and $C_{1-6}$ alkylsulfonyl, bb) 5-membered heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl and halo-$C_{1-6}$ alkoxy, and cc) 6-membered heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl and halo-$C_{1-6}$ alkoxy);

$A^2$ is a group selected from the group consisting of the following dd), ee) and f):

dd) $C_{6-10}$ aryl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano, amino, nitro, carboxy and $(C_{7-10}$ aralkyloxy)carbonyl, ee) heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, cyano, mono(di)$C_{1-6}$ alkylamino, $C_{1-6}$ alkylsulfanyl, amino, $(C_{7-10}$ aralkyloxy)carbonyl, hydroxy-$C_{1-6}$ alkyl, $C_{2-6}$ alkenyl, morpholino and $(C_{1-6}$ alkyl)carbonyl, and f) $C_{3-6}$ cycloalkyl;

X is CH or N;

Y is —$CR^1R^2$— or an oxygen atom;

$R^1$ and $R^2$ independently represent a hydrogen atom, a halogen atom or $C_{1-6}$ alkyl;

$R^3$ and $R^4$ independently represent a hydrogen atom, a halogen atom, $C_{1-6}$ alkyl, $C_{1-6}$ alkoxy, halo-$C_{1-6}$ alkyl, halo-$C_{1-6}$ alkoxy, hydroxy-$C_{1-6}$ alkoxy, $C_{3-6}$ cycloalkyl, $C_{3-6}$ cycloalkoxy, $C_{2-6}$ alkenyl or cyano with the proviso that when X is CH, and $R^1$ and $R^2$ are hydrogen atoms, $R^3$ and $R^4$ are not hydrogen atoms at the same time; and n is 1 or 2).

[18] The compound according to [17] or a pharmaceutically acceptable salt thereof, wherein X is CH; and n is 1.

[19] The compound according to [18] or a pharmaceutically acceptable salt thereof, wherein a group represented by the general formula:

[chem. 12]

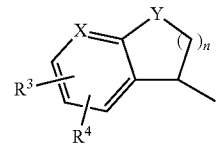

(II)

is a group represented by the following general formula:

[Chem. 13]

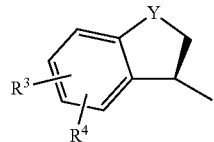

(III)

(wherein $R^3$ and $R^4$ independently represent a hydrogen atom, a halogen atom, $C_{1-6}$ alkyl, $C_{1-6}$ alkoxy, halo-$C_{1-6}$ alkyl, halo-$C_{1-6}$ alkoxy, hydroxy-$C_{1-6}$ alkoxy, $C_{3-6}$ cycloalkyl, $C_{3-6}$ cycloalkoxy, $C_{2-6}$ alkenyl or cyano with the proviso that $R^3$ and $R^4$ are not hydrogen atoms at the same time).

[20] The compound according to [19] or a pharmaceutically acceptable salt thereof, wherein Y is —$CR^1R^2$—.

[21] The compound according to [20] or a pharmaceutically acceptable salt thereof, wherein a group represented by the general formula:

[chem. 14]

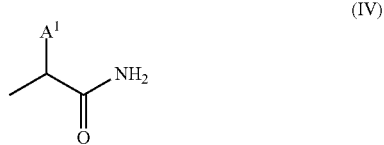

(IV)

is a group represented by the following general formula:

[chem. 15]

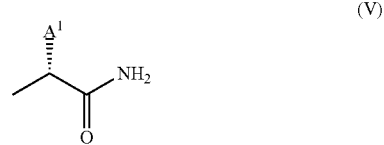

(V)

(wherein $A^1$ is a group selected from the group consisting of the following aa1), bb) or cc):

aa1) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, $C_{1-6}$ alkoxycarbonyl and $C_{1-6}$ alkylsulfonyl, bb) 5-membered heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl and halo-$C_{1-6}$ alkoxy, and cc) 6-membered heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl and halo-$C_{1-6}$ alkoxy).

[22] The compound according to [21] or a pharmaceutically acceptable salt thereof, wherein a group represented by the general formula:

[chem. 16]

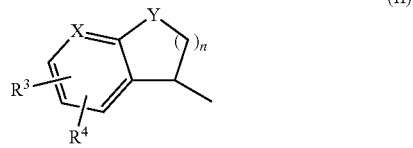

(II)

is a group represented by the following general formula:

[chem. 17]

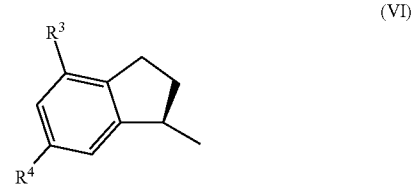

(VI)

(wherein $R^3$ and $R^4$ independently represent a hydrogen atom, a halogen atom, $C_{1-6}$ alkyl, $C_{1-6}$ alkoxy, halo-$C_{1-6}$ alkyl, halo-$C_{1-6}$ alkoxy, hydroxy-$C_{1-6}$ alkoxy, $C_{3-6}$ cycloalkyl, $C_{2-6}$ alkenyl or cyano with the proviso that $R^3$ and $R^4$ are not hydrogen atoms at the same time).

[23] The compound according to [22] or a pharmaceutically acceptable salt thereof, wherein $A^2$ is a group selected from the group consisting of the following dd1) and ee):

dd1) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano, amino, nitro, carboxy and ($C_{7-10}$ aralkyloxy)carbonyl, and ee) heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, cyano, mono(di)$C_{1-6}$ alkylamino, $C_{1-6}$ alkylsulfanyl, amino, ($C_{7-10}$ aralkyloxy)carbonyl, hydroxy-$C_{1-6}$ alkyl, $C_{2-6}$ alkenyl, morpholino and ($C_{1-6}$ alkyl)carbonyl.

[24] The compound according to [23] or a pharmaceutically acceptable salt thereof, wherein $A^1$ is a group selected from the group consisting of the following aa2), bb1) and cc1):

aa2) phenyl, wherein the ring is unsubstituted or substituted with 1 to 2 substituents independently selected from the group consisting of the following: a halogen atom, hydroxy and $C_{1-6}$ alkoxy, bb1) thiazolyl, and cc1) a group selected from the group consisting of pyridyl, pyrimidinyl and pyrazinyl, wherein the each ring is unsubstituted or substituted with 1 to 2 halogen atoms;

$A^2$ is a group selected from the group consisting of the following dd2) and e1):

dd2) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano and amino, and e1) heterocycle, wherein the ring is unsubstituted or substituted with 1 to 2 substituents independently selected from the group consisting of the following: a halogen atom, $C_{1-6}$ alkyl, $C_{1-6}$ alkoxy, cyano, mono(di)$C_{1-6}$ alkylamino, $C_{1-6}$ alkylsulfanyl, amino, hydroxy-$C_{1-6}$ alkyl and $C_{2-6}$ alkenyl; and $R^3$ and $R^4$ independently represent a hydrogen atom, a halogen atom, $C_{1-6}$ alkyl, $C_{1-6}$ alkoxy, halo-$C_{1-6}$ alkyl, halo-$C_{1-6}$ alkoxy, $C_{3-6}$ cycloalkyl or cyano with the proviso that $R^3$ and $R^4$ are not hydrogen atoms at the same time.

[25] The compound according to [24] or a pharmaceutically acceptable salt thereof, wherein $A^2$ is a group selected from the group consisting of dd2) and e2):

dd2) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano and amino, and e2) a group selected from the group consisting of pyridyl, pyrimidinyl, pyrazinyl, thienyl, thiazolyl, isothiazolyl, 2,3-dihydrobenzofuranyl, pyrazolyl, imidazolyl, isoxazolyl, oxazolyl, furazanyl and a benzo[1,3]dioxolyl, wherein the each ring is unsubstituted or substituted with 1 to 2 substituents independently selected from the group consisting of the following: a halogen atom, $C_{1-6}$ alkyl, $C_{1-6}$ alkoxy, cyano, mono(di)$C_{1-6}$ alkylamino, $C_{1-6}$ alkylsulfanyl, amino, hydroxy-$C_{1-6}$ alkyl and $C_{2-6}$ alkenyl.

[26] The compound according to [25] or a pharmaceutically acceptable salt thereof, wherein $A^1$ is phenyl, pyridyl or pyrazinyl, in which the each ring is unsubstituted or substituted with selected from the group consisting of the following: a halogen atom or hydroxy;

$A^2$ is a group selected from the group consisting of d4) and e3):

d4) phenyl, wherein the ring is unsubstituted or substituted with 1 to 2 substituents independently selected from the group consisting of the following: a halogen atom, hydroxy, $C_{1-6}$ alkoxy and amino, and e3) a group selected from the group consisting of pyridyl, pyrimidinyl, pyrazinyl, thiazolyl, 2,3-dihydrobenzofuranyl, pyrazolyl, isoxazolyl and benzo[1,3]dioxolyl, wherein the each ring is unsubstituted or substituted with 1 to 2 substituents independently selected from the group consisting of the following: a halogen atom, $C_{1-6}$ alkyl, $C_{1-6}$ alkoxy, mono(di)$C_{1-6}$ alkylamino, $C_{1-6}$ alkylsulfanyl, and amino, and $R^3$ and $R^4$ independently represent a hydrogen atom, a halogen atom, $C_{1-6}$ alkyl, $C_{1-6}$ alkoxy, halo-$C_{1-6}$ alkoxy, $C_{3-6}$ cycloalkyl or cyano with the proviso that $R^3$ and $R^4$ are not hydrogen atoms at the same time.

[27] The compound according to [17] selected from the following group or a pharmaceutically acceptable salt thereof:

N-[(R)-carbamoylphenylmethyl]-N-[(R)-4,6-difluoroindan-1-yl]nicotinamide (Example 1-1);

N-[(R)-carbamoylphenylmethyl]-N-[(R)-6-methoxyindan-1-yl]nicotinamide (Example 1-6);

N-[(R)-carbamoylphenylmethyl]-N-[(R)-6-chloroindan-1-yl]benzamide (Example 2-2LP);

N-[(R)-carbamoylphenylmethyl]-N-[(R)-6-methoxyindan-1-yl]benzamide (Example 2-4LP);

N-[(R)-carbamoylphenylmethyl]-N-[(R)-6-cyclopropylindan-1-yl]benzamide (Example 2-5LP);

N-[(R)-carbamoylphenylmethyl]-N-[(R)-6-difluoromethoxyindan-1-yl]benzamide (Example 2-11LP);

N-[(R)-carbamoylphenylmethyl]-N-[(R)-6-difluoromethoxyindan-1-yl]nicotinamide (Example 2-26LP);

2-amino-N-[(R)-carbamoylphenylmethyl]-N-[(R)-6-difluoromethoxyindan-1-yl]nicotinamide (Example 2-27LP);

N-[(R)-carbamoylphenylmethyl]-N-[(R)-6-chloroindan-1-yl]nicotinamide (Example 2-31LP);

2-amino-N-[(R)-carbamoylphenylmethyl]-N-[(R)-6-chloroindan-1-yl]nicotinamide (Example 2-33LP);

N-[(R)-carbamoylphenylmethyl]-N-[(R)-4-fluoro-6-methoxyindan-1-yl]nicotinamide (Example 2-39LP);

N-[(R)-carbamoylphenylmethyl]-N-[(R)-4-fluoro-6-methylindan-1-yl]nicotinamide (Example 2-40LP);

N-[(R)-carbamoylphenylmethyl]-N-[(R)-4-fluoroindan-1-yl]nicotinamide (Example 2-56LP);

N-[(R)-carbamoylpyridin-3-ylmethyl]-N-[(R)-6-chloro-4-fluoroindan-1-yl]benzamide (Example 2-66LP);

N-[(R)-carbamoylphenylmethyl]-N-[(R)-6-chloroindan-1-yl]thiazole-5-carboxamide (Example 2-71LP);

N-[(R)-carbamoylpyridin-3-ylmethyl]-N-[(R)-4,6-difluoroindan-1-yl]benzamide (Example 2-76LP);

N-[(R)-carbamoylphenylmethyl]-N-[(R)-6-chloro-4-fluoroindan-1-yl]-5-fluoronicotinamide (Example 2-86LP);

N-[(R)-carbamoylphenylmethyl]-N-[(R)-4,6-difluoroindan-1-yl]benzamide (Example 2-221LP);

N-[(R)-carbamoylphenylmethyl]-N-[(R)-6-cyanoindan-1-yl]-2-hydroxybenzamide (Example 3-2);

N-[(R)-carbamoylphenylmethyl]-N-[(S)-5-chloro-2,3-dihydrobenzofuran-3-yl]-2-hydroxybenzamide (Example 4-2);

2-amino-N-[(R)-carbamoylphenylmethyl]-N-[(R)-4,6-difluoroindan-1-yl]benzamide (Example 6-1);

N-[(R)-carbamoylpyridin-3-ylmethyl]-N-[(R)-6-chloro-4-fluoroindan-1-yl]-2-methylnicotinamide (Example 12);

2-amino-N-[(R)-carbamoylphenylmethyl]-N-[(R)-4,6-difluoroindan-1-yl]nicotinamide (Example 1-3);

N-[(R)-carbamoylphenylmethyl]-N-[(R)-6-chloro-4-fluoroindan-1-yl]benzamide (Example 2-6LP);

N-[(R)-carbamoylphenylmethyl]-N-[(R)-6-chloro-4-fluoroindan-1-yl]nicotinamide (Example 2-23LP);

N-[(R)-carbamoylphenylmethyl]-N-[(R)-4,6-difluoroindan-1-yl]-2-methoxynicotinamide (Example 2-36LP);

N-[(R)-carbamoylphenylmethyl]-N-[(R)-6-chloroindan-1-yl]-2-methoxynicotinamide (Example 2-46LP);

N-[(R)-carbamoylpyridin-3-ylmethyl]-N-[(R)-6-chloroindan-1-yl]benzamide (Example 2-87LP);

N-[(R)-carbamoylphenylmethyl]-N-[(R)-6-chloroindan-1-yl]-4-methylthiazole-5-carboxamide (Example 2-88LP);

N-[(R)-carbamoylphenylmethyl]-N-[(R)-6-chloro-4-fluoroindan-1-yl]-2-methoxybenzamide (Example 2-89LP);

N-[(R)-carbamoylphenylmethyl]-2-chloro-N-[(R)-6-chloro-4-fluoroindan-1-yl]nicotinamide (Example 2-93LP);

N-[(R)-carbamoylpyridin-3-ylmethyl]-2-chloro-N-[(R)-6-chloro-4-fluoroindan-1-yl]benzamide (Example 2-97LP);

N-[(R)-carbamoylphenylmethyl]-N-[(R)-6-chloro-4-fluoroindan-1-yl]-4-methylnicotinamide (Example 2-100LP);

N-[(R)-carbamoylphenylmethyl]-N-[(R)-6-chloro-4-fluoroindan-1-yl]-2-(methylamino)nicotinamide (Example 2-107LP);

N-[(R)-carbamoylphenylmethyl]-N-[(R)-6-chloro-4-fluoroindan-1-yl]-2,3-dihydrobenzofuran-7-carboxamide (Example 2-111LP);

N-[(R)-carbamoylpyridin-3-ylmethyl]-N-[(R)-6-chloro-4-fluoroindan-1-yl]-2-methoxybenzamide (Example 2-118LP);

N-[(R)-carbamoylphenylmethyl]-N-[(R)-6-chloroindan-1-yl]-2-(methylsulfanyl)nicotinamide (Example 2-125LP);

N-[(R)-carbamoylphenylmethyl]-N-[(R)-6-chloro-4-fluoroindan-1-yl]-2-(methylsulfanyl)nicotinamide (Example 2-128LP);

N-[(R)-carbamoylphenylmethyl]-N-[(R)-4,6-difluoroindan-1-yl]-2-methylnicotinamide (Example 2-131LP);

N-[(R)-carbamoylphenylmethyl]-N-[(R)-4,6-difluoroindan-1-yl]-4-methylthiazole-5-carboxamide (Example 2-132LP);

N-[(R)-carbamoylphenylmethyl]-N-[(R)-6-chloro-4-fluoroindan-1-yl]-2-methyl-2H-pyrazole-3-carboxamide (Example 2-133LP);

N-[(R)-carbamoylphenylmethyl]-N-[(R)-6-chloroindan-1-yl]-2-methylnicotinamide (Example 2-137LP);

N-[(R)-carbamoylphenylmethyl]-N-[(R)-6-chloro-4-fluoroindan-1-yl]-5-methylthiazole-4-carboxamide (Example 2-147LP);

N-[(R)-carbamoylphenylmethyl]-N-[(R)-6-chloro-4-fluoroindan-1-yl]-4-methylisoxazole-5-carboxamide (Example 2-150LP);

N-[(R)-carbamoylphenylmethyl]-N-[(R)-6-chloro-4-fluoroindan-1-yl]-3-methylpyridine-2-carboxamide (Example 2-152LP);

N-[(R)-carbamoylphenylmethyl]-N-[(R)-6-chloro-4-fluoroindan-1-yl]-4-methylpyrimidine-5-carboxamide (Example 2-154LP);

N-[(R)-carbamoyl-(3-fluorophenyl)methyl]-N-[(R)-6-chloro-4-fluoroindan-1-yl]-2-methylnicotinamide (Example 2-161LP);

N-[(R)-carbamoylphenylmethyl]-N-[(R)-6-chloro-4-fluoroindan-1-yl]-3-methylisonicotinamide (Example 2-167LP);

N-[(R)-carbamoyl-(3-hydroxyphenyl)methyl]-N-[(R)-6-chloro-4-fluoroindan-1-yl]-2-methylnicotinamide (Example 2-168LP);

N-[(R)-carbamoylpyridin-3-ylmethyl]-N-[(R)-6-chloro-4-fluoroindan-1-yl]benzo[1,3]dioxole-4-carboxamide (Example 2-172LP);

N-[(R)-carbamoylphenylmethyl]-N-[(R)-6-chloro-4-fluoroindan-1-yl]benzo[1,3]dioxole-4-carboxamide (Example 2-173LP);

N-[(R)-carbamoylphenylmethyl]-N-[(R)-6-chloro-4-fluoroindan-1-yl]-3-methylpyrazine-2-carboxamide (Example 2-175LP);

N-[(R)-carbamoylphenylmethyl]-N-[(R)-6-chloro-4-fluoroindan-1-yl]pyrazine-2-carboxamide (Example 2-179LP);

N-[(R)-carbamoylpyridin-3-ylmethyl]-N-[(R)-6-chloro-4-fluoroindan-1-yl]-2-methoxynicotinamide (Example 2-180LP);

N-[(RS)-carbamoylphenylmethyl]-N-[(SR)-5-chloro-7-fluoro-2,3-dihydrobenzofuran-3-yl]benzamide (Example 2-252M);

N-[(R)-carbamoylpyridin-3-ylmethyl]-N-[(R)-6-chloro-4-fluoroindan-1-yl]-2-hydroxybenzamide (Example 4-5);

N-[(R)-carbamoylpyrazin-2-ylmethyl]-N-[(R)-6-chloro-4-fluoroindan-1-yl]-2-hydroxybenzamide (Example 4-8);

N-[(R)-carbamoylphenylmethyl]-N-[(R)-6-chloro-4-fluoroindan-1-yl]-2-hydroxy-3-methylbenzamide (Example 4-9);

N-[(R)-carbamoylphenylmethyl]-N-[(R)-6-chloro-4-fluoroindan-1-yl]-2-methoxynicotinamide (Example 11);

2-amino-N-[(R)-carbamoylphenylmethyl]-N-[(R)-6-chloro-4-fluoroindan-1-yl]nicotinamide (Example 13);

N-[(R)-carbamoylphenylmethyl]-N-[(R)-6-chloro-4-fluoroindan-1-yl]-2-methylnicotinamide (Example 14LP); and N-[(R)-carbamoylphenylmethyl]-N-[(R)-6-chloro-4-fluoroindan-1-yl]-4-methylthiazole-5-carboxamide (Example 15LP).

[28] A pharmaceutical composition comprising the compound according to any one of [17] to [27] or a pharmaceutically acceptable salt thereof.

[29] The pharmaceutical composition according to [28], which is an agent for the treatment or prevention of a disease or a symptom caused by hyperexcitability or a disorder of the afferent neuron.

[30] A method for preventing or treating a disease or a symptom caused by hyperexcitability or a disorder of afferent neurons, comprising administering an effective amount of the compound according to any one of [17] to [27] or a pharmaceutically acceptable salt thereof.

[31] Use of the compound according to any one of [17] to [27] or a pharmaceutically acceptable salt thereof for the manufacture of a pharmaceutical composition for preventing or treating a disease or a symptom caused by hyperexcitability or a disorder of afferent neurons.

Effects of the Invention

The compound (I) of the present invention or a pharmaceutically acceptable salt thereof exhibits a potent inhibitory effect in for example a confirmation test of inhibitory effects on icilin-induced wet-dog shakes which is a similar method described in International publication No. WO2009/012430. Therefore, the compound (I) of the present invention or a pharmaceutically acceptable salt thereof is useful as an agent for treating or preventing diseases or symptoms caused by hyperexcitability or disorder of afferent neurons.

EMBODIMENTS FOR CARRYING OUT THE INVENTION

The terms in the specification are defined.

The "halogen atom" means a fluorine atom, a chlorine atom, a bromine atom, or an iodine atom. It is preferably a fluorine atom or a chlorine atom.

The term "$C_{1-6}$ alkyl" means alkyl having 1 to 6 carbon atoms, which may be branched. Examples thereof include methyl, ethyl, propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, n-hexyl, isohexyl, and the like.

The term "$C_{1-6}$ alkoxy" means alkoxy having 1 to 6 carbon atoms, which may be branched. Examples thereof include methoxy, ethoxy, propoxy, isopropoxy, butoxy, isobutoxy, sec-butoxy, tert-butoxy, pentyloxy, hexyloxy, and the like.

The term "halo-$C_{1-6}$ alkyl" means the above $C_{1-6}$ alkyl substituted by 1 to 5 of the same or different halogen atoms. Examples thereof include monofluoromethyl, difluoromethyl, trifluoromethyl, 2-chloroethyl, 2-fluoroethyl, 2,2-difluoroethyl, 1,1-difluoroethyl, 1,2-difluoroethyl, 2,2,2-trifluoroethyl, 1,1,2,2,2-pentafluoroethyl, 2,2,2-trichloroethyl, 3-fluoropropyl, 2-fluoropropyl, 1-fluoropropyl, 3,3-difluoropropyl, 2,2-difluoropropyl, 1,1-difluoropropyl, 1-fluorobutyl, 1-fluoropentyl, 1-fluorohexyl, and the like.

The term "halo-$C_{1-6}$ alkoxy" means the above $C_{1-6}$ alkoxy substituted by 1 to 5 of the same or different halogen atoms. Examples thereof include monofluoromethoxy, difluoromethoxy, trifluoromethoxy, 2-chloroethoxy, 2-fluoroethoxy, 2,2-difluoroethoxy, 1,1-difluoroethoxy, 1,2-difluoroethoxy, 2,2,2-trifluoroethoxy, 1,1,2,2,2-pentafluoroethoxy, 2,2,2-trichloroethoxy, 3-fluoropropoxy, 2-fluoropropoxy, 1-fluoropropoxy, 3,3-difluoropropoxy, 2,2-difluoropropoxy, 1,1-difluoropropoxy, 4-fluorobutoxy, 5-fluoropentyloxy, 6-fluorohexyloxy, and the like.

The term "hydroxy-$C_{1-6}$ alkyl" means the above $C_{1-6}$ alkyl substituted by hydroxy. Examples thereof include hydroxymethyl, 1-hydroxyethyl, 1-hydroxy-1,1-dimethylmethyl, 2-hydroxyethyl, 2-hydroxy-2-methylpropyl, 3-hydroxypropyl, and the like.

The term "hydroxy-$C_{1-6}$ alkoxy" means the above $C_{1-6}$ alkoxy substituted by hydroxy. Examples thereof include hydroxymethoxy, 1-hydroxyethoxy, 1-hydroxy-1,1-dimethylmethoxy, 2-hydroxyethoxy, 2-hydroxy-2-methylpropoxy, 3-hydroxypropoxy, and the like.

The term "$C_{6-10}$ aryl" means phenyl or naphthyl.

The term "($C_{7-10}$ aralkyloky)carbonyl" means carbonyl substituted by alkoxy having 1 to 4 carbon atoms substituted by phenyl. Examples thereof include benzyloxycarbonyl, phenethyloxycarbonyl, 1-phenylethyloxycarbonyl, 3-phenylpropyloxycarbonyl, 4-phenylbutyloxycarbonyl, and the like.

The term "mono(di)$C_{1-6}$ alkylamino" means amino mono- or di-substituted by the above $C_{1-6}$ alkyl. These $C_{1-6}$ alkyl may be different in the case of di-substitution.

The term "$C_{1-6}$ alkylsulfanyl" means a group represented by ($C_{1-6}$ alkyl)-S—. Examples thereof include methylsulfanyl, ethylsulfanyl, propylsulfanyl, isopropylsulfanyl, butylsulfanyl, isobutylsulfanyl, sec-butylsulfanyl, pentylsulfanyl, hexylsulfanyl, and the like.

The term "$C_{1-6}$ alkylsulfonyl" means a group represented by ($C_{1-6}$ alkyl)-$SO_2$—. Examples thereof include methylsulfonyl, ethylsulfonyl, propylsulfonyl, isopropylsulfonyl, butylsulfonyl, isobutylsulfonyl, sec-butylsulfonyl, pentylsulfonyl, hexylsulfonyl, and the like.

The term "($C_{1-6}$ alkyl)carbonyl" means carbonyl substituted by the above $C_{1-6}$ alkyl. Examples thereof include acetyl, ethylcarbonyl, propylcarbonyl, isopropylcarbonyl, isobutylcarbonyl, butylcarbonyl, sec-butylcarbonyl, tert-butylcarbonyl, pentylcarbonyl, hexylcarbonyl, and the like.

The term "$C_{1-6}$ alkoxycarbonyl" means carbonyl substituted by the above $C_{1-6}$ alkoxy. Examples thereof include methoxycarbonyl, ethoxycarbonyl, propoxycarbonyl, isopropoxycarbonyl, isobutoxycarbonyl, butoxycarbonyl, sec-butoxycarbonyl, tert-butoxycarbonyl, pentyloxycarbonyl, hexyloxycarbonyl, and the like.

The term "$C_{3-6}$ cycloalkyl" means monocyclic saturated alicyclic hydrocarbon having 3 to 6 carbon atoms. Examples thereof include cyclopropyl, cyclobutyl, cyclopentyl, and cyclohexyl.

The term "$C_{3-6}$ cycloalkoxy" means alkoxy having monocyclic saturated alicyclic hydrocarbon having 3 to 6 carbon atoms. Examples thereof include cyclopropoxy, cyclobutyloxy, cyclopentyloxy, and cyclohexyloxy.

The term "heterocycle" means 5 or 6-membered heterocycle having any 1 to 4 atoms selected from a sulfur atom, an oxygen atom and a nitrogen atom, examples thereof include aromatic heterocycle such as furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, 1-oxidopyridyl, pyridazinyl, pyrimidinyl, pyrazinyl, furazanyl and the like, unsaturated heterocycle such as pyrrolinyl, imidazolinyl, pyrazolinyl, dihydropyranyl, dihydrothiopyranyl, dihydropyridyl and the like, and saturated heterocycle such as morphonyl, thiomorphonyl, pyrrolidinyl, imidazolinyl, pyrazolidinyl, piperidyl, piperazinyl, tetrahydrofuranyl and the like. Furthermore, the above "heterocycle" may be fused with other cyclic groups, examples thereof include isobenzofuranyl, benzoxazolyl, benzoisoxazolyl, benzothiazolyl, benzoisothiazolyl, chromenyl, chromanonyl, xanthenyl, phenoxathiinyl, indolizinyl, isoindolizinyl, indolyl, indazolyl, purinyl, quinolizinyl, isoquinolyl, quinolyl, phthalazinyl, naphthyridinyl, quinoxalinyl, quinazolinyl, carbazolyl, carbolinyl, acridinyl, isoindolinyl, 2,3-dihydrobenzofuranyl, imidazo[1,2-a]pyridyl, imidazo[1,2-a]pyrazinyl, benzo[1,3]dioxolyl, benzothienyl, 5,6,7,8-tetrahydroimidazo[1,2-a]pyrazinyl, and the like.

Preferably, examples of the "heterocycle" of $A^2$ include thienyl, pyrazolyl, imidazolyl, oxazolyl, isoxazolyl, thiazolyl, isothiazolyl, pyridyl, pyrimidinyl, pyrazinyl, furazanyl, 2,3-dihydrobenzofuranyl or benzo[1,3]dioxolyl, further preferably pyrazolyl, thiazolyl, pyridyl or benzo[1,3]dioxolyl.

As "5-membered heterocycle" of $A^1$, isoxazolyl or thiazolyl is preferable.

As "6-membered heterocycle" of $A^1$, pyridyl, pyridazinyl, pyrimidinyl or pyrazinyl is preferable, and pyridyl, pyrimidinyl or pyrazinyl is more preferable.

The term "($C_{7-10}$ aralkyloxy)$C_{1-6}$ alkoxy" means the above $C_{1-6}$ alkoxy substituted by alkoxy having 1 to 4 carbon atoms substituted by phenyl.

The term "$C_{2-6}$ alkenyl" means straight chained or branched unsaturated hydrocarbon having 2 to 6 carbon atoms, which has at least one double bond. Examples thereof include vinyl, 2-propenyl, 1-propenyl, 1-buten-1-yl, 1-buten-2-yl, 1-buten-3-yl, 1-buten-4-yl, 2-buten-1-yl, 2-buten-2-yl, 1-penten-1-yl, 1-penten-2-yl, 1-penten-3-yl, 2-penten-1-yl, 2-penten-2-yl, 2-penten-3-yl, 1-hexen-1-yl, 1-hexen-2-yl, 1-hexen-3-yl, 2-methyl-1-propen-1-yl, and the like.

The term "($C_{1-6}$ alkyl)carbonylamino" means amino substituted by the above ($C_{1-6}$ alkyl)carbonyl.

The term "$C_{1-6}$ alkylsulfonylamino" means amino substituted by the above $C_{1-6}$ alkylsulfonyl.

The term "$C_{1-6}$ alkoxycarbonylamino-$C_{1-6}$ alkyl" means the above $C_{1-6}$ alkyl substituted by amino substituted by the above ($C_{1-6}$ alkoxy)carbonyl.

The term "($C_{1-6}$ alkyl)carbonyloxy" means carbonyloxy substituted by the above $C_{1-6}$ alkyl.

Hereinafter, the present invention is described in more detail.

The compound (I) of the present invention also include stereoisomers such as optical isomers, geometric isomers and the like thereof.

The optical isomer of the compound (I) of the present invention may have either of an R configuration and an S configuration at the respective asymmetric carbon atoms. Also, any of the optical isomers thereof and a mixture of the optical isomers are encompassed by the present invention. Further, in the mixture of the optical active bodies, racemic bodies including equal amounts of the respective optical isomers are also encompassed within the scope of the present invention. In the case where the compound (I) of the present invention is a solid or crystal racemic body, the racemic compound, the racemic mixture, and the racemic solid solution are also encompassed within the scope of the present invention.

In the case where geometric isomers of the compound (I) of the present invention exist, the present invention includes any of the geometric isomers.

Furthermore, in the case where tautomers of the compound (I) of the present invention exist, the present invention includes any of the tautomers.

The compound (I) of the present invention can be converted to a pharmaceutically acceptable salt thereof according to a usual method, as necessary. Such a salt may be presented as an acid addition salt or a salt with a base.

Examples of the acid addition salt can include acid addition salts with mineral acids such as hydrochloric acid, hydrobromic acid, hydroiodic acid, sulfuric acid, nitric acid, phosphoric acid and the like, and acid addition salts with organic acids such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid, and the like.

Examples of the salt with a base can include salts with inorganic bases, such as a sodium salt, a potassium salt, a calcium salt, a magnesium salt, and the like, and salts with organic bases such as piperidine, morpholine, pyrrolidine, arginine, lysine, and the like.

In addition, the compound (I) of the present invention or a pharmaceutically acceptable salt thereof also encompasses hydrates, and solvates with pharmaceutically acceptable solvents such as ethanol and the like.

TRPM8 is a cation channel that expression is observed in dorsal root ganglion and trigeminal ganglion. The TRPM8 inhibitor reduces the amount of cations influxing into cells through TRPM8 and thus suppresses the increase of the intracellular cation concentration. Based on this mechanism, the TRPM8 inhibitor is useful as an agent for treating or preventing lower urinary tract symptoms (LUTS), in particular overactive bladder syndrome (OAB) and the like by supression of hyperexcited afferent neuron activity.

Further, TRPM8 inhibitory activity can be evaluated by the efficacy inhibiting the wet-dog shake action which is induced by the administration of Icilin, TRPM8 agonist. Furthermore, an effect on overactive bladder (OAB) can be evaluated by an elongation of micturition interval against overactive bladder induced by acetic acid in accordance with a method described in J. Urol., 2001, 166, 1142.

As other embodiment of a compound represented by the general formula (I) of the present invention, $A^1$ is a group selected from the group consisting of the following aa3), bb2) and cc2):

aa3) $C_{6-10}$ aryl, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, $C_{1-6}$ alkoxycarbonyl and $C_{1-6}$ alkylsulfonyl, b2) isoxazolyl or thiazolyl, and c2) 6-membered heterocycle, wherein the ring is unsubstituted or substituted with 1 to 2 substituents independently selected from the group consisting of the following: a halogen atom and $C_{1-6}$ alkyl;

$A^2$ is a group selected from the group consisting of the following dd), ee) and f):

dd) $C_{6-10}$ aryl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano, amino, nitro, carboxy and ($C_{7-10}$ aralkyloxy)carbonyl, ee) heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, cyano, mono(di)$C_{1-6}$ alkylamino, $C_{1-6}$ alkylsulfanyl, amino, ($C_{7-10}$ aralkyloxy)carbonyl, hydroxy-$C_{1-6}$ alkyl, $C_{2-6}$ alkenyl, morpholino and ($C_{1-6}$ alkyl)carbonyl, and f) $C_{3-6}$ cycloalkyl;

X is CH or N;

Y is —$CR^1R^2$— or an oxygen atom;

$R^1$ and $R^2$ independently represent a hydrogen atom, a halogen atom or $C_{1-6}$ alkyl;

$R^3$ and $R^4$ independently represent a hydrogen atom, a halogen atom, $C_{1-6}$ alkyl, $C_{1-6}$ alkoxy, halo-$C_{1-6}$ alkyl, halo-$C_{1-6}$ alkoxy, hydroxy-$C_{1-6}$ alkoxy, $C_{3-6}$ cycloalkyl, $C_{2-6}$ alkenyl or cyano with the proviso that when X is CH, and $R^1$ and $R^2$ are hydrogen atoms, $R^3$ and $R^4$ are not hydrogen atoms at the same time; and n is 1 or 2.

Methods for Producing Compound (I) of the Present Invention

The compound (I) of the present invention or a pharmaceutically acceptable salt thereof can be prepared by a method shown in the following or a similar method thereto, or a method described in literatures or a similar method thereto.

Scheme 1

[Chem. 18]

(wherein, $A^1$, $A^2$, $R^1$ to $R^4$, X, Y and n have the same meanings as defined above;

$R^5$ and $R^6$ respectively represent $C_{1-6}$ alkyl group or $R^5$ and $R^6$ are bound to form a group represented by —$(CH_2)_m$—$(CHR^7)_m$—$(CH_2)_m$—;

m is 1 or 2; and $R^7$ represent a hydrogen atom or a phenyl group.)

Step 1-1

Compound (5) can be prepared by allowing Compound (1), Compound (2) and Compound (3) to react with Compound (4) in a solvent. Such reaction is well-known to those skilled in the art as Ugi reaction, and can be prepared, for example, by using the methods described in Domling A., Ugi I. Angewandte Chemie International Edition 2000, 39, 3168-3210. The reaction temperature is at −78° C. to solvent reflux temperature, and the reaction time is usually from 10 minutes to 6 days, varying based on a used starting material, solvent and reaction temperature or the like.

Step 1-2

The compound (I) can be prepared by hydrolysis of Compound (5) in a solvent under acidic condition. Examples of the solvent include tetrahydrofuran, 1,4-dioxane, and the like. Examples of the acid include hydrochloric acid, sulfuric acid, trifluoroacetic acid, and the like. The reaction temperature is at room temperature to solvent reflux temperature, and the reaction time is usually from 10 minutes to 1 day, varying based on a used starting material, solvent and reaction temperature or the like.

Respectively, Compound (2) and Compound (3) can be commercially available, or can be prepared by a method described in literature or a similar method thereto.

Compound (1) can be commercially available, and can be prepared, for example, by using the methods described in Jonathan A. Ellman et al., Accounts of Chemical Research 2002, 35, 984-995 or a similar method thereto. Compound (4) can be commercially available, and can be prepared, for example, by using the methods described in W. Maison et al., Bioorganic Medicinal Chemistry 2000, 8, 1343-1360 or a similar method thereto.

The schemes shown above are exemplifications of methods for preparing the compound (I) of the present invention or production intermediates thereof. These can be variously modified into schemes which can be easily understood by those skilled in the art.

Moreover, where a protecting group is required depending on the type of the functional group, introduction and removal operations can be appropriately carried out in combination according to conventional methods. Examples regarding the type of protecting groups, introduction, and removal can include the methods described in Theodora W. Greene & Peter G.M. Wuts Eds., "Greene's Protective Groups in Organic Synthesis," fourth edition, Wiley-Interscience, 2006.

The compound (I) of the present invention or a pharmaceutically acceptable salt thereof, and a manufacturing intermediate used for preparing these compounds can be isolated/purified, as necessary, by solvent extraction, crystallization/recrystallization, chromatography, preparative high performance liquid chromatography, or the like, which are isolation/purification means well-known to a skilled person in the art of the relevant field.

A pharmaceutical composition comprising the compound (I) of the present invention or a pharmaceutically acceptable salt thereof as an active ingredient is used in various dosage forms according to the usage. Examples of such dosage forms include powders, granules, fine granules, dry syrups, tablets, capsules, injections, liquids, ointments, suppositories, plasters, sublinguals, and the like, which are administered orally or parenterally.

These pharmaceutical compositions can be prepared by appropriately mixing or diluting/dissolving with appropriate pharmaceutical additives such as an excipient, a disintegrant, a binder, a lubricant, a diluent, a buffering agent, a tonicity agent, a preservative, a wetting agent, an emulsifier, a dispersant, a stabilizer, a solubilizing aid, and the like by a publicly-known method according to the dosage form. In addition, when the compound (I) of the present invention or a pharmaceutically acceptable salt thereof is used in combination with agents other than the TRPM8 inhibitor, the pharmaceutical compositions can be prepared by formulating the respective active ingredients simultaneously or separately in the same way as described above.

The compound (I) of the present invention or a pharmaceutically acceptable salt thereof exhibits potent inhibitory effects based on its TRPM8 inhibition in the confirmation test of inhibitory effects on icilin-induced wet-dog shakes. Accordingly, a pharmaceutical comprising the compound (I) of the present invention or a pharmaceutically acceptable salt thereof as an active ingredient can be used as an agent for treating or preventing diseases or symptoms caused by the activation of TRPM8.

"A disease or a symptom caused by the activation of TRPM8" means a disease or a symptom caused by hyperexcitability or a disorder of afferent neurons.

Examples of "a disease or a symptom caused by hyperexcitability or a disorder of afferent neurons" include anxietas, depression, lower urinary tract symptoms (LUTS), algi, circulatory disorder, itch, pins-and-needles sensation, hives and the like.

"Lower urinary tract symptoms (LUTS)" means symptom caused by lower urinary tract dysfunction and the like, and examples of "lower urinary tract dysfunction" include overactive bladder, detrusor overactivity, nocturia, cystitis such as interstitial cystitis and the like, prostatitis such as chronic prostatitis and the like, painful bladder syndrome, hypersensitive bladder syndrome, urinary incontinence, benign prostatic hyperplasia, ankylurethria and the like.

Examples of "circulatory disorder" include cold-induced rhinitis, Raynaud disease and the like.

The compound (I) of the present invention or a pharmaceutically acceptable salt thereof can also be appropriately used in combination with at least one agent other than the TRPM8 inhibitor.

Examples of the agent that can be used in combination with the compound (I) of the present invention or a pharmaceutically acceptable salt thereof include an opioid analgesic agent, a non-steroidal anti-inflammatory drug (NSAID), a barbiturate sedative, a benzodiazepine drug having sedating properties, a $H_1$ blocker having sedating properties, a sedative, a skeletal muscle relaxant, a NMDA receptor antagonist, an α-adrenoceptor modulator, a tricyclic antidepressant, an anti-seizure drug, a tachykinin antagonist (NK antagonist), a muscarinic receptor antagonist, a COX-2 selective inhibitor, a coal tar analgesic, a neuroleptic agent, a TRPV1 agonist, a TRPV1 inhibitor, a β blocker, a local anesthetic agent, a corticosteroid, a 5-HT receptor agonist, a $5-HT_{2A}$ receptor antagonist, a cholinergic analgesic, PDE5 inhibitor, PDE9 inhibitor, α2δ ligand, a cannabinoid, a metabotropic glutamate receptor 1 antagonist (mGluR1 antagonist), a metabotropic glutamate receptor 5 antagonist (mGluR5 antagonist), a serotonin reuptake inhibitor, a noradrenaline reuptake inhibitor, a serotonin-noradrenaline reuptake inhibitor, an inducible nitric oxide synthase inhibitor (iNOS inhibitor), an acetylcholine esterase inhibitor (AChE inhibitor), an EP4 antagonist, a leukotriene B4 antagonist, a 5-lipoxygenase inhibitor, a sodium channel blocker, a 5-HT3 antagonist, a chemotherapeutic agent, an EP1 antagonist, a β3 adrenoceptor agonist, a TRPA1 inhibitor, a TRPV3 inhibitor, a TRPV4 inhibitor, a T-type calcium channel inhibitor, a an ASIC inhibitor, a P2X inhibitor, a Trk inhibitor, a FAAH inhibitor, a botulinus toxin, a 5α-reductase inhibitor, an anti-NGF antibody, a NGF modulator, an depressant of IgE production, a histamine H2 inhibitor, a bladder mucosal protectant, a NOS activity regulator, a bladder muscle relaxant, a GABA reuptake inhibitor, a GABA receptor regulator, GABA aminotransferase inhibitor and the like.

Furthermore, concrete examples of the agent that is used in combination are illustrated as below, but the content of the present invention is not limited thereto. Further, examples of the concrete compounds include a free form thereof and other pharmaceutically acceptable salts.

Examples of "an α-adrenoceptor modulator" can include doxazosin, tamsulosin, silodosin, clonidine, guanfacine, dexmedetomidine, modafinil, tizanidine, moxonidine, and the like.

Examples of "a muscarinic receptor antagonist" can include oxybutynin, tolterodine, propiverine, darifenacin, solifenacin, temiverine, ipratropium bromide, trospium, propantheline, temiverine, imidafenacin, fesoterodine, and the like.

Examples of "EP1 antagonist" can include GSK-269984A, ONO-8539 and the like.

Examples of "a β3 adrenoceptor agonist" can include mirabegron, solabegron, TRK-380, and the like.

Examples of "a bladder mucosal protectant" can include pentosan polysulphate, hyaluronic acid, chondroitin sulfate, and the like.

When the compound (I) of the present invention or a pharmaceutically acceptable salt thereof is administered in combination with one or more of the above-described agents, the present invention includes all administration methods following 1) to 5):
1) simultaneous administration by a combination preparation,
2) simultaneous administration by the same administration pathway as a separate formulation,
3) simultaneous administration by a different administration pathway as a separate formulation,
4) administration at different times by the same administration pathway as a separate formulation, and
5) administration at different times by a different administration pathway as a separate formulation.

Further, in the case of administration at different times as a separate formulation as in 4) or 5), the order of administration of the compound (I) of the present invention or a pharmaceutically acceptable salt thereof and the above-described agents that is administered in combination is not particularly limited.

Furthermore, the compounds of the present invention or a pharmaceutically acceptable salt thereof can be administered appropriately in combination with one or more of the above-described agents to achieve an advantageous effect that is equal to or more than an additive effect in prevention or treatment of the above-described diseases. Alternatively, as compared with a case of being administrated alone, the amount used can be reduced, or the side effect of the agent(s) without TRPM8 inhibitor used together can be mitigated, or the side effect of the agent(s) without TRPM8 inhibitor used together can be avoided or mitigated.

The pharmaceutical composition of the present invention can be administered systemically or locally, and orally or parenterally (nasal, pulmonary, intravenous, rectal, subcutaneous, intramuscular, transdermal routes, and the like).

When the pharmaceutical composition of the present invention is employed for actual therapy, the administration amount of the active ingredient, which is the compound (I) of the present invention or a pharmaceutically acceptable salt thereof, is appropriately determined depending on the age, gender, and weight of the patient, the extent of disease and therapy and the like. For example, in the case of oral administration, it can be appropriately administered in the range of about 6 to 3000 mg per day for an adult (regarded as a body weight of 60 kg), in one portion or in several divided portions. The daily dose as an oral administration agent is preferably from 10 to 1000 mg, and more preferably from 60 to 600 mg. For example, in the case of parenteral administration, it can be appropriately administered in the range of about 0.6 to 300 mg per day for an adult, in one portion or in several divided portions. The daily dose as a parenteral administration agent is preferably from 1 to 100 mg, and more preferably from 6 to 60 mg. In addition, the administration amount of the compound (I) or a pharmaceutically acceptable salt thereof which is the active ingredient of the TRPM8 inhibitor of the present invention can be reduced according to the administration amount of agents other than TRPM8 inhibitor.

Hereinbelow, the present invention is illustrated in detail with reference to Examples, Reference Examples, and Test Examples, but the scope of the present invention is not limited thereto.

Among the symbols used in each of the Reference Examples, Examples, and Tables, Ref. Ex. means Reference Example Number, Ex. No. means Example Number, Strc. means a chemical structural formula, $^1$H-NMR means a proton nuclear magnetic resonance spectrum, CDCl$_3$ means chloroform-d, and DMSO-d$_6$ means dimethylsulfoxide-d$_6$, CD$_3$OD means methanol-d$_4$. Further, ESI-MS means electrospray ionization mass spectrometry. RT means retention time of high-performance liquid chromatography. When a mixture of two diastereomer was separated/purified using normal-phase column chromatography, low polarity product means a former eluted compound, high polarity product means a latter eluted compound. In the end of Example Number, LP means low polarity product, HP means high polarity product, and M means a mixture of optical isomers. [α]$_D$ means specific optical rotation.

In each Reference Example, the irradiation of the microwave used Biotage Initiator.

In each Example, high-performance liquid chromatography and mass spectrometry analysis was performed on the following conditions.

Instrument: 6520 Accurate-Mass Q-TOF instrument (Agilent)
Column: Inertsil ODS-4 (GL-science) 2.1×50 mm, 3 µm
Flow rate: 0.75 mL/min.
Gradient:

TABLE 1

| Time (minute) | 0.1% HCO$_2$H/H$_2$O | 0.1% HCO$_2$H/MeCN |
|---|---|---|
| 0 | 80 | 20 |
| 5 | 10 | 90 |
| 6 | 10 | 90 |

EXAMPLES

Reference Example 1-1

6-Cyclopropylindan-1-one

To a suspension of 6-bromoindan-1-one (0.60 g), cyclopropylboronic acid monohydrate (0.47 g), tricyclohexylphosphine (0.081 g) and tripotassium phosphate (2.11 g) in toluene (10 mL) and distilled water (0.5 mL) was added palladium(II) acetate (0.064 g), and the mixture was stirred for 1 hour at 150° C. under microwave irradiation. The reaction mixture was allowed to cool to room temperature, and water was added. The mixture was extracted with ethyl acetate. The organic layer was washed with brine, and dried over anhydrous magnesium sulfate, then filtrated. The filtrate was concentrated under reduced pressure. The residue was purified by silica gel column chromatography (eluent: ethyl acetate/n-hexane=0/100 to 20/80) to afford the title compound (0.462 g).

$^1$H-NMR (CDCl$_3$) δ: 0.68-0.75 (2H, m), 0.95-1.05 (2H, m), 1.90-2.00 (1H, m), 2.64-2.73 (2H, m), 3.05-3.13 (2H, m), 7.34-7.38 (2H, m), 7.40-7.43 (1H, m).

Reference Example 1-2

6-Cyclopropyl-4-fluoroindan-1-one

The title compound was synthesized in a manner similar to that of Reference Example 1-1 by using the corresponding starting material. The spectrum data of the title compound is shown as follows, and the structural formula is shown in Table 2.

$^1$H-NMR (CDCl$_3$) δ: 0.69-0.76 (2H, m), 0.99-1.07 (2H, m), 1.90-1.98 (1H, m), 2.67-2.75 (2H, m), 3.05-3.13 (2H, m), 7.02 (1H, dd, J=1.3, 9.9 Hz), 7.24 (1H, d, J=1.3 Hz).

Reference Example 2

4-Fluoro-6-vinylindan-1-one

A mixture of 6-bromo-4-fluoroindan-1-one (0.36 g), tetrakis(triphenylphosphine)palladium(0) (0.182 g), tributylvinyltin (600 μL) and toluene (6 mL) was stirred overnight under reflux. The reaction mixture was allowed to cool to room temperature, to the mixture were added an aqueous solution of 0.5 mol/L potassium fluoride and ethyl acetate, and the mixture was stirred for 0.5 hours at room temperature. The insoluble material was removed by filtration through a pad of Celite. The organic layer of the filtrate was washed with water and brine successively, and dried over anhydrous magnesium sulfate. The solvent was removed under reduced pressure, and the residue was purified by silica gel column chromatography (eluent:ethyl acetate/n-hexane=0/100 to 15/85) to afford the title compound (0.235 g). The structural formula is shown in Table 2.

$^1$H-NMR (CDCl$_3$) δ: 2.72-2.77 (2H, m), 3.11-3.17 (2H, m), 5.37 (1H, d, J=10.8 Hz), 5.81 (1H, d, J=17.5 Hz), 6.72 (1H, dd, J=10.8, 17.5 Hz), 7.33 (1H, dd, J=1.2, 9.8 Hz), 7.56-7.59 (1H, m).

Reference Example 3-1

(R)-6-Chloro-4-fluoroindan-1-ylamine hydrochloride

To a solution of 6-chloro-4-fluoroindan-1-one (0.43 g) in toluene (5 mL) were added (R)-tert-butylsulfinamide (0.29 g) and tetraethyl orthotitanate (0.79 g), and the mixture was stirred for 23 hrs at 60° C. under argon atmosphere. The reaction mixture was poured into a saturated aqueous solution of sodium bicarbonate, and the obtained two-layer mixture was stirred vigorously. The insoluble material was removed by filtration through a pad of Celite. The organic layer was separated, and the water layer was extracted with toluene. The combined organic layer was washed with brine, and dried over anhydrous sodium sulfate. The solvent was removed under reduced pressure, and the residue was purified by silica gel column chromatography (eluent:ethyl acetate/n-hexane=14/86 to 35/65) to afford (R-N-(6-chloro-4-fluoroindan-1-ylidene)-tert-butylsulfinamide (0.18 g). To a solution of (R)-N-(6-chloro-4-fluoroindan-1-ylidene)-tert-butylsulfinamide (0.32 g) in tetrahydrofuran (5.4 mL) were added water (0.11 mL) and sodium borohydride (0.13 g) at 0° C., and the mixture was stirred for 15 minutes at same temperature, and for 45 minutes at room temperature. The reaction mixture was partitioned between dichloromethane and water, and the organic layer was concentrated under reduced pressure. The residue was purified by silica gel column chromatography (eluent:ethyl acetate/n-hexane=19/81 to 40/60) to afford (R)-N-[(R)-6-chloro-4-fluoroindan-1-yl]-tert-butylsulfinamide (0.26 g). To a solution of (R)-N-[(R)-6-chloro-4-fluoroindan-1-yl]-tert-butylsulfinamide (0.39 g) in methanol (3.4 mL) was added a solution of 4 mol/L hydrogen chloride in 1,4-dioxane (1.0 mL) at room temperature, and the mixture was stirred for 1 hr at same temperature. Diisopropyl ether (approx. 20 mL) was added dropwise to the reaction mixture, and the precipitated salt was collected by filtration to afford the title compound (0.26 g). The structural formula is shown in Table 2.

$^1$H-NMR (DMSO-d$_6$) δ: 1.98-2.11 (1H, m), 2.44-2.59 (1H, m), 2.83-2.93 (1H, m), 3.00-3.11 (1H, m), 4.74-4.81 (1H, m), 7.44 (1H, dd, J=1.6, 9.0 Hz), 7.51-7.55 (1H, m), 8.25-8.55 (3H, m).

Reference Examples 3-2 to 3-6

Reference Examples 3-2 to 3-6 were synthesized in a manner similar to that of Reference Example 3-1 by using the corresponding starting materials. The spectrum data of Reference Example 3-2 to 3-6 are shown as follows, and the structural formulae are shown in Table 2.

Reference Example 3-2

(R)-4-Fluoroindan-1-ylamine hydrochloride $^1$H-NMR (DMSO-d$_6$) δ: 1.95-2.15 (1H, m), 2.40-2.60 (1H, m), 2.80-3.00 (1H, m), 3.00-3.15 (1H, m), 4.70-4.80 (1H, m), 7.10-7.25 (1H, m), 7.30-7.55 (2H, m), 8.20-8.70 (2H, m).

Reference Example 3-3

(R)-5-Fluoroindan-1-ylamine hydrochloride $^1$H-NMR (DMSO-d$_6$) δ: 1.95-2.10 (1H, m), 2.40-2.60 (1H, m), 2.80-2.95 (1H, m), 3.00-3.15 (1H, m), 4.60-4.75 (1H, m), 7.05-7.25 (2H, m), 7.55-7.70 (1H, m), 8.20-8.65 (2H, m).

Reference Example 3-4

(R)-4,6-Difluoroindan-1-ylamine hydrochloride $^1$H-NMR (DMSO-d$_6$) δ: 1.95-2.15 (1H, m), 2.40-2.60 (1H, m), 2.80-2.95 (1H, m), 2.95-3.10 (1H, m), 4.76 (1H, dd, J=7.0 Hz), 7.20-7.40 (2H, m), 8.15-8.60 (2H, m).

Reference Example 3-5

(R)-3,3-Dimethylindan-1-ylamine hydrochloride $^1$H-NMR (DMSO-d$_6$) δ: 1.17 (3H, s), 1.38 (3H, s), 1.83 (1H, dd, J=8.5, 13.3 Hz), 2.38 (1H, dd, J=7.5, 13.3 Hz), 4.75-4.81 (1H, m), 7.27-7.40 (3H, m), 7.54-7.61 (1H, m), 8.47 (3H, br s).

Reference Example 3-6

(R)-6-Cyclopropylindan-1-ylamine hydrochloride $^1$H-NMR (DMSO-d$_6$) δ: 0.55-0.72 (2H, m), 0.90-1.00 (2H, m), 1.86-2.03 (2H, m), 2.37-2.52 (1H, m), 2.74-2.87 (1H, m), 2.92-3.05 (1H, m), 4.60-4.67 (1H, m), 7.08 (1H, dd, J=1.6, 8.0 Hz), 7.19 (1H, d, J=8.0 Hz), 7.29 (1H, s), 8.33 (3H, br s).

Reference Example 4-1

(R)-N-[(R)-6-Cyclopropyl-4-fluoroindan-1-yl]-tert-butylsulfinamide

To a solution of 6-cyclopropyl-4-fluoroindan-1-one (0.083 g) and (R)-tert-butylsulfinamide (0.053 g) in tetrahydrofuran (1 mL) was added tetraethyl orthotitanate (180 μL) at room temperature, and the mixture was stirred for a day under reflux. The reaction mixture was allowed to cool to 0° C., and sodium borohydride (0.017 g) was added. The mixture was stirred for 0.5 hours under ice-cooling, and for 1 hour at room temperature. To the reaction mixture were added water and methanol, and the mixture was extracted with ethyl acetate. The organic layer was washed with brine, and dried over anhydrous magnesium sulfate, then filtered. The filtrate was concentrated under reduced pressure. The residue was purified by silica gel column chromatography (eluent:ethyl acetate/n-hexane=2/8 to 1/1) to afford the title compound (0.032 g). The structural formula is shown in Table 2.

$^1$H-NMR (CDCl$_3$) δ: 0.61-0.73 (2H, m), 0.91-1.00 (2H, m), 1.23 (9H, s), 1.84-1.94 (1H, m), 1.95-2.05 (1H, m), 2.40-2.54 (1H, m), 2.71-2.82 (1H, m), 2.93-3.03 (1H, m), 3.39 (1H, d, J=6.0 Hz), 4.80-4.90 (1H, m), 6.62 (1H, d, J=10.4 Hz), 7.10 (1H, s).

Reference Example 4-2

(R)-N-[(R)-4-Fluoro-6-vinylindan-1-yl]-tert-butyl-sulfinamide

The title compound was synthesized in a manner similar to that of Reference Example 4-1 by using the corresponding starting material. The spectrum data of the title compound is shown as follows, and the structural formula is shown in Table 2.

$^1$H-NMR (CDCl$_3$) δ: 1.24 (9H, s), 1.98-2.09 (1H, m), 2.45-2.57 (1H, m), 2.75-2.87 (1H, m), 2.97-3.08 (1H, m), 3.42 (1H, d, J=6.2 Hz), 4.85-4.95 (1H, m), 5.26 (1H, d, J=10.9 Hz), 5.74 (1H, d, J=17.6 Hz), 6.68 (1H, dd, J=10.9, 17.6 Hz), 7.00 (1H, d, J=10.0 Hz), 7.40 (1H, s).

Reference Example 5

[(R)-6-(2-Benzyloxyethoxy)indan-1-yl]carbamic acid tert-butyl ester

To a mixture of N-[(R)-6-hydroxyindan-1-yl]carbamic acid tert-butyl ester (0.148 g), cesium carbonate (0.386 g) and sodium iodide (0.018 g) in N,N-dimethylformamide (2 mL) was added (2-bromoethoxymethyl)benzene (117 μL) at room temperature, and the mixture was stirred for 3 hours at 70° C. The reaction mixture was allowed to cool to room temperature. To the mixture was added water, and this was extracted with ethyl acetate. The organic layer was washed with water and brine, and dried over anhydrous magnesium sulfate. The solvent was removed under reduced pressure, and the residue was purified by silica gel column chromatography (eluent:ethyl acetate/n-hexane=1/9 to 9/1) to afford the title compound (0.20 g). The structural formula is shown in Table 2.

$^1$H-NMR (CDCl$_3$) δ: 1.49 (9H, br s), 1.71-1.85 (1H, m), 2.50-2.64 (1H, m), 2.69-2.95 (2H, m), 3.75-3.86 (2H, m), 4.08-4.20 (2H, m), 4.58-4.77 (3H, m), 5.06-5.21 (1H, m), 6.81 (1H, dd, J=2.4, 8.3 Hz), 6.88 (1H, d, J=1.9 Hz), 7.10 (1H, d, J=8.3 Hz), 7.24-7.42 (5H, m).

TABLE 2

| Ref. Ex. | Strc. |
|---|---|
| 1-1 | |
| 1-2 | |
| 2 | |
| 3-1 | |
| 3-2 | |
| 3-3 | |
| 3-4 | |
| 3-5 | |
| 3-6 | |

TABLE 2-continued

| Ref. Ex. | Strc. |
|---|---|
| 4-1 | (structure: 4-fluoro-6-cyclopropyl indan with N-H-S(=O)-tBu sulfinamide) |
| 4-2 | (structure: 4-fluoro-6-vinyl indan with N-H-S(=O)-tBu sulfinamide) |
| 5 | (structure: 6-(2-benzyloxyethoxy)indan-1-yl NHC(=O)O-tBu) |

Example 1-1

N-[(R)-Carbamoylphenylmethyl]-N-[(R)-4,6-difluoroindan-1-yl]nicotinamide

To a solution of (R)-4,6-difluoroindan-1-ylamine (0.1 g) in methanol (1 mL) was added benzaldehyde (0.063 g), and the mixture was stirred for 1 hour at 60° C. The reaction mixture was allowed to cool to room temperature, and to the mixture were added nicotinic acid (0.073 g) and 4-phenylcyclohexen-1-ylisocyanide (0.108 g). The mixture was stirred overnight at 60° C., allowed to cool to room temperature, and concentrated under reduced pressure. To the residue were added tetrahydrofuran (3 mL), water (12 μL) and a solution of 4 mol/L hydrogen chloride in 1,4-dioxane (440 μL), and the mixture was stirred for 1.5 hours at room temperature. To the reaction mixture were added water and a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by silica gel column chromatography (eluent: methanol/ethyl acetate/n-hexane=0/70/30 to 0/100/0 to 20/80/0) to afford the title compound (0.076 g). The structural formula is shown in Table 3.

RT (min.): 2.727
MS (ESI, m/z): 406.1371 (M−H)⁻
$^1$H-NMR (CDCl$_3$) δ: 1.69-1.90 (1H, m), 1.93-2.15 (1H, m), 2.42-2.90 (2H, m), 4.54-4.88 (1H, br), 5.28-5.70 (3H, m), 6.65-6.79 (1H, m), 7.34-7.66 (7H, m), 7.77-7.97 (1H, m), 8.64-8.73 (1H, m), 8.82 (1H, br s).

Examples 1-2 to 1-6

Examples 1-2 to 1-6 were synthesized in a manner similar to that of Example 1-1 by using the corresponding starting materials. The spectrum data of Examples 1-2 to 1-6 are shown as follows, and the structural formulae are shown in Table 3.

Example 1-2

N-[(R)-Carbamoylphenylmethyl]-N-[(R)-6-cyanoindan-1-yl]nicotinamide

RT (min.): 2.356
MS (ESI, m/z): 395.1513 (M−H)⁻
$^1$H-NMR (CDCl$_3$) δ: 1.74-2.19 (2H, m), 2.57-2.90 (2H, m), 4.56-5.78 (4H, m), 7.21-7.61 (8H, m), 7.81-7.92 (1H, m), 8.19-8.37 (1H, m), 8.64-8.75 (1H, m), 8.81 (1H, br s).

Example 1-3

2-Amino-N-[(R)-carbamoylphenylmethyl]-N-[(R)-4,6-difluoroindan-1-yl]nicotinamide RT (min.): 2.161
MS (ESI, m/z): 421.1480 (M−H)⁻
$^1$H-NMR (CDCl$_3$) δ: 1.61-1.82 (1H, m), 1.92-2.18 (1H, m), 2.43-2.80 (2H, m), 4.50-4.80 (1H, br), 5.23-5.62 (5H, m), 6.62-6.78 (2H, m), 7.35-7.55 (7H, m), 8.13 (1H, dd, J=1.9, 5.0 Hz).

Example 1-4

2-Amino-N-[(R)-carbamoylphenylmethyl]-N-[(R)-6-cyanoindan-1-yl]nicotinamide

RT (min.): 1.813
MS (ESI, m/z): 410.1621 (M−H)⁻
$^1$H-NMR (CDCl$_3$) δ: 1.63-1.86 (1H, m), 1.93-2.20 (1H, m), 2.58-2.90 (2H, m), 4.46-4.77 (1H, br), 5.08-5.81 (5H, m), 6.65-6.75 (1H, m), 7.35-7.62 (8H, m), 8.14 (1H, dd, J=1.5, 5.1 Hz), 8.21 (1H, br s).

Example 1-5

N-[(R)-Carbamoylphenylmethyl]-N-[(R)-6-trifluoromethylindan-1-yl]nicotinamide

RT (min.): 2.964
MS (ESI, m/z): 438.1435 (M−H)⁻
$^1$H-NMR (CDCl$_3$) δ: 1.76-1.94 (1H, m), 2.05-2.20 (1H, m), 2.58-2.90 (2H, m), 4.55-4.97 (1H, br), 5.20-5.81 (3H, m), 7.20-7.63 (8H, m), 7.78-7.97 (1H, m), 8.26 (1H, br s), 8.62-8.73 (1H, m), 8.82 (1H, br s).

Example 1-6

N-[(R)-Carbamoylphenylmethyl]-N-[(R)-6-methoxyindan-1-yl]nicotinamide

RT (min.): 2.432
MS (ESI, m/z): 400.1663 (M−H)⁻
$^1$H-NMR (CDCl$_3$) δ: 1.67-1.82 (1H, m), 1.97-2.09 (1H, m), 2.47-2.75 (2H, m), 3.89 (3H, s), 4.66-4.82 (1H, br), 5.28-5.67 (3H, m), 6.81-6.88 (1H, m), 7.07 (1H, d, J=8.4

Hz), 7.34-7.54 (6H, m), 7.60-7.65 (1H, m), 7.90-7.96 (1H, m), 8.69 (1H, dd, J=1.6, 5.0 Hz), 8.86-8.89 (1H, m).

Example 2-1

N-[(R)-Carbamoylphenylmethyl]-N-[(R)-5-chloroindan-1-yl]benzamide

N-[(S)-Carbamoylphenylmethyl]-N-[(R)-5-chloroindan-1-yl]benzamide

To a solution of (R)-5-chloroindan-1-ylamine hydrochloride (0.05 g) in methanol (1 mL) were added triethylamine (35 μL) and benzaldehyde (0.026 g), and the mixture was stirred for 1.5 hours at 50° C. The reaction mixture was allowed to cool to room temperature, and to the mixture were added benzoic acid (0.03 g) and 4-phenylcyclohexen-1-ylisocyanide (0.045 g). The mixture was stirred for 3 days at 50° C., then allowed to cool to room temperature, and concentrated under reduced pressure. To the obtained residue were added tetrahydrofuran (2 mL), water (5 μL) and a solution of 4 mol/L hydrogen chloride in 1,4-dioxane (185 μL), and the mixture was stirred for 1 hour at room temperature. To the reaction mixture were added water and a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by silica gel column chromatography (eluent:ethyl acetate/n-hexane=55/45 to 75/25 to 100/0) to afford N-[(R)-carbamoylphenylmethyl]-N-[(R)-5-chloroindan-1-yl]benzamide (Example 2-1LP, 0.040 g) as low polarity product and N-[(S)-carbamoylphenylmethyl]-N-[(R)-5-chloroindan-1-yl]benzamide (Example 2-1HP, 0.023 g) as high polarity product. The structural formulae are shown in Table 4.

Example 2-1LP

N-[(R)-Carbamoylphenylmethyl]-N-[(R)-5-chloroindan-1-yl]benzamide

RT (min.): 3.627
MS (ESI, m/z): 403.1217 (M–H)⁻
¹H-NMR (CDCl₃) δ: 1.64-1.88 (1H, m), 1.95-2.15 (1H, m), 2.46-2.84 (2H, m), 4.63 (1H, br s), 5.20-5.90 (3H, m), 7.15 (1H, br s), 7.25-7.65 (11H, m), 7.91 (1H, d, J=8.0 Hz).

Example 2-1HP

N-[(S)-Carbamoylphenylmethyl]-N-[(R)-5-chloroindan-1-yl]benzamide

RT (min.): 3.534
MS (ESI, m/z): 403.1219 (M–H)⁻
¹H-NMR (CDCl₃) δ: 2.34-2.53 (1H, m), 2.58-2.86 (2H, m), 2.98-3.15 (1H, m), 4.35-4.53 (1H, m), 5.31-6.05 (3H, m), 6.51-6.70 (1H, m), 6.78 (1H, dd, J=1.8, 8.2 Hz), 7.16 (1H, br s), 7.27-7.63 (10H, m).

Examples 2-2 to 2-260

Examples 2-2 to 2-260 were synthesized in a manner similar to that of Example 2-1 by using the corresponding starting materials. The spectrum data of Examples 2-2 to 2-260 are shown as follows, and the structural formulae are shown in Tables 4 to 28.

Example 2-2LP

N-[(R)-Carbamoylphenylmethyl]-N-[(R)-6-chloroindan-1-yl]benzamide

RT (min.): 3.583
MS (ESI, m/z): 403.1219 (M–H)⁻
¹H-NMR (CDCl₃) δ: 1.70-1.86 (1H, m), 2.00-2.14 (1H, m), 2.48-2.78 (2H, m), 4.66 (1H, s), 5.23-5.93 (3H, m), 7.09 (1H, d, J=7.8 Hz), 7.17-7.65 (11H, m), 7.97 (1H, s).

Example 2-2HP

N-[(S)-Carbamoylphenylmethyl]-N-[(R)-6-chloroindan-1-yl]benzamide

RT (min.): 3.447
MS (ESI, m/z): 403.1213 (M–H)⁻
¹H-NMR (CDCl₃) δ: 2.35-2.56 (1H, m), 2.59-2.83 (2H, m), 2.95-3.13 (1H, m), 4.40 (1H, br s), 5.31-5.92 (3H, m), 6.49-6.64 (1H, m), 7.04-7.14 (2H, m), 7.27-7.63 (10H, m).

Example 2-3LP

N-[(R)-Carbamoylphenylmethyl]-N-[(R)-4-trifluoromethylindan-1-yl]benzamide

RT (min.): 3.760
MS (ESI, m/z): 437.1482 (M–H)⁻
¹H-NMR (CDCl₃) δ: 1.65-1.90 (1H, m), 2.00-2.20 (1H, m), 2.60-2.85 (1H, m), 2.85-3.05 (1H, m), 4.63 (1H, br s), 5.20-5.85 (3H, m), 7.30-7.65 (12H, m), 8.15-8.30 (1H, m).

Example 2-3HP

N-[(S)-Carbamoylphenylmethyl]-N-[(R)-4-trifluoromethylindan-1-yl]benzamide

RT (min.): 3.641
MS (ESI, m/z): 437.1483 (M–H)⁻
¹H-NMR (CDCl₃) δ: 2.40-2.60 (1H, m), 2.60-2.80 (1H, m), 2.80-3.00 (1H, m), 3.15-3.35 (1H, m), 4.30-4.55 (1H, m), 5.25-5.90 (3H, m), 6.75-6.95 (2H, m), 7.20-7.35 (4H, m), 7.35-7.50 (5H, m), 7.50-7.65 (2H, m).

Example 2-4LP

N-[(R)-Carbamoylphenylmethyl]-N-[(R)-6-methoxyindan-1-yl]benzamide

RT (min.): 3.332
MS (ESI, m/z): 399.1711 (M–H)⁻
¹H-NMR (CDCl₃) δ: 1.65-1.82 (1H, m), 1.96-2.11 (1H, m), 2.46-2.75 (2H, m), 3.90 (3H, s), 4.69 (1H, br s), 5.20-5.90 (3H, m), 6.78-6.87 (1H, m), 7.06 (1H, d, J=8.3 Hz), 7.24-7.67 (11H, m).

Example 2-5LP

N-[(R)-Carbamoylphenylmethyl]-N-[(R)-6-cyclopropylindan-1-yl]benzamide

RT (min.): 3.803
MS (ESI, m/z): 409.1919 (M–H)⁻
¹H-NMR (CDCl₃) δ: 0.74-1.06 (4H, m), 1.63-1.82 (1H, m), 1.91-2.11 (2H, m), 2.44-2.76 (2H, m), 4.65 (1H, br s), 5.19-5.98 (3H, m), 6.97-7.09 (2H, m), 7.29-7.68 (11H, m).

Example 2-5HP

N-[(S)-Carbamoylphenylmethyl]-N-[(R)-6-cyclopropylindan-1-yl]benzamide

RT (min.): 3.653
MS (ESI, m/z): 409.1913 (M−H)⁻
$^1$H-NMR (CDCl$_3$) δ: −0.03-0.09 (1H, m), 0.26-0.36 (1H, m), 0.61-0.79 (2H, m), 1.46-1.59 (1H, m), 2.29-2.47 (1H, m), 2.56-2.78 (2H, m), 2.93-3.08 (1H, m), 4.45 (1H, br s), 5.25-5.95 (3H, m), 6.35 (1H, br s), 6.89 (1H, dd, J=1.3, 8.0 Hz), 7.02-7.08 (1H, m), 7.27-7.66 (10H, m).

Example 2-6LP

N-[(R)-Carbamoylphenylmethyl]-N-[(R)-6-chloro-4-fluoroindan-1-yl]benzamide

RT (min.): 3.720
MS (ESI, m/z): 421.1130 (M−H)⁻
$^1$H-NMR (CDCl$_3$) δ: 1.65-1.90 (1H, m), 1.90-2.20 (1H, m), 2.40-2.65 (1H, m), 2.65-2.90 (1H, m), 4.66 (1H, br s), 5.20-5.85 (3H, m), 6.75-7.05 (1H, m), 7.25-7.90 (11H, m).

Example 2-6HP

N-[(S)-Carbamoylphenylmethyl]-N-[(R)-6-chloro-4-fluoroindan-1-yl]benzamide

RT (min.): 3.595
MS (ESI, m/z): 421.1129 (M−H)⁻
$^1$H-NMR (CDCl$_3$) δ: 2.35-2.60 (1H, m), 2.60-2.90 (2H, m), 2.95-3.25 (1H, m), 4.30-4.50 (1H, m), 5.20-5.90 (3H, m), 6.25-6.45 (1H, m), 6.83 (1H, d, J=8.3 Hz), 7.25-7.60 (10H, m).

Example 2-7LP

N-[(R)-Carbamoylphenylmethyl]-N-[(R)-4-chloroindan-1-yl]benzamide

RT (min.): 3.627
MS (ESI, m/z): 403.1217 (M−H)⁻
$^1$H-NMR (CDCl$_3$) δ: 1.65-1.87 (1H, m), 1.99-2.16 (1H, m), 2.47-2.64 (1H, m), 2.74-2.92 (1H, m), 4.65 (1H, br s), 5.19-5.98 (3H, m), 7.23-7.62 (12H, m), 7.83-7.95 (1H, m).

Example 2-7HP

N-[(S)-Carbamoylphenylmethyl]-N-[(R)-4-chloroindan-1-yl]benzamide

RT (min.): 3.526
MS (ESI, m/z): 403.1216 (M−H)⁻
$^1$H-NMR (CDCl$_3$) δ: 2.34-3.23 (4H, m), 4.47 (1H, br s), 5.31-5.93 (3H, m), 6.52-6.68 (1H, m), 6.74-6.80 (1H, m), 7.11 (1H, d, J=7.9 Hz), 7.23-7.63 (10H, m).

Example 2-8LP

N-[(R)-Carbamoylphenylmethyl]-N-[(R)-4-chloro-6-fluoroindan-1-yl]benzamide

RT (min.): 3.779
MS (ESI, m/z): 421.1115 (M−H)⁻
$^1$H-NMR (CDCl$_3$) δ: 1.65-1.90 (1H, m), 1.90-2.15 (1H, m), 2.40-2.65 (1H, m), 2.65-2.85 (1H, m), 4.50-4.80 (1H, m), 5.20-5.85 (3H, m), 6.85-7.10 (1H, m), 7.25-7.80 (11H, m).

Example 2-8HP

N-[(S)-Carbamoylphenylmethyl]-N-[(R)-4-chloro-6-fluoroindan-1-yl]benzamide

RT (min.): 3.609
MS (ESI, m/z): 421.1121 (M−H)⁻
$^1$H-NMR (CDCl$_3$) δ: 2.40-2.60 (1H, m), 2.60-2.85 (2H, m), 2.95-3.20 (1H, m), 4.35-4.55 (1H, m), 5.30-5.90 (3H, m), 6.10-6.35 (1H, m), 6.75-6.95 (1H, m), 7.25-7.60 (10H, m).

Example 2-9LP

N-[(R)-Carbamoylphenylmethyl]-N-[(S)-2,3-dihydrobenzofuran-3-yl]benzamide

RT (min.): 2.882
MS (ESI, m/z): 371.1406 (M−H)⁻
$^1$H-NMR (CDCl$_3$) δ: 4.12 (1H, dd, J=5.3, 10.2 Hz), 4.26 (1H, br s), 4.66 (1H, br s), 5.28-5.88 (3H, m), 6.78 (1H, d, J=8.1 Hz), 6.93-7.04 (1H, m), 7.19-7.73 (12H, m).

Example 2-9HP

N-[(S)-Carbamoylphenylmethyl]-N-[(S)-2,3-dihydrobenzofuran-3-yl]benzamide

RT (min.): 2.900
MS (ESI, m/z): 371.1402 (M−H)⁻
$^1$H-NMR (CDCl$_3$) δ: 4.48-4.61 (2H, m), 5.13-5.22 (1H, m), 5.43-5.70 (3H, m), 6.51 (1H, t, J=7.5 Hz), 6.68 (1H, br s), 6.80 (1H, d, J=8.2 Hz), 7.07-7.54 (11H, m).

Example 2-10LP

N-[(R)-Carbamoylphenylmethyl]-N-[(R)-5-chloro-6-methoxyindan-1-yl]benzamide

RT (min.): 3.671
MS (ESI, m/z): 433.1329 (M−H)⁻
$^1$H-NMR (CDCl$_3$) δ: 1.60-1.80 (1H, m), 1.95-2.10 (1H, m), 2.45-2.70 (2H, m), 4.03 (3H, s), 4.55-4.70 (1H, m), 5.20-5.75 (3H, m), 7.17 (1H, s), 7.30-7.65 (10H, m), 7.75 (1H, br s).

Example 2-11LP

N-[(R)-Carbamoylphenylmethyl]-N-[(R)-6-difluoromethoxyindan-1-yl]benzamide

RT (min.): 3.562
MS (ESI, m/z): 435.1535 (M−H)⁻
$^1$H-NMR (CDCl$_3$) δ: 1.75-1.95 (1H, m), 2.05-2.25 (1H, m), 2.50-2.85 (2H, m), 4.55-4.70 (1H, m), 5.25-5.65 (2H, m), 5.80-6.10 (1H, m), 6.67 (1H, dd, J=74.6, 74.6 Hz), 6.95-7.20 (2H, m), 7.30-7.65 (10H, m), 7.65-7.75 (1H, m).

Example 2-11HP

N-[(S)-Carbamoylphenylmethyl]-N-[(R)-6-difluoromethoxyindan-1-yl]benzamide

RT (min.): 3.351
MS (ESI, m/z): 435.1527 (M−H)⁻
$^1$H-NMR (CDCl$_3$) δ: 2.40-2.60 (1H, m), 2.65-2.85 (2H, m), 3.00-3.15 (1H, m), 4.35-4.50 (1H, m), 5.30-5.90 (4H, m), 6.30-6.45 (1H, m), 6.87 (1H, dd, J=2.0, 8.0 Hz), 7.14 (1H, d, J=8.3 Hz), 7.25-7.65 (10H, m).

Example 2-12LP

N-[(R)-Carbamoylphenylmethyl]-N-[(R)-5,6-difluoroindan-1-yl]benzamide

RT (min.): 3.469
MS (ESI, m/z): 405.1423 (M−H)$^-$
$^1$H-NMR (CDCl$_3$) δ: 1.68-1.86 (1H, m), 1.99-2.19 (1H, m), 2.46-2.79 (2H, m), 4.55-4.77 (1H, br), 5.21-5.94 (3H, m), 6.83-7.01 (1H, m), 7.32-7.62 (10H, m) 7.71-7.88 (1H, m).

Example 2-12HP

N-[(S)-Carbamoylphenylmethyl]-N-[(R)-5,6-difluoroindan-1-yl]benzamide

RT (min.): 3.330
MS (ESI, m/z): 405.1424 (M−H)$^-$
$^1$H-NMR (CDCl$_3$) δ: 2.36-2.56 (1H, m), 2.62-2.81 (2H, m), 2.94-3.15 (1H, m), 4.35-4.47 (1H, br), 5.32-5.87 (3H, m), 6.29-6.48 (1H, m), 6.88-7.00 (1H, m), 7.27-7.40 (5H, m) 7.41-7.60 (5H, m).

Example 2-13LP

N-[(R)-Carbamoylphenylmethyl]-N-[(R)-6-cyanoindan-1-yl]benzamide

RT (min.): 3.144
MS (ESI, m/z): 394.1567 (M−H)$^-$
$^1$H-NMR (CDCl$_3$) δ: 1.16-2.24 (2H, m), 2.56-3.22 (2H, m), 4.48-5.95 (4H, m), 7.12-7.64 (12H, m), 8.15-8.34 (1H, m).

Example 2-14LP

N-[(R)-Carbamoylphenylmethyl]-N-[(R)-4-difluoromethoxyindan-1-yl]benzamide

RT (min.): 3.470
MS (ESI, m/z): 435.1531 (M−H)$^-$
$^1$H-NMR (CDCl$_3$) δ: 1.65-1.85 (1H, m), 2.00-2.15 (1H, m), 2.45-2.65 (1H, m), 2.75-2.90 (1H, m), 4.66 (1H, br s), 5.20-6.00 (3H, m), 6.49 (1H, dd, J=74.0, 74.0 Hz), 6.95-7.10 (1H, m), 7.30-7.65 (11H, m), 7.80-7.90 (1H, m).

Example 2-14HP

N-[(S)-Carbamoylphenylmethyl]-N-[(R)-4-difluoromethoxyindan-1-yl]benzamide

RT (min.): 3.382
MS (ESI, m/z): 435.1533 (M−H)$^-$
$^1$H-NMR (CDCl$_3$) δ: 2.35-2.55 (1H, m), 2.60-2.85 (2H, m), 3.05-3.25 (1H, m), 4.40-4.55 (1H, m), 5.30-6.00 (3H, m), 6.49 (1H, dd, J=73.9, 73.9 Hz), 6.55-6.65 (1H, m), 6.75-6.95 (2H, m), 7.20-7.65 (10H, m).

Example 2-15LP

N-[(R)-Carbamoylphenylmethyl]-N-[(S)-5-chloro-2,3-dihydrobenzofuran-3-yl]benzamide RT (min.): 3.292
MS (ESI, m/z): 405.1019 (M−H)$^-$
$^1$H-NMR (CDCl$_3$) δ: 3.61-5.90 (6H, m), 6.65 (1H, d, J=8.6 Hz), 7.05-7.19 (1H, m), 7.36-7.80 (11H, m).

Example 2-15HP

N-[(S)-Carbamoylphenylmethyl]-N-[(S)-5-chloro-2,3-dihydrobenzofuran-3-yl]benzamide RT (min.): 3.215
MS (ESI, m/z): 405.1016 (M−H)$^-$
$^1$H-NMR (CDCl$_3$) δ: 4.45-4.65 (2H, m), 5.07-5.21 (1H, m), 5.42-5.72 (3H, m), 6.51 (1H, br s), 6.65-6.74 (1H, m), 7.03 (1H, d, J=8.2 Hz), 7.13-7.53 (10H, m).

Example 2-16LP

N-[(R)-Carbamoylphenylmethyl]-N-[(R)-6-ethylindan-1-yl]benzamide

RT (min.): 3.752
MS (ESI, m/z): 397.1924 (M−H)$^-$
$^1$H-NMR (CDCl$_3$) δ: 1.29 (3H, t, J=7.6 Hz), 1.66-1.87 (1H, m), 1.97-2.13 (1H, m), 2.49-2.80 (4H, m), 4.67 (1H, br s), 5.20-6.05 (3H, m), 7.05-7.15 (2H, m), 7.30-7.53 (8H, m), 7.57-7.65 (2H, m), 7.77 (1H, br s).

Example 2-17LP

N-[(R)-Carbamoylphenylmethyl]-N-[(R)-6-methylindan-1-yl]benzamide

RT (min.): 3.516
MS (ESI, m/z): 383.1769 (M−H)$^-$
$^1$H-NMR (CDCl$_3$) δ: 1.65-1.82 (1H, m), 1.98-2.11 (1H, m), 2.43 (3H, s), 2.48-2.78 (2H, m), 4.67 (1H, br s), 5.38-5.98 (3H, m), 7.02-7.12 (2H, m), 7.30-7.53 (8H, m), 7.58-7.66 (2H, m), 7.74 (1H, br s).

Example 2-18LP

N-[(R)-Carbamoylphenylmethyl]-N-[(R)-4-methylindan-1-yl]benzamide

RT (min.): 3.493
MS (ESI, m/z): 383.1766 (M−H)$^-$
$^1$H-NMR (CDCl$_3$) δ: 1.66-1.83 (1H, m), 2.00-2.13 (1H, m), 2.20 (3H, s), 2.41-2.77 (2H, m), 4.70 (1H, br s), 5.21-6.01 (3H, m), 7.09 (1H, d, J=7.2 Hz), 7.22-7.29 (1H, m), 7.31-7.64 (10H, m), 7.77 (1H, d, J=7.2 Hz).

Example 2-19LP

N-[(R)-6-Bromoindan-1-yl]-N-[(R)-carbamoylphenylmethyl]benzamide

RT (min.): 3.654
MS (ESI, m/z): 447.0716 (M−H)$^-$
$^1$H-NMR (CDCl$_3$) δ: 1.68-1.86 (1H, m), 1.97-2.14 (1H, m), 2.46-2.77 (2H, m), 4.66 (1H, br s), 5.25-5.94 (3H, m), 6.98-7.07 (1H, m), 7.30-7.63 (11H, m), 8.11 (1H, br s).

Example 2-20LP

N-[(R)-Carbamoylphenylmethyl]-N-[(R)-6-trifluoromethylindan-1-yl]benzamide

RT (min.): 3.737
MS (ESI, m/z): 437.1487 (M−H)$^-$
$^1$H-NMR (CDCl$_3$) δ: 1.77-1.94 (1H, m), 2.06-2.26 (1H, m), 2.59-2.92 (2H, m), 4.56-4.74 (1H, m), 5.22-6.03 (3H, m), 7.17-7.65 (12H, m), 8.23 (1H, br s).

Example 2-21LP

N-[(R)-Carbamoylphenylmethyl]-N-[(R)-6-trifluoromethoxyindan-1-yl]benzamide

RT (min.): 3.822
MS (ESI, m/z): 453.1434 (M−H)⁻
$^1$H-NMR (CDCl$_3$) δ: 1.75-1.95 (1H, m), 2.00-2.20 (1H, m), 2.50-2.85 (2H, m), 4.55-4.80 (1H, m), 5.20-6.00 (3H, m), 7.05-7.20 (2H, m), 7.30-7.65 (10H, m), 7.85 (1H, br s).

Example 2-22LP

N-[(R)-Carbamoylphenylmethyl]-N-[(R)-4,6-difluoroindan-1-yl]-2-nitrobenzamide

RT (min.): 3.534
MS (ESI, m/z): 450.1273 (M−H)⁻
$^1$H-NMR (CDCl$_3$) δ: 1.65-1.85 (1H, m), 2.05-2.20 (1H, m), 2.35-2.50 (1H, m), 2.65-2.80 (1H, m), 4.63 (1H, s), 5.05-5.20 (1H, m), 5.35-5.50 (2H, m), 6.65-6.80 (1H, m), 7.35-7.85 (9H, m), 8.25 (1H, d, J=8.2 Hz).

Example 2-23LP

N-[(R)-Carbamoylphenylmethyl]-N-[(R)-6-chloro-4-fluoroindan-1-yl]nicotinamide

RT (min.): 2.937
MS (ESI, m/z): 422.1074 (M−H)⁻
$^1$H-NMR (CDCl$_3$) δ: 1.70-1.90 (1H, m), 1.95-2.20 (1H, m), 2.40-2.65 (1H, m), 2.65-2.90 (1H, m), 4.55-4.90 (1H, m), 5.25-5.75 (3H, m), 6.90-7.10 (1H, m), 7.30-7.55 (6H, m), 7.70-7.95 (2H, m), 8.65-8.75 (1H, m), 8.82 (1H, br s).

Example 2-23HP

N-[(S)-Carbamoylphenylmethyl]-N-[(R)-6-chloro-4-fluoroindan-1-yl]nicotinamide

RT (min.): 2.767
MS (ESI, m/z): 422.1077 (M−H)⁻
$^1$H-NMR (CDCl$_3$) δ: 2.40-2.65 (1H, m), 2.65-2.85 (2H, m), 3.00-3.20 (1H, m), 4.30-4.55 (1H, m), 5.30-5.70 (3H, m), 6.20-6.40 (1H, m), 6.85 (1H, d, J=8.3 Hz), 7.25-7.45 (6H, m), 7.80-7.95 (1H, m), 8.71 (1H, dd, J=1.6, 4.9 Hz), 8.75-8.85 (1H, br s).

Example 2-24LP

N-[(R)-Carbamoylphenylmethyl]-N-[(S)-5-chloro-2,3-dihydrobenzofuran-3-yl]nicotinamide RT (min.): 2.486
MS (ESI, m/z): 406.0972 (M−H)⁻
$^1$H-NMR (CDCl$_3$) δ: 4.05-4.20 (2H, m), 5.00-5.90 (4H, m), 6.40-6.80 (1H, m), 7.00-7.95 (9H, m), 8.45-8.90 (2H, m).

Example 2-24HP

N-[(S)-Carbamoylphenylmethyl]-N-[(S)-5-chloro-2,3-dihydrobenzofuran-3-yl]nicotinamide RT (min.): 2.507
MS (ESI, m/z): 406.0960 (M−H)⁻
$^1$H-NMR (CDCl$_3$) δ: 4.40-5.80 (5H, m), 6.35-6.80 (2H, m), 7.06 (1H, d, J=1.7, 8.6 Hz), 7.15-7.60 (7H, m), 7.65-7.90 (1H, m), 8.60-8.75 (2H, m).

Example 2-25LP

2-Amino-N-[(R)-carbamoylphenylmethyl]-N-[(S)-5-chloro-2,3-dihydrobenzofuran-3-yl]nicotinamide RT (min.): 1.824
MS (ESI, m/z): 421.1071 (M−H)⁻
$^1$H-NMR (CDCl$_3$) δ: 4.01 (1H, dd, J=4.7, 10.1 Hz), 5.35-5.65 (5H, m), 6.65-6.75 (2H, m), 7.16-7.23 (1H, m), 7.40-7.58 (6H, m), 7.70-7.72 (1H, m), 8.14 (1H, dd, J=1.8, 5.1 Hz).

Example 2-26LP

N-[(R)-Carbamoylphenylmethyl]-N-[(R)-6-difluoromethoxyindan-1-yl]nicotinamide

RT (min.): 2.778
MS (ESI, m/z): 436.1476 (M−H)⁻
$^1$H-NMR (CDCl$_3$) δ: 1.75-1.90 (1H, m), 2.05-2.20 (1H, m), 2.55-2.80 (2H, m), 4.55-4.85 (1H, m), 5.25-5.90 (3H, m), 6.65 (1H, dd, J=74.1, 74.1 Hz), 6.95-7.20 (2H, m), 7.35-7.55 (6H, m), 7.75 (1H, br s), 7.85-7.95 (1H, m), 8.65-8.75 (1H, m), 8.84 (1H, br s).

Example 2-27LP

2-Amino-N-[(R)-carbamoylphenylmethyl]-N-[(R)-6-difluoromethoxyindan-1-yl]nicotinamide RT (min.): 2.243
MS (ESI, m/z): 451.1583 (M−H)⁻
$^1$H-NMR (CDCl$_3$) δ: 1.40-1.90 (1H, m), 1.95-2.20 (1H, m), 2.50-2.80 (2H, m), 4.50-4.75 (1H, m), 5.30-5.60 (5H, m), 6.58 (1H, dd, J=74.1, 74.1 Hz), 6.68 (1H, dd, J=5.0, 7.3 Hz), 6.95-7.10 (1H, m), 7.16 (1H, d, J=8.2 Hz), 7.35-7.55 (6H, m), 7.70 (1H, br s), 8.12 (1H, dd, J=1.8, 5.0 Hz).

Example 2-28LP

N-[(R)-Carbamoylphenylmethyl]-N-[(S))-5-fluoro-2,3-dihydrobenzofuran-3-yl]benzamide RT (min.): 3.030
MS (ESI, m/z): 389.1307 (M−H)⁻
$^1$H-NMR (CDCl$_3$) δ: 4.10-5.84 (6H, m), 6.60-6.99 (2H, m), 7.32-7.66 (11H, m).

Example 2-28HP

N-[(S)-Carbamoylphenylmethyl]-N-[(S)-5-fluoro-2,3-dihydrobenzofuran-3-yl]benzamide RT (min.): 2.979
MS (ESI, m/z): 389.1305 (M−H)⁻
$^1$H-NMR (CDCl$_3$) δ: 4.50-4.65 (1H, m), 5.11-5.23 (1H, m), 5.40-5.66 (3H, m), 6.25-6.36 (1H, m), 6.66-6.84 (2H, m), 7.17-7.34 (4H, m), 7.43-7.50 (6H, m).

Example 2-29LP

N-[(R)-Carbamoylphenylmethyl]-N-[(S)-5,7-difluoro-2,3-dihydrobenzofuran-3-yl]benzamide RT (min.): 3.239
MS (ESI, m/z): 407.1211 (M−H)⁻
$^1$H-NMR (CDCl$_3$) δ: 4.16-5.86 (6H, m), 6.64-6.81 (1H, m), 7.16-7.68 (11H, m).

Example 2-29HP

N-[(S)-Carbamoylphenylmethyl]-N-[(S)-5,7-difluoro-2,3-dihydrobenzofuran-3-yl]benzamide RT (min.): 3.165
MS (ESI, m/z): 407.1208 (M–H)$^-$
$^1$H-NMR (CDCl$_3$) δ: 4.60-6.20 (6H, m), 6.60-6.68 (1H, m), 7.24-7.50 (11H, m).

Example 2-30LP

N-[(R)-Carbamoylphenylmethyl]-N-[(R)-4-fluoro-6-methoxyindan-1-yl]benzamide

RT (min.): 3.499
MS (ESI, m/z): 417.1614 (M–H)$^-$
$^1$H-NMR (CDCl$_3$) δ: 1.66-1.81 (1H, m), 1.99-2.11 (1H, m), 2.41-2.53 (1H, m), 2.69-2.79 (1H, m), 3.89 (3H, s), 4.67 (1H, br s), 5.30-5.78 (3H, m), 6.54 (1H, d, J=10.5 Hz), 7.33-7.52 (9H, m), 7.56-7.61 (2H, m).

Example 2-30HP

N-[(S)-Carbamoylphenylmethyl]-N-[(R)-4-fluoro-6-methoxyindan-1-yl]benzamide

RT (min.): 3.301
MS (ESI, m/z): 417.1618 (M–H)$^-$
$^1$H-NMR (CDCl$_3$) δ: 2.39-2.51 (1H, m), 2.61-2.77 (2H, m), 2.99-3.11 (1H, m), 3.28 (3H, s), 4.47 (1H, br s), 5.37-5.54 (2H, m), 5.73 (1H, br), 5.95 (1H, br s), 6.40 (1H, dd, J=2.0, 10.4 Hz), 7.28-7.39 (5H, m), 7.42-7.48 (3H, m), 7.53-7.59 (2H, m).

Example 2-31LP

N-[(R)-Carbamoylphenylmethyl]-N-[(R)-6-chloroindan-1-yl]nicotinamide

RT (min.): 2.732
MS (ESI, m/z): 404.1171 (M–H)$^-$
$^1$H-NMR (CDCl$_3$) δ: 1.70-1.90 (1H, m), 1.90-2.15 (1H, m), 2.50-2.80 (2H, m), 4.55-4.90 (1H, m), 5.20-5.75 (3H, m), 7.05-7.15 (1H, m), 7.15-7.30 (1H, m), 7.30-7.55 (6H, m), 7.85-8.05 (2H, m), 8.60-8.75 (1H, m), 8.84 (1H, br s).

Example 2-31HP

N-[(S)-Carbamoylphenylmethyl]-N-[(R)-6-chloroindan-1-yl]nicotinamide

RT (min.): 2.606
MS (ESI, m/z): 404.1170 (M–H)$^-$
$^1$H-NMR (CDCl$_3$) δ: 2.40-2.60 (1H, m), 2.65-2.85 (2H, m), 2.95-3.15 (1H, m), 4.30-4.60 (1H, m), 5.25-5.75 (3H, m), 6.40-6.60 (1H, m), 7.10 (2H, s), 7.25-7.45 (6H, m), 7.80-7.95 (1H, m), 8.70 (1H, dd, J=1.5, 4.8 Hz), 8.83 (1H, br s).

Example 2-32LP

N-[(R)-Carbamoylphenylmethyl]-N-[(R)-4,6-difluoroindan-1-yl]pyrimidine-5-carboxamide RT (min.): 2.715
MS (ESI, m/z): 407.1326 (M–H)$^-$
$^1$H-NMR (CDCl$_3$) δ: 1.70-1.91 (1H, m), 1.94-2.14 (1H, m), 2.44-2.90 (2H, m), 4.45-5.00 (1H, br), 5.25-5.77 (3H, m), 6.63-6.86 (1H, m), 7.25-7.78 (6H, m), 8.77-9.02 (2H, m), 9.22-9.36 (1H, m).

Example 2-33LP

2-Amino-N-[(R)-carbamoylphenylmethyl]-N-[(R)-6-chloroindan-1-yl]nicotinamide

RT (min.): 2.166
MS (ESI, m/z): 419.1276 (M–H)$^-$
$^1$H-NMR (CDCl$_3$) δ: 1.45-1.80 (1H, m), 1.90-2.15 (1H, m), 2.45-2.75 (2H, m), 4.55-4.80 (1H, m), 5.25-5.65 (5H, m), 6.67 (1H, dd, J=5.1, 7.3 Hz), 7.10 (1H, d, J=8.0 Hz), 7.20-7.30 (1H, m), 7.35-7.55 (6H, m), 7.87 (1H, br s), 8.12 (1H, dd, J=1.7, 5.0 Hz).

Example 2-34LP

N-[(R)-Carbamoylphenylmethyl]-N-[(R)-4,6-difluoroindan-1-yl]pyrazine-2-carboxamide RT (min.): 2.944
MS (ESI, m/z): 407.1323 (M–H)$^-$
$^1$H-NMR (DMSO-d$_6$) δ: 1.20-1.40 (1H, m), 2.00-2.15 (1H, m), 2.45-2.65 (1H, m), 2.80-2.95 (1H, m), 5.05-5.15 (1H, m), 5.54 (1H, s), 6.85-7.00 (1H, m), 7.20-7.55 (9H, m), 8.65-8.95 (2H, m).

Example 2-35LP

N-[(R)-Carbamoylphenylmethyl]-N-[(R)-4-fluoro-6-methylindan-1-yl]benzamide

RT (min.): 3.586
MS (ESI, m/z): 401.1671 (M–H)$^-$
$^1$H-NMR (CDCl$_3$) δ: 1.68-1.82 (1H, m), 2.00-2.12 (1H, m), 2.39-2.56 (4H, m), 2.71-2.82 (1H, m), 4.65 (1H, br s), 5.25-5.85 (3H, m), 6.78 (1H, d, J=9.6 Hz), 7.25-7.63 (11H, m).

Example 2-35HP

N-[(S)-Carbamoylphenylmethyl]-N-[(R)-4-fluoro-6-methylindan-1-yl]benzamide

RT (min.): 3.544
MS (ESI, m/z): 401.1669 (M–H)$^-$
$^1$H-NMR (CDCl$_3$) δ: 1.93 (3H, s), 2.39-2.76 (3H, m), 3.02-3.14 (1H, m), 4.39 (1H, br s), 5.35-5.55 (2H, m), 5.67-5.79 (1H, m), 6.19 (1H, br s), 6.62 (1H, d, J=9.9 Hz), 7.25-7.33 (4H, m), 7.42-7.47 (3H, m), 7.53-7.61 (2H, m).

Example 2-36LP

N-[(R)-Carbamoylphenylmethyl]-N-[(R)-4,6-difluoroindan-1-yl]-2-methoxynicotinamide RT (min.): 3.204
MS (ESI, m/z): 436.1478 (M–H)$^-$
$^1$H-NMR (CDCl$_3$) δ: 1.69-2.27 (2H, m), 2.44-3.08 (2H, m), 3.93-4.12 (3H, m), 4.49-4.85 (1H, m), 5.15-6.05 (3H, m), 6.51-6.79 (1H, m), 6.88-7.10 (1H, m), 7.30-7.88 (7H, m), 8.17-8.33 (1H, m).

Example 2-37LP

N-[(R)-Carbamoylphenylmethyl]-N-[(R)-6-fluoroindan-1-yl]nicotinamide

RT (min.): 2.492
MS (ESI, m/z): 388.1465 (M–H)$^-$
$^1$H-NMR (CDCl$_3$) δ: 1.69-1.88 (1H, m), 1.97-2.13 (1H, m), 2.46-2.78 (2H, m), 4.61-4.86 (1H, br), 5.28-5.75 (3H, m), 6.89-7.02 (1H, m), 7.05-7.16 (1H, m), 7.33-7.55 (6H, m), 7.66-7.79 (1H, m), 7.83-7.95 (1H, m), 8.69 (1H, dd, J=1.5, 4.9 Hz), 8.80-8.89 (1H, m).

Example 2-38LP

2-Amino-N-[(R)-carbamoylphenylmethyl]-N-[(R)-6-fluoroindan-1-yl]nicotinamide

RT (min.): 1.979
MS (ESI, m/z): 403.1574 (M−H)⁻
$^1$H-NMR (CDCl$_3$) δ: 1.50-2.11 (2H, m), 2.43-2.75 (2H, m), 4.54-4.79 (1H, br), 5.30-5.62 (5H, m), 6.67 (1H, dd, J=5.0, 7.4 Hz), 6.93-7.00 (1H, m), 7.09-7.15 (1H, m), 7.36-7.54 (6H, m), 7.59-7.64 (1H, m), 8.12 (1H, dd, J=1.7, 5.0 Hz).

Example 2-39LP

N-[(R)-Carbamoylphenylmethyl]-N-[(R)-4-fluoro-6-methoxyindan-1-yl]nicotinamide

RT (min.): 2.674
MS (ESI, m/z): 418.1569 (M−H)⁻
$^1$H-NMR (CDCl$_3$) δ: 1.67-1.81 (1H, m), 1.97-2.10 (1H, m), 2.42-2.55 (1H, m), 2.68-2.80 (1H, m), 3.88 (3H, s), 4.72 (1H, br s), 5.32-5.61 (3H, m), 6.56 (1H, d, J=10.5 Hz), 7.34-7.53 (7H, m), 7.86-7.95 (1H, m), 8.67-8.72 (1H, m), 8.86 (1H, s).

Example 2-39HP

N-[(S)-Carbamoylphenylmethyl]-N-[(R)-4-fluoro-6-methoxyindan-1-yl]nicotinamide

RT (min.): 2.479
MS (ESI, m/z): 418.1570 (M−H)⁻
$^1$H-NMR (CDCl$_3$) δ: 2.43-2.55 (1H, m), 2.64-2.80 (2H, m), 2.98-3.11 (1H, m), 3.26 (3H, s), 4.50 (1H, br), 5.37-5.62 (3H, m), 5.88 (1H, s), 6.41 (1H, dd, J=2.0, 10.4 Hz), 7.30-7.44 (6H, m), 7.85-7.92 (1H, m), 8.69-8.73 (1H, m), 8.84 (1H, s).

Example 2-40LP

N-[(R)-Carbamoylphenylmethyl]-N-[(R)-4-fluoro-6-methylindan-1-yl]nicotinamide

RT (min.): 2.744
MS (ESI, m/z): 402.1620 (M−H)⁻
$^1$H-NMR (CDCl$_3$) δ: 1.69-1.83 (1H, m), 2.00-2.10 (1H, m), 2.42 (3H, s), 2.45-2.57 (1H, m), 2.70-2.83 (1H, m), 4.72 (1H, br s), 5.33-5.64 (3H, m), 6.79 (1H, d, J=9.7 Hz), 7.35-7.60 (7H, m), 7.91 (1H, d, J=7.8 Hz), 8.69 (1H, dd, J=1.6, 4.9 Hz), 8.86 (1H, s).

Example 2-40HP

N-[(S)-Carbamoylphenylmethyl]-N-[(R)-4-fluoro-6-methylindan-1-yl]nicotinamide

RT (min.): 2.672
MS (ESI, m/z): 402.1621 (M−H)⁻
$^1$H-NMR (CDCl$_3$) δ: 1.92 (3H, s), 2.40-2.58 (1H, m), 2.65-2.81 (2H, m), 3.00-3.15 (1H, m), 4.42 (1H, br), 5.37-5.64 (3H, m), 6.14 (1H, s), 6.63 (1H, d, J=9.8 Hz), 7.25-7.44 (6H, m), 7.86-7.92 (1H, m), 8.70 (1H, dd, J=1.7, 4.9 Hz), 8.83 (1H, s).

Example 2-41LP

2-Amino-N-[(R)-carbamoylphenylmethyl]-N-[(S)-5-fluoro-2,3-dihydrobenzofuran-3-yl]nicotinamide RT (min.): 1.545
MS (ESI, m/z): 405.1367 (M−H)⁻
$^1$H-NMR (CDCl$_3$) δ: 4.01 (1H, dd, J=4.6, 10.2 Hz), 4.07-4.85 (1H, m), 5.35-5.64 (4H, m), 6.65-6.78 (2H, m), 6.90-7.01 (1H, m), 7.39-7.60 (7H, m), 8.15 (1H, dd, J=1.7, 5.1 Hz).

Example 2-42LP

2-Amino-N-[(R)-carbamoylphenylmethyl]-N-[(S)-5,7-difluoro-2,3-dihydrobenzofuran-3-yl]nicotinamide RT (min.): 1.848
MS (ESI, m/z): 423.1271 (M−H)⁻
$^1$H-NMR (CDCl$_3$) δ: 4.07-4.80 (2H, m), 5.30-5.65 (4H, m), 6.67-6.87 (2H, m), 7.30-7.60 (7H, m), 8.13-8.17 (1H, m).

Example 2-43LP

N-[(R)-Carbamoylphenylmethyl]-N-[(R)-4,6-difluoroindan-1-yl]pyridine-2-carboxamide RT (min.): 3.085
MS (ESI, m/z): 406.1373 (M−H)⁻
$^1$H-NMR (CDCl$_3$) δ: 1.66-3.18 (4H, m), 4.69-6.24 (4H, m), 6.48-6.78 (1H, m), 6.97-8.06 (9H, m), 8.56-8.64 (1H, m).

Example 2-44LP

N-[(R)-Carbamoylphenylmethyl]-N-[(R)-4,6-difluoroindan-1-yl]pyridazine-4-carboxamide RT (min.): 2.633
MS (ESI, m/z): 407.1318 (M−H)⁻
$^1$H-NMR (CDCl$_3$) δ: 1.68-1.89 (1H, m), 1.95-2.13 (1H, m), 2.45-2.88 (2H, m), 4.48-5.76 (4H, m), 6.56-6.84 (1H, m), 7.37-7.72 (7H, m), 9.21-9.42 (2H, m).

Example 2-45LP

N-[(R)-Carbamoylphenylmethyl]-N-[(R)-4,6-difluoroindan-1-yl]-6-methoxynicotinamide RT (min.): 3.324
MS (ESI, m/z): 436.1470 (M−H)⁻
$^1$H-NMR (CDCl$_3$) δ: 1.72-1.93 (1H, m), 1.95-2.20 (1H, m), 2.47-2.94 (2H, m), 3.97 (3H, s), 4.50-5.94 (4H, m), 6.64-6.77 (1H, br), 6.80 (1H, d, J=8.7 Hz), 7.31-7.68 (6H, m), 7.74-7.86 (1H, m), 8.43 (1H, d, J=1.7 Hz).

Example 2-46LP

N-[(R)-Carbamoylphenylmethyl]-N-[(R)-6-chloroindan-1-yl]-2-methoxynicotinamide

RT (min.): 3.261
MS (ESI, m/z): 434.1276 (M−H)⁻
$^1$H-NMR (CDCl$_3$) δ: 1.65-1.85 (1H, m), 1.85-2.25 (1H, m), 2.45-2.80 (2H, m), 3.95-4.10 (3H, m), 4.55-4.90 (1H, m), 5.10-6.20 (3H, m), 6.90-7.15 (2H, m), 7.15-7.30 (1H, m), 7.30-8.05 (7H, m), 8.22 (1H, dd, J=1.8, 5.0 Hz).

Example 2-47LP

N-[(R)-Carbamoylphenylmethyl]-N-[(R)-4,6-difluoroindan-1-yl]isonicotinamide

RT (min.): 2.620
MS (ESI, m/z): 406.1370 (M–H)⁻
$^1$H-NMR (CDCl$_3$) δ: 1.68-1.86 (1H, m), 1.93-2.12 (1H, m), 2.43-2.85 (2H, m), 4.50-5.05 (1H, m), 5.24-5.77 (3H, m), 6.53-6.80 (1H, m), 7.20-7.66 (8H, m), 8.66-8.80 (2H, m).

Example 2-48LP

N-[(R)-Carbamoylphenylmethyl]-N-[(R)-7-chloro-1,2,3,4-tetrahydronaphthalen-1-yl]nicotinamide RT (min.): 2.804
MS (ESI, m/z): 418.1329 (M–H)⁻
$^1$H-NMR (CDCl$_3$) δ: 1.34-1.64 (2H, m), 1.66-1.83 (2H, m), 2.55-2.65 (2H, m), 4.65 (1H, br s), 4.99-5.10 (1H, m), 5.28-5.69 (2H, m), 7.01 (1H, d, J=8.2 Hz), 7.17-7.23 (1H, m), 7.35-7.45 (4H, m), 7.47-7.55 (2H, m), 7.89-7.95 (1H, m), 8.22 (1H, d, J=1.3 Hz), 8.70 (1H, dd, J=1.6, 4.9 Hz), 8.86 (1H, d, J=1.6 Hz).

Example 2-48HP

N-[(S)-Carbamoylphenylmethyl]-N-[(R)-7-chloro-1,2,3,4-tetrahydronaphthalen-1-yl]nicotinamide RT (min.): 2.701
MS (ESI, m/z): 418.1324 (M–H)⁻
$^1$H-NMR (CDCl$_3$) δ: 1.37-1.68 (1H, m), 1.90-2.07 (1H, m), 2.14-2.35 (2H, m), 2.58-2.83 (2H, m), 4.45 (1H, br s), 4.99-5.09 (1H, m), 5.34-5.72 (2H, m), 6.77 (1H, br s), 6.93-7.02 (2H, m), 7.22-7.43 (6H, m), 7.83-7.91 (1H, m), 8.70 (1H, dd, J=1.5, 4.9 Hz), 8.81-8.85 (1H, m).

Example 2-49LP

N-[(R)-Carbamoylphenylmethyl]-N-[(R)-7-chloro-1,2,3,4-tetrahydronaphthalen-1-yl]benzamide RT (min.): 3.691
MS (ESI, m/z): 417.1379 (M–H)⁻
$^1$H-NMR (CDCl$_3$) δ: 1.32-1.55 (2H, m), 1.70-1.84 (2H, m), 2.54-2.63 (2H, m), 4.62 (1H, br s), 5.07-5.18 (1H, m), 5.24-5.99 (2H, m), 7.00 (1H, d, J=8.2 Hz), 7.16-7.22 (1H, m), 7.32-7.61 (10H, m), 8.13-8.18 (1H, m).

Example 2-49HP

N-[(S)-Carbamoylphenylmethyl]-N-[(R)-7-chloro-1,2,3,4-tetrahydronaphthalen-1-yl]benzamide RT (min.): 3.583
MS (ESI, m/z): 417.1376 (M–H)⁻
$^1$H-NMR (CDCl$_3$) δ: 1.40-1.53 (1H, m), 1.89-2.02 (1H, m), 2.13-2.33 (2H, m), 2.56-2.67 (1H, m), 2.70-2.83 (1H, m), 4.42 (1H, br s), 5.07-5.17 (1H, m), 5.31-5.93 (2H, m), 6.85 (1H, br s), 6.93-7.02 (2H, m), 7.28-7.32 (5H, m), 7.42-7.46 (3H, m), 7.53-7.57 (2H, m).

Example 2-50LP

N-[(R)-Carbamoylphenylmethyl]-N-[(R)-6-chloro-4-fluoroindan-1-yl]thiophene-2-carboxamide RT (min.): 3.682
MS (ESI, m/z): 427.0689 (M–H)⁻
$^1$H-NMR (CDCl$_3$) δ: 1.80-2.40 (2H, m), 2.55-2.70 (1H, m), 2.80-3.00 (1H, m), 4.40-6.30 (4H, m), 6.90-7.05 (1H, m), 7.07 (1H, dd, J=3.8, 5.0 Hz), 7.30-7.50 (6H, m), 7.52 (1H, dd, J=1.0, 5.0 Hz), 7.65-7.85 (1H, m).

Example 2-51LP

N-[(R)-Carbamoylphenylmethyl]-N-[(R)-6-chloro-4-fluoroindan-1-yl]thiazole-5-carboxamide RT (min.): 3.173
MS (ESI, m/z): 428.0639 (M–H)⁻
$^1$H-NMR (CDCl$_3$) δ: 1.75-2.30 (2H, m), 2.50-2.70 (1H, m), 2.75-3.00 (1H, m), 4.50-6.05 (4H, m), 6.85-7.10 (1H, m), 7.30-7.55 (5H, m), 7.65-7.90 (1H, m), 8.20 (1H, br s), 8.92 (1H, s).

Example 2-52LP

N-[(R)-Carbamoylphenylmethyl]-N-[(R)-6-isopropoxyindan-1-yl]nicotinamide

RT (min.): 2.840
MS (ESI, m/z): 428.1983 (M–H)⁻
$^1$H-NMR (CDCl$_3$) δ: 1.34-1.42 (6H, m), 1.69-1.82 (1H, m), 1.96-2.07 (1H, m), 2.44-2.73 (2H, m), 4.60-4.85 (2H, m), 5.29-5.66 (3H, m), 6.77-6.86 (1H, m), 7.02-7.10 (1H, m), 7.33-7.62 (7H, m), 7.86-7.97 (1H, m), 8.64-8.72 (1H, m), 8.84-8.92 (1H, m).

Example 2-53LP

N-[(R)-Carbamoylphenylmethyl]-N-[(R)-6-isopropoxyindan-1-yl]benzamide

RT (min.): 3.742
MS (ESI, m/z): 427.2028 (M–H)⁻
$^1$H-NMR (CDCl$_3$) δ: 1.34-1.43 (6H, m), 1.67-1.81 (1H, m), 1.97-2.08 (1H, m), 2.45-2.71 (2H, m), 4.61-4.76 (2H, m), 5.24-5.84 (3H, m), 6.77-6.84 (1H, m), 7.05 (1H, d, J=8.1 Hz), 7.30-7.64 (11H, m).

Example 2-54LP

N-[(R)-Carbamoylphenylmethyl]-6-cyano-N-[(R)-4,6-difluoroindan-1-yl]nicotinamide RT (min.): 3.276
MS (ESI, m/z): 431.1326 (M–H)⁻
$^1$H-NMR (CDCl$_3$) δ: 1.67-2.16 (2H, m), 2.44-2.90 (2H, m), 4.50-5.85 (4H, m), 6.62-6.84 (1H, m), 7.37-8.09 (8H, m), 8.79-8.95 (1H, m).

Example 2-55LP

N-[(R)-Carbamoylphenylmethyl]-N-[(R)-4,6-difluoroindan-1-yl]thiazole-5-carboxamide RT (min.): 2.959
MS (ESI, m/z): 412.0941 (M–H)⁻
$^1$H-NMR (CDCl$_3$) δ: 1.77-1.98 (1H, m), 2.00-2.30 (1H, m), 2.54-2.69 (1H, m), 2.77-2.96 (1H, m), 4.37-5.14 (1H, m), 5.19-6.08 (3H, m), 6.55-6.88 (1H, m), 7.33-7.70 (6H, m), 8.17-8.24 (1H, m), 8.93 (1H, s).

Example 2-56LP

N-[(R)-Carbamoylphenylmethyl]-N-[(R)-4-fluoroindan-1-yl]nicotinamide

RT (min.): 2.502
MS (ESI, m/z): 388.1467 (M–H)⁻

¹H-NMR (CDCl₃) δ: 1.68-1.88 (1H, m), 1.97-2.15 (1H, m), 2.47-2.66 (1H, m), 2.72-2.92 (1H, m), 4.60-4.83 (1H, br), 5.29-5.73 (3H, m), 6.91-7.04 (1H, m), 7.29-7.55 (7H, m), 7.78 (1H, d, J=7.7 Hz), 7.91 (1H, d, J=7.7 Hz), 8.65-8.73 (1H, m), 8.80-8.90 (1H, m).

Example 2-57LP

N-[(R)-Carbamoylphenylmethyl]-N-[(R)-4,6-difluoroindan-1-yl]thiazole-2-carboxamide RT (min.): 3.495
MS (ESI, m/z): 412.0940 (M−H)⁻
¹H-NMR (CDCl₃) δ: 1.55-3.19 (4H, m), 4.50-5.90 (2H, m), 6.50-7.10 (2H, m), 7.32-7.68 (8H, m), 7.85-8.00 (1H, m).

Example 2-58LP

N-[(R)-Carbamoylphenylmethyl]-N-[(R)-4-chloro-6-fluoroindan-1-yl]nicotinamide

RT (min.): 2.986
MS (ESI, m/z): 422.1078 (M−H)⁻
¹H-NMR (CDCl₃) δ: 1.70-1.90 (1H, m), 1.95-2.15 (1H, m), 2.40-2.65 (1H, m), 2.65-2.85 (1H, m), 4.50-5.80 (4H, m), 6.85-7.10 (1H, m), 7.20-7.95 (8H, m), 8.65-8.75 (1H, m), 8.81 (1H, br s).

Example 2-59LP

2-Amino-N-[(R)-carbamoylphenylmethyl]-N-[(R)-6-chloro-4-fluoroindan-1-yl]thiazole-5-carboxamide RT (min.): 2.752
MS (ESI, m/z): 443.0751 (M−H)⁻
¹H-NMR (CDCl₃) δ: 1.75-2.35 (2H, m), 2.45-2.75 (1H, m), 2.75-3.00 (1H, m), 4.20-6.30 (6H, m), 6.85-7.10 (1H, m), 7.10-7.80 (7H, m).

Example 2-60LP

N-[(R)-Carbamoylphenylmethyl]-N-[(R)-6-chloro-4-fluoroindan-1-yl]thiazole-4-carboxamide RT (min.): 3.294
MS (ESI, m/z): 428.0643 (M−H)⁻
¹H-NMR (CDCl₃) δ: 1.45-2.05 (1H, m), 2.10-2.45 (1H, m), 2.55-2.75 (1H, m), 2.75-3.20 (1H, m), 4.50-7.05 (4H, m), 7.10-7.85 (7H, m), 8.18 (1H, br s), 8.75-8.95 (1H, m).

Example 2-61LP

2-Amino-N-[(R)-carbamoylphenylmethyl]-N-[(R)-4,6-difluoroindan-1-yl]thiazole-5-carboxamide RT (min.): 2.540
MS (ESI, m/z): 427.1046 (M−H)⁻
¹H-NMR (CDCl₃) δ: 1.78-2.36 (2H, m), 2.51-2.73 (1H, m), 2.80-2.95 (1H, m), 4.33-5.00 (1H, m), 5.21-6.30 (5H, m), 6.56-6.84 (1H, m), 7.31-7.58 (7H, m).

Example 2-62LP

N-[(R)-Carbamoylphenylmethyl]-N-[(R)-4,6-difluoroindan-1-yl]terephthalamic acid benzyl ester RT (min.): 4.269
MS (ESI, m/z): 539.1791 (M−H)⁻
¹H-NMR (CDCl₃) δ: 1.63-2.12 (2H, m), 2.37-3.13 (2H, m), 4.50-5.07 (1H, m), 5.13-5.71 (5H, m), 6.53-6.73 (1H, m), 7.23-7.67 (13H, m), 8.08-8.22 (2H, m).

Example 2-63LP

N-[(R)-Carbamoylphenylmethyl]-N-[(R)-6-chloro-4-fluoroindan-1-yl]thiophene-3-carboxamide RT (min.): 3.586
MS (ESI, m/z): 427.0690 (M−H)⁻
¹H-NMR (CDCl₃) δ: 1.70-2.25 (2H, m), 2.45-2.65 (1H, m), 2.70-3.00 (1H, m), 4.50-5.95 (4H, m), 6.85-7.10 (1H, m), 7.20-7.90 (9H, m).

Example 2-64LP

N-[(R)-Carbamoylphenylmethyl]-N-[(R)-6-chloro-4-fluoroindan-1-yl]-5-fluorothiophene-2-carboxamide RT (min.): 3.923
MS (ESI, m/z): 445.0597 (M−H)⁻
¹H-NMR (CDCl₃) δ: 1.22-1.34 (1H, m), 1.81-1.95 (1H, m), 2.56-2.69 (1H, m), 2.85-2.96 (1H, m), 4.10-6.30 (4H, m), 6.47 (1H, dd, J=1.4, 4.2 Hz), 6.94-7.03 (1H, m), 7.11-7.16 (1H, m), 7.34-7.43 (5H, m), 7.70-7.78 (1H, m).

Example 2-64HP

N-[(S)-Carbamoylphenylmethyl]-N-[(R)-6-chloro-4-fluoroindan-1-yl]-5-fluorothiophene-2-carboxamide RT (min.): 3.747
MS (ESI, m/z): 445.0596 (M−H)⁻
¹H-NMR (CDCl₃) δ: 2.63-2.94 (3H, m), 3.13-3.23 (1H, m), 4.28-6.48 (4H, m), 6.49 (1H, dd, J=1.4, 4.2 Hz), 6.85-6.90 (1H, m), 7.13-7.18 (1H, m), 7.20-7.35 (6H, m).

Example 2-65LP

2-Amino-N-[(R)-carbamoylphenylmethyl]-N-[(R)-4-fluoroindan-1-yl]nicotinamide

RT (min.): 1.997
MS (ESI, m/z): 403.1575 (M−H)⁻
¹H-NMR (CDCl₃) δ: 1.60-1.77 (1H, m), 1.97-2.16 (1H, m), 2.50-2.82 (2H, m), 4.52-4.82 (1H, br), 5.24-5.64 (5H, m), 6.67 (1H, dd, J=5.0, 7.4 Hz), 6.93-7.01 (1H, m), 7.25-7.55 (7H, m), 7.67 (1H, d, J=7.4 Hz), 8.12 (1H, d, J=1.8, 5.0 Hz).

Example 2-66LP

N-[(R)-Carbamoylpyridin-3-ylmethyl]-N-[(R)-6-chloro-4-fluoroindan-1-yl]benzamide RT (min.): 2.520
MS (ESI, m/z): 422.1078 (M−H)⁻
¹H-NMR (CDCl₃) δ: 1.74-1.94 (1H, m), 2.10-2.31 (1H, m), 2.48-2.68 (1H, m), 2.76-2.96 (1H, m), 4.63-4.77 (1H, m), 5.34-6.14 (3H, m), 6.95-7.06 (1H, m), 7.32-7.59 (6H, m), 7.70 (1H, br s), 7.85-8.02 (1H, m), 8.56-8.72 (2H, m).

Example 2-66HP

N-[(S)-Carbamoylpyridin-3-ylmethyl]-N-[(R)-6-chloro-4-fluoroindan-1-yl]benzamide RT (min.): 2.275
MS (ESI, m/z): 422.1079 (M−H)⁻

¹H-NMR (CDCl₃) δ: 2.42-3.20 (4H, m), 4.37-4.48 (1H, m), 5.41-5.92 (3H, m), 6.86-6.92 (1H, m), 7.28-7.34 (1H, m), 7.43-7.60 (6H, m), 7.86-7.94 (1H, m), 8.30-8.38 (1H, m), 8.56-8.63 (1H, m).

Example 2-67LP

N-[(R)-Carbamoylphenylmethyl]-N-[(R)-4,6-difluoroindan-1-yl]isothiazole-5-carboxamide RT (min.): 3.228
MS (ESI, m/z): 412.0937 (M−H)⁻
¹H-NMR (CDCl₃) δ: 1.71-1.93 (1H, m), 2.05-2.34 (1H, m), 2.48-2.66 (1H, m), 2.71-2.96 (1H, m), 4.45-5.90 (4H, m), 6.54-6.88 (1H, m), 7.32-7.65 (7H, m), 8.48 (1H, br s).

Example 2-68LP

N-[(R)-Carbamoylpyridin-2-ylmethyl]-N-[(R)-6-chloro-4-fluoroindan-1-yl]benzamide RT (min.): 3.223
MS (ESI, m/z): 422.1075 (M−H)⁻
¹H-NMR (CDCl₃) δ: 1.90-2.09 (1H, m), 2.21-2.37 (1H, m), 2.50-2.69 (1H, m), 2.80-3.11 (1H, m), 4.66-5.95 (4H, m), 6.83-7.09 (1H, m), 7.40-7.83 (9H, m), 8.49-8.65 (1H, m).

Example 2-69LP

N-[(R)-Carbamoylphenylmethyl]-N-[(R)-6-chloro-4-fluoroindan-1-yl]pyridine-2-carboxamide RT (min.): 3.300
MS (ESI, m/z): 422.1077 (M−H)⁻
¹H-NMR (CDCl₃) δ: 1.60-2.10 (1H, m), 2.15-2.40 (1H, m), 2.45-3.20 (2H, m), 4.70-6.30 (3H, m), 6.80-7.00 (1H, m), 7.30-7.60 (7H, m), 7.60-8.00 (3H, m), 8.55-8.65 (1H, m).

Example 2-70LP

N-[(R)-Carbamoylpyridin-4-ylmethyl]-N-[(R)-6-chloro-4-fluoroindan-1-yl]benzamide RT (min.): 2.385
MS (ESI, m/z): 422.1077 (M−H)⁻
¹H-NMR (CDCl₃) δ: 1.87-2.96 (4H, m), 4.56-4.73 (1H, br), 5.29-6.33 (3H, m), 6.94-7.09 (1H, m), 7.34-7.66 (8H, m), 8.62-8.68 (2H, m).

Example 2-71LP

N-[(R)-Carbamoylphenylmethyl]-N-[(R)-6-chloroindan-1-yl]thiazole-5-carboxamide

RT (min.): 2.972
MS (ESI, m/z): 410.0736 (M−H)⁻
¹H-NMR (CDCl₃) δ: 1.75-1.95 (1H, m), 2.00-2.30 (1H, m), 2.55-2.90 (2H, m), 4.50-4.90 (1H, m), 5.20-6.00 (3H, m), 7.05-7.30 (2H, m), 7.35-7.50 (5H, m), 7.90-8.00 (1H, m), 8.15-8.30 (1H, m), 8.92 (1H, s).

Example 2-72LP

N-[(R)-Carbamoylphenylmethyl]-N-[(R)-6-chloroindan-1-yl]thiophene-3-carboxamide

RT (min.): 3.440
MS (ESI, m/z): 409.0783 (M−H)⁻
¹H-NMR (CDCl₃) δ: 1.70-1.95 (1H, m), 1.95-2.20 (1H, m), 2.50-2.85 (2H, m), 4.55-4.80 (1H, m), 5.20-5.95 (3H, m), 7.05-7.30 (2H, m), 7.30-7.65 (7H, m), 7.71 (1H, br s), 7.90-8.05 (1H, m).

Example 2-73LP

N-[(R)-Carbamoylphenylmethyl]-N-[(R)-6-chloroindan-1-yl]pyridine-2-carboxamide

RT (min.): 3.112
MS (ESI, m/z): 404.1172 (M−H)⁻
¹H-NMR (CDCl₃) δ: 1.55-2.05 (1H, m), 2.15-2.40 (1H, m), 2.50-3.20 (2H, m), 4.60-5.25 (1H, m), 5.40-6.25 (3H, m), 7.00-7.25 (2H, m), 7.25-8.30 (9H, m), 8.61 (1H, d, J=4.6 Hz).

Example 2-74LP

N-[(R)-Carbamoylphenylmethyl]-N-[(R)-6-chloroindan-1-yl]thiazole-4-carboxamide

RT (min.): 3.116
MS (ESI, m/z): 410.0738 (M−H)⁻
¹H-NMR (CDCl₃) δ: 1.45-2.05 (1H, m), 2.10-2.50 (1H, m), 2.55-3.20 (2H, m), 4.50-5.35 (1H, m), 5.35-6.85 (3H, m), 6.95-8.25 (9H, m), 8.75-8.95 (1H, m).

Example 2-75LP

N-[(R)-Carbamoylphenylmethyl]-N-[(R)-6-chloro-4-fluoroindan-1-yl]thiazole-2-carboxamide RT (min.): 3.711
MS (ESI, m/z): 428.0640 (M−H)⁻
¹H-NMR (CDCl₃) δ: 1.50-2.05 (1H, m), 2.10-2.45 (1H, m), 2.45-3.20 (2H, m), 4.50-7.10 (4H, m), 7.25-8.25 (9H, m).

Example 2-76LP

N-[(R)-Carbamoylpyridin-3-ylmethyl]-N-[(R)-4,6-difluoroindan-1-yl]benzamide

RT (min.): 2.302
MS (ESI, m/z): 406.1371 (M−H)⁻
¹H-NMR (CDCl₃) δ: 1.74-1.92 (1H, m), 2.12-2.29 (1H, m), 2.50-2.66 (1H, m), 2.75-2.95 (1H, m), 4.59-4.84 (1H, m), 5.28-6.16 (3H, m), 6.62-6.83 (1H, m), 7.32-7.61 (7H, m), 7.86-8.04 (1H, m), 8.51-8.74 (2H, m).

Example 2-77LP

N-[(R)-Carbamoylpyridin-2-ylmethyl]-N-[(R)-4,6-difluoroindan-1-yl]benzamide

RT (min.): 3.011
MS (ESI, m/z): 406.1373 (M−H)⁻
¹H-NMR (CDCl₃) δ: 1.90-2.04 (1H, m), 2.21-2.37 (1H, m), 2.50-2.68 (1H, m), 2.76-2.95 (1H, m), 4.69-4.86 (1H, m), 5.27-5.68 (2H, m), 6.61-6.79 (1H, m), 7.16-7.85 (10H, m), 8.54-8.62 (1H, m).

Example 2-77HP

N-[(S)-Carbamoylpyridin-2-ylmethyl]-N-[(R)-4,6-difluoroindan-1-yl]benzamide

RT (min.): 2.800
MS (ESI, m/z): 406.1374 (M−H)⁻

¹H-NMR (CDCl₃) δ: 2.33-2.78 (3H, m), 2.95-3.14 (1H, m), 4.69-4.84 (1H, m), 5.40-5.72 (2H, m), 6.55-6.65 (1H, m), 6.95-7.06 (1H, m), 7.16-7.83 (9H, m), 8.49-8.60 (1H, m).

Example 2-78LP

N-[(R)-Carbamoylpyridin-2-ylmethyl]-N-[(R)-4,6-difluoroindan-1-yl]nicotinamide

RT (min.): 2.141
MS (ESI, m/z): 407.1324 (M−H)⁻
¹H-NMR (CDCl₃) δ: 1.87-2.06 (1H, m), 2.22-2.40 (1H, m), 2.52-2.69 (1H, m), 2.78-2.95 (1H, m), 4.75-4.95 (1H, m), 5.39-5.68 (2H, m), 6.61-6.80 (1H, m), 7.20-7.90 (6H, m), 7.92-8.08 (1H, m), 8.53-8.65 (1H, m), 8.66-8.81 (1H, m), 8.93 (1H, br s).

Example 2-79LP

N-[(R)-Carbamoylphenylmethyl]-N-[(R)-6-chloroindan-1-yl]thiazole-2-carboxamide

RT (min.): 3.543
MS (ESI, m/z): 410.0736 (M−H)⁻
¹H-NMR (CDCl₃) δ: 1.45-2.00 (1H, m), 2.15-2.45 (1H, m), 2.55-3.15 (2H, m), 4.60-5.90 (2H, m), 6.95-7.65 (11H, m), 7.80-8.00 (1H, m).

Example 2-80LP

N-[(R)-Carbamoylphenylmethyl]-N-[(R)-6-chloro-4-fluoroindan-1-yl]isonicotinamide RT (min.): 2.829
MS (ESI, m/z): 422.1075 (M−H)⁻
¹H-NMR (CDCl₃) δ: 1.30-3.20 (4H, m), 4.35-5.70 (4H, m), 6.80-7.90 (9H, m), 8.65-8.80 (2H, m).

Example 2-81LP

N-[(R)-Carbamoylpyridin-3-ylmethyl]-N-[(R)-4,6-difluoroindan-1-yl]nicotinamide

RT (min.): 1.447
MS (ESI, m/z): 407.1326 (M−H)⁻
¹H-NMR (CDCl₃) δ: 1.71-1.92 (1H, m), 2.08-2.27 (1H, m), 2.47-2.66 (1H, m), 2.74-2.94 (1H, m), 4.46-4.95 (1H, m), 5.33-5.84 (3H, m), 6.65-6.84 (1H, m), 7.35-7.62 (3H, m), 7.79-8.08 (2H, m), 8.57-8.91 (4H, m).

Example 2-82LP

N-[(R)-Carbamoylphenylmethyl]-N-[(R)-6-chloro-4-fluoroindan-1-yl]isothiazole-5-carboxamide RT (min.): 3.444
MS (ESI, m/z): 428.0640 (M−H)⁻
¹H-NMR (CDCl₃) δ: 1.70-1.95 (1H, m), 2.00-2.25 (1H, m), 2.50-2.65 (1H, m), 2.70-2.95 (1H, m), 4.50-5.90 (4H, m), 6.85-7.10 (1H, m), 7.30-7.90 (7H, m), 8.48 (1H, s).

Example 2-83LP

N-[(R)-Carbamoylpyridin-3-ylmethyl]-N-[(R)-6-chloro-4-fluoroindan-1-yl]nicotinamide RT (min.): 1.774
MS (ESI, m/z): 423.1029 (M−H)⁻
¹H-NMR (CDCl₃) δ: 1.70-1.90 (1H, m), 2.05-2.30 (1H, m), 2.45-2.70 (1H, m), 2.70-2.95 (1H, m), 4.65-4.90 (1H, m), 5.30-5.85 (3H, m), 6.95-7.10 (1H, m), 7.25-7.50 (2H, m), 7.70-8.05 (3H, m), 8.60-8.85 (4H, m).

Example 2-84LP

N-[(R)-Carbamoylpyridin-3-ylmethyl]-N-[(R)-6-chloro-4-fluoroindan-1-yl]-5-fluorothiophene-2-carboxamide RT (min.): 2.650
MS (ESI, m/z): 446.0547 (M−H)⁻
¹H-NMR (CDCl₃) δ: 1.85-1.98 (1H, m), 2.06-2.41 (1H, m), 2.64-2.78 (1H, m), 2.90-3.04 (1H, m), 4.41-6.23 (4H, m), 6.49 (1H, dd, J=1.4, 4.2 Hz), 7.04 (1H, d, J=8.5 Hz), 7.15-7.19 (1H, m), 7.35 (1H, dd, J=4.8, 8.0 Hz), 7.67 (1H, s), 7.84-7.90 (1H, m), 8.59-8.64 (2H, m).

Example 2-85LP

N-[(R)-Carbamoylpyridin-2-ylmethyl]-N-[(R)-6-chloro-4-fluoroindan-1-yl]nicotinamide RT (min.): 2.381
MS (ESI, m/z): 423.1031 (M−H)⁻
¹H-NMR (CDCl₃) δ: 1.87-3.16 (4H, m), 4.52-5.86 (3H, m), 6.79-8.09 (8H, m), 8.44-8.98 (3H, m).

Example 2-86LP

N-[(R)-Carbamoylphenylmethyl]-N-[(R)-6-chloro-4-fluoroindan-1-yl]-5-fluoronicotinamide RT (min.): 3.319
MS (ESI, m/z): 440.0983 (M−H)⁻
¹H-NMR (CDCl₃) δ: 1.72-2.17 (2H, m), 2.44-2.86 (2H, m), 4.58-5.82 (4H, m), 6.87-7.09 (1H, m), 7.30-7.90 (7H, m), 8.50-8.70 (2H, m).

Example 2-87LP

N-[(R)-Carbamoylpyridin-3-ylmethyl]-N-[(R)-6-chloroindan-1-yl]benzamide

RT (min.): 2.318
MS (ESI, m/z): 404.1171 (M−H)⁻
¹H-NMR (CDCl₃) δ: 1.70-1.95 (1H, m), 2.10-2.30 (1H, m), 2.55-2.70 (1H, m), 2.70-2.90 (1H, m), 4.60-4.80 (1H, m), 5.20-6.30 (3H, m), 7.05-7.20 (1H, m), 7.20-7.30 (1H, m), 7.30-7.40 (1H, m), 7.40-7.50 (3H, m), 7.50-7.65 (2H, m), 7.80-7.90 (1H, m), 7.90-8.05 (1H, m), 8.55-8.70 (2H, m), Example 2-88LP N-[(R)-Carbamoylphenylmethyl]-N-[(R)-6-chloroindan-1-yl]-4-methylthiazole-5-carboxamide RT (min.): 3.052
MS (ESI, m/z): 424.0892 (M−H)⁻

¹H-NMR (CDCl₃) δ: 1.65-2.20 (2H, m), 2.45-2.90 (5H, m), 4.50-4.90 (1H, m), 5.20-5.70 (3H, m), 7.05-7.15 (1H, m), 7.20-7.50 (6H, m), 7.90 (1H, s), 8.76 (1H, s).

Example 2-89LP

N-[(R)-Carbamoylphenylmethyl]-N-[(R)-6-chloro-4-fluoroindan-1-yl]-2-methoxybenzamide RT (min.): 3.654
MS (ESI, m/z): 451.1227 (M−H)⁻
¹H-NMR (CDCl₃) δ: 1.70-1.90 (1H, m), 1.95-2.25 (1H, m), 2.40-3.10 (2H, m), 3.85-3.95 (3H, m), 4.50-6.35 (4H, m), 6.80-7.15 (3H, m), 7.20-7.80 (8H, m).

Example 2-90LP

N-[(R)-Carbamoylphenylmethyl]-N-[(R)-6-chloro-4-fluoroindan-1-yl]cyclohexylcarboxamide RT (min.): 4.058
MS (ESI, m/z): 427.1595 (M−H)⁻
¹H-NMR (CDCl₃) δ: 1.05-3.04 (15H, m), 4.31-6.60 (4H, m), 6.90-7.06 (1H, m), 7.25-7.85 (6H, m).

Example 2-91LP

N-[(R)-Carbamoylphenylmethyl]-N-[(R)-6-chloro-4-fluoroindan-1-yl]-6-trifluoromethylnicotinamide RT (min.): 3.845
MS (ESI, m/z): 490.0953 (M−H)⁻
¹H-NMR (CDCl₃) δ: 1.69-1.87 (1H, m), 1.95-2.12 (1H, m), 2.45-3.15 (2H, m), 4.58-5.78 (4H, m), 6.84-7.06 (1H, m), 7.37-7.56 (5H, m), 7.69-7.88 (2H, m), 7.98-8.11 (1H, m), 8.89 (1H, br s).

Example 2-91HP

N-[(S)-Carbamoylphenylmethyl]-N-[(R)-6-chloro-4-fluoroindan-1-yl]-6-trifluoromethylnicotinamide RT (min.): 3.694
MS (ESI, m/z): 490.0953 (M−H)⁻
¹H-NMR (CDCl₃) δ: 2.46-2.61 (1H, m), 2.69-2.83 (2H, m), 3.02-3.17 (1H, m), 4.47 (1H, br s), 5.27-5.57 (3H, m), 6.26 (1H, br s), 6.86 (1H, d, J=8.3 Hz), 7.25-7.43 (5H, m), 7.79 (1H, d, J=8.0 Hz), 8.00-8.08 (1H, m), 8.89 (1H, br s).

Example 2-92LP

N-[(R)-Carbamoylphenylmethyl]-N-[(R)-5,7-difluoroindan-1-yl]benzamide

RT (min.): 3.970
MS (ESI, m/z): 405.1422 (M−H)⁻
¹H-NMR (CDCl₃) δ: 2.00-2.30 (1H, m), 2.30-2.65 (1H, m), 2.65-2.90 (1H, m), 2.90-3.15 (1H, m), 4.40-4.80 (1H, m), 5.00-6.20 (2H, m), 6.60-6.80 (2H, m), 6.90-7.15 (1H, m), 7.25-7.55 (8H, m), 7.55-7.65 (2H, m).

Example 2-92HP

N-[(S)-Carbamoylphenylmethyl]-N-[(R)-5,7-difluoroindan-1-yl]benzamide

RT (min.): 3.259
MS (ESI, m/z): 405.1422 (M−H)⁻
¹H-NMR (CDCl₃) δ: 2.40-2.60 (1H, m), 2.65-3.00 (2H, m), 3.15-3.40 (1H, m), 4.28 (1H, br s), 5.40-5.90 (3H, m), 6.10-6.20 (1H, m), 6.65-6.75 (1H, m), 7.15-7.30 (5H, m), 7.40-7.50 (3H, m), 7.55-7.65 (2H, m).

Example 2-93LP

N-[(R)-Carbamoylphenylmethyl]-2-chloro-N-[(R)-6-chloro-4-fluoroindan-1-yl]nicotinamide RT (min.): 3.441
MS (ESI, m/z): 456.0688 (M−H)⁻
¹H-NMR (CDCl₃) δ: 1.72-1.86 (1H, m), 2.25-2.60 (2H, m), 2.75-3.13 (1H, m), 4.56 (1H, br s), 5.13-5.26 (1H, m), 5.34-5.50 (2H, m), 6.86-7.04 (1H, m), 7.34-7.94 (8H, m), 8.41-8.50 (1H, m).

Example 2-94LP

N-[(R)-Carbamoylphenylmethyl]-N-[(R)-6-chloro-4-fluoroindan-1-yl]-2-trifluoromethylnicotinamide RT (min.): 3.722
MS (ESI, m/z): 490.0951 (M−H)⁻
¹H-NMR (CDCl₃) δ: 1.67-2.15 (2H, m), 2.43-3.11 (2H, m), 4.56 (1H, s), 5.03-5.20 (1H, m), 5.31-5.53 (2H, m), 6.85-7.05 (1H, m), 7.35-8.14 (8H, m), 8.78-8.82 (1H, m).

Example 2-95LP

N-[(R)-Carbamoylphenylmethyl]-N-[(R)-6-chloroindan-1-yl]isothiazole-5-carboxamide RT (min.): 3.551
MS (ESI, m/z): 410.0735 (M−H)⁻
¹H-NMR (CDCl₃) δ: 1.45-2.00 (1H, m), 2.15-2.45 (1H, m), 2.55-3.15 (2H, m), 4.60-5.90 (2H, m), 6.90-7.65 (11H, m), 7.80-8.00 (1H, m).

Example 2-96LP

N-[(S)-Carbamoylthiazol-2-ylmethyl]-N-[(R)-6-chloro-4-fluoroindan-1-yl]benzamide RT (min.): 3.358
MS (ESI, m/z): 428.0639 (M−H)⁻
¹H-NMR (CDCl₃) δ: 1.85-2.04 (1H, m), 2.18-2.33 (1H, m), 2.48-2.67 (1H, m), 2.84-2.99 (1H, m), 4.94-5.07 (1H, m), 5.36-5.66 (2H, m), 6.83-7.05 (2H, m), 7.38-7.91 (8H, m).

Example 2-97LP

N-[(R)-Carbamoylpyridin-3-ylmethyl]-2-chloro-N-[(R)-6-chloro-4-fluoroindan-1-yl]benzamide RT (min.): 2.778
MS (ESI, m/z): 456.0686 (M−H)⁻
¹H-NMR (CDCl₃) δ: 1.66-2.96 (4H, m), 4.55-5.70 (4H, m), 6.80-7.07 (1H, m), 7.30-8.81 (9H, m).

Example 2-98LP

N-[(R)-Carbamoylphenylmethyl]-3-chloro-N-[(R)-6-chloro-4-fluoroindan-1-yl]isonicotinamide RT (min.): 3.402
MS (ESI, m/z): 456.0687 (M−H)⁻

¹H-NMR (CDCl₃) δ: 1.71-3.17 (4H, m), 4.52-5.82 (4H, m), 6.83-7.07 (1H, m), 7.30-7.88 (7H, m), 8.50-8.80 (2H, m).

Example 2-99LP

N-[(R)-Carbamoyl-(2-chlorophenyl)methyl]-N-[(R)-6-chloro-4-fluoroindan-1-yl]nicotinamide RT (min.): 3.170
MS (ESI, m/z): 456.0685 (M–H)⁻
¹H-NMR (CDCl₃) δ: 1.60-3.18 (4H, m), 4.80-5.80 (4H, m), 6.79-7.01 (1H, m), 7.28-8.02 (7H, m), 8.57-8.89 (2H, m).

Example 2-100LP

N-[(R)-Carbamoylphenylmethyl]-N-[(R)-6-chloro-4-fluoroindan-1-yl]-4-methylnicotinamide RT (min.): 2.796
MS (ESI, m/z): 436.1237 (M–H)⁻
¹H-NMR (CDCl₃) δ: 1.68-2.17 (2H, m), 2.40-2.62 (4H, m), 2.71-3.14 (1H, m), 4.58-5.11 (1H, m), 5.19-5.28 (1H, m), 5.36-5.53 (2H, m), 6.86-7.03 (1H, m), 7.17-7.60 (6H, m), 7.71-7.90 (1H, m), 8.48-8.72 (2H, m).

Example 2-101LP

N-[(R)-Carbamoylphenylmethyl]-4-chloro-N-[(R)-6-chloro-4-fluoroindan-1-yl]nicotinamide RT (min.): 3.312
MS (ESI, m/z): 456.0687 (M–H)⁻
¹H-NMR (DMSO-d₆) δ: 1.30-1.44 (1H, m), 2.01-2.21 (1H, m), 2.48-2.66 (1H, m), 2.83-2.94 (1H, m), 4.92-5.00 (0.5H, m), 5.22-5.30 (1H, m), 5.40 (0.5H, s), 7.10-7.17 (1H, m), 7.35-7.81 (9H, m), 8.33 (0.5H, s), 8.62-8.68 (1H, m), 8.90 (0.5H, s).

Example 2-102LP

N-[(R)-Carbamoylphenylmethyl]-N-[(R)-6-chloro-4-fluoroindan-1-yl]-2-ethoxynicotinamide RT (min.): 3.596
MS (ESI, m/z): 466.1339 (M–H)⁻
¹H-NMR (CDCl₃) δ: 1.47 (3H, t, J=7.1 Hz), 1.65-1.90 (1H, m), 2.10-2.30 (1H, m), 2.40-2.65 (1H, m), 2.65-3.10 (1H, m), 4.30-4.70 (3H, m), 5.20-5.80 (3H, m), 6.80-7.05 (2H, m), 7.30-7.90 (7H, m), 8.15-8.30 (1H, m).

Example 2-103LP

N-[(R)-Carbamoyl-(2-fluorophenyl)methyl]-N-[(R)-6-chloro-4-fluoroindan-1-yl]nicotinamide RT (min.): 3.039
MS (ESI, m/z): 440.0982 (M–H)⁻
¹H-NMR (CDCl₃) δ: 1.69-3.21 (4H, m), 4.82-5.82 (4H, m), 6.78-8.00 (8H, m), 8.62-8.86 (2H, m).

Example 2-104LP

5-{N-[(R)-Carbamoylphenylmethyl]-N-[(R)-6-chloro-4-fluoroindan-1-yl]carbamoyl}pyridine-2-carboxylic acid benzyl ester RT (min.): 3.976
MS (ESI, m/z): 556.1451 (M–H)⁻
¹H-NMR (CDCl₃) δ: 1.64-2.11 (2H, m), 2.40-2.87 (2H, m), 4.56-5.71 (6H, m), 6.80-7.10 (1H, m), 7.28-8.28 (13H, m), 8.85-8.99 (1H, m).

Example 2-105LP

N-[(R)-Carbamoylphenylmethyl]-3-chloro-N-[(R)-6-chloro-4-fluoroindan-1-yl]pyridine-2-carboxamide RT (min.): 3.500
MS (ESI, m/z): 456.0688 (M–H)⁻
¹H-NMR (CDCl₃) δ: 1.61-3.17 (4H, m), 4.66-6.08 (4H, m), 6.78-7.01 (1H, m), 7.22-7.90 (8H, m), 8.48-8.62 (1H, m).

Example 2-106LP

N-[(R)-Carbamoylphenylmethyl]-N-[(R)-6-chloro-4-fluoroindan-1-yl]-6-methoxynicotinamide RT (min.): 3.510
MS (ESI, m/z): 452.1181 (M–H)⁻
¹H-NMR (CDCl₃) δ: 1.68-2.23 (2H, m), 2.43-2.95 (2H, m), 3.97 (3H, s), 4.38-4.95 (1H, m), 5.22-5.88 (3H, m), 6.80 (1H, d, J=8.6 Hz), 6.89-7.06 (1H, m), 7.31-7.53 (5H, m), 7.69-7.90 (2H, m), 8.38-8.48 (1H, m).

Example 2-106HP

N-[(S)-Carbamoylphenylmethyl]-N-[(R)-6-chloro-4-fluoroindan-1-yl]-6-methoxynicotinamide RT (min.): 3.366
MS (ESI, m/z): 452.1187 (M–H)⁻
¹H-NMR (CDCl₃) δ: 2.48-2.83 (3H, m), 3.03-3.19 (1H, m), 3.97 (3H, s), 4.22-4.63 (1H, m), 5.32-5.83 (3H, m), 6.18-6.53 (1H, m), 6.75-6.89 (2H, m), 7.18-7.49 (5H, m), 7.73-7.85 (1H, m), 8.33-8.46 (1H, m).

Example 2-107LP

N-[(R)-Carbamoylphenylmethyl]-N-[(R)-6-chloro-4-fluoroindan-1-yl]-2-(methylamino)nicotinamide RT (min.): 2.362
MS (ESI, m/z): 451.1341 (M–H)⁻
¹H-NMR (CDCl₃) δ: 1.62-2.14 (2H, m), 2.45-2.83 (2H, m), 3.00-3.13 (3H, m), 4.48-4.82 (1H, m), 5.19-5.67 (3H, m), 6.00-6.31 (1H, m), 6.57 (1H, dd, J=5.1, 7.2 Hz), 6.91-7.05 (1H, m), 7.34-7.68 (7H, m), 8.20 (1H, dd, J=1.7, 5.1 Hz).

Example 2-107HP

N-[(S)-Carbamoylphenylmethyl]-N-[(R)-6-chloro-4-fluoroindan-1-yl]-2-(methylamino)nicotinamide RT (min.): 2.357
MS (ESI, m/z): 451.1343 (M–H)⁻
¹H-NMR (CDCl₃) δ: 2.49-2.90 (3H, m), 2.99-3.15 (4H, m), 4.21-4.56 (1H, m), 5.32-5.66 (3H, m), 5.89-6.32 (1H, m), 6.56 (1H, dd, J=5.1, 7.3 Hz), 6.81 (1H, dd, J=1.3, 8.6 Hz), 7.25-7.43 (7H, m), 8.20 (1H, dd, J=1.7, 5.1 Hz).

Example 2-108LP

N-[(R)-Carbamoylphenylmethyl]-N-[(R)-6-chloro-4-fluoroindan-1-yl]-4-trifluoromethylnicotinamide RT (min.): 3.616
MS (ESI, m/z): 490.0952 (M−H)−
$^1$H-NMR (CDCl$_3$) δ: 1.65-3.13 (4H, m), 4.56-4.78 (1H, m), 5.05-5.20 (1H, m), 5.30-6.03 (2H, m), 6.85-7.05 (1H, m), 7.33-7.56 (5H, m), 7.60-7.93 (2H, m), 8.76-9.10 (2H, m).

Example 2-109LP

N-[(R)-Carbamoyl-(5-fluoropyridin-3-yl)methyl]-N-[(R)-6-chloro-4-fluoroindan-1-yl]benzamide RT (min.): 3.217
MS (ESI, m/z): 440.0984 (M−H)−
$^1$H-NMR (CDCl$_3$) δ: 1.71-2.00 (1H, m), 2.13-2.40 (1H, m), 2.50-3.02 (2H, m), 4.64-4.86 (1H, m), 5.34-6.35 (3H, m), 6.92-7.08 (1H, m), 7.42-7.87 (7H, m), 8.40-8.56 (2H, m).

Example 2-110LP

N-[(R)-Carbamoylphenylmethyl]-N-[(R)-6-chloro-4-fluoroindan-1-yl]imidazo[1,2-a]pyrazine-3-carboxamide RT (min.): 2.970
MS (ESI, m/z): 462.1140 (M−H)−
$^1$H-NMR (CDCl$_3$) δ: 1.61-3.13 (4H, m), 4.40-6.40 (4H, m), 6.86-7.14 (1H, m), 7.36-8.22 (8H, m), 8.80-9.30 (2H, m).

Example 2-111LP

N-[(R)-Carbamoylphenylmethyl]-N-[(R)-6-chloro-4-fluoroindan-1-yl]-2,3-dihydrobenzofuran-7-carboxamide RT (min.): 3.737
MS (ESI, m/z): 463.1227 (M−H)−
$^1$H-NMR (CDCl$_3$) δ: 1.76-2.33 (2H, m), 2.45-2.90 (2H, m), 3.20-3.35 (2H, m), 4.56-6.17 (6H, m), 6.80-7.02 (2H, m), 7.19-7.72 (8H, m).

Example 2-112LP

N-[(R)-Carbamoylpyridin-3-ylmethyl]-N-[(R)-4-chloroindan-1-yl]nicotinamide

RT (min.): 1.615
MS (ESI, m/z): 405.1139 (M−H)−
$^1$H-NMR (CDCl$_3$) δ: 1.68-1.86 (1H, m), 2.07-2.23 (1H, m), 2.57-2.72 (1H, m), 2.79-2.99 (1H, m), 4.66-4.92 (1H, m), 5.26-5.91 (3H, m), 7.24-7.45 (4H, m), 7.77-8.05 (3H, m), 8.62-8.74 (3H, m), 8.81-8.87 (1H, m).

Example 2-113LP

N-[(R)-Carbamoylpyridin-3-ylmethyl]-N-[(R)-6-chloro-4-fluoroindan-1-yl]-2-fluorobenzamide RT (min.): 2.623
MS (ESI, m/z): 440.0983 (M−H)−
$^1$H-NMR (CDCl$_3$) δ: 1.74-1.89 (1H, m), 2.17-2.40 (1H, m), 2.54-2.67 (1H, m), 2.79-2.93 (1H, m), 4.57-4.87 (1H, m), 5.33-6.10 (3H, m), 6.98-7.04 (1H, m), 7.14-7.21 (1H, m), 7.24-7.68 (5H, m), 7.90-8.03 (1H, m), 8.59-8.72 (2H, m).

Example 2-114LP

N-[(R)-Carbamoylphenylmethyl]-N-[(R)-6-chloro-4-fluoroindan-1-yl]-4-methoxynicotinamide RT (min.): 2.295
MS (ESI, m/z): 452.1177 (M−H)−
$^1$H-NMR (CDCl$_3$) δ: 1.68-2.21 (2H, m), 2.38-3.09 (2H, m), 3.89-4.03 (3H, m), 4.44-5.89 (4H, m), 6.80-7.05 (2H, m), 7.24-7.89 (6H, m), 8.40-8.66 (2H, m).

Example 2-115LP

N-[(R)-Carbamoylphenylmethyl]-N-[(R)-6-chloro-4-fluoroindan-1-yl]imidazo[1,2-a]pyridine-6-carboxamide RT (min.): 2.250
MS (ESI, m/z): 461.1184 (M−H)−
$^1$H-NMR (CDCl$_3$) δ: 1.69-3.14 (4H, m), 4.45-6.60 (4H, m), 6.83-7.10 (1H, m), 7.27-8.00 (10H, m), 8.40-8.56 (1H, m).

Example 2-116LP

N-[(R)-Carbamoylphenylmethyl]-N-[(R)-6-chloro-4-fluoroindan-1-yl]-2-hydroxymethylnicotinamide RT (min.): 2.665
MS (ESI, m/z): 452.1184 (M−H)−
$^1$H-NMR (CDCl$_3$) δ: 1.69-1.82 (1H, m), 2.00-2.18 (1H, m), 2.45-3.12 (2H, m), 4.55-5.71 (6H, m), 6.85-7.04 (1H, m), 7.25-7.87 (8H, m), 8.59-8.67 (1H, m).

Example 2-117LP

N-[(R)-Carbamoylpyridin-3-ylmethyl]-N-[(R)-6-chloro-4-fluoroindan-1-yl]-2-methylbenzamide RT (min.): 2.788
MS (ESI, m/z): 436.1235 (M−H)−
$^1$H-NMR (CDCl$_3$) δ: 1.68-1.81 (1H, m), 2.03-2.22 (1H, m), 2.37-2.58 (4H, m), 2.77-3.17 (1H, m), 4.61-4.70 (1H, m), 5.23-5.96 (3H, m), 6.85-7.03 (1H, m), 7.20-7.49 (5H, m), 7.61-7.82 (1H, m), 7.97-8.15 (1H, m), 8.51-8.74 (2H, m).

Example 2-118LP

N-[(R)-Carbamoylpyridin-3-ylmethyl]-N-[(R)-6-chloro-4-fluoroindan-1-yl]-2-methoxybenzamide RT (min.): 2.518
MS (ESI, m/z): 452.1183 (M−H)−
$^1$H-NMR (CDCl$_3$) δ: 1.75-1.91 (1H, m), 2.09-2.32 (1H, m), 2.52-2.67 (1H, m), 2.79-3.13 (1H, m), 3.90-3.97 (3H, m), 4.68-4.77 (1H, m), 5.31-6.75 (3H, m), 6.84-7.10 (3H, m), 7.25-7.58 (4H, m), 7.89-8.02 (1H, m), 8.50-8.76 (2H, m).

Example 2-119LP

N-[(R)-Carbamoylpyridin-3-ylmethyl]-N-[(R)-6-chloro-4-fluoroindan-1-yl]-2-trifluoromethylbenzamide RT (min.): 3.003
MS (ESI, m/z): 490.0953 (M–H)⁻
$^1$H-NMR (DMSO-$d_6$) δ: 1.22-2.22 (2H, m), 2.46-2.70 (1H, m), 2.82-2.94 (1H, m), 4.94-5.28 (1H, m), 5.31-5.36 (1H, m), 7.10-7.56 (5H, m), 7.63-8.03 (5H, m), 8.39-8.73 (2H, m).

Example 2-120LP

N-[(R)-Carbamoylpyridin-3-ylmethyl]-N-[(R)-6-chloro-4-fluoroindan-1-yl]-2-ethylbenzamide RT (min.): 3.028
MS (ESI, m/z): 450.1387 (M–H)⁻
$^1$H-NMR (CDCl$_3$) δ: 1.28-1.35 (3H, m), 1.66-1.83 (1H, m), 2.01-2.25 (1H, m), 2.45-2.59 (1H, m), 2.70-3.14 (3H, m), 4.61-4.69 (1H, m), 5.18-6.04 (3H, m), 6.85-7.03 (1H, m), 7.19-7.84 (6H, m), 7.98-8.13 (1H, m), 8.53-8.73 (2H, m).

Example 2-121LP

N-[(R)-Carbamoylphenylmethyl]-N-[(R)-6-chloro-4-fluoroindan-1-yl]-6-oxo-1,6-dihydropyridazine-3-carboxamide RT (min.): 2.761
MS (ESI, m/z) 439.0979 (M–H)⁻
$^1$H-NMR (CDCl$_3$) δ: 1.35-2.14 (2H, m), 2.51-2.64 (1H, m), 2.73-3.07 (1H, m), 5.04-6.35 (4H, m), 6.77-7.03 (2H, m), 7.35-7.79 (7H, m), 11.52 (1H, br).

Example 2-122LP

N-[(R)-Carbamoylpyridin-3-ylmethyl]-N-[(R)-6-chloro-4-fluoroindan-1-yl]-2-cyanobenzamide RT (min.): 2.498
MS (ESI, m/z): 447.1031 (M–H)⁻
$^1$H-NMR (DMSO-$d_6$) δ: 1.29-2.14 (2H, m), 2.42-2.69 (1H, m), 2.84-2.97 (1H, m), 5.05-5.42 (2H, m), 7.11-8.09 (10H, m), 8.48-8.73 (2H, m).

Example 2-123LP

N-[(R)-Carbamoylpyridin-3-ylmethyl]-N-[(R)-6-chloro-4-fluoroindan-1-yl]-2-trifluoromethoxybenzamide RT (min.): 3.072
MS (ESI, m/z): 506.0900 (M–H)⁻
$^1$H-NMR (CDCl$_3$) δ: 1.65-1.97 (1H, m), 2.13-2.24 (1H, m), 2.48-2.66 (1H, m), 2.77-3.16 (1H, m), 4.57-5.00 (1H, m), 5.20-5.78 (3H, m), 6.85-7.05 (1H, m), 7.32-7.77 (6H, m), 7.87-8.11 (1H, m), 8.59-8.69 (2H, m).

Example 2-124LP

N-[(R)-Carbamoylpyridin-3-ylmethyl]-N-[(R)-5-methoxyindan-1-yl]nicotinamide

RT (min.): 0.998
MS (ESI, m/z): 401.1626 (M–H)⁻
$^1$H-NMR (CDCl$_3$) δ: 1.69-1.83 (1H, m), 2.08-2.25 (1H, m), 2.57-2.87 (2H, m), 3.81 (3H, s), 4.71-4.83 (1H, m), 5.24-6.05 (3H, m), 6.72-6.76 (1H, m), 6.86-6.91 (1H, m), 7.34-7.42 (2H, m), 7.73 (1H, d, J=8.4 Hz), 7.87-7.94 (1H, m), 7.96-8.05 (1H, m), 8.60-8.73 (3H, m), 8.83-8.88 (1H, m).

Example 2-125LP

N-[(R)-Carbamoylphenylmethyl]-N-[(R)-6-chloroindan-1-yl]-2-(methylsulfanyl)nicotinamide RT (min.): 3.518
MS (ESI, m/z): 450.1050 (M–H)⁻
$^1$H-NMR (CDCl$_3$) δ: 1.65-1.90 (1H, m), 2.10-2.35 (1H, m), 2.45-2.75 (5H, m), 4.45-4.90 (1H, m), 5.10-5.65 (3H, m), 7.00-7.15 (2H, m), 7.20-7.30 (1H, m), 7.30-7.80 (6H, m), 7.95 (1H, s), 8.49 (1H, dd, J=1.6, 4.9 Hz).

Example 2-126LP

N-[(R)-Carbamoylphenylmethyl]-N-[(R)-6-chloro-4-fluoroindan-1-yl]imidazo[1,2-a]pyrazine-2-carboxamide RT (min.): 2.961
MS (ESI, m/z): 462.1148 (M–H)⁻
$^1$H-NMR (DMSO-$d_6$) δ: 1.19-1.36 (1H, m), 1.91-2.07 (1H, m), 2.42-2.64 (1H, m), 2.78-2.95 (1H, m), 5.06-5.17 (1H, m), 6.63 (1H, s), 7.08-7.15 (1H, m), 7.33-7.64 (8H, m), 7.96-8.01 (1H, m), 8.46 (1H, s), 8.60-8.67 (1H, m), 9.14 (1H, s).

Example 2-127LP

N-[(R)-Carbamoylpyridin-3-ylmethyl]-N-[(R)-6-chloro-4-fluoroindan-1-yl]-2,3-dihydrobenzofuran-7-carboxamide RT (min.): 2.574
MS (ESI, m/z): 464.1186 (M–H)⁻
$^1$H-NMR (CDCl$_3$) δ: 1.82-2.00 (1H, m), 2.26-2.43 (1H, m), 2.56-2.71 (1H, m), 2.80-2.96 (1H, m), 3.20-3.38 (2H, m), 4.60-4.86 (3H, m), 5.30-5.80 (2H, m), 6.87-7.07 (2H, m), 7.22-7.57 (5H, m), 7.85-7.98 (1H, m), 8.50-8.75 (2H, m).

Example 2-128LP

N-[(R)-Carbamoylphenylmethyl]-N-[(R)-6-chloro-4-fluoroindan-1-yl]-2-(methylsulfanyl)nicotinamide RT (min.): 3.627
MS (ESI, m/z): 468.0959 (M–H)⁻
$^1$H-NMR (CDCl$_3$) δ: 1.70-1.90 (1H, m), 2.10-2.45 (1H, m), 2.45-2.60 (1H, m), 2.65 (3H, s), 2.65-3.15 (1H, m), 4.40-4.95 (1H, m), 5.00-5.75 (3H, m), 6.80-7.15 (2H, m), 7.35-7.85 (7H, m), 8.45-8.55 (1H, m).

Example 2-129LP

N-[(R)-Carbamoylphenylmethyl]-N-[(R)-6-chloro-4-fluoroindan-1-yl]-2-hydroxynicotinamide RT (min.): 2.598
MS (ESI, m/z): 438.1035 (M–H)⁻

¹H-NMR (CDCl₃) δ: 1.35-2.00 (2H, m), 2.15-3.15 (3H, m), 4.70-5.20 (1H, m), 5.35-5.65 (1H, m), 6.05-6.80 (2H, m), 6.80-7.05 (1H, m), 7.25-7.85 (9H, m).

Example 2-130LP

N-[(R)-Carbamoylphenylmethyl]-N-[(R)-6-chloro-4-fluoroindan-1-yl]-2-methylthiazole-4-carboxamide RT (min.): 3.464
MS (ESI, m/z): 442.0805 (M−H)⁻
¹H-NMR (CDCl₃) δ: 1.59-3.24 (7H, m), 4.44-7.06 (4H, m), 7.12-8.06 (8H, m).

Example 2-131LP

N-[(R)-Carbamoylphenylmethyl]-N-[(R)-4,6-difluoroindan-1-yl]-2-methylnicotinamide RT (min.): 2.495
MS (ESI, m/z): 420.1532 (M−H)⁻
¹H-NMR (CDCl₃) δ: 1.56-2.22 (2H, m), 2.34-3.18 (5H, m), 4.46-5.68 (4H, m), 6.55-6.86 (1H, m), 7.14-7.83 (8H, m), 8.51-8.65 (1H, m).

Example 2-132LP

N-[(R)-Carbamoylphenylmethyl]-N-[(R)-4,6-difluoroindan-1-yl]-4-methylthiazole-5-carboxamide RT (min.): 3.005
MS (ESI, m/z): 426.1101 (M−H)⁻
¹H-NMR (CDCl₃) δ: 1.61-2.23 (2H, m), 2.44-2.95 (5H, m), 4.43-4.90 (1H, m), 5.27-5.84 (3H, m), 6.57-6.86 (1H, m), 7.28-7.81 (6H, m), 8.77 (1H, s).

Example 2-133LP

N-[(R)-Carbamoylphenylmethyl]-N-[(R)-6-chloro-4-fluoroindan-1-yl]-2-methyl-2H-pyrazole-3-carboxamide RT (min.): 3.183
MS (ESI, m/z): 425.1189 (M−H)⁻
¹H-NMR (CDCl₃) δ: 1.68-2.25 (2H, m), 2.51-3.10 (2H, m), 3.86-4.18 (3H, m), 4.50-6.00 (4H, m), 6.46 (1H, br s), 6.80-7.11 (1H, m), 7.29-7.85 (7H, m).

Example 2-134LP

N-[(R)-Carbamoylphenylmethyl]-N-[(R)-6-chloro-4-fluoroindan-1-yl]-3-methyl-3H-imidazole-4-carboxamide RT (min.): 2.272
MS (ESI, m/z): 425.1193 (M−H)⁻
¹H-NMR (CDCl₃) δ: 1.75-2.36 (2H, m), 2.51-3.00 (2H, m), 3.86 (3H, br s), 4.30-6.50 (4H, m), 6.88-7.07 (1H, m), 7.33-7.85 (8H, m).

Example 2-135LP

N-[(R)-Carbamoylphenylmethyl]-N-[(R)-6-chloro-4-fluoroindan-1-yl]-5-methylisoxazole-4-carboxamide RT (min.): 3.377
MS (ESI, m/z): 426.1032 (M−H)⁻
¹H-NMR (CDCl₃) δ: 1.69-2.25 (2H, m), 2.40-3.04 (5H, m), 4.38-5.10 (1H, m), 5.16-5.90 (3H, m), 6.87-7.13 (1H, m), 7.30-7.53 (5H, m), 7.61-7.87 (1H, m), 8.26 (1H, br s).

Example 2-136LP

N-[(R)-Carbamoylpyridin-3-ylmethyl]-2-chloro-N-[(R)-6-chloroindan-1-yl]benzamide RT (min.): 2.567
MS (ESI, m/z): 438.0787 (M−H)⁻
¹H-NMR (CDCl₃) δ: 1.65-1.99 (1H, m), 2.11-2.34 (1H, m), 2.53-2.90 (2H, m), 4.60-4.85 (1H, m), 5.17-5.80 (3H, m), 7.07-8.22 (9H, m), 8.56-8.74 (2H, m).

Example 2-137LP

N-[(R)-Carbamoylphenylmethyl]-N-[(R)-6-chloroindan-1-yl]-2-methylnicotinamide

RT (min.): 2.483
MS (ESI, m/z): 418.1332 (M−H)⁻
¹H-NMR (CDCl₃) δ: 1.60-1.85 (1H, m), 1.90-2.15 (1H, m), 2.40-2.60 (1H, m), 2.60-2.85 (4H, m), 4.55-4.80 (1H, m), 5.19 (1H, dd, J=8.6, 8.6 Hz), 5.25-5.65 (2H, m), 7.05-7.15 (1H, m), 7.15-7.30 (2H, m), 7.30-7.90 (6H, m), 7.90-8.05 (1H, m), 8.50-8.65 (1H, m).

Example 2-138LP

N-[(R)-Carbamoylpyridin-3-ylmethyl]-N-[(R)-6-chloroindan-1-yl]-2-methoxybenzamide RT (min.): 2.331
MS (ESI, m/z): 434.1285 (M−H)⁻
¹H-NMR (CDCl₃) δ: 1.70-1.90 (1H, m), 2.05-2.30 (1H, m), 2.55-2.70 (1H, m), 2.70-2.85 (1H, m), 3.94 (3H, s), 4.72 (1H, s), 5.20-5.80 (2H, m), 5.90-6.95 (1H, m), 6.97 (1H, d, J=8.4 Hz), 7.06 (1H, ddd, J=0.7, 7.5, 7.5 Hz), 7.11 (1H, dd, J=8.0, 17.4 Hz), 7.15-7.50 (4H, m), 7.68 (1H, s), 7.90-8.05 (1H, m), 8.50-8.80 (2H, m).

Example 2-139LP

N-[(R)-Carbamoylphenylmethyl]-N-[(R)-6-chloro-4-fluoroindan-1-yl]-2-ethylnicotinamide RT (min.): 3.006
MS (ESI, m/z): 450.1399 (M−H)⁻
¹H-NMR (CDCl₃) δ: 1.35-1.45 (3H, m), 1.67-1.83 (1H, m), 1.97-2.08 (1H, m), 2.43-3.21 (4H, m), 4.53-4.72 (1H, m), 5.16-5.57 (3H, m), 6.84-7.04 (1H, m), 7.16-7.86 (8H, m), 8.58-8.66 (1H, m).

Example 2-140LP

N-[(R)-Carbamoylphenylmethyl]-N-[(R)-6-chloro-4-fluoroindan-1-yl]-2-vinylnicotinamide RT (min.): 3.366
MS (ESI, m/z): 448.1238 (M−H)⁻
¹H-NMR (CDCl₃) δ: 1.64-1.85 (1H, m), 1.91-2.13 (1H, m), 2.40-3.18 (2H, m), 4.50-4.98 (1H, m), 5.13-5.78 (4H, m), 6.48-6.63 (1H, m), 6.85-7.87 (10H, m), 8.60-8.69 (1H, m).

Example 2-141LP

N-[(R)-Carbamoylphenylmethyl]-N-[(R)-6-chloro-4-fluoroindan-1-yl]-4-methyloxazole-5-carboxamide RT (min.): 3.196
MS (ESI, m/z): 426.1034 (M−H)⁻
$^1$H-NMR (CDCl$_3$) δ: 1.82-2.32 (2H, m), 2.46 (3H, br s), 2.54-3.05 (2H, m), 4.46-5.27 (1H, m), 5.30-6.19 (3H, m), 6.84-7.05 (1H, m), 7.33-7.52 (5H, m), 7.54-7.87 (2H, m).

Example 2-142LP

N-[(R)-Carbamoylphenylmethyl]-N-[(R)-6-chloro-4-fluoroindan-1-yl]-2,4-dimethylthiazole-5-carboxamide RT (min.): 3.333
MS (ESI, m/z): 456.0961 (M−H)⁻
$^1$H-NMR (CDCl$_3$) δ: 1.67-1.93 (1H, m), 1.94-2.23 (1H, m), 2.45-2.96 (8H, m), 4.37-5.93 (4H, m), 6.87-7.08 (1H, m), 7.33-7.52 (5H, m), 7.63-7.79 (1H, m).

Example 2-143LP

2-{N-[(R)-Carbamoylphenylmethyl]-N-[(R)-6-chloro-4-fluoroindan-1-yl]carbamoyl}pyridine N-oxide RT (min.): 2.727
MS (ESI, m/z): 438.1036 (M−H)⁻
$^1$H-NMR (CDCl$_3$) δ: 1.75-2.25 (1H, m), 2.40-3.20 (3H, m), 4.60-6.00 (4H, m), 6.85-7.10 (1H, m), 7.25-7.70 (9H, m), 8.20-8.35 (1H, m).

Example 2-144LP

N-[(R)-Carbamoylphenylmethyl]-N-[(R)-6-chloro-4-fluoroindan-1-yl]imidazo[1,2-a]pyridine-8-carboxamide RT (min.): 2.221
MS (ESI, m/z): 461.1193 (M−H)⁻
$^1$H-NMR (CDCl$_3$) δ: 1.90-3.20 (4H, m), 4.76-5.97 (3H, m), 6.78-6.99 (2H, m), 7.22-7.48 (5H, m), 7.49-7.82 (4H, m), 8.15-8.28 (1H, m).

Example 2-145LP

3-{N-[(R)-Carbamoylphenylmethyl]-N-[(R)-6-chloro-4-fluoroindan-1-yl]carbamoyl}pyridine N-oxide RT (min.): 2.536
MS (ESI, m/z): 438.1030 (M−H)⁻
$^1$H-NMR (CDCl$_3$) δ: 1.65-1.85 (1H, m), 1.90-2.15 (1H, m), 2.45-3.20 (2H, m), 4.50-5.90 (4H, m), 6.80-7.20 (1H, m), 7.25-7.55 (7H, m), 7.60-7.90 (1H, m), 8.15-8.30 (1H, m), 8.36 (1H, s).

Example 2-146LP

N-[(R)-Carbamoylpyridin-3-ylmethyl]-N-[(R)-6-chloro-4-fluoroindan-1-yl]-4-methylthiazole-5-carboxamide RT (min.): 2.101
MS (ESI, m/z): 443.0758 (M−H)⁻
$^1$H-NMR (CDCl$_3$) δ: 1.69-1.89 (1H, m), 1.99-2.29 (1H, m), 2.54-2.69 (4H, m), 2.80-2.97 (1H, m), 4.52-4.97 (1H, m), 5.32-5.75 (3H, m), 6.97-7.06 (1H, m), 7.39 (1H, dd, J=4.8, 8.0 Hz), 7.69 (1H, br s), 7.85-8.00 (1H, br), 8.59-8.71 (2H, m), 8.78 (1H, s).

Example 2-147LP

N-[(R)-Carbamoylphenylmethyl]-N-[(R)-6-chloro-4-fluoroindan-1-yl]-5-methylthiazole-4-carboxamide RT (min.): 3.225
MS (ESI, m/z): 442.0803 (M−H)⁻
$^1$H-NMR (CDCl$_3$) δ: 1.69-1.92 (1H, m), 1.95-2.23 (1H, m), 2.47-2.70 (4H, m), 2.71-3.00 (1H, m), 4.45-4.91 (1H, m), 5.22-5.77 (3H, m), 6.85-7.08 (1H, m), 7.32-7.54 (5H, m), 7.72 (1H, br s), 8.77 (1H, s).

Example 2-148LP

N-[(R)-Carbamoylphenylmethyl]-N-[(R)-6-chloro-4-fluoroindan-1-yl]-5-methyloxazole-4-carboxamide RT (min.): 3.435
MS (ESI, m/z): 426.1031 (M−H)⁻
$^1$H-NMR (CDCl$_3$) δ: 1.80-3.19 (7H, m), 4.26-6.11 (2H, m), 6.40-8.11 (10H, m).

Example 2-149LP

N-[(R)-Carbamoylphenylmethyl]-N-[(R)-6-chloro-4-fluoroindan-1-yl]-6-morpholin-4-ylnicotinamide RT (min.): 3.170
MS (ESI, m/z): 507.1618 (M−H)⁻
$^1$H-NMR (CDCl$_3$) δ: 1.76-2.25 (2H, m), 2.47-2.97 (2H, m), 3.54-3.64 (4H, m), 3.75-3.86 (4H, m), 4.42-6.08 (3H, m), 6.64 (1H, d, J=8.8 Hz), 6.90-7.03 (1H, m), 7.30-7.51 (6H, m), 7.70-7.82 (2H, m), 8.45 (1H, d, J=2.0 Hz).

Example 2-149HP

N-[(S)-Carbamoylphenylmethyl]-N-[(R)-6-chloro-4-fluoroindan-1-yl]-6-morpholin-4-ylnicotinamide RT (min.): 3.004
MS (ESI, m/z): 507.1613 (M−H)⁻
$^1$H-NMR (CDCl$_3$) δ: 2.48-2.81 (3H, m), 3.05-3.17 (1H, m), 3.56-3.63 (4H, m), 3.78-3.86 (4H, m), 4.27-4.71 (1H, m), 5.34-5.98 (3H, m), 6.19-6.51 (1H, m), 6.65 (1H, d, J=8.9 Hz), 6.82-6.88 (1H, m), 7.27-7.37 (5H, m), 7.74 (1H, dd, J=2.1, 8.9 Hz), 8.42 (1H, d, J=2.1 Hz).

Example 2-150LP

N-[(R)-Carbamoylphenylmethyl]-N-[(R)-6-chloro-4-fluoroindan-1-yl]-4-methylisoxazole-5-carboxamide RT (min.): 3.507
MS (ESI, m/z): 426.1034 (M−H)⁻

¹H-NMR (CDCl₃) δ: 1.85-2.30 (5H, m), 2.50-2.67 (1H, m), 2.81-3.06 (1H, m), 4.82-5.92 (4H, m), 6.80-7.00 (1H, m), 7.34-7.72 (6H, m), 7.93-8.25 (1H, m).

Example 2-151LP

N-[(R)-Carbamoylphenylmethyl]-N-[(R)-6-chloroindan-1-yl]-3-methylpyridine-2-carboxamide RT (min.): 3.205
MS (ESI, m/z): 418.1330 (M–H)⁻
¹H-NMR (CDCl₃) δ: 1.70-1.95 (1H, m), 2.10-2.30 (1H, m), 2.45-2.60 (4H, m), 2.60-2.75 (1H, m), 4.65-4.95 (1H, m), 5.17 (1H, dd, J=8.5, 8.5 Hz), 5.25-5.95 (2H, m), 7.00-7.50 (6H, m), 7.50-7.65 (3H, m), 7.92 (1H, br s), 8.40-8.50 (1H, m).

Example 2-152LP

N-[(R)-Carbamoylphenylmethyl]-N-[(R)-6-chloro-4-fluoroindan-1-yl]-3-methylpyridine-2-carboxamide RT (min.): 3.372
MS (ESI, m/z): 436.1240 (M–H)⁻
¹H-NMR (CDCl₃) δ: 1.70-2.00 (1H, m), 2.10-2.40 (1H, m), 2.40-3.20 (5H, m), 4.60-5.90 (4H, m), 6.80-7.00 (1H, m), 7.15-7.25 (1H, m), 7.25-7.70 (6H, m), 7.76 (1H, s), 8.40-8.50 (1H, m).

Example 2-153LP

N-[(R)-Carbamoyl-(2-methylphenyl)methyl]-N-[(R)-6-chloro-4-fluoroindan-1-yl]nicotinamide RT (min.): 3.165
MS (ESI, m/z): 436.1241 (M–H)⁻
¹H-NMR (CDCl₃) δ: 1.79-3.13 (7H, m), 4.76-5.08 (1H, m), 5.26-5.73 (3H, m), 6.79-7.00 (1H, m), 7.17-7.50 (5H, m), 7.60-7.99 (2H, m), 8.54-8.90 (2H, m).

Example 2-154LP

N-[(R)-Carbamoylphenylmethyl]-N-[(R)-6-chloro-4-fluoroindan-1-yl]-4-methylpyrimidine-5-carboxamide RT (min.): 2.937
MS (ESI, m/z): 437.1192 (M–H)⁻
¹H-NMR (CDCl₃) δ: 1.68-1.84 (1H, m), 1.95-2.13 (1H, m), 2.44-2.92 (5H, m), 4.54-4.87 (1H, m), 5.09-5.62 (3H, m), 6.95-7.06 (1H, m), 7.38-7.61 (5H, m), 7.78 (1H, s), 8.50-8.80 (1H, m), 9.05-9.20 (1H, m).

Example 2-155LP

N-[(R)-Carbamoyl-(3-methylphenyl)methyl]-N-[(R)-6-chloro-4-fluoroindan-1-yl]-2-methylnicotinamide RT (min.): 2.965
MS (ESI, m/z): 450.1399 (M–H)⁻
¹H-NMR (CDCl₃) δ: 1.38-1.87 (1H, m), 1.94-2.14 (1H, m), 2.38 (3H, s), 2.41-3.13 (5H, m), 4.52-5.00 (1H, m), 5.14-5.68 (3H, m), 6.84-7.40 (6H, m), 7.51-7.83 (2H, m), 8.52-8.60 (1H, m).

Example 2-156LP

N-[(R)-Carbamoyl-(4-methylphenyl)methyl]-N-[(R)-6-chloro-4-fluoroindan-1-yl]-2-methylnicotinamide RT (min.): 2.975
MS (ESI, m/z): 450.1395 (M–H)⁻
¹H-NMR (CDCl₃) δ: 1.39-1.88 (1H, m), 1.94-2.14 (1H, m), 2.35-2.41 (3H, m), 2.42-2.55 (1H, m), 2.61-3.13 (4H, m), 4.49-5.62 (4H, m), 6.84-7.02 (1H, m), 7.13-7.28 (3H, m), 7.34-7.82 (4H, m), 8.51-8.60 (1H, m).

Example 2-157LP

N-[(R)-Carbamoylphenylmethyl]-N-[(R)-6-chloroindan-1-yl]-6-(2,2,2-trifluoroethoxy)nicotinamide RT (min.): 3.951
MS (ESI, m/z): 502.1156 (M–H)⁻
¹H-NMR (CDCl₃) δ: 1.65-2.20 (2H, m), 2.50-2.85 (2H, m), 4.55-4.90 (3H, m), 5.25-5.80 (3H, m), 6.92 (1H, d, J=8.5 Hz), 7.05-7.15 (1H, m), 7.15-7.30 (1H, m), 7.30-7.55 (5H, m), 7.88 (1H, dd, J=2.0, 8.6 Hz), 7.97 (1H, br s), 8.37-8.45 (1H, m).

Example 2-158LP

3-Amino-N-[(R)-carbamoylphenylmethyl]-N-[(R)-6-chloroindan-1-yl]pyrazine-2-carboxamide RT (min.): 2.928
MS (ESI, m/z): 420.1241 (M–H)⁻
¹H-NMR (CDCl₃) δ: 1.70-1.95 (1H, m), 2.05-2.35 (1H, m), 2.50-2.90 (2H, m), 4.55-4.95 (1H, m), 5.30-5.95 (5H, m), 7.08 (1H, d, J=8.0 Hz), 7.10-7.25 (1H, m), 7.30-7.55 (5H, m), 7.70-7.95 (2H, m), 7.95-8.15 (1H, m).

Example 2-159LP

N-[(R)-Carbamoyl-(2-fluorophenyl)methyl]-N-[(R)-6-chloro-4-fluoroindan-1-yl]-2-methylnicotinamide RT (min.): 2.815
MS (ESI, m/z): 454.1144 (M–H)⁻
¹H-NMR (CDCl₃) δ: 1.40-2.20 (2H, m), 2.40-3.20 (5H, m), 4.85-5.65 (4H, m), 6.80-8.10 (8H, m), 8.50-8.60 (1H, m).

Example 2-160LP

N-[(R)-Carbamoyl-(2-trifluoromethylphenyl)methyl]-N-[(R)-6-chloro-4-fluoroindan-1-yl]-2-methylnicotinamide RT (min.): 3.031
MS (ESI, m/z): 504.1114 (M–H)⁻
¹H-NMR (CDCl₃) δ: 1.40-1.75 (1H, m), 1.80-2.10 (1H, m), 2.35-2.55 (1H, m), 2.55-2.85 (4H, m), 4.80-5.60 (4H, m), 6.90-7.05 (1H, m), 7.15-7.30 (1H, m), 7.50-7.90 (5H, m), 8.15-8.40 (1H, m), 8.50-8.70 (1H, m).

Example 2-161LP

N-[(R)-Carbamoyl-(3-fluorophenyl)methyl]-N-[(R)-6-chloro-4-fluoroindan-1-yl]-2-methylnicotinamide RT (min.): 2.836
MS (ESI, m/z): 454.1147 (M−H)⁻
¹H-NMR (CDCl₃) δ: 1.64-1.83 (1H, m), 2.00-2.15 (1H, m), 2.45-2.87 (5H, m), 4.53-4.74 (1H, m), 5.21 (1H, t, J=8.7 Hz), 5.37-5.67 (2H, m), 6.86-7.82 (8H, m), 8.54-8.62 (1H, m).

Example 2-162LP

N-[(R)-Carbamoyl-(4-fluorophenyl)methyl]-N-[(R)-6-chloro-4-fluoroindan-1-yl]-2-methylnicotinamide RT (min.): 2.839
MS (ESI, m/z): 454.1147 (M−H)⁻
¹H-NMR (CDCl₃) δ: 1.40-1.85 (1H, m), 1.96-2.13 (1H, m), 2.44-3.16 (5H, m), 4.52-4.96 (1H, m), 5.16-5.66 (3H, m), 6.86-7.34 (4H, m), 7.46-7.81 (4H, m), 8.53-8.62 (1H, m).

Example 2-163LP

N-[(R)-Carbamoyl-(3-methoxyphenyl)methyl]-N-[(R)-6-chloro-4-fluoroindan-1-yl]-2-methylnicotinamide RT (min.): 2.785
MS (ESI, m/z): 466.1347 (M−H)⁻
¹H-NMR (CDCl₃) δ: 1.68-1.88 (1H, m), 1.97-2.15 (1H, m), 2.42-3.16 (5H, m), 3.82 (3H, s), 4.50-4.99 (1H, m), 5.15-5.62 (3H, m), 6.77-7.40 (6H, m), 7.51-7.83 (2H, m), 8.53-8.61 (1H, m).

Example 2-164LP

N-[(R)-Carbamoyl-(4-methoxyphenyl)methyl]-N-[(R)-6-chloro-4-fluoroindan-1-yl]-2-methylnicotinamide RT (min.): 2.760
MS (ESI, m/z): 466.1347 (M−H)⁻
¹H-NMR (CDCl₃) δ: 1.42-1.90 (1H, m), 1.94-2.11 (1H, m), 2.42-3.14 (5H, m), 3.84 (3H, s), 4.46-4.95 (1H, m), 5.13-5.60 (3H, m), 6.84-7.03 (3H, m), 7.14-7.81 (5H, m), 8.52-8.61 (1H, m).

Example 2-165LP

N-[(R)-Carbamoyl-(3-trifluoromethylphenyl)methyl]-N-[(R)-6-chloro-4-fluoroindan-1-yl]-2-methylnicotinamide RT (min.): 3.239
MS (ESI, m/z): 504.1115 (M−H)⁻
¹H-NMR (CDCl₃) δ: 1.61-1.75 (1H, m), 2.03-2.14 (1H, m), 2.46-2.58 (1H, m), 2.61-2.87 (4H, m), 4.65-4.83 (1H, m), 5.23 (1H, t, J=8.7 Hz), 5.33-5.70 (2H, m), 6.99-7.05 (1H, m), 7.20-7.30 (1H, m), 7.48-7.94 (6H, m), 8.55-8.63 (1H, m).

Example 2-166LP

N-[(R)-Carbamoyl-(4-trifluoromethylphenyl)methyl]-N-[(R)-6-chloro-4-fluoroindan-1-yl]-2-methylnicotinamide RT (min.): 3.298
MS (ESI, m/z): 504.1113 (M−H)⁻
¹H-NMR (CDCl₃) δ: 1.62-1.77 (1H, m), 2.03-2.15 (1H, m), 2.46-2.58 (1H, m), 2.61-3.15 (4H, m), 4.62-4.98 (1H, m), 5.15-5.73 (3H, m), 6.86-7.30 (2H, m), 7.41-7.83 (6H, m), 8.54-8.64 (1H, m).

Example 2-167LP

N-[(R)-Carbamoylphenylmethyl]-N-[(R)-6-chloro-4-fluoroindan-1-yl]-3-methylisonicotinamide RT (min.): 2.769
MS (ESI, m/z): 436.1235 (M−H)⁻
¹H-NMR (CDCl₃) δ: 1.67-1.84 (1H, m), 1.92-2.12 (1H, m), 2.35-3.12 (5H, m), 4.52-4.72 (1H, m), 5.09-5.62 (3H, m), 6.83-7.65 (7H, m), 7.69-7.87 (1H, m), 8.50-8.60 (2H, m).

Example 2-168LP

N-[(R)-Carbamoyl-(3-hydroxyphenyl)methyl]-N-[(R)-6-chloro-4-fluoroindan-1-yl]-2-methylnicotinamide RT (min.): 2.314
MS (ESI, m/z): 452.1191 (M−H)⁻
¹H-NMR (DMSO-d₆) δ: 1.36-1.57 (1H, m), 2.02-2.15 (1H, m), 2.35-2.69 (4H, m), 2.85-2.97 (1H, m), 4.93-5.30 (2H, m), 6.66-7.49 (8H, m), 7.57-7.86 (2H, m), 8.51-8.59 (1H, m), 9.65 (1H, br).

Example 2-169LP

N-[(R)-Carbamoyl-(4-hydroxyphenyl)methyl]-N-[(R)-6-chloro-4-fluoroindan-1-yl]-2-methylnicotinamide RT (min.): 2.212
MS (ESI, m/z): 452.1178 (M−H)⁻
¹H-NMR (DMSO-d₆) δ: 1.31-1.51 (1H, m), 1.98-2.10 (1H, m), 2.35-2.68 (4H, m), 2.84-2.95 (1H, m), 4.91-5.27 (2H, m), 6.75-6.86 (2H, m), 7.02-7.17 (3H, m), 7.25-7.90 (5H, m), 8.50-8.58 (1H, m), 9.68 (1H, br).

Example 2-170LP

N-[(R)-Carbamoylphenylmethyl]-N-[(R)-6-chloro-4-fluoroindan-1-yl]-4-methylfurazan-3-carboxamide RT (min.): 3.830
MS (ESI, m/z): 427.0986 (M−H)⁻
¹H-NMR (CDCl₃) δ: 1.80-3.05 (7H, m), 5.06-5.87 (4H, m), 6.76-6.97 (1H, m), 7.40-7.55 (5H, m), 7.58-7.67 (1H, m).

Example 2-171LP

N-[(R)-Carbamoylphenylmethyl]-N-[(R)-6-chloro-4-fluoroindan-1-yl]-2-cyanonicotinamide RT (min.): 3.372
MS (ESI, m/z): 447.1035 (M−H)⁻
¹H-NMR (CDCl₃) δ: 1.78-1.91 (1H, m), 2.12-2.33 (1H, m), 2.45-3.16 (2H, m), 4.50-5.64 (4H, m), 6.85-7.02 (1H, m), 7.36-7.66 (6H, m), 7.72-8.12 (2H, m), 8.72-8.81 (1H, m).

Example 2-172LP

N-[(R)-Carbamoylpyridin-3-ylmethyl]-N-[(R)-6-chloro-4-fluoroindan-1-yl]benzo[1,3]dioxole-4-carboxamide RT (min.): 2.594
MS (ESI, m/z): 466.0982 (M−H)⁻
¹H-NMR (CDCl₃) δ: 1.79-1.99 (1H, m), 2.21-2.42 (1H, m), 2.58-2.71 (1H, m), 2.79-2.98 (1H, m), 4.65-4.82 (1H, m), 5.37-5.78 (2H, m), 5.98-6.36 (3H, m), 6.85-7.08 (4H, m), 7.31-7.39 (1H, m), 7.49-7.62 (1H, m), 7.82-7.97 (1H, m), 8.55-8.70 (2H, m).

Example 2-173LP

N-[(R)-Carbamoylphenylmethyl]-N-[(R)-6-chloro-4-fluoroindan-1-yl]benzo[1,3]dioxole-4-carboxamide RT (min.): 3.674
MS (ESI, m/z): 465.1034 (M−H)⁻
¹H-NMR (CDCl₃) δ: 1.69-1.92 (1H, m), 2.10-2.31 (1H, m), 2.50-2.63 (1H, m), 2.71-2.89 (1H, m), 4.56-5.95 (4H, m), 5.98-6.12 (2H, m), 6.81-7.03 (4H, m), 7.29-7.80 (6H, m).

Example 2-174LP

N-[(R)-Carbamoylpyridin-3-ylmethyl]-N-[(R)-5-methoxyindan-1-yl]-2-methylnicotinamide RT (min.): 0.838
MS (ESI, m/z): 415.1781 (M−H)⁻
¹H-NMR (CDCl₃) δ: 1.61-1.76 (1H, m), 2.01-2.14 (1H, m), 2.51-2.87 (5H, m), 3.80 (3H, s), 4.61-4.80 (1H, m), 5.14-5.83 (3H, m), 6.70-6.76 (1H, m), 6.84-6.91 (1H, m), 7.17-7.24 (1H, m), 7.32-8.22 (4H, m), 8.50-8.73 (3H, m).

Example 2-175LP

N-[(R)-Carbamoylphenylmethyl]-N-[(R)-6-chloro-4-fluoroindan-1-yl]-3-methylpyrazine-2-carboxamide RT (min.): 3.170
MS (ESI, m/z): 437.1194 (M−H)⁻
¹H-NMR (CDCl₃) δ: 1.80-2.30 (2H, m), 2.40-2.55 (1H, m), 2.60-2.85 (4H, m), 5.10-5.25 (1H, m), 5.35-5.80 (2H, m), 6.85-7.00 (1H, m), 7.35-7.50 (4H, m), 7.50-7.60 (2H, m), 7.77 (1H, s), 8.30-8.60 (2H, m).

Example 2-176LP

N-[(R)-Carbamoylphenylmethyl]-N-[(R)-6-chloro-4-fluoroindan-1-yl]-2,2-dimethyl-2,3-dihydrobenzofuran-7-carboxamide RT (min.): 4.092
MS (ESI, m/z): 491.1551 (M−H)⁻
¹H-NMR (CDCl₃) δ: 1.29-1.65 (6H, m), 1.76-1.94 (1H, m), 2.12-2.36 (1H, m), 2.47-2.66 (1H, m), 2.73-2.88 (1H, m), 2.94-3.14 (2H, m), 4.58-4.77 (1H, m), 5.24-6.33 (3H, m), 6.87-7.01 (2H, m), 7.17-7.23 (1H, m), 7.28-7.76 (7H, m).

Example 2-177LP

3-[(R)-Carbamoyl-{[(R)-6-chloro-4-fluoroindan-1-yl]-(2-methylpyridin-3-carbonyl)amino}methyl] benzoic acid methyl ester RT (min.): 2.776
MS (ESI, m/z): 494.1296 (M−H)⁻
¹H-NMR (CDCl₃) δ: 1.60-1.78 (1H, m), 2.00-2.12 (1H, m), 2.43-2.56 (1H, m), 2.62-2.87 (4H, m), 3.94 (3H, m), 4.63-4.85 (1H, m), 5.26-5.76 (3H, m), 6.92-7.27 (2H, m), 7.43-7.92 (4H, m), 7.95-8.27 (2H, m), 8.54-8.64 (1H, m).

Example 2-177HP

3-[(S)-Carbamoyl-{[(R)-6-chloro-4-fluoroindan-1-yl]-(2-methylpyridin-3-carbonyl)amino}methyl] benzoic acid methyl ester RT (min.): 2.513
MS (ESI, m/z): 494.1294 (M−H)⁻
¹H-NMR (CDCl₃) δ: 2.30-3.23 (7H, m), 3.93 (3H, m), 4.35-4.45 (1H, m), 5.06-5.76 (3H, m), 6.80-8.14 (8H, m), 8.60 (1H, dd, J=1.6, 5.0 Hz).

Example 2-178LP

N-[(R)-Carbamoyl-(3-methanesulfonylphenyl)methyl]-N-[(R)-6-chloro-4-fluoroindan-1-yl]-2-methylnicotinamide RT (min.): 2.342
MS (ESI, m/z): 514.1018 (M−H)⁻
¹H-NMR (CDCl₃) δ: 1.40-1.80 (1H, m), 2.05-2.25 (1H, m), 2.45-2.90 (5H, m), 3.10 (3H, s), 4.70-4.90 (1H, m), 5.25 (1H, dd, J=8.5, 8.5 Hz), 5.30-6.10 (2H, m), 6.99-7.06 (1H, m), 7.20-7.32 (1H, m), 7.53-8.22 (6H, m), 8.55-8.67 (1H, m).

Example 2-179LP

N-[(R)-Carbamoylphenylmethyl]-N-[(R)-6-chloro-4-fluoroindan-1-yl]pyrazine-2-carboxamide RT (min.): 3.081
MS (ESI, m/z): 423.1028 (M−H)⁻
¹H-NMR (CDCl₃) δ: 1.85-2.30 (2H, m), 2.45-2.70 (1H, m), 2.70-3.15 (1H, m), 4.50-6.70 (4H, m), 6.80-7.05 (1H, m), 7.30-7.85 (6H, m), 8.40-9.20 (3H, m).

Example 2-180LP

N-[(R)-Carbamoylpyridin-3-ylmethyl]-N-[(R)-6-chloro-4-fluoroindan-1-yl]-2-methoxynicotinamide RT (min.): 2.219
MS (ESI, m/z): 453.1144 (M−H)⁻
¹H-NMR (CDCl₃) δ: 1.70-3.10 (4H, m), 3.97-4.10 (3H, m), 4.60-6.50 (4H, m), 6.95-8.75 (9H, m).

Example 2-181LP

3-Amino-N-[(R)-carbamoylphenylmethyl]-N-[(R)-6-chloro-4-fluoroindan-1-yl]pyrazine-2-carboxamide RT (min.): 3.074
MS (ESI, m/z): 438.1146 (M−H)⁻
¹H-NMR (CDCl₃) δ: 1.70-2.35 (2H, m), 2.45-3.20 (2H, m), 4.50-6.00 (6H, m), 6.85-7.00 (1H, m), 7.35-7.55 (6H, m), 7.80-7.92 (1H, m), 7.95-8.13 (1H, m).

Example 2-182LP

N-[(R)-Carbamoylphenylmethyl]-N-[(R)-6-chloro-4-fluoroindan-1-yl]benzo[b]thiophene-2-carboxamide RT (min.): 4.158
MS (ESI, m/z): 477.0856 (M−H)⁻
¹H-NMR (CDCl₃) δ: 1.79-2.35 (2H, m), 2.54-3.06 (2H, m), 4.39-4.97 (1H, m), 5.26-6.33 (3H, m), 6.84-7.09 (1H, m), 7.32-7.54 (7H, m), 7.64 (1H, s), 7.77-7.91 (3H, m).

Example 2-183LP

N-[(R)-Carbamoylphenylmethyl]-N-[(R)-6-chloro-4-fluoroindan-1-yl]naphthalene-2-carboxamide RT (min.): 4.087
MS (ESI, m/z): 471.1290 (M−H)⁻
¹H-NMR (CDCl₃) δ: 1.73-2.22 (2H, m), 2.35-2.87 (2H, m), 4.45-5.88 (4H, m), 6.83-7.04 (1H, m), 7.34-7.99 (12H, m), 8.05 (1H, s).

Example 2-184LP

N-[(R)-Carbamoylphenylmethyl]-N-[(R)-6-chloro-4-fluoroindan-1-yl]quinoline-3-carboxamide RT (min.): 3.463
MS (ESI, m/z): 472.1243 (M−H)⁻
¹H-NMR (CDCl₃) δ: 1.73-2.22 (2H, m), 2.37-3.17 (2H, m), 4.50-5.89 (4H, m), 6.80-7.09 (1H, m), 7.35-7.69 (6H, m), 7.75-7.98 (3H, m), 8.14 (1H, d, J=8.6 Hz), 8.37 (1H, s), 9.09 (1H, s).

Example 2-185LP

N-[(R)-Carbamoylphenylmethyl]-N-[(R)-6-chloro-4-fluoroindan-1-yl]isoquinoline-4-carboxamide RT (min.): 3.206
MS (ESI, m/z): 472.1239 (M−H)⁻
¹H-NMR (CDCl₃) δ: 1.73-1.82 (1H, m), 2.10-2.18 (1H, m), 2.38-2.48 (1H, m), 2.69-2.76 (1H, m), 4.70 (1H, br), 5.50 (2H, br), 5.23-5.27 (1H, m), 6.93-6.96 (1H, m), 7.43-7.75 (7H, m), 7.93-8.04 (2H, m), 8.52-8.57 (2H, m), 9.31 (1H, br).

Example 2-186LP

N-[(R)-Carbamoylphenylmethyl]-N-[(R)-6-chloro-4-fluoroindan-1-yl]naphthalene-1-carboxamide RT (min.): 4.078
MS (ESI, m/z): 471.1294 (M−H)⁻
¹H-NMR (CDCl₃) δ: 1.67-1.75 (1H, m), 2.00-2.08 (1H, m), 2.28-2.41 (1H, m), 2.28-2.41 (1H, m), 2.64-2.70 (1H, m), 4.67 (1H, br), 5.19-5.28 (2H, m), 6.90-6.92 (1H, m), 7.34-7.92 (12H, m), 8.48-8.51 (1H, m).

Example 2-187LP

4-Amino-N-[(R)-carbamoylphenylmethyl]-N-[(R)-6-chloro-4-fluoroindan-1-yl]thiazole-5-carboxamide RT (min.): 3.131
MS (ESI, m/z): 443.0761 (M−H)⁻
¹H-NMR (CDCl₃) δ: 1.82-3.08 (4H, m), 4.45-6.40 (6H, m), 6.94-7.05 (1H, m), 7.30-7.56 (5H, m), 7.64 (1H, s), 8.56 (1H, s).

Example 2-187HP

4-Amino-N-[(S)-carbamoylphenylmethyl]-N-[(R)-6-chloro-4-fluoroindan-1-yl]thiazole-5-carboxamide RT (min.): 3.009
MS (ESI, m/z): 443.0759 (M−H)⁻
¹H-NMR (CDCl₃) δ: 2.67-2.97 (3H, m), 3.12-3.27 (1H, m), 4.33-4.60 (1H, m), 5.34-5.56 (1H, br), 5.92-6.23 (3H, m), 6.39-6.56 (1H, br), 6.87 (1H, dd, J=1.5, 8.6 Hz), 7.24-7.45 (6H, m), 8.58 (1H, s).

Example 2-188LP

N-[(R)-Carbamoylphenylmethyl]-N-[(R)-6-chloro-4-fluoroindan-1-yl]-2-methoxy-3-methylbenzamide RT (min.): 3.939
MS (ESI, m/z): 465.1397 (M−H)⁻
¹H-NMR (CDCl₃) δ: 1.63-3.18 (7H, m), 3.69-4.01 (3H, m), 4.55-5.96 (4H, m), 6.80-7.89 (10H, m).

Example 2-189LP

N-[(R)-Carbamoylpyridin-3-ylmethyl]-N-[(R)-5-fluoroindan-1-yl]-2-methylnicotinamide RT (min.): 0.979
MS (ESI, m/z): 403.1590 (M−H)⁻
¹H-NMR (CDCl₃) δ: 1.62-1.80 (1H, m), 2.01-2.16 (1H, m), 2.54-2.88 (5H, m), 4.56-4.83 (1H, m), 5.17-5.89 (3H, m), 6.86-6.94 (1H, m), 6.98-7.07 (1H, m), 7.18-7.24 (1H, m), 7.32-8.23 (4H, m), 8.50-8.74 (3H, m).

Example 2-190LP

N-[(R)-Carbamoylpyridin-3-ylmethyl]-N-[(R)-5-fluoroindan-1-yl]-4-methylthiazole-5-carboxamide RT (min.): 1.527
MS (ESI, m/z): 409.1151 (M−H)⁻
¹H-NMR (CDCl₃) δ: 1.68-1.83 (1H, m), 2.10-2.27 (1H, m), 2.60-2.89 (5H, m), 4.59-4.85 (1H, m), 5.24-5.79 (3H, m), 6.89-6.94 (1H, m), 6.99-7.06 (1H, m), 7.35-7.40 (1H, m), 7.75-7.81 (1H, m), 7.94-8.00 (1H, m), 8.61 (1H, d, J=2.3 Hz), 8.64 (1H, dd, J=1.5, 4.8 Hz), 8.78 (1H, s).

Example 2-191LP

N-[(R)-Carbamoylpyridin-3-ylmethyl]-N-[(R)-5-fluoroindan-1-yl]benzamide

RT (min.): 2.057
MS (ESI, m/z): 388.1475 (M−H)⁻

¹H-NMR (CDCl₃) δ: 1.74-1.90 (1H, m), 2.11-2.28 (1H, m), 2.60-2.89 (2H, m), 4.62-4.82 (1H, m), 5.21-6.25 (3H, m), 6.85-6.94 (1H, m), 6.96-7.07 (1H, m), 7.32-7.39 (1H, m), 7.41-7.50 (3H, m), 7.53-7.61 (2H, m), 7.77-7.84 (1H, m), 7.91-8.00 (1H, m), 8.61 (1H, dd, J=1.6, 4.8 Hz), 8.65 (1H, d, J=2.3 Hz).

Example 2-192LP

N-[(R)-Carbamoylpyridin-3-ylmethyl]-N-[(R)-6-cyanoindan-1-yl]benzamide

RT (min.): 1.908
MS (ESI, m/z): 395.1525 (M−H)⁻
¹H-NMR (CDCl₃) δ: 1.67-1.78 (1H, m), 1.84-1.94 (1H, m), 2.20-2.28 (1H, m), 2.86-2.95 (1H, m), 4.66 (1H, br), 5.43-6.11 (3H, m), 7.34-7.55 (8H, m), 8.17 (1H, s), 8.62 (3H, br).

Example 2-192HP

N-[(S)-Carbamoylpyridin-3-ylmethyl]-N-[(R)-6-cyanoindan-1-yl]benzamide

RT (min.): 1.749
MS (ESI, m/z): 395.1524 (M−H)⁻
¹H-NMR (CDCl₃) δ: 2.51-2.60 (1H, m), 2.68-2.77 (1H, m), 2.85-2.93 (1H, m), 3.18-3.26 (1H, m), 4.33-4.41 (1H, m), 5.53-5.74 (3H, m), 6.89 (1H, br), 7.31-7.57 (8H, m), 7.91-7.93 (1H, m), 8.21 (1H, br), 8.61-8.62 (1H, m).

Example 2-193LP

N-[(R)-Carbamoylpyridin-3-ylmethyl]-N-[(R)-6-fluoroindan-1-yl]benzamide

RT (min.): 2.078
MS (ESI, m/z): 388.1474 (M−H)⁻
¹H-NMR (CDCl₃) δ: 1.78-1.92 (1H, m), 2.13-2.27 (1H, m), 2.56-2.68 (1H, m), 2.71-2.89 (1H, m), 4.63-4.80 (1H, m), 5.26-6.25 (3H, m), 6.92-7.03 (1H, m), 7.09-7.17 (1H, m), 7.32-7.37 (1H, m), 7.42-7.50 (3H, m), 7.53-7.62 (3H, m), 7.91-8.02 (1H, m), 8.59-8.68 (2H, m).

Example 2-193HP

N-[(S)-Carbamoylpyridin-3-ylmethyl]-N-[(R)-6-fluoroindan-1-yl]benzamide

RT (min.): 1.895
MS (ESI, m/z): 388.1473 (M−H)⁻
¹H-NMR (CDCl₃) δ: 2.43-2.54 (1H, m), 2.62-2.83 (2H, m), 3.05-3.16 (1H, m), 4.41-4.57 (1H, m), 5.35-5.73 (2H, m), 5.83-6.18 (1H, m), 6.35-6.53 (1H, m), 6.85-6.91 (1H, m), 7.13-7.19 (1H, m), 7.25-7.31 (1H, m), 7.44-7.50 (3H, m), 7.52-7.59 (2H, m), 7.87-7.93 (1H, m), 8.30 (1H, s), 8.53-8.58 (1H, m).

Example 2-194LP

N-[(R)-Carbamoylpyridin-3-ylmethyl]-N-[(R)-6-fluoroindan-1-yl]nicotinamide

RT (min.): 1.139
MS (ESI, m/z): 389.1429 (M−H)⁻
¹H-NMR (CDCl₃) δ: 1.75-1.88 (1H, m), 2.09-2.23 (1H, m), 2.56-2.86 (2H, m), 4.64-4.94 (1H, m), 5.28-5.95 (3H, m), 6.93-7.04 (1H, m), 7.09-7.19 (1H, m), 7.34-7.44 (2H, m), 7.58-7.68 (1H, m), 7.84-8.07 (2H, m), 8.60-8.73 (3H, m), 8.83 (1H, s).

Example 2-195LP

N-[(R)-Carbamoylpyridin-3-ylmethyl]-N-[(R)-6-fluoroindan-1-yl]-2-methylnicotinamide RT (min.): 0.987
MS (ESI, m/z): 403.1586 (M−H)⁻
¹H-NMR (CDCl₃) δ: 1.66-1.81 (1H, m), 2.04-2.14 (1H, m), 2.52-2.85 (5H, m), 4.56-4.83 (1H, m), 5.07-5.90 (3H, m), 6.93-7.04 (1H, m), 7.10-7.25 (2H, m), 7.32-8.25 (4H, m), 8.50-8.75 (3H, m).

Example 2-196LP

N-[(R)-Carbamoylpyridin-3-ylmethyl]-N-[(R)-6-fluoroindan-1-yl]-4-methylthiazole-5-carboxamide RT (min.): 1.539
MS (ESI, m/z): 409.1147 (M−H)⁻
¹H-NMR (CDCl₃) δ: 1.73-1.83 (1H, m), 2.08-2.27 (1H, m), 2.60-2.85 (5H, m), 4.57-4.95 (1H, m), 5.24-5.86 (3H, m), 6.95-7.04 (1H, m), 7.12-7.19 (1H, m), 7.34-7.40 (1H, m), 7.53-7.60 (1H, m), 7.90-8.04 (1H, m), 8.61 (1H, d, J=2.2 Hz), 8.64 (1H, dd, J=1.3, 4.8 Hz), 8.78 (1H, s).

Example 2-197LP

N-[(R)-Carbamoylpyridin-3-ylmethyl]-N-[(R)-6-cyanoindan-1-yl]-2-methylnicotinamide RT (min.): 0.834
MS (ESI, m/z): 410.1634 (M−H)⁻
¹H-NMR (CDCl₃) δ: 1.71-1.80 (1H, m), 2.09-2.16 (1H, m), 2.65-2.86 (5H, m), 4.59-4.70 (1H, m), 5.26 (1H, t, J=8.6 Hz), 5.37-5.79 (2H, m), 7.21-7.80, (5H, m), 8.00-8.25 (2H, m), 8.59-8.67 (3H, m).

Example 2-198LP

N-[(R)-Carbamoyl-(2-methylpyridin-3-yl)methyl]-N-[(R)-6-chloro-4-fluoroindan-1-yl]benzamide RT (min.): 2.367
MS (ESI, m/z): 436.1249 (M−H)⁻
¹H-NMR (CDCl₃) δ: 1.00-3.22 (7H, m), 4.65-5.78 (4H, m), 6.75-8.16 (9H, m), 8.49-8.61 (1H, m).

Example 2-199LP

N-[(R)-Carbamoyl-(2-methylpyridin-3-yl)methyl]-N-[(R)-6-chloro-4-fluoroindan-1-yl]-2-methylnicotinamide RT (min.): 1.566
MS (ESI, m/z): 451.1357 (M−H)⁻
¹H-NMR (CDCl₃) δ: 1.38-1.62 (1H, m), 1.93-2.08 (1H, m), 2.24-2.88 (8H, m), 4.76-5.06 (1H, m), 5.14-5.62 (3H, m), 6.96-7.07 (1H, m), 7.17-7.34 (2H, m), 7.48-7.88 (2H, m), 8.02-8.29 (1H, m), 8.51-8.66 (2H, m).

Example 2-200LP

N-[(R)-Carbamoyl-(6-methylpyridin-3-yl)methyl]-N-[(R)-6-chloro-4-fluoroindan-1-yl]benzamide RT (min.): 2.317
MS (ESI, m/z): 436.1246 (M−H)⁻
$^1$H-NMR (CDCl$_3$) δ: 1.75-1.99 (1H, m), 2.06-2.30 (1H, m), 2.40-2.96 (5H, m), 4.53-4.82 (1H, m), 5.21-6.07 (3H, m), 6.88-7.24 (2H, m), 7.39-7.60 (5H, m), 7.64-7.93 (2H, m), 8.39-8.60 (1H, m).

Example 2-201LP

N-[(R)-Carbamoyl-(6-methylpyridin-3-yl)methyl]-N-[(R)-6-chloro-4-fluoroindan-1-yl]nicotinamide RT (min.): 1.643
MS (ESI, m/z): 437.1196 (M−H)⁻
$^1$H-NMR (CDCl$_3$) δ: 1.75-1.93 (1H, m), 2.05-2.23 (1H, m), 2.48-2.93 (5H, m), 4.53-4.93 (1H, m), 5.28-5.81 (3H, m), 6.91-7.08 (1H, m), 7.23 (1H, d, J=8.1 Hz), 7.35-7.44 (1H, m), 7.68-7.96 (3H, m), 8.44-8.56 (1H, m), 8.66-8.74 (1H, m), 8.76-8.83 (1H, m).

Example 2-202LP

N-[(R)-Carbamoyl-(6-methylpyridin-3-yl)methyl]-N-[(R)-6-chloro-4-fluoroindan-1-yl]-2-methylnicotinamide RT (min.): 1.545
MS (ESI, m/z): 451.1353 (M−H)⁻
$^1$H-NMR (CDCl$_3$) δ: 1.66-1.86 (1H, m), 2.00-2.17 (1H, m), 2.44-2.89 (8H, m), 4.52-4.78 (1H, m), 5.14-5.71 (3H, m), 6.96-7.07 (1H, m), 7.13-7.31 (2H, m), 7.43-8.08 (3H, m), 8.41-8.66 (2H, m).

Example 2-203LP

N-[(R)-Carbamoylpyridin-3-ylmethyl]-N-[(R)-6-chloroindan-1-yl]-2-methylnicotinamide RT (min.): 1.378
MS (ESI, m/z): 419.1290 (M−H)⁻
$^1$H-NMR (CDCl$_3$) δ: 1.62-1.81 (1H, m), 2.00-2.14 (1H, m), 2.50-2.87 (5H, m), 4.60-4.80 (1H, m), 5.17-5.76 (3H, m), 7.09-7.16 (1H, m), 7.17-8.23 (6H, m), 8.51-8.74 (3H, m).

Example 2-204LP

N-[(R)-Carbamoylpyridazin-4-ylmethyl]-N-[(R)-6-chloro-4-fluoroindan-1-yl]-2-methoxybenzamide RT (min.): 2.708
MS (ESI, m/z): 453.1148 (M−H)⁻
$^1$H-NMR (CDCl$_3$) δ: 1.50-3.02 (4H, m), 3.89-4.07 (3H, m), 4.61-4.74 (1H, m), 5.32-5.82 (3H, m), 6.96-7.72 (7H, m), 9.17-9.23 (2H, m).

Example 2-205LP

N-[(R)-Carbamoylpyridazin-3-ylmethyl]-N-[(R)-6-chloro-4-fluoroindan-1-yl]-2-methoxybenzamide RT (min.): 2.807
MS (ESI, m/z): 453.1147 (M−H)⁻
$^1$H-NMR (CDCl$_3$) δ: 1.49-3.31 (4H, m), 3.93-3.99 (3H, m), 4.93-5.05 (1H, m), 5.24-5.82 (2H, m), 6.93-7.72 (8H, m), 7.94-8.14 (1H, m), 9.08-9.17 (1H, m).

Example 2-206LP

N-[(R)-Carbamoylpyridin-3-ylmethyl]-N-[(R)-5-chloroindan-1-yl]benzamide

RT (min.): 2.349
MS (ESI, m/z): 404.1182 (M−H)⁻
$^1$H-NMR (CDCl$_3$) δ: 1.71-1.87 (1H, m), 2.06-2.26 (1H, m), 2.58-2.88 (2H, m), 4.60-4.79 (1H, m), 5.27-6.20 (3H, m), 7.17-7.21 (1H, m), 7.25-7.40 (2H, m), 7.40-7.50 (3H, m), 7.52-7.62 (2H, m), 7.81 (1H, d, J=8.0 Hz), 7.91-8.02 (1H, m), 8.58-8.68 (2H, m).

Example 2-207LP

N-[(R)-Carbamoylpyridin-3-ylmethyl]-N-[(R)-5-chloroindan-1-yl]-2-methylnicotinamide RT (min.): 1.496
MS (ESI, m/z): 419.1294 (M−H)⁻
$^1$H-NMR (CDCl$_3$) δ: 1.61-1.80 (1H, m), 2.00-2.16 (1H, m), 2.50-2.88 (5H, m), 4.56-4.77 (1H, m), 5.15-5.77 (3H, m), 7.13-7.34 (3H, m), 7.34-8.20 (4H, m), 8.52-8.73 (3H, m).

Example 2-208LP

N-[(R)-Carbamoylpyridin-3-ylmethyl]-N-[(R)-5-chloroindan-1-yl]-4-methylthiazole-5-carboxamide RT (min.): 1.901
MS (ESI, m/z): 425.0856 (M−H)⁻
$^1$H-NMR (CDCl$_3$) δ: 1.66-1.81 (1H, m), 2.02-2.23 (1H, m), 2.60-2.89 (5H, m), 4.54-4.86 (1H, m), 5.31-5.75 (3H, m), 7.18-7.23 (1H, m), 7.28-7.33 (1H, m), 7.35-7.40 (1H, m), 7.75-7.81 (1H, m), 7.92-8.00 (1H, m), 8.59-8.67 (2H, m), 8.78 (1H, s).

Example 2-209LP

N-[(R)-Carbamoylpyridin-3-ylmethyl]-N-[(R)-6-chloroindan-1-yl]nicotinamide

RT (min.): 1.490
MS (ESI, m/z): 405.1134 (M−H)⁻
$^1$H-NMR (CDCl$_3$) δ: 1.67-2.26 (2H, m), 2.54-2.98 (2H, m), 4.64-4.92 (1H, m), 5.28-6.05 (3H, m), 7.09-7.15 (1H, m), 7.18-7.44 (3H, m), 7.85-8.05 (3H, m), 8.61-8.67 (2H, m), 8.71 (1H, dd, J=1.6, 5.0 Hz), 8.81-8.86 (1H, m).

Example 2-210LP

N-[(R)-Carbamoylpyridin-3-ylmethyl]-N-[(R)-6-chloroindan-1-yl]-4-methylthiazole-5-carboxamide RT (min.): 1.819
MS (ESI, m/z): 425.0851 (M−H)⁻
¹H-NMR (CDCl$_3$) δ: 1.71-1.84 (1H, m), 2.07-2.27 (1H, m), 2.57-2.87 (5H, m), 4.57-4.95 (1H, m), 5.31-5.81 (3H, m), 7.10-7.17 (1H, m), 7.23-7.30 (1H, m), 7.34-7.40 (1H, m), 7.82 (1H, s), 7.90-8.00 (1H, m), 8.61 (1H, d, J=2.3 Hz), 8.64 (1H, dd, J=1.5, 4.8 Hz), 8.78 (1H, s).

Example 2-211LP

N-[(R)-Carbamoylpyrimidin-5-ylmethyl]-N-[(R)-6-chloro-4-fluoroindan-1-yl]-2-methoxybenzamide RT (min.): 2.770
MS (ESI, m/z): 453.1147 (M−H)⁻
¹H-NMR (CDCl$_3$) δ: 1.58-3.00 (4H, m), 3.92-4.04 (3H, m), 4.64-4.79 (1H, m), 5.04-6.00 (3H, m), 6.96-7.56 (6H, m), 8.82-8.95 (2H, m), 9.16-9.24 (1H, m).

Example 2-212LP

N-[(R)-Carbamoylpyridin-3-ylmethyl]-N-[(R)-6-methoxyindan-1-yl]benzamide

RT (min.): 2.046
MS (ESI, m/z): 400.1679 (M−H)⁻
¹H-NMR (CDCl$_3$) δ: 1.70-1.84 (1H, m), 2.06-2.22 (1H, m), 2.52-2.80 (2H, m), 3.88 (3H, s), 4.67-4.82 (1H, m), 5.28-6.20 (3H, m), 6.85 (1H, dd, J=2.3, 8.3 Hz), 7.10 (1H, d, J=8.3 Hz), 7.32-7.37 (1H, m), 7.41-7.51 (4H, m), 7.55-7.64 (2H, m), 7.92-8.04 (1H, m), 8.60 (1H, dd, J=1.5, 4.8 Hz), 8.65 (1H, d, J=2.3 Hz).

Example 2-213LP

N-[(R)-Carbamoylpyridin-3-ylmethyl]-N-[(R)-6-methoxyindan-1-yl]nicotinamide

RT (min.): 1.154
MS (ESI, m/z): 401.1633 (M−H)⁻
¹H-NMR (CDCl$_3$) δ: 1.67-1.82 (1H, m), 2.05-2.18 (1H, m), 2.53-2.79 (2H, m), 3.88 (3H, s), 4.72-4.87 (1H, m), 5.28-5.83 (3H, m), 6.83-6.90 (1H, m), 7.07-7.14 (1H, m), 7.34-7.44 (2H, m), 7.50-7.56 (1H, m), 7.88-8.05 (2H, m), 8.61-8.73 (3H, m), 8.84-8.89 (1H, m).

Example 2-214LP

N-[(R)-Carbamoylpyridin-3-ylmethyl]-N-[(R)-6-methoxyindan-1-yl]-2-methylnicotinamide RT (min.): 1.017
MS (ESI, m/z): 415.1790 (M−H)⁻
¹H-NMR (CDCl$_3$) δ: 1.61-1.77 (1H, m), 1.99-2.11 (1H, m), 2.47-2.89 (5H, m), 3.80-3.94 (3H, m), 4.64-4.83 (1H, m), 5.15-5.85 (3H, m), 6.81-6.89 (1H, m), 7.04-7.14 (1H, m), 7.18-7.24 (1H, m), 7.32-8.23 (4H, m), 8.50-8.72 (3H, m).

Example 2-215LP

N-[(R)-Carbamoylpyridin-3-ylmethyl]-N-[(R)-6-methoxyindan-1-yl]-4-methylthiazole-5-carboxamide RT (min.): 1.517
MS (ESI, m/z): 421.1352 (M−H)⁻
¹H-NMR (CDCl$_3$) δ: 1.64-1.79 (1H, m), 2.07-2.22 (1H, m), 2.55-2.81 (5H, m), 3.86 (3H, s), 4.68-4.83 (1H, m), 5.32-5.70 (3H, m), 6.84-6.89 (1H, m), 7.08-7.14 (1H, m), 7.33-7.40 (1H, m), 7.43-7.48 (1H, m), 7.93-8.03 (1H, m), 8.60-8.65 (2H, m), 8.77 (1H, s).

Example 2-216LP

N-[(R)-Carbamoylpyrazin-2-ylmethyl]-N-[(R)-6-chloro-4-fluoroindan-1-yl]-2-methoxybenzamide RT (min.): 2.973
MS (ESI, m/z): 453.1152 (M−H)⁻
¹H-NMR (CDCl$_3$) δ: 1.78-3.09 (4H, m), 3.92-4.04 (3H, m), 4.72-4.80 (1H, m), 5.20-5.80 (2H, m), 6.92-7.64 (7H, m), 8.48-8.58 (2H, m), 8.90-9.13 (1H, m).

Example 2-217LP

N-[(R)-Carbamoylpyridin-3-ylmethyl]-N-[(R)-4-chloroindan-1-yl]benzamide

RT (min.): 2.344
MS (ESI, m/z): 404.1180 (M−H)⁻
¹H-NMR (CDCl$_3$) δ: 1.69-1.89 (1H, m), 2.08-2.27 (1H, m), 2.56-2.99 (2H, m), 4.60-4.80 (1H, m), 5.20-6.21 (3H, m), 7.22-7.33 (2H, m), 7.33-7.40 (1H, m), 7.41-7.50 (3H, m), 7.53-7.62 (2H, m), 7.73-7.83 (1H, m), 7.87-8.01 (1H, m), 8.62 (1H, dd, J=1.4, 4.8 Hz), 8.64-8.68 (1H, m).

Example 2-218LP

N-[(R)-Carbamoylphenylmethyl]-N-[(R)-6-fluoroindan-1-yl]benzamide

RT (min.): 4.044
MS (ESI, m/z): 387.1521 (M−H)⁻
¹H-NMR (CDCl$_3$) δ: 1.70-1.90 (1H, m), 1.95-2.20 (1H, m), 2.45-2.80 (2H, m), 4.67 (1H, br s), 5.15-6.00 (3H, m), 6.85-7.20 (2H, m), 7.30-7.80 (11H, m).

Example 2-218HP

N-[(S)-Carbamoylphenylmethyl]-N-[(R)-6-fluoroindan-1-yl]benzamide

RT (min.): 3.879
MS (ESI, m/z): 387.1516 (M−H)⁻
¹H-NMR (CDCl$_3$) δ: 2.35-2.55 (1H, m), 2.60-2.85 (2H, m), 2.95-3.15 (1H, m), 4.46 (1H, br s), 5.30-5.65 (2H, m), 5.70-6.05 (1H, m), 6.25-6.45 (1H, m), 6.75-6.90 (1H, m), 7.10 (1H, dd, J=5.1, 8.1 Hz), 7.25-7.35 (5H, m), 7.40-7.50 (3H, m), 7.50-7.60 (2H, m).

Example 2-219LP

N-[(R)-Carbamoylphenylmethyl]-N-[(R)-4-fluoroindan-1-yl]benzamide

RT (min.): 4.008
MS (ESI, m/z): 387.1520 (M−H)⁻

¹H-NMR (CDCl₃) δ: 1.65-1.90 (1H, m), 2.00-2.20 (1H, m), 2.45-2.65 (1H, m), 2.70-2.95 (1H, m), 4.66 (1H, br s), 5.20-5.95 (3H, m), 6.85-7.05 (1H, m), 7.25-7.65 (11H, m), 7.70-7.85 (1H, m).

Example 2-219HP

N-[(S)-Carbamoylphenylmethyl]-N-[(R)-4-fluoroindan-1-yl]benzamide

RT (min.): 3.946
MS (ESI, m/z): 387.1517 (M−H)⁻
¹H-NMR (CDCl₃) δ: 2.35-2.55 (1H, m), 2.60-2.85 (2H, m), 3.05-3.25 (1H, m), 4.47 (1H, br s), 5.25-6.10 (3H, m), 6.40-6.65 (1H, m), 6.75-6.85 (2H, m), 7.20-7.35 (5H, m), 7.40-7.50 (3H, m), 7.50-7.65 (2H, m).

Example 2-220LP

N-[(R)-Carbamoylphenylmethyl]-N-[(R)-5-fluoroindan-1-yl]benzamide

RT (min.): 4.027
MS (ESI, m/z): 387.1521 (M−H)⁻
¹H-NMR (CDCl₃) δ: 1.65-1.90 (1H, m), 2.00-2.20 (1H, m), 2.50-2.85 (2H, m), 4.65 (1H, br s), 5.20-5.95 (3H, m), 6.80-6.90 (1H, m), 6.95-7.10 (1H, m), 7.30-7.55 (8H, m), 7.55-7.65 (2H, m), 7.85-7.95 (1H, m).

Example 2-220HP

N-[(S)-Carbamoylphenylmethyl]-N-[(R)-5-fluoroindan-1-yl]benzamide

RT (min.): 3.932
MS (ESI, m/z): 387.1517 (M−H)⁻
¹H-NMR (CDCl₃) δ: 2.35-2.55 (1H, m), 2.60-2.85 (2H, m), 3.00-3.20 (1H, m), 4.44 (1H, br s), 5.35-5.65 (2H, m), 5.75-6.00 (1H, m), 6.45-6.55 (1H, m), 6.55-6.70 (1H, m), 6.86 (1H, dd, J=2.0, 8.8 Hz), 7.25-7.35 (5H, m), 7.40-7.50 (3H, m), 7.50-7.60 (2H, m).

Example 2-221LP

N-[(R)-Carbamoylphenylmethyl]-N-[(R)-4,6-difluoroindan-1-yl]benzamide

RT (min.): 4.171
MS (ESI, m/z): 405.1424 (M−H)⁻
¹H-NMR (CDCl₃) δ: 1.65-1.90 (1H, m), 1.90-2.20 (1H, m), 2.40-2.65 (1H, m), 2.65-2.90 (1H, m), 4.66 (1H, br s), 5.20-5.85 (3H, m), 6.60-6.80 (1H, m), 7.30-7.65 (11H, m).

Example 2-221HP

N-[(S)-Carbamoylphenylmethyl]-N-[(R)-4,6-difluoroindan-1-yl]benzamide

RT (min.): 4.022
MS (ESI, m/z): 405.1426 (M−H)⁻
¹H-NMR (CDCl₃) δ: 2.35-2.65 (1H, m), 2.65-2.85 (2H, m), 2.95-3.20 (1H, m), 4.45 (1H, br s), 5.30-6.00 (3H, m), 6.05-6.25 (1H, m), 6.45-6.65 (1H, m), 7.25-7.40 (5H, m), 7.40-7.60 (5H, m).

Example 2-222LP

N-[(R)-Carbamoylphenylmethyl]-N-[(R)-6-chloro-4-fluoroindan-1-yl]-2,6-dimethylnicotinamide RT (min.): 2.439
MS (ESI, m/z): 450.1406 (M−H)⁻
¹H-NMR (CDCl₃) δ: 1H-NMR (CDCl3) δppm: 1.34-1.85 (1H, m), 1.95-2.11 (1H, m), 2.41-3.13 (8H, m), 4.52-5.00 (1H, m), 5.17-5.61 (3H, m), 6.83-7.84 (9H, m).

Example 2-223LP

N-[(R)-Carbamoylpyridin-3-ylmethyl]-N-[(R)-4-chloroindan-1-yl]-2-methylnicotinamide RT (min.): 1.514
MS (ESI, m/z): 419.1298 (M−H)⁻
¹H-NMR (CDCl₃) δ: 1.61-1.81 (1H, m), 2.02-2.16 (1H, m), 2.53-2.95 (5H, m), 4.60-4.83 (1H, m), 5.22-5.89 (3H, m), 7.15-7.24 (1H, m), 7.24-8.20 (6H, m), 8.52-8.75 (3H, m).

Example 2-224LP

N-[(R)-Carbamoylpyridin-3-ylmethyl]-N-[(R)-4-chloroindan-1-yl]-4-methylthiazole-5-carboxamide RT (min.): 1.911
MS (ESI, m/z): 425.0858 (M−H)⁻
¹H-NMR (CDCl₃) δ: 1.65-1.81 (1H, m), 2.07-2.25 (1H, m), 2.59-2.98 (5H, m), 4.56-4.91 (1H, m), 5.27-5.80 (3H, m), 7.25-7.33 (2H, m), 7.34-7.42 (1H, m), 7.72-7.80 (1H, m), 7.91-8.00 (1H, m), 8.60-8.69 (2H, m), 8.77 (1H, s).

Example 2-225LP

N-[(R)-Carbamoylpyridin-3-ylmethyl]-N-[(R)-4-fluoroindan-1-yl]benzamide

RT (min.): 2.070
MS (ESI, m/z): 388.1485 (M−H)⁻
¹H-NMR (CDCl₃) δ: 1.74-1.92 (1H, m), 2.11-2.28 (1H, m), 2.54-2.70 (1H, m), 2.85-3.00 (1H, m), 4.64-4.82 (1H, m), 5.21-6.20 (3H, m), 6.94-7.02 (1H, m), 7.25-7.39 (2H, m), 7.41-7.50 (3H, m), 7.53-7.70 (3H, m), 7.87-8.01 (1H, m), 8.58-8.70 (2H, m).

Example 2-226LP

N-[(R)-Carbamoylpyridin-3-ylmethyl]-N-[(R)-4-fluoroindan-1-yl]nicotinamide

RT (min.): 1.207
MS (ESI, m/z): 389.1432 (M−H)⁻
¹H-NMR (CDCl₃) δ: 1.70-1.87 (1H, m), 2.07-2.25 (1H, m), 2.56-2.98 (2H, m), 4.65-4.87 (1H, m), 5.28-5.93 (3H, m), 6.96-7.04 (1H, m), 7.29-7.45 (3H, m), 7.66-7.76 (1H, m), 7.85-8.05 (2H, m), 8.62-8.74 (3H, m), 8.82-8.89 (1H, m).

Example 2-227LP

N-[(R)-Carbamoylpyridin-3-ylmethyl]-N-[(R)-4-fluoroindan-1-yl]-2-methylnicotinamide RT (min.): 1.052
MS (ESI, m/z): 403.1592 (M−H)⁻
$^1$H-NMR (CDCl$_3$) δ: 1.63-1.82 (1H, m), 2.01-2.17 (1H, m), 2.52-2.96 (5H, m), 4.60-4.80 (1H, m), 5.20-5.85 (3H, m), 6.95-7.04 (1H, m), 7.17-7.24 (1H, m), 7.29-8.20 (5H, m), 8.52-8.76 (3H, m).

Example 2-228LP

N-[(R)-Carbamoylpyridin-3-ylmethyl]-N-[(R)-4-fluoroindan-1-yl]-4-methylthiazole-5-carboxamide RT (min.): 1.577
MS (ESI, m/z): 409.1155 (M−H)⁻
$^1$H-NMR (CDCl$_3$) δ: 1.68-1.84 (1H, m), 2.09-2.27 (1H, m), 2.60-2.74 (4H, m), 2.84-2.99 (1H, m), 4.62-4.85 (1H, m), 5.32-5.79 (3H, m), 6.95-7.04 (1H, m), 7.27-7.42 (2H, m), 7.63 (1H, d, J=7.7 Hz), 7.92-8.01 (1H, m), 8.60-8.67 (2H, m), 8.78 (1H, s).

Example 2-229LP

N-[(R)-Carbamoylpyridin-3-ylmethyl]-N-[(R)-7-fluoroindan-1-yl]benzamide

RT (min.): 1.868
MS (ESI, m/z): 388.1492 (M−H)⁻
$^1$H-NMR (CDCl$_3$) δ: 2.08-2.23 (1H, m), 2.38-2.63 (1H, m), 2.79-3.21 (2H, m), 4.50-4.82 (1H, m), 5.21-6.00 (3H, m), 6.87-6.97 (1H, m), 7.01-7.09 (1H, m), 7.24-7.37 (2H, m), 7.43-7.63 (5H, m), 7.79-7.91 (1H, m), 8.52-8.58 (1H, m), 8.60-8.67 (1H, m).

Example 2-230LP

N-[(R)-Carbamoylpyridin-2-ylmethyl]-N-[(R)-6-chloro-4-fluoroindan-1-yl]-4-methylthiazole-5-carboxamide RT (min.): 2.698
MS (ESI, m/z): 443.0770 (M−H)⁻
$^1$H-NMR (CDCl$_3$) δ: 1.90-2.45 (2H, m), 2.55-3.00 (5H, m), 4.60-5.10 (1H, m), 5.35-5.75 (2H, m), 6.90-7.05 (1H, m), 7.20-7.85 (5H, m), 8.50-8.65 (1H, m), 8.78 (1H, s).

Example 2-231LP

N-[(R)-Carbamoylpyridin-3-ylmethyl]-N-[(R)-5-methoxyindan-1-yl]-4-methylthiazole-5-carboxamide RT (min.): 1.394
MS (ESI, m/z): 421.1347 (M−H)⁻
$^1$H-NMR (CDCl$_3$) δ: 1.65-1.79 (1H, m), 2.11-2.24 (1H, m), 2.59-2.85 (5H, m), 3.81 (3H, s), 4.67-4.80 (1H, m), 5.21-5.84 (3H, m), 6.73-6.78 (1H, m), 6.85-6.91 (1H, m), 7.33-7.40 (1H, m), 7.67 (1H, d, J=8.6 Hz), 7.94-8.00 (1H, m), 8.58-8.65 (2H, m), 8.77 (1H, s).

Example 2-232LP

N-[(R)-Carbamoylpyridin-3-ylmethyl]-N-[(R)-7-chloroindan-1-yl]benzamide

RT (min.): 2.034
MS (ESI, m/z): 404.1175 (M−H)⁻
$^1$H-NMR (CDCl$_3$) δ: 2.28-2.40 (1H, m), 2.55-2.72 (1H, m), 2.92-3.04 (1H, m), 3.20-3.33 (1H, m), 4.49-4.61 (1H, m), 5.08-5.88 (2H, m), 7.17-7.34 (4H, m), 7.43-7.68 (6H, m), 7.79-7.88 (1H, m), 8.50-8.55 (1H, m), 8.64-8.70 (1H, m).

Example 2-233LP

N-[(R)-Carbamoylpyridin-3-ylmethyl]-N-[(R)-4-methylindan-1-yl]benzamide

RT (min.): 2.163
MS (ESI, m/z): 384.1723 (M−H)⁻
$^1$H-NMR (CDCl$_3$) δ: 1.71-1.89 (1H, m), 2.12-2.31 (4H, m), 2.47-2.86 (2H, m), 4.65-4.83 (1H, m), 5.26-6.48 (3H, m), 7.08-7.15 (1H, m), 7.20-7.30 (1H, m), 7.31-7.38 (1H, m), 7.40-7.50 (3H, m), 7.54-7.68 (3H, m), 7.92-8.00 (1H, m), 8.60 (1H, dd, J=1.5, 4.9 Hz), 8.65 (1H, d, J=2.3 Hz).

Example 2-234LP

N-[(R)-Carbamoylpyridin-3-ylmethyl]-N-[(R)-4-methylindan-1-yl]nicotinamide

RT (min.): 1.303
MS (ESI, m/z): 385.1676 (M−H)⁻
$^1$H-NMR (CDCl$_3$) δ: 1.70-1.84 (1H, m), 2.07-2.28 (4H, m), 2.47-2.83 (2H, m), 4.71-4.89 (1H, m), 5.25-6.03 (3H, m), 7.10-7.16 (1H, m), 7.23-7.30 (1H, m), 7.34-7.42 (2H, m), 7.65-7.74 (1H, m), 7.85-8.05 (2H, m), 8.60-8.74 (3H, m), 8.82-8.89 (1H, m).

Example 2-235LP

N-[(R)-Carbamoylpyridin-3-ylmethyl]-2-methyl-N-[(R)-4-methylindan-1-yl]nicotinamide RT (min.): 1.128
MS (ESI, m/z): 399.1831 (M−H)⁻
$^1$H-NMR (CDCl$_3$) δ: 1.62-1.77 (1H, m), 2.00-2.15 (1H, m), 2.22 (3H, s), 2.44-2.97 (5H, m), 4.63-4.87 (1H, m), 5.19-5.94 (3H, m), 7.09-8.23 (7H, m), 8.50-8.75 (3H, m).

Example 2-236LP

N-[(R)-Carbamoylpyridin-3-ylmethyl]-N-[(R)-4-methylindan-1-yl]-4-methylthiazole-5-carboxamide RT (min.): 1.654
MS (ESI, m/z): 405.1397 (M−H)⁻
$^1$H-NMR (CDCl$_3$) δ: 1.67-1.80 (1H, m), 2.11-2.30 (4H, m), 2.51-2.83 (5H, m), 4.69-4.83 (1H, m), 5.28-5.93 (3H, m), 7.10-7.16 (1H, m), 7.22-7.29 (1H, m), 7.33-7.39 (1H, m), 7.59-7.65 (1H, m), 7.94-8.00 (1H, m), 8.57-8.65 (2H, m), 8.76 (1H, s).

Example 2-237LP

N-[(R)-Carbamoylpyridin-3-ylmethyl]-N-[(R)-5-methylindan-1-yl]benzamide

RT (min.): 2.198
MS (ESI, m/z): 384.1725 (M−H)⁻
$^1$H-NMR (CDCl$_3$) δ: 1.71-1.87 (1H, m), 2.08-2.25 (1H, m), 2.35 (3H, s), 2.57-2.86 (2H, m), 4.64-4.80 (1H, m), 5.17-6.47 (3H, m), 7.00-7.07 (1H, m), 7.10-7.17 (1H, m), 7.30-7.37 (1H, m), 7.40-7.49 (3H, m), 7.54-7.63 (2H, m), 7.65-7.72 (1H, m), 7.92-8.00 (1H, m), 8.56-8.68 (2H, m).

Example 2-238LP

N-[(R)-Carbamoylpyridin-3-ylmethyl]-2-methyl-N-[(R)-5-methylindan-1-yl]nicotinamide RT (min.): 1.207
MS (ESI, m/z): 399.1832 (M−H)⁻
$^1$H-NMR (CDCl$_3$) δ: 1.60-1.74 (1H, m), 2.00-2.12 (1H, m), 2.35 (3H, s), 2.52-2.86 (5H, m), 4.59-4.82 (1H, m), 5.16-5.89 (3H, m), 7.03 (1H, s), 7.10-7.18 (1H, m), 7.18-7.23 (1H, m), 7.32-7.43 (1H, m), 7.50-7.87 (2H, m), 7.95-8.20 (1H, m), 8.50-8.72 (3H, m).

Example 2-239LP

N-[(R)-Carbamoylpyridin-3-ylmethyl]-N-[(R)-5-methylindan-1-yl]-4-methylthiazole-5-carboxamide RT (min.): 1.695
MS (ESI, m/z): 405.1396 (M−H)⁻
$^1$H-NMR (CDCl$_3$) δ: 1.65-1.78 (1H, m), 2.09-2.22 (1H, m), 2.36 (3H,), 2.60-2.83 (5H, m), 4.67-4.81 (1H, m), 5.27-5.91 (3H, m), 7.05 (1H, s), 7.12-7.17 (1H, m), 7.33-7.39 (1H, m), 7.66 (1H, d, J=7.9 Hz), 7.94-8.00 (1H, m), 8.58-8.61 (1H, m), 8.62 (1H, dd, J=1.5, 4.8 Hz), 8.77 (1H, s).

Example 2-240LP

N-[(R)-Carbamoylpyridin-3-ylmethyl]-N-[(R)-6-methylindan-1-yl]benzamide

RT (min.): 2.168
MS (ESI, m/z): 384.1725 (M−H)⁻
$^1$H-NMR (CDCl$_3$) δ: 1.72-1.87 (1H, m), 2.07-2.23 (1H, m), 2.42 (3H, s), 2.55-2.84 (2H, m), 4.66-4.78 (1H, m), 5.28-6.30 (3H, m), 7.06-7.14 (2H, m), 7.31-7.36 (1H, m), 7.42-7.50 (3H, m), 7.55-7.65 (3H, m), 7.90-8.00 (1H, m), 8.59 (1H, dd, J=1.6, 5.0 Hz), 8.64 (1H, d, J=2.3 Hz).

Example 2-241LP

N-[(R)-Carbamoylpyridin-3-ylmethyl]-N-[(R)-6-methylindan-1-yl]nicotinamide

RT (min.): 1.328
MS (ESI, m/z): 385.1678 (M−H)⁻
$^1$H-NMR (CDCl$_3$) δ: 1.67-1.82 (1H, m), 2.06-2.18 (1H, m), 2.42 (3H, s), 2.53-2.83 (2H, m), 4.70-4.85 (1H, m), 5.28-5.95 (3H, m), 7.06-7.16 (2H, m), 7.33-7.44 (2H, m), 7.64-7.70 (1H, m), 7.88-8.04 (2H, m), 8.60-8.75 (3H, m), 8.84-8.91 (1H, m).

Example 2-242LP

N-[(R)-Carbamoylpyridin-3-ylmethyl]-2-methyl-N-[(R)-6-methylindan-1-yl]nicotinamide RT (min.): 1.141
MS (ESI, m/z): 399.1833 (M−H)⁻
$^1$H-NMR (CDCl$_3$) δ: 1.60-1.75 (1H, m), 1.98-2.12 (1H, m), 2.41 (3H, s), 2.50-2.90 (5H, m), 4.62-4.80 (1H, m), 5.15-5.87 (3H, m), 7.05-7.15 (2H, m), 7.17-7.24 (1H, m), 7.32-8.22 (4H, m), 8.50-8.74 (3H, m).

Example 2-243LP

N-[(R)-Carbamoylpyridin-3-ylmethyl]-N-[(R)-6-methylindan-1-yl]-4-methylthiazole-5-carboxamide RT (min.): 1.648
MS (ESI, m/z): 405.1398 (M−H)⁻
$^1$H-NMR (CDCl$_3$) δ: 1.66-1.78 (1H, m), 2.09-2.21 (1H, m), 2.41 (3H, s), 2.59-2.82 (5H, m), 4.67-4.81 (1H, m), 5.27-5.86 (3H, m), 7.08-7.15 (2H, m), 7.33-7.39 (1H, m), 7.55-7.60 (1H, m), 7.94-8.00 (1H, m), 8.58-8.64 (2H, m), 8.77 (1H, s).

Example 2-244LP

N-[(R)-Carbamoylpyridin-3-ylmethyl]-N-[(R)-4-fluoro-6-methylindan-1-yl]-2-methylnicotinamide RT (min.): 1.471
MS (ESI, m/z): 417.1740 (M−H)⁻
$^1$H-NMR (CDCl$_3$) δ: 1.61-1.78 (1H, m), 2.03-2.13 (1H, m), 2.33-2.88 (8H, m), 4.63-4.81 (1H, m), 5.14-5.84 (3H, m), 6.81 (1H, d, J=9.9 Hz), 7.18-7.24 (1H, m), 7.32-8.23 (4H, m), 8.52-8.76 (3H, m).

Example 2-245LP

N-[(R)-Carbamoylpyridin-3-ylmethyl]-N-[(R)-4-fluoro-6-methoxyindan-1-yl]-2-methylnicotinamide RT (min.): 1.445
MS (ESI, m/z): 433.1691 (M−H)⁻
$^1$H-NMR (CDCl$_3$) δ: 1.61-1.77 (1H, m), 2.00-2.13 (1H, m), 2.43-2.87 (5H, m), 3.78-3.93 (3H, m), 4.63-4.83 (1H, m), 5.14-5.75 (3H, m), 6.56 (1H, dd, J=1.7, 10.5 Hz), 7.18-7.24 (1H, m), 7.31-8.21 (4H, m), 8.52-8.75 (3H, m).

Example 2-246LP

N-[(R)-Carbamoylpyridin-3-ylmethyl]-N-[(R)-6-chloro-4-fluoroindan-1-yl]-2,6-dimethylnicotinamide RT (min.): 1.520
MS (ESI, m/z): 451.1355 (M−H)⁻
$^1$H-NMR (CDCl$_3$) δ: 1.64-1.81 (1H, m), 2.03-2.15 (1H, m), 2.47-3.17 (8H, m), 4.58-4.98 (1H, m), 5.25 (1H, t, J=8.7 Hz), 5.32-5.78 (2H, m), 6.85-7.13 (2H, m), 7.33-7.79 (3H, m), 7.94-8.16 (1H, m), 8.60-8.72 (2H, m).

Example 2-247LP

N-[(R)-Carbamoylpyridin-3-ylmethyl]-N-[(R)-6-chloro-4-fluoroindan-1-yl]-2-isopropoxybenzamide RT (min.): 2.925
MS (ESI, m/z): 480.1508 (M−H)⁻

¹H-NMR (CDCl₃) δ: 1.38-1.49 (6H, m), 1.71-1.97 (1H, m), 2.14-2.37 (1H, m), 2.50-2.97 (2H, m), 4.62-4.79 (2H, m), 5.26-6.18 (3H, m), 6.92-7.08 (3H, m), 7.18-7.47 (3H, m), 7.56-7.63 (1H, m), 7.87-8.10 (1H, m), 8.54-8.67 (1H, m), 8.72-8.83 (1H, m).

Example 2-248LP

N-[(R)-Carbamoylpyridin-3-ylmethyl]-N-[(R)-6-chloro-4-fluoroindan-1-yl]-2-(2-hydroxyethoxy)benzamide RT (min.): 2.232
MS (ESI, m/z): 482.1302 (M−H)⁻
¹H-NMR (CDCl₃) δ: 1.55-1.83 (1H, m), 1.98-2.37 (1H, m), 2.44-2.88 (2H, m), 3.89-4.41 (4H, m), 4.61-4.79 (1H, m), 5.22-5.69 (3H, m), 6.94-7.13 (3H, m), 7.31-7.46 (3H, m), 7.50-8.07 (2H, m), 8.48-8.69 (1.4H, m), 9.12-9.23 (0.6H, m).

Example 2-249LP

N-[(R)-Carbamoylphenylmethyl]-N-[(R)-6-chloro-4-fluoroindan-1-yl]-2,5-dimethylnicotinamide RT (min.): 2.675
MS (ESI, m/z): 450.1399 (M−H)⁻
¹H-NMR (CDCl₃) δ: 1.35-1.83 (1H, m), 1.93-2.13 (1H, m), 2.30-3.16 (8H, m), 4.52-4.97 (1H, m), 5.21 (t, 1H, J=8.7 Hz), 5.31-5.60 (2H, m), 6.84-7.03 (1H, m), 7.24-7.61 (6H, m), 7.71-7.84 (1H, m), 8.34-8.43 (1H, m).

Example 2-250LP

N-[(R)-Carbamoylpyridin-3-ylmethyl]-N-[(R)-6-chloro-4-fluoroindan-1-yl]-2,5-dimethylnicotinamide RT (min.): 1.746
MS (ESI, m/z): 451.1354 (M−H)⁻
¹H-NMR (CDCl₃) δ: 1.65-1.81 (1H, m), 2.00-2.16 (1H, m), 2.26-2.39 (3H, m), 2.47-3.21 (5H, m), 4.58-4.97 (1H, m), 5.24 (t, 1H, J=8.7 Hz), 5.32-5.78 (2H, m), 6.87-7.05 (1H, m), 7.21-7.80 (3H, m), 7.95-8.17 (1H, m), 8.35-8.45 (1H, m), 8.54-8.72 (2H, m).

Example 2-251LP

N-[(R)-Carbamoylphenylmethyl]-N-[(R)-6,7-dihydro-5H-[1]pyrindin-5-yl]benzamide

RT (min.): 0.978
MS (ESI, m/z): 370.1559 (M−H)⁻
¹H-NMR (CDCl₃) δ: 1.68-1.91 (1H, m), 2.05-2.21 (1H, m), 2.65-2.98 (2H, m), 4.52-4.67 (1H, m), 5.20-5.80 (3H, m), 7.31-7.66 (11H, m), 8.20-8.55 (2H, m).

Example 2-251HP

N-[(S)-Carbamoylphenylmethyl]-N-[(R)-6,7-dihydro-5H-[1]pyrindin-5-yl]benzamide

RT (min.): 0.811
MS (ESI, m/z): 370.1551 (M−H)⁻
¹H-NMR (CDCl₃) δ: 2.41-2.62 (1H, m), 2.65-3.00 (2H, m), 3.10-3.31 (1H, m), 4.37-4.53 (1H, m), 5.31-5.82 (3H, m), 6.65-6.73 (1H, m), 6.80-6.98 (1H, m), 7.24-7.64 (10H, m), 8.33 (1H, d, J=4.4 Hz).

Example 2-252M

N-[(RS)-Carbamoylphenylmethyl]-N-[(SR)-5-chloro-7-fluoro-2,3-dihydrobenzofuran-3-yl]benzamide RT (min.): 3.489
MS (ESI, m/z): 423.0914 (M−H)⁻
¹H-NMR (CDCl₃) δ: 3.60-4.41 (2H, m), 5.20-5.88 (4H, m), 6.91-6.99 (1H, m), 7.15-7.68 (11H, m).

Example 2-253M

N-(Carbamoylphenylmethyl)-N-[(R)-3,3-dimethylindan-1-yl]benzamide

RT (min.): 3.623
MS (ESI, m/z): 397.1920 (M−H)⁻
¹H-NMR (CDCl₃) δ: 0.94 (2H, s), 1.02 (1H, s), 1.19 (2H, s), 1.45 (1H, s), 1.64-1.73 (0.67H, m), 1.83-1.92 (0.67H, m), 2.19-2.29 (0.33H, m), 2.47-2.59 (0.33H, m), 4.52 (0.33H, s), 4.68 (0.67H, s), 5.25-6.10 (3H, m), 6.68 (0.33H, d, J=7.5 Hz), 6.81-6.87 (0.33H, m), 7.10-7.66 (12.67H, m), 7.96 (0.67H, d, J=7.5 Hz).

Example 2-254M

N-(Carbamoylphenylmethyl)-N-(3-methylindan-1-yl)benzamide

RT (min.): 3.483
MS (ESI, m/z): 383.1767 (M−H)⁻
¹H-NMR (CDCl₃) δ: 1.00-1.43 (3H, m), 1.67-3.21 (3H, m), 4.50-4.63 (0.3H, br), 4.71 (0.7H, br s), 5.20-6.16 (3H, m), 6.68-8.10 (14H, m).

Example 2-255M

N-(Carbamoylphenylmethyl)-N-[(R)-4-methoxyindan-1-yl]benzamide

RT (min.): 3.203
MS (ESI, m/z): 399.1708 (M−H)⁻
RT (min.): 3.259
MS (ESI, m/z): 399.1715 (M−H)⁻
¹H-NMR (CDCl₃) δ: 1.65-3.15 (4H, m), 3.80 (1.4H, s), 3.81 (1.6H, s), 4.45-4.75 (1H, m), 5.35-6.90 (4H, m), 7.20-8.15 (12H, m).

Example 2-256M

N-(Carbamoylphenylmethyl)-N-(3,3-difluoroindan-1-yl)benzamide

RT (min.): 3.180
MS (ESI, m/z): 405.1431 (M−H)⁻
RT (min.): 3.229
MS (ESI, m/z): 405.1432 (M−H)⁻
¹H-NMR (CDCl₃) δ: 2.16-3.46 (2H, m), 4.20-4.55 (1H, m), 4.93-5.84 (3H, m), 6.64-7.11 (1H, m), 7.17-7.72 (12H, m), 7.90-8.17 (1H, m).

Example 2-257M

N-(Carbamoylpyridin-3-ylmethyl)-N-[(R)-7-fluorolindan-1-yl]nicotinamide

RT (min.): 0.759
MS (ESI, m/z): 389.1434 (M−H)⁻

¹H-NMR (CDCl₃) δ: 2.08-2.24 (0.5H, m), 2.42-3.40 (3.5H, m), 4.30-4.41 (0.5H, m), 4.56-4.80 (0.5H, m), 5.24-5.86 (2.5H, m), 6.43-6.53 (0.5H, m), 6.88-7.48 (4.5H, m), 7.80-8.01 (3H, m), 8.45-8.92 (3.5H, m).

Example 2-258M

N-(Carbamoylpyridin-3-ylmethyl)-N-[(R)-7-fluorolindan-1-yl]-4-methylthiazole-5-carboxamide RT (min.): 1.046
MS (ESI, m/z): 409.1141 (M–H)⁻
RT (min.): 1.166
MS (ESI, m/z): 409.1146 (M–H)⁻
¹H-NMR (CDCl₃) δ: 2.08-2.22 (0.6H, m), 2.42-3.40 (6.4H, m), 4.32-4.37 (0.4H, m), 4.58-4.80 (0.6H, m), 5.32-5.88 (2.6H, m), 6.40-6.48 (0.4H, m), 6.88-7.40 (4H, m), 7.80-7.98 (1.4H, m), 8.46-8.62 (1.6H, m), 8.80 (0.4H, s), 8.82 (0.6H, s).

Example 2-259M

N-(Carbamoylpyridin-3-ylmethyl)-N-[(R)-7-chlorolindan-1-yl]nicotinamide

RT (min.): 0.838
MS (ESI, m/z): 405.1122 (M–H)⁻
RT (min.): 1.016
MS (ESI, m/z: 405.1126 (M–H)⁻
¹H-NMR (CDCl₃) δ: 2.27-2.49 (4H, m), 4.18-4.26 (0.4H, m), 4.53-4.64 (0.6H, m), 5.18-5.70 (2.6H, m), 6.70-6.78 (0.4H, m), 7.08-7.51 (5H, m), 7.75-8.11 (2.4H, m), 8.43-8.93 (3.6H, m).

Example 2-260HP

2-Amino-N-[(S)-carbamoylphenylmethyl]-N-[(R)-6-chloro-4-fluoroindan-1-yl]nicotinamide RT (min.): 2.295
MS (ESI, m/z): 437.1187 (M–H)⁻
¹H-NMR (CDCl₃) δ: 2.50-2.85 (3H, m), 2.95-3.20 (1H, m), 4.25-4.55 (1H, m), 5.20-5.65 (4H, m), 6.10-6.35 (1H, m), 6.67 (1H, dd, J=5.0, 7.3 Hz), 6.81 (1H, dd, J=1.3, 8.5 Hz), 7.20-7.40 (6H, m), 7.47 (1H, dd, J=1.8, 7.2 Hz), 8.13 (1H, dd, J=1.8, 5.0 Hz).

Example 3-1

N-[(R)-Carbamoylphenylmethyl]-2-hydroxy-N-[(R)-6-trifluoromethylindan-1-yl]benzamide To a solution of (R)-6-trifluoromethylindan-1-ylamine (0.06 g) in methanol (1 mL) was added benzaldehyde (0.032 g), and the mixture was stirred for 20 minutes under reflux. The reaction mixture was allowed to cool to room temperature. To the mixture were added acetylsalicylic acid (0.054 g) and 4-phenylcyclohexen-1-ylisocyanide (0.055 g). The mixture was stirred overnight under reflux, then allowed to cool to room temperature, and concentrated under reduced pressure. To the obtained residue were added tetrahydrofuran (2 mL), water (6 μL) and a solution of 4 mol/L hydrogen chloride in 1,4-dioxane (225 μL), and the mixture was stirred for 3 hours at room temperature. To the reaction mixture were added water and a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane=55/45 to 75/25 to 100/0) to afford 2-{N-[(R)-carbamoylphenylmethyl]-N-[(R)-6-trifluoromethylindan-1-yl]carbamoyl}phenyl acetate as low polarity product. The product was passed through aminopropyl silica gel column chromatography (eluent: methanol/ethyl acetate=0/100 to 35/65) to afford the title compound (0.039 g). The structural formula is shown in Table 29.
RT (min.): 3.397
MS (ESI, m/z): 453.1431 (M–H)⁻
¹H-NMR (CDCl₃) δ: 1.67-2.33 (2H, m), 2.61-3.00 (2H, m), 4.29-6.00 (4H, m), 6.89-6.95 (1H, m), 7.01-7.07 (1H, m), 7.22-7.57 (9H, m), 8.13 (1H, s), 8.67-8.86 (1H, m).

Example 3-2 to 3-3

Examples 3-2 to 3-3 were synthesized in a manner similar to that of Example 3-1 by using the corresponding starting materials. The spectrum data of Examples 3-2 to 3-3 are shown as follows, and the structural formulae are shown in Table 29.

Example 3-2

N-[(R)-Carbamoylphenylmethyl]-N-[(R)-6-cyanoindan-1-yl]-2-hydroxybenzamide

RT (min.): 2.837
MS (ESI, m/z): 410.1510 (M–H)⁻
¹H-NMR (CDCl₃) δ: 1.48-1.99 (2H, m), 2.61-3.07 (2H, m), 4.40-6.21 (4H, m), 6.90-6.97 (1H, m), 7.00-7.07 (1H, m), 7.22-7.65 (9H, m), 8.15 (1H, s), 8.50-8.94 (1H, br).

Example 3-3

N-[(R)-Carbamoylphenylmethyl]-N-[(R)-4,6-difluoroindan-1-yl]-2-hydroxybenzamide

RT (min.): 3.165
MS (ESI, m/z): 421.1370 (M–H)⁻
¹H-NMR (CDCl₃) δ: 1.64-2.25 (2H, m), 2.47-2.90 (2H, m), 4.30-5.00 (1H, br), 5.27-6.00 (3H, m), 6.62-6.78 (1H, m), 6.88-6.95 (1H, m), 7.00-7.06 (1H, m), 7.30-7.54 (8H, m), 8.54-8.84 (1H, br).

Example 4-1

N-[(R)-Carbamoylphenylmethyl]-N-[(R)-6-chloro-4-fluoroindan-1-yl]-2-hydroxybenzamide To a solution of (R)-6-chloro-4-fluoroindan-1-ylamine hydrochloride (98 mg) in methanol (2.2 mL) were added benzaldehyde (47 mg) and triethylamine (45 mg), and the mixture was stirred for 3 hours at 60° C. The reaction mixture was allowed to cool to room temperature. To the mixture were added acetylsalicylic acid (79 mg) and 4-phenylcyclohexen-1-ylisocyanide (81 mg). The mixture was stirred for 19 hours at 60° C., and concentrated under reduced pressure. The obtained residue was suspended in tetrahydrofuran (2.2 mL), and water (9 μL) and a solution of 4 mol/L hydrogen chloride in 1,4-dioxane (0.33 mL) were added. The mixture was stirred for 1.5 hours at room temperature. To the reaction mixture were added a saturated aqueous solution of sodium bicarbonate and dichloromethane, and the formed two-layer mixture was stirred vigorously. The organic layer was separated by ISOLUTE (registered trademark) Phase Separator, and concentrated under reduced pressure. The residue was purified by silica gel column chromatography (eluent: ethyl acetate/n-hexane=52/48 to 73/27) to afford 2-{N-[(R)-carbamoylphenylmethyl]-N-[(R)-6-chloro-4-fluoroindan-1-yl]carbamoy}phenyl acetate as low polarity product. The product was passed through aminopropyl silica gel column chromatography (eluent: methanol/ethyl acetate=14/86 to 20/80) to afford the title compound (69 mg). The structural formula is shown in Table 30.

RT (min.): 3.364
MS (ESI, m/z): 437.1070 (M–H)⁻
¹H-NMR (CDCl₃) δ: 1.65-2.30 (2H, m), 2.50-2.95 (2H, m), 4.35-5.05 (1H, m), 5.20-6.00 (3H, m), 6.85-7.10 (3H, m), 7.30-7.55 (7H, m), 7.66 (1H, br s), 8.50-9.00 (1H, m).

Example 4-2 to 4-9

Examples 4-2 to 4-9 were synthesized in a manner similar to that of Example 4-1 by using the corresponding starting materials. The spectrum data of Examples 4-2 to 4-9 are shown as follows, and the structural formulae are shown in Tables 30 and 31.

Example 4-2

N-[(R)-Carbamoylphenylmethyl]-N-[(S)-5-chloro-2,3-dihydrobenzofuran-3-yl]-2-hydroxybenzamide RT (min.): 2.974
MS (ESI, m/z): 421.0959 (M–H)⁻
¹H-NMR (CDCl₃) δ: 4.06 (1H, dd, J=4.7, 9.9 Hz), 4.40-6.00 (4H, m), 6.65-6.80 (1H, m), 6.90-7.00 (1H, m), 7.05 (1H, dd, J=0.6, 8.3 Hz), 7.10-7.70 (10H, m), 8.60-9.00 (1H, m).

Example 4-3

N-[(R)-Carbamoylphenylmethyl]-N-[(S)-5-fluoro-2,3-dihydrobenzofuran-3-yl]-2-hydroxybenzamide RT (min.): 2.721
MS (ESI, m/z): 405.1253 (M–H)⁻
¹H-NMR (CDCl₃) δ: 4.02-5.00 (2H, m), 5.45-5.75 (3H, m), 6.70-6.78 (1H, m), 6.90-6.99 (2H, m), 7.02-7.08 (1H, m), 7.23-7.30 (1H, m), 7.33-7.65 (8H, m), 8.73 (1H, br).

Example 4-4

N-[(R)-Carbamoylphenylmethyl]-N-[(S)-5,7-difluoro-2,3-dihydrobenzofuran-3-yl]-2-hydroxybenzamide RT (min.): 2.910
MS (ESI, m/z): 423.1162 (M–H)⁻
¹H-NMR (CDCl₃) δ: 3.70-4.40 (2H, m), 5.38-5.88 (3H, m), 6.73-6.83 (1H, m), 6.91-6.97 (1H, m), 7.02-7.07 (1H, m), 7.25-7.31 (2H, m), 7.34-7.68 (7H, m), 8.70 (1H, br).

Example 4-5

N-[(R)-Carbamoylpyridin-3-ylmethyl]-N-[(R)-6-chloro-4-fluoroindan-1-yl]-2-hydroxybenzamide RT (min.): 2.155
MS (ESI, m/z): 438.1031 (M–H)⁻
¹H-NMR (CDCl₃) δ: 1.70-2.38 (2H, m), 2.53-2.94 (2H, m), 4.43-5.10 (1H, m), 5.27-6.41 (3H, m), 6.88-7.04 (3H, m), 7.28-7.35 (2H, m), 7.39 (1H, dd, J=4.8, 7.9 Hz), 7.50-7.55 (1H, m), 7.86-8.07 (1H, m), 8.62 (1H, dd, J=1.5, 4.8 Hz), 8.69-8.86 (1H, m), 8.89-9.79 (1H, m).

Example 4-6

N-[(R)-Carbamoylpyridin-3-ylmethyl]-N-[(R)-6-chloroindan-1-yl]-2-hydroxybenzamide RT (min.): 1.984
MS (ESI, m/z): 420.1128 (M–H)⁻
¹H-NMR (CDCl₃) δ: 1.67-1.87 (1H, m), 2.00-2.38 (1H, m), 2.54-2.86 (2H, m), 4.57-4.98 (1H, m), 5.30-6.35 (3H, m), 6.87-7.02 (2H, m), 7.13 (1H, d, J=8.0 Hz), 7.22-7.42 (4H, m), 7.70 (1H, br s), 7.96-8.06 (1H, m), 8.57-8.64 (1H, m), 8.66-8.72 (1H, m), 8.81-9.76 (1H, br).

Example 4-7

N-[(R)-Carbamoylpyrimidin-5-ylmethyl]-N-[(R)-6-chloro-4-fluoroindan-1-yl]-2-hydroxybenzamide RT (min.): 2.463
MS (ESI, m/z): 439.0998 (M–H)⁻
¹H-NMR (DMSO-d₆) δ: 1.25-2.96 (4H, m), 4.64-5.61 (2H, m), 6.72-7.79 (8H, m), 8.64-8.93 (2H, m), 9.01-9.26 (1H, m), 10.09-10.49 (1H, m).

Example 4-8

N-[(R)-Carbamoylpyrazin-2-ylmethyl]-N-[(R)-6-chloro-4-fluoroindan-1-yl]-2-hydroxybenzamide RT (min.): 2.691
MS (ESI, m/z): 439.0998 (M–H)⁻
¹H-NMR (CDCl₃) δ: 1.88-2.02 (1H, m), 2.45-2.98 (3H, m), 4.80-4.96 (1H, m), 5.52-5.94 (2H, m), 6.94-7.07 (3H, m), 7.34-7.43 (3H, m), 7.86-8.28 (1H, m), 8.51-8.54 (1H, m), 8.60-8.64 (1H, m), 8.88 (1H, s), 9.22 (1H, s).

Example 4-9

N-[(R)-Carbamoylphenylmethyl]-N-[(R)-6-chloro-4-fluoroindan-1-yl]-2-hydroxy-3-methylbenzamide RT (min.): 3.811
MS (ESI, m/z): 451.1236 (M–H)⁻
¹H-NMR (CDCl₃) δ: 1.67-2.22 (2H, m), 2.30 (3H, s), 2.49-2.62 (1H, m), 2.63-2.94 (1H, m), 4.46-4.91 (1H, m), 5.28-5.95 (3H, m), 6.82 (1H, t, J=7.6 Hz), 6.91-7.06 (1H, m), 7.18-7.25 (2H, m), 7.34-7.52 (5H, m), 7.61-7.71 (1H, m), 8.60-8.95 (1H, br).

Example 5-1

2-Amino-N-[(R)-carbamoylphenylmethyl]-N-[(R)-6-trifluoromethylindan-1-yl]benzamide To a solution of (R)-6-trifluoromethylindan-1-ylamine (0.06 g) in methanol (1 mL) was added benzaldehyde (0.032 g), and the mixture was stirred for 20 minutes under reflux. The reaction mixture was allowed to cool to room temperature. To the mixture were added 2-nitrobenzoic acid (0.049 g) and 4-phenylcyclohexen-1-ylisocyanide (0.055 g). The mixture was stirred overnight under reflux, then allowed to cool to room temperature, and concentrated under reduced pressure. To the obtained residue were added tetrahydrofuran (2 mL), water (6 µL) and a solution of 4 mol/L hydrogen chloride in 1,4-dioxane (225 µL), and the mixture was stirred for 3 hours at room temperature. To the reaction mixture were added water and a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by silica gel column chromatography (eluent:ethyl acetate/n-hexane=55/45 to 75/25 to 100/0) to afford N-[(R)-carbamoylphenylmethyl]-2-nitro-N-[(R)-6-trifluoromethylindan-1-yl]benzamide. To N-[(R)-carbamoylphenylmethyl]-2-nitro-N-[(R)-6-trifluoromethylindan-1-yl]benzamide (0.030 g) were added ethanol (2 mL) and 10% palladium carbon (0.030 g) at room temperature, and the mixture was stirred for 4 hours under hydrogen atmosphere. The catalyst was removed by filtration, and the filtrate was concentrated under reduced pressure. The residue was purified by aminopropyl silica gel column chromatography (eluent: ethyl acetate/n-hexane=45/55 to 65/35) to afford the title compound (0.015 g). The structural formula is shown in Table 32.

RT (min.): 3.695
MS (ESI, m/z): 452.1591 (M−H)⁻
$^1$H-NMR (CDCl$_3$) δ: 1.63-1.86 (1H, m), 2.00-2.25 (1H, m), 2.50-2.88 (2H, m), 4.29-4.74 (3H, m), 5.15-5.73 (3H, m), 6.67-6.80 (2H, m), 7.12-7.57 (9H, m), 8.17-8.29 (1H, br).

Example 5-2

2-Amino-N-[(R)-carbamoylphenylmethyl]-N-[(R)-6-cyanoindan-1-yl]benzamide

The title compound was synthesized in a manner similar to that of Example 5-1 by using the corresponding starting material. The spectrum data of the title compound is shown as follows, and the structural formula is shown in Table 32.

RT (min.): 3.124
MS (ESI, m/z): 409.1668 (M−H)⁻
$^1$H-NMR (CDCl$_3$) δ: 1.59-1.82 (1H, m), 1.91-2.22 (1H, m), 2.48-2.90 (2H, m), 4.22-5.80 (6H, m), 6.64-6.88 (2H, m), 7.12-7.62 (9H, m), 8.13-8.34 (1H, m).

Example 6-1

2-Amino-N-[(R)-carbamoylphenylmethyl]-N-[(R)-4,6-difluoroindan-1-yl]benzamide

To a solution of (R)-4,6-difluoroindan-1-ylamine hydrochloride (0.13 g) in methanol (1.6 mL) were added benzaldehyde (67 mg) and triethylamine (64 mg), and the mixture was stirred for 2 hours at 60° C. The reaction mixture was allowed to cool to room temperature. To the mixture were added 2-nitrobenzoic acid (0.1 g) and 4-phenylcyclohexen-1-ylisocyanide (0.12 g). The mixture was stirred for 15 hours at 60° C., and concentrated under reduced pressure. The obtained residue was suspended in tetrahydrofuran (3.2 mL), and water (13 µL) and a solution of 4 mol/L hydrogen chloride in 1,4-dioxane (0.47 mL) were added. The mixture was stirred for 2 hours at room temperature. To the reaction mixture were added a saturated aqueous solution of sodium bicarbonate and dichloromethane, and the formed two-layer mixture was stirred vigorously. The organic layer was separated by ISOLUTE (registered trademark) Phase Separator, and concentrated under reduced pressure. The residue was purified by silica gel column chromatography (eluent: ethyl acetate/n-hexane=55/45 to 76/24) to afford N-[(R)-carbamoylphenylmethyl]-N-[(R)-4,6-difluoroindan-1-yl]-2-nitrobenzamide (0.16 g). A mixture of N-[(R)-carbamoylphenylmethyl]-N-[(R)-4,6-difluoroindan-1-yl]-2-nitrobenzamide (0.16 g), 10% palladium carbon (16 mg) and tetrahydrofuran (3.5 mL) was stirred vigorously for 18 hours at room temperature under hydrogen atmosphere. The catalyst was removed by filtration through a pad of Celite, and the filtrate was concentrated under reduced pressure. The residue was purified by silica gel column chromatography (eluent: ethyl acetate/n-hexane=53/47 to 74/26) to afford the title compound (0.11 g). The structural formula is shown in Table 33.

RT (min.): 3.462
MS (ESI, m/z): 420.1531 (M−H)⁻
$^1$H-NMR (CDCl$_3$) δ: 1.30-2.85 (6H, m), 4.50-4.75 (1H, m), 5.30-5.65 (3H, m), 6.60-6.80 (3H, m), 7.15-7.25 (2H, m), 7.30-7.60 (6H, m).

Example 6-2 to 6-5

Examples 6-2 to 6-5 were synthesized in a manner similar to that of Example 6-1 by using the corresponding starting materials. The spectrum data of Examples 6-2 to 6-5 are shown as follows, and the structural formulae are shown in Tables 33 and 34.

Example 6-2

2-Amino-N-[(R)-carbamoylphenylmethyl]-N-[(R)-6-chloro-4-fluoroindan-1-yl]benzamide RT (min.): 3.664
MS (ESI, m/z): 436.1232 (M−H)⁻
$^1$H-NMR (CDCl$_3$) δ: 1.35-1.85 (3H, m), 1.90-2.25 (1H, m), 2.40-2.60 (1H, m), 2.60-2.80 (1H, m), 4.50-4.75 (1H, m), 5.30-5.70 (3H, m), 6.65-6.80 (2H, m), 6.90-7.05 (1H, m), 7.15-7.25 (2H, m), 7.30-7.60 (5H, m), 7.65-7.85 (1H, m).

Example 6-3

2-Amino-N-[(R)-carbamoylphenylmethyl]-N-[(S)-5-chloro-2,3-dihydrobenzofuran-3-yl]benzamide RT (min.): 3.239
MS (ESI, m/z): 420.1117 (M−H)⁻
$^1$H-NMR (CDCl$_3$) δ: 3.99-4.70 (5H, m), 5.28-5.80 (3H, m), 6.66-6.80 (3H, m), 7.07-7.24 (3H, m), 7.36-7.65 (5H, m), 7.72-7.77 (1H, m).

Example 6-4

2-Amino-N-[(R)-carbamoylpyridin-3-ylmethyl]-N-[(R)-6-chloro-4-fluoroindan-1-yl]benzamide RT (min.): 2.498
MS (ESI, m/z): 437.1196 (M−H)⁻
$^1$H-NMR (CDCl$_3$) δ: 1.50-1.81 (1H, m), 1.99-2.27 (1H, m), 2.48-2.96 (2H, m), 4.00-5.00 (3H, m), 5.28-5.80 (3H, m), 6.67-6.82 (2H, m), 6.93-7.06 (1H, m), 7.12-7.24 (2H, m), 7.38 (1H, dd, J=5.0, 8.0 Hz), 7.70 (1H, br s), 7.92-8.17 (1H, br), 8.58-8.68 (2H, m).

Example 6-5

2-Amino-N-[(R)-carbamoylpyridin-3-ylmethyl]-N-[(R)-6-chloro-4-fluoroindan-1-yl]nicotinamide RT (min.): 1.243
MS (ESI, m/z): 438.1144 (M–H)⁻
$^1$H-NMR (CDCl$_3$) δ: 1.55-1.79 (1H, m), 1.96-2.24 (1H, m), 2.50-2.63 (1H, m), 2.68-2.87 (1H, m), 4.51-4.94 (1H, m), 5.27-5.79 (5H, m), 6.69 (1H, dd, J=5.0, 7.3 Hz), 6.98-7.05 (1H, m), 7.39 (1H, ddd, J=0.5, 4.7, 8.0 Hz), 7.47 (1H, dd, J=1.6, 4.7 Hz), 7.67 (1H, s), 7.95-8.10 (1H, m), 8.14 (1H, dd, J=1.8, 5.0 Hz), 8.60-8.63 (1H, m), 8.66 (1H, dd, J=1.6, 4.7 Hz).

Example 7

N-[(R)-Carbamoylphenylmethyl]-N-[(R)-6-(2-hydroxyethoxy)indan-1-yl]benzamide

To a solution of [(R)-6-(2-benzyloxyethoxy)indan-1-yl]carbamic acid tert-butyl ester (0.20 g) in dichloromethane (1 mL) was added trifluoroacetic acid (1 mL) at room temperature, and the mixture was stirred for 1 hour at same temperature. The reaction mixture was concentrated under reduced pressure. To the residue was added a saturated aqueous solution of sodium bicarbonate, and the mixture was extracted with ethyl acetate. The organic layer was washed with brine, and dried over anhydrous magnesium sulfate. The solvent was removed under reduced pressure. A mixture of the obtained residue, triethylamine (145 μL) and benzaldehyde (0.056 g) in methanol (1 mL) was stirred for 2 hours at 60° C. The reaction mixture was allowed to cool to room temperature. To the mixture were added benzoic acid (0.064 g) and 4-phenylcyclohexen-1-ylisocyanide (0.095 g), and the mixture was stirred for 5 days at external temperature of 60° C. The reaction mixture was concentrated under reduced pressure. To the obtained residue was added tetrahydrofuran (3 mL) to dissolve. To the mixture were added water (11 μL) and a solution of 4 mol/L hydrogen chloride in 1,4-dioxane (0.39 mL), and stirred for 1.5 hours at room temperature. To the reaction mixture were added water and a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane=55/45 to 75/25) to afford N-[(R)-carbamoylphenylmethyl]-N-[6-(2-benzyloxyethoxy)indan-1-yl]benzamide (0.62 g). To a solution of N-[(R)-carbamoylphenylmethyl]-N-[6-(2-benzyloxyethoxy)indan-1-yl]benzamide (0.62 g) in tetrahydrofuran (1 mL) was added 10% palladium carbon (0.02 g) at room temperature, and the mixture was stirred for 2 hours under hydrogen atmosphere. The catalyst was removed by filtration, and the filtrate was concentrated under reduced pressure. The residue was purified by silica gel column chromatography (eluent: ethyl acetate/methanol=100/0 to 85/15) to afford the title compound (0.019 g). The structural formula is shown in Table 34.

RT (min.): 2.832
MS (ESI, m/z): 429.1823 (M–H)⁻
$^1$H-NMR (CDCl$_3$) δ: 1.65-1.82 (1H, m), 1.97-2.13 (1H, m), 2.40-2.74 (3H, m), 3.90-4.00 (2H, m), 4.16-4.32 (2H, m), 4.67 (1H, br s), 5.34-5.90 (3H, m), 6.82-6.91 (1H, m), 7.04-7.10 (1H, m), 7.32-7.68 (11H, m).

Example 8-1

N-[(R)-Carbamoylphenylmethyl]-N-[(R)-6-cyclopropyl-4-fluoroindan-1-yl]benzamide

To a solution of (R)-N-[(R)-6-cyclopropyl-4-fluoroindan-1-yl]-tert-butansulfinamide (0.03 g) in methanol (1 mL) was added a solution of 4 mol/L hydrogen chloride in 1,4-dioxane (35 μL) at room temperature, and the mixture was stirred for 3 hours at same temperature. The reaction mixture was concentrated under reduced pressure. A mixture of the obtained residue, triethylamine (14 μL) and benzaldehyde (0.011 g) in methanol (2 mL) was heated under reflux for 0.5 hours. The reaction mixture was allowed to cool to room temperature. Benzoic acid (0.013 g) and 4-phenylcyclohexen-1-ylisocyanide (0.019 g) were added, and the mixture was heated for 2 days under reflux. The reaction mixture was concentrated under reduced pressure. To the residue was added tetrahydrofuran (2 mL) to dissolve. To the mixture were added water (3 μL) and a solution of 4 mol/L hydrogen chloride in 1,4-dioxane (75 μL), and the mixture was stirred for 1 hour at room temperature. To the reaction mixture were added water and a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane=55/45 to 75/25 to 100/0) to afford the title compound (0.006 g). The structural formula is shown in Table 34.

RT (min.): 3.848
MS (ESI, m/z): 427.1832 (M–H)⁻
$^1$H-NMR (CDCl$_3$) δ: 0.72-1.07 (4H, m), 1.66-1.79 (1H, m), 1.90-2.12 (2H, m), 2.42-2.87 (2H, m), 4.63 (1H, br s), 5.28-5.86 (3H, m), 6.64-6.74 (1H, m), 7.29-7.63 (11H, m).

Example 8-2

N-[(R)-Carbamoylphenylmethyl]-N-[(R)-4-fluoro-6-vinylindan-1-yl]benzamide

The title compound was synthesized in a manner similar to that of Example 8-1 by using the corresponding starting material. The spectrum data of the title compound is shown as follows, and the structural formula is shown in Table 34.

RT (min.): 3.712
MS (ESI, m/z): 413.1676 (M–H)⁻
$^1$H-NMR (CDCl$_3$) δ: 1.68-1.84 (1H, m), 2.00-2.14 (1H, m), 2.44-2.88 (2H, m), 4.60-4.73 (1H, m), 5.21-5.96 (5H, m), 6.76 (1H, dd, J=11.0, 17.2 Hz), 6.96-7.04 (1H, m), 7.32-7.65 (10H, m), 7.89 (1H, br s).

Example 9

N-[(R)-Carbamoylphenylmethyl]-N-[(R)-6-ethyl-4-fluoroindan-1-yl]benzamide

To a solution of N-[(R)-carbamoylphenylmethyl]-N-[(R)-4-fluoro-6-vinylindan-1-yl]benzamide (0.04 g, Example 8-2) in tetrahydrofuran (1 mL) was added 10% palladium carbon (0.01 g) at room temperature, and the mixture was stirred for 3 hours under hydrogen atmosphere. The catalyst was removed by filtration, and the filtrate was concentrated under reduced pressure. The residue was purified by silica gel column chromatography (eluent: ethyl acetate/n-hexane=55/45 to 75/25 to 100/0) to afford the title compound (0.030 g). The structural formula is shown in Table 34.

RT (min.): 3.803
MS (ESI, m/z): 415.1832 (M−H)⁻
$^1$H-NMR (CDCl$_3$) δ: 1.28 (3H, t, J=7.6 Hz), 1.69-1.91 (1H, m), 2.00-2.16 (1H, m), 2.44-2.87 (4H, m), 4.66 (1H, br s), 5.26-5.93 (3H, m), 6.80 (1H, d, J=9.8 Hz), 7.32-7.66 (11H, m).

Example 10

N-[(R)-Carbamoylphenylmethyl]-N-[(R)-4,6-difluoroindan-1-yl]terephthalamidic acid To a solution of N-[(R)-carbamoylphenylmethyl]-N-[(R)-4,6-difluoroindan-1-yl]terephthalamidic acid benzyl ester (0.068 g, Example 2-62LP) in tetrahydrofuran (2 mL) was added 10% palladium carbon (0.02 g) at room temperature, and the mixture was stirred for 2 hours under hydrogen atmosphere. The catalyst was removed by filtration, and the filtrate was concentrated under reduced pressure. The residue was purified by silica gel column chromatography (eluent: ethyl acetate/methanol=100/0 to 80/20) to afford the title compound (0.032 g). The structural formula is shown in Table 34.

RT (min.): 3.057
MS (ESI, m/z): 449.1322 (M−H)⁻
$^1$H-NMR (DMSO-d$_6$) δ: 1.11-1.28 (1H, m), 1.88-2.08 (1H, m), 2.43-2.64 (1, m), 2.75-2.94 (1H, m), 4.96-5.08 (1H, m), 5.37 (1H, br s), 6.88-6.98 (1H, m), 7.21-7.62 (10H, m), 7.99-8.12 (2H, m), 13.08-13.33 (1H, br).

Example 11

N-[(R)-Carbamoylphenylmethyl]-N-[(R)-6-chloro-4-fluoroindan-1-yl]-2-methoxynicotinamide To a solution of (R)-6-chloro-4-fluoroindan-1-ylamine hydrochloride (0.33 g) in methanol (7.5 mL) were added benzaldehyde (0.16 g) and triethylamine (0.15 g), and the mixture was stirred for 1 hour at 65° C. The reaction mixture was allowed to cool to room temperature. To the mixture were added 2-methoxynicotinic acid (0.24 g) and 4-phenylcyclohexen-1-ylisocyanide (0.27 g). The mixture was stirred for 23 hours at 65° C., and the reaction mixture concentrated under reduced pressure. The obtained residue was suspended in tetrahydrofuran (7.5 mL), and water (30 μL) and a solution of 4 mol/L hydrogen chloride in 1,4-dioxane (1.1 mL) were added. The mixture was stirred for 1 hour at room temperature. To the reaction mixture were added a saturated aqueous solution of sodium bicarbonate and dichloromethane, and the formed two-layer mixture was stirred vigorously. The organic layer was separated by ISOLUTE (registered trademark) Phase Separator, and concentrated under reduced pressure. The residue was purified by silica gel column chromatography (eluent: ethyl acetate/n-hexane=64/36 to 85/15) to afford the crude product. The crude product was purified by aminopropyl silica gel column chromatography (eluent: ethyl acetate/n-hexane=58/42 to 100/0) to afford the title compound (0.20 g). The structural formula is shown in Table 34.

RT (min.): 3.409
MS (ESI, m/z): 452.1182 (M−H)⁻
$^1$H-NMR (CDCl$_3$) δ: 1.70-3.10 (4H, m), 3.95-4.10 (3H, m), 4.50-6.10 (4H, m), 6.80-7.10 (2H, m), 7.30-7.90 (7H, m), 8.20-8.30 (1H, m).

Example 12

N-[(R)-Carbamoylpyridin-3-ylmethyl]-N-[(R)-6-chloro-4-fluoroindan-1-yl]-2-methylnicotinamide To a solution of (R)-6-chloro-4-fluoroindan-1-ylamine hydrochloride (103 mg) in methanol (2.3 mL) were added 3-pyridinecarboxaldehyde (50 mg) and triethylamine (47 mg), and the mixture was stirred for 2 hours at 65° C. The reaction mixture was allowed to cool to room temperature, and to the mixture were added 2-methylnicotinic acid (67 mg) and 4-phenylcyclohexen-1-ylisocyanide (85 mg). The mixture was stirred for 5 hours at 65° C., and the reaction mixture was concentrated under reduced pressure. The obtained residue was suspended in tetrahydrofuran (2.3 mL), and water (9 L) and a solution of 4 mol/L hydrogen chloride in 1,4-dioxane (0.46 mL) were added. The mixture was stirred for 1 hour at room temperature. To the reaction mixture were added a saturated aqueous solution of sodium bicarbonate and dichloromethane, and the formed two-layer mixture was stirred vigorously. The organic layer was separated by ISOLUTE (registered trademark) Phase Separator, and concentrated under reduced pressure. The residue was purified by aminopropyl silica gel column chromatography (eluent: methanol/ethyl acetate=0/100 to 9/91) to afford a mixture of diastereomers. The mixture was purified by preparative reverse phase liquid chromatography (Inertsil ODS-3, eluent: acetonitrile/water=10/90 to 90/10) to afford the title compound (32 mg). The structural formula is shown in Table 34.

RT (min.): 1.694
MS (ESI, m/z): 437.1191 (M−H)⁻
$^1$H-NMR (CDCl$_3$) δ: 1.65-1.85 (1H, m), 2.00-2.20 (1H, m), 2.45-2.90 (5H, m), 4.55-5.00 (1H, m), 5.23 (1H, dd, J=8.8, 8.8 Hz), 5.30-5.80 (2H, m), 7.02 (1H, dd, J=0.8, 8.6 Hz), 7.15-7.30 (1H, m), 7.35-7.90 (3H, m), 7.90-8.25 (1H, m), 8.50-8.80 (3H, m).
$[α]^{25}{}_D$: +54.4° (c=0.40, MeOH)

Example 13

2-Amino-N-[(R)-carbamoylphenylmethyl]-N-[(R)-6-chloro-4-fluoroindan-1-yl]nicotinamide To a solution of (R)-6-chloro-4-fluoroindan-1-ylamine hydrochloride (0.1 g) in methanol (3 mL) were added triethylamine (0.046 g) and benzaldehyde (0.048 g), and the mixture was stirred for 0.5 hours at 65° C. The reaction mixture was allowed to cool to room temperature, and to the mixture were added 2-nitronicotinic acid (0.083 g) and 4-phenylcyclohexen-1-ylisocyanide (0.083 g). The mixture was stirred overnight at 65° C., then allowed to cool to room temperature, and concentrated under reduced pressure. To the obtained residue were added tetrahydrofuran (4 mL), water (40 μL) and a solution of 4 mol/L hydrogen chloride in 1,4-dioxane (340 μL), and the mixture was stirred for 1 hour at room temperature. To the reaction mixture were added water and a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by silica gel column chromatography (eluent:

methanol/ethyl acetate/n-hexane=0/60/40 to 0/100/0 to 20/80/0) to afford 2-nitro-N-[(R)-carbamoylphenylmethyl]-N-[(R)-6-chloro-4-fluoroindan-1-yl]nicotinamide (0.090 g). A suspension of Raney catalyst was prepared as follows. A mixture of Raney (registered trademark) 2800 nickel slurry in water, active catalyst (Sigma-Aldrich) (200 μL) and ethanol was stirred, and the solvent was removed by decantation. The catalyst was washed 3 times with ethanol, and ethanol (1 mL) was added to form a suspension. To a solution of 2-nitro-N-[(R)-carbamoylphenylmethyl]-N-[(R)-6-chloro-4-fluoroindan-1-yl]nicotinamide (0.090 g) in ethanol (1 mL) was added the suspension of Raney catalyst at room temperature, and the mixture was stirred for 5 hours under hydrogen atmosphere. The catalyst was removed by filtration, and the filtrate was concentrated under reduced pressure. The residue was purified by aminopropyl silica gel column chromatography (eluent: ethyl acetate/n-hexane=90/10 to 100/0) to afford the title compound (0.071 g). The structural formula is shown in Table 34.

RT (min.): 2.330
MS (ESI, m/z): 437.1182 (M−H)⁻
$^1$H-NMR (CDCl$_3$) δ: 1.60-1.85 (1H, m), 1.90-2.20 (1H, m), 2.45-2.85 (2H, m), 4.50-4.85 (1H, m), 5.20-5.65 (5H, m), 6.69 (1H, dd, J=5.1, 7.3 Hz), 6.90-7.05 (1H, m), 7.35-7.55 (6H, m), 7.70 (1H, br s), 8.13 (1H, dd, J=1.7, 5.1 Hz).
$[\alpha]^{26}_D$: +44.9° (c=1.08, MeOH)

Example 14

N-[(R)-Carbamoylphenylmethyl]-N-[(R)-6-chloro-4-fluoroindan-1-yl]-2-methylnicotinamide N-[(S)-Carbamoylphenylmethyl]-N-[(R)-6-chloro-4-fluoroindan-1-yl]-2-methylnicotinamide To a mixture of (R)-6-chloro-4-fluoroindan-1-ylamine hydrochloride (444 mg) and benzaldehyde (212 mg) in methanol (8 mL) was added triethylamine (202 mg), and the mixture was stirred for 2 hours at 60° C. The reaction mixture was allowed to cool to room temperature, and 2-methylnicotinic acid (274 mg) and 4-phenylcyclohexen-1-ylisocyanide (366 mg) were added, and the mixture was stirred overnight at 60° C. The solvent was removed under reduced pressure. To the residue were added 1,4-dioxane (3.5 mL), water (0.5 mL) and a solution of 4 mol/L hydrogen chloride in 1,4-dioxane (0.5 mL) at room temperature, and the mixture was stirred for 3 hours. To the reaction mixture was added a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane=5/1) to afford the each diastereomer as a crude. These crude products were purified by aminopropyl silica gel column chromatography (eluent: ethyl acetate/n-hexane=3/1) to afford N-[(R)-carbamoylphenylmethyl]-N-[(R)-6-chloro-4-fluoroindan-1-yl]-2-methylnicotinamide (Example 14LP, 279 mg) as low polarity product and N-[(S)-carbamoylphenylmethyl]-N-[(R)-6-chloro-4-fluoroindan-1-yl]-2-methylnicotinamide (Example 14HP, 166 mg) as high polarity product. The structural formulae are shown in Tables 34 and 35.

Example 14LP

N-[(R)-Carbamoylphenylmethyl]-N-[(R)-6-chloro-4-fluoroindan-1-yl]-2-methylnicotinamide RT (min.): 2.728
MS (ESI, m/z): 436.1233 (M−H)⁻
$^1$H-NMR (CDCl$_3$) δ: 1.65-1.85 (1H, m), 1.96-2.11 (1H, m), 2.41-2.55 (1H, m), 2.61-3.14 (4H, m), 4.55-5.00 (1H, m), 5.17-5.24 (1H, m), 5.30-5.57 (2H, m), 6.84-7.04 (1H, m), 7.15-7.84 (8H, m), 8.53-8.61 (1H, m).
$[\alpha]^{25}_D$: +24.9° (c=0.58, MeOH)

Example 14HP

N-[(S)-Carbamoylphenylmethyl]-N-[(R)-6-chloro-4-fluoroindan-1-yl]-2-methylnicotinamide RT (min.): 2.569
MS (ESI, m/z): 436.1240 (M−H)⁻
$^1$H-NMR (CDCl$_3$) δ: 2.31-3.17 (7H, m), 4.36 (1H, br s), 5.07-5.61 (3H, m), 6.12-6.28 (1H, m), 6.76-6.87 (1H, m), 7.17-7.73 (7H, m), 8.56-8.61 (1H, m).
$[\alpha]^{25}_D$: +85.3° (c=1.18, MeOH)

Example 15LP

N-[(R)-Carbamoylphenylmethyl]-N-[(R)-6-chloro-4-fluoroindan-1-yl]-4-methylthiazole-5-carboxamide To a solution of (R)-6-chloro-4-fluoroindan-1-ylamine hydrochloride (0.45 g) in methanol (10 mL) were added benzaldehyde (0.22 g) and triethylamine (0.21 g), and the mixture was stirred for 2.5 hours at 65° C. The reaction mixture was allowed to cool to room temperature. To the mixture were added 4-methylthiazole-5-carboxylic acid (0.31 g) and 4-phenylcyclohexen-1-ylisocyanide (0.37 g). The mixture was stirred for 20 hours at 65° C. The reaction mixture was concentrated under reduced pressure, and the obtained residue was suspended in tetrahydrofuran (5 mL), and water (40 μL) and a solution of 4 mol/L hydrogen chloride in 1,4-dioxane (1.5 mL) were added. The mixture was stirred for 1 hour at room temperature. To the reaction mixture were added a saturated aqueous solution of sodium bicarbonate and dichloromethane, and the formed two-layer mixture was stirred vigorously. The organic layer was separated by ISOLUTE (registered trademark) Phase Separator, and concentrated under reduced pressure. The residue was purified by silica gel column chromatography (eluent: ethyl acetate/n-hexane=71/29 to 92/8) to afford the title compound (0.35 g). The structural formula is shown in Table 35.

RT (min.): 3.241
MS (ESI, m/z): 442.0800 (M−H)⁻
$^1$H-NMR (CDCl$_3$) δ: 1.65-2.30 (2H, m), 2.45-3.05 (5H, m), 4.40-6.00 (4H, m), 6.85-7.10 (1H, m), 7.30-7.60 (5H, m), 7.72 (1H, br s), 8.77 (1H, s).
$[\alpha]^{26}_D$: +33.6° (c=1.07, MeOH)

Example 15HP

N-[(S)-Carbamoylphenylmethyl]-N-[(R)-6-chloro-4-fluoroindan-1-yl]-4-methylthiazole-5-carboxamide The title compound was synthesized in a manner similar to that of Example 15LP as the corresponding high polarity diastereomer. The spectrum data of the title compound is shown as follows, and the structural formula is shown in Table 35.

RT (min.): 3.046

MS (ESI, m/z): 442.0802 (M−H)⁻

$^1$H-NMR (CDCl$_3$) δ: 2.24-2.85 (6H, m), 3.05-3.20 (1H, m), 4.20-4.70 (1H, m), 5.20-5.75 (3H, m), 6.00-6.45 (1H, m), 6.84 (1H, dd, J=1.0, 8.6 Hz), 7.20-7.45 (5H, m), 8.79 (1H, s).

$[α]^{25}_D$: +72.3° (c=1.04, MeOH)

Example 16

7-Acetyl-N-[(R)-carbamoylphenylmethyl]-N-[(R)-6-chloro-4-fluoroindan-1-yl]-5,6,7,8-tetrahydroimidazo[1,2-a]pyrazine-3-carboxamide To a solution of 5,6,7,8-tetrahydroimidazo[1,2-a]pyrazine-3-carboxylic acid ethyl ester (0.225 g) in tetrahydrofuran (3 mL) was added acetic anhydride (130 μL), and the mixture was stirred for 1 hour at room temperature. The reaction mixture was concentrated under reduced pressure, and the residue was purified by aminopropyl silica gel column chromatography (eluent: ethyl acetate/n-hexane=60/40 to 85/15) to afford 7-acetyl-5,6,7,8-tetrahydroimidazo[1,2-a]pyrazine-3-carboxylic acid ethyl ester (0.12 g). To a solution of 7-acetyl-5,6,7,8-tetrahydroimidazo[1,2-a]pyrazine-3-carboxylic acid ethyl ester (0.12 g) in ethanol (3 mL) was added an aqueous solution of 2 mol/L sodium hydroxide (330 μL), and the mixture was stirred for 30 minutes under reflux. The reaction mixture was allowed to cool to room temperature, and 2 mol/L hydrochloric acid (330 μL) was added to the mixture. The mixture was concentrated under reduced pressure to afford 7-acetyl-5,6,7,8-tetrahydroimidazo[1,2-a]pyrazine-3-carboxylic acid (0.106 g). To a mixture of (R)-6-chloro-4-fluoroindan-1-ylamine hydrochloride (0.112 g) and triethylamine (0.051 g) in methanol (2 mL) was added benzaldehyde (0.054 g), and the mixture was stirred for 30 minutes at 65° C. The reaction mixture was allowed to cool to room temperature. To the mixture were added 7-Acetyl-5,6,7,8-tetrahydroimidazo[1,2-a]pyrazine-3-carboxylic acid (0.106 g) and 4-phenylcyclohexen-1-ylisocyanide (0.093 g). The mixture was stirred overnight at 65° C., then allowed to cool to room temperature, and concentrated under reduced pressure. To the obtained residue were added tetrahydrofuran (4 mL), water (100 μL) and a solution of 4 mol/L hydrogen chloride in 1,4-dioxane (500 μL), and the mixture was stirred for 30 minutes at room temperature. To the reaction mixture were added water and a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by aminopropyl silica gel column chromatography (eluent: methanol/ethyl acetate=4/96) to afford the title compound (0.033 g) as a low polarity diastereomer. The structural formula is shown in Table 35.

RT (min.): 2.458

MS (ESI, m/z): 508.1561 (M−H)⁻

$^1$H-NMR (CDCl$_3$) δ: 1.75-2.28 (5H, m), 2.55-2.97 (2H, m), 3.70-5.08 (7H, m), 5.23-6.26 (3H, m), 6.89-7.10 (1H, m), 7.33-7.49 (6H, m), 7.57-7.81 (1H, m).

Example 17

N-[(R)-Carbamoylphenylmethyl]-N-[(R)-6-chloro-4-fluoroindan-1-yl]-5,6,7,8-tetrahydroimidazo[1,2-a]pyrazine-3-carboxamide To a suspension of imidazo[1,2-a]pyrazine-3-carboxylic acid ethyl ester (0.21 g) and a solution of 4 mol/L hydrogen chloride in ethyl acetate (360 μL) in ethanol (3 mL) was added 10% palladium carbon (0.080 g) at room temperature, and the mixture was stirred overnight under hydrogen atmosphere. The catalyst was removed by filtration, and the filtrate was concentrated under reduced pressure. To the residue were added tetrahydrofuran (3 mL), triethylamine (460 μL) and benzyloxycarbonyl chloride (250 μL), and the mixture was stirred overnight at room temperature. To the reaction mixture were added water and a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by aminopropyl silica gel column chromatography (eluent: ethyl acetate/n-hexane=60/40 to 85/15) to afford 5,6-dihydro-8H-imidazo[1,2-a]pyrazine-3,7-dicarboxylic acid 7-benzyl-3-ethyl ester (0.16 g). To a solution of 5,6-dihydro-8H-imidazo[1,2-a]pyrazine-3,7-dicarboxylic acid 7-benzyl-3-ethyl ester (0.16 g) in ethanol (3 mL) was added an aqueous solution of 2 mol/L sodium hydroxide (315 μL). The mixture was stirred for 30 minutes under reflux, and allowed to cool to room temperature. To the mixture was added 2 mol/L hydrochloric acid (315 μL), and concentrated under reduced pressure to afford 5,6-dihydro-8H-imidazo[1,2-a]pyrazine-3,7-dicarboxylic acid 7-benzyl ester (0.146 g). To a solution of (R)-6-chloro-4-fluoroindan-1-ylamine hydrochloride (0.108 g) and triethylamine (0.049 g) in methanol (2 mL) was added benzaldehyde (0.052 g), and the mixture was stirred for 30 minutes at 65° C. The reaction mixture was allowed to cool to room temperature. To the mixture were added 5,6-dihydro-8H-imidazo[1,2-a]pyrazine-3,7-dicarboxylic acid 7-benzyl ester (0.146 g) and 4-phenylcyclohexen-1-ylisocyanide (0.089 g). The mixture was stirred overnight at 65° C., then allowed to cool to room temperature, and concentrated under reduced pressure. To the obtained residue were added tetrahydrofuran (4 mL), water (100 μL) and a solution of 4 mol/L hydrogen chloride in 1,4-dioxane (500 μL), and the mixture was stirred for 30 minutes at room temperature. To the reaction mixture were added water and a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by aminopropyl silica gel column chromatography (eluent: methanol/ethyl acetate=4/96) to afford 3-{N-[(R)-carbamoylphenylmethyl]-N-[(R)-6-chloro-4-fluoroindan-1-yl]carbamoyl}-5,6-dihydro-8H-imidazo[1,2-a]pyrazine-7-carboxylic acid benzyl ester (0.038 g) as a low polarity diastereomer. To a suspension of 3-{N-[(R)-carbamoylphenylmethyl]-N-[(R)-6-chloro-4-fluoroindan-1-yl]carbamoyl}-5,6-dihydro-8H-imidazo[1,2-a]pyrazine-7-carboxylic acid benzyl ester (0.038 g) in tetrahydrofuran (3 mL) was added 10% palladium carbon (0.020 g) at room temperature, and the mixture was stirred for a day under hydrogen atmosphere. The catalyst was removed by filtration, and the filtrate was concentrated under reduced pressure. The residue was purified by aminopropyl silica gel column chromatography (eluent: methanol/ethyl acetate=0/

100 to 20/80) to afford the title compound (0.23 g). The structural formula is shown in Table 35.

RT (min.): 2.045

MS (ESI, m/z): 466.1450 (M−H)⁻

$^1$H-NMR (CDCl$_3$) δ: 1.76-2.36 (2H, m), 2.50-3.00 (2H, m), 3.16-3.33 (2H, m), 3.56-5.00 (6H, m), 5.20-6.34 (3H, m), 6.86-7.09 (1H, m), 7.30-7.48 (6H, m), 7.55-7.81 (1H, m).

TABLE 3

| Ex. No. | Strc. |
|---|---|
| 1-1 | |
| 1-2 | |
| 1-3 | |
| 1-4 | |
| 1-5 | |
| 1-6 | |

TABLE 4

| Ex. No. | Strc. |
|---|---|
| 2-1LP | |
| 2-1HP | |

TABLE 4-continued
| Ex. No. | Strc. |
|---|---|
| 2-2LP | 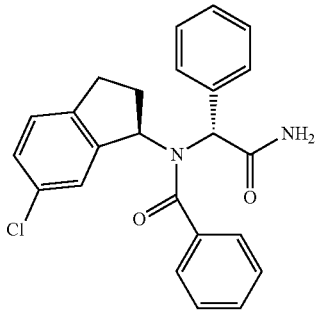 [SMILES: NC(=O)[C@@H](c1ccccc1)N(C(=O)c1ccccc1)[C@@H]1CCc2ccc(Cl)cc21] |
| 2-2HP | 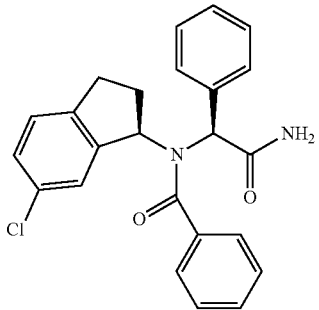 [SMILES: NC(=O)[C@H](c1ccccc1)N(C(=O)c1ccccc1)[C@@H]1CCc2ccc(Cl)cc21] |
| 2-3LP | 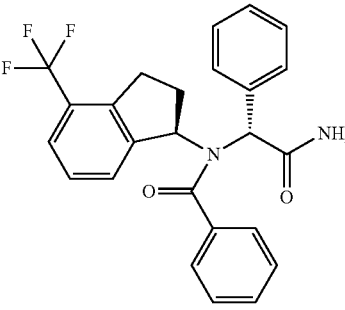 |
| 2-3HP | 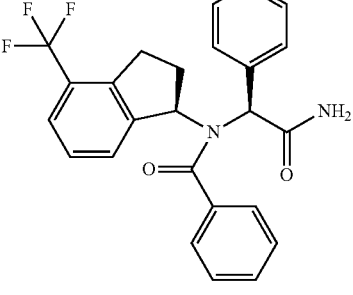 |
| 2-4LP | 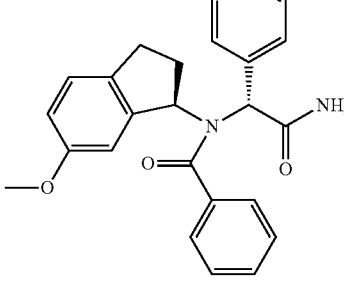 |
TABLE 4-continued
| Ex. No. | Strc. |
|---|---|
| 2-5LP | 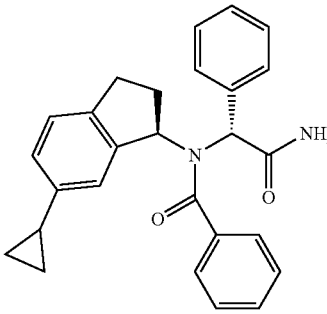 |
| 2-5HP | 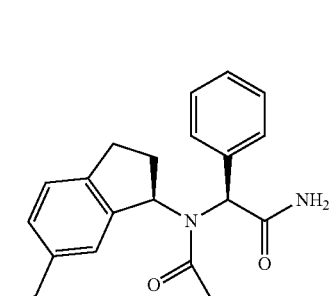 |
| 2-6LP | 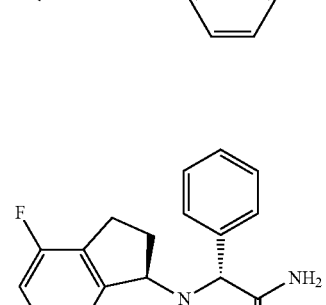 |
| 2-6HP | 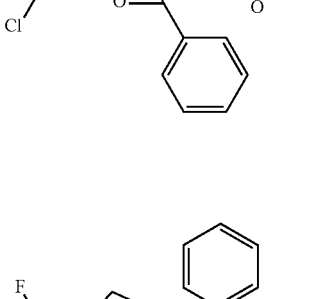 |

TABLE 4-continued
| Ex. No. | Strc. |
|---|---|
| 2-7LP | 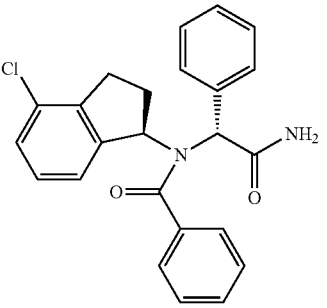 [SMILES: NC(=O)[C@@H](c1ccccc1)N(C(=O)c1ccccc1)[C@@H]1CCc2c(Cl)cccc21] |
TABLE 5
| Ex. No. | Strc. |
|---|---|
| 2-7HP | 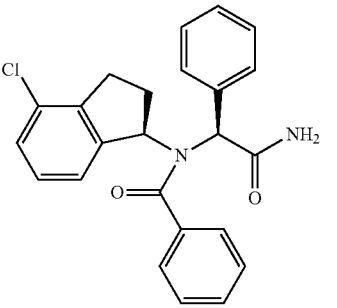 [SMILES: NC(=O)[C@H](c1ccccc1)N(C(=O)c1ccccc1)[C@@H]1CCc2c(Cl)cccc21] |
| 2-8LP | 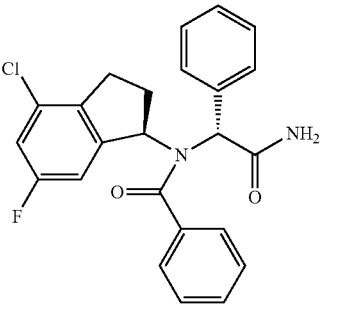 [SMILES: NC(=O)[C@@H](c1ccccc1)N(C(=O)c1ccccc1)[C@@H]1CCc2c(Cl)cc(F)cc21] |
| 2-8HP | 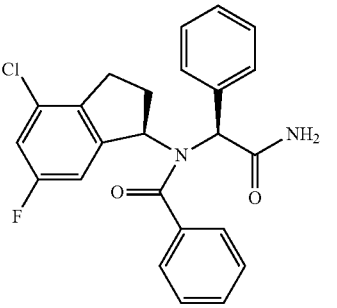 [SMILES: NC(=O)[C@H](c1ccccc1)N(C(=O)c1ccccc1)[C@@H]1CCc2c(Cl)cc(F)cc21] |
TABLE 5-continued
| Ex. No. | Strc. |
|---|---|
| 2-9LP | 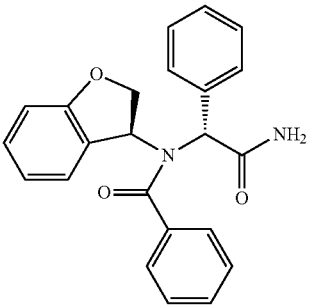 [SMILES: NC(=O)[C@@H](c1ccccc1)N(C(=O)c1ccccc1)[C@@H]1COc2ccccc21] |
| 2-9HP | 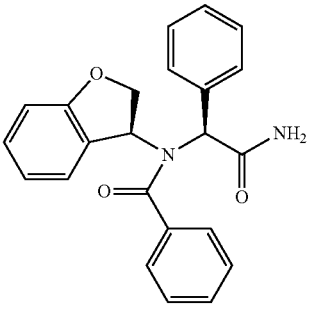 [SMILES: NC(=O)[C@H](c1ccccc1)N(C(=O)c1ccccc1)[C@@H]1COc2ccccc21] |
| 2-10LP | 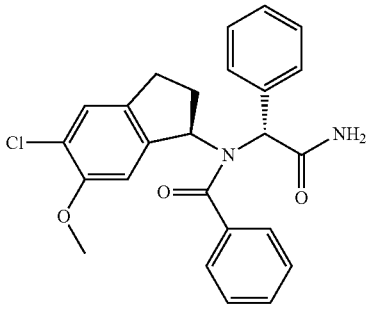 [SMILES: COc1cc2c(cc1Cl)CC[C@H]2N(C(=O)c1ccccc1)[C@@H](C(N)=O)c1ccccc1] |
| 2-11LP | 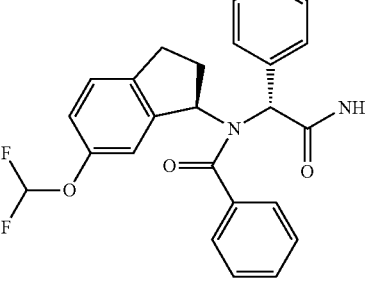 |
| 2-11HP | 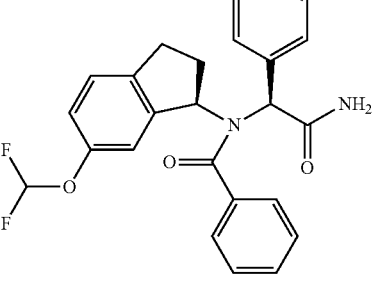 |

TABLE 5-continued

| Ex. No. | Strc. |
|---|---|
| 2-12LP | |
| 2-12HP | |
| 2-13LP | |
| 2-14LP | |

TABLE 6

| Ex. No. | Strc. |
|---|---|
| 2-14HP | |
| 2-15LP | |
| 2-15HP | |
| 2-16LP | |
| 2-17LP | |

TABLE 6-continued
| Ex. No. | Strc. |
|---|---|
| 2-18LP | 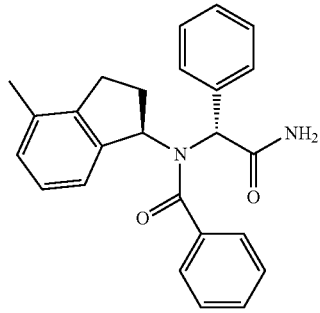 [SMILES: Cc1cccc2c1CC[C@H]2N(C(=O)c1ccccc1)[C@@H](C(N)=O)c1ccccc1] |
| 2-19LP | 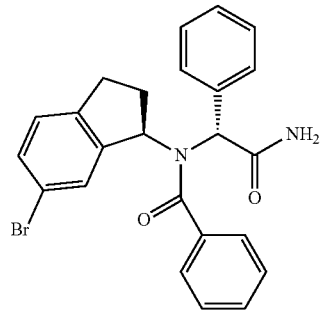 |
| 2-20LP | 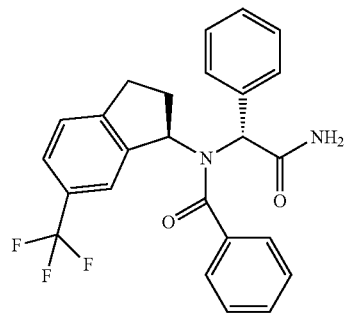 [SMILES: NC(=O)[C@@H](c1ccccc1)N(C(=O)c1ccccc1)[C@@H]1CCc2ccc(C(F)(F)F)cc21] |
| 2-21LP | 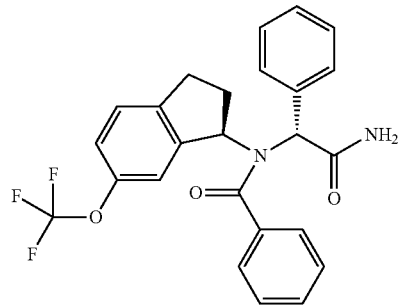 [SMILES: NC(=O)[C@@H](c1ccccc1)N(C(=O)c1ccccc1)[C@@H]1CCc2ccc(OC(F)(F)F)cc21] |
TABLE 6-continued
| Ex. No. | Strc. |
|---|---|
| 2-22LP | 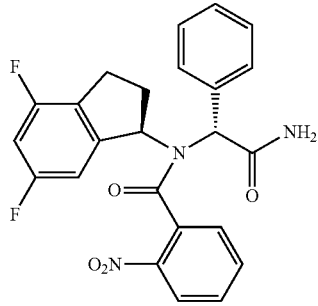 [SMILES: NC(=O)[C@@H](c1ccccc1)N(C(=O)c1ccccc1[N+](=O)[O-])[C@@H]1CCc2c(F)cc(F)cc21] |
| 2-23LP | 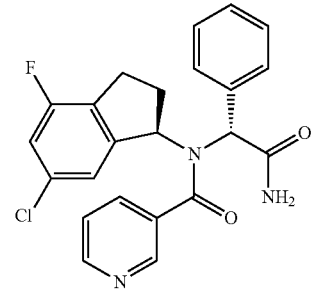 [SMILES: NC(=O)[C@@H](c1ccccc1)N(C(=O)c1cccnc1)[C@@H]1CCc2c(F)cc(Cl)cc21] |
| 2-23HP | 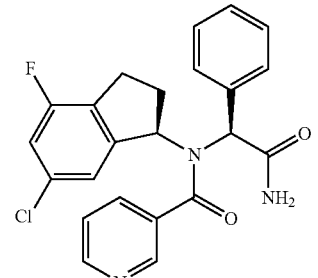 |
TABLE 7
| Ex. No. | Strc. |
|---|---|
| 2-24LP | 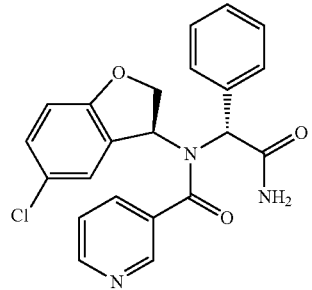 [SMILES: NC(=O)[C@@H](c1ccccc1)N(C(=O)c1cccnc1)[C@@H]1COc2ccc(Cl)cc21] |

TABLE 7-continued
| Ex. No. | Strc. |
|---|---|
| 2-24HP | 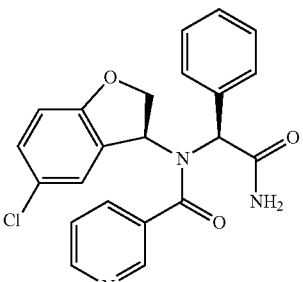 |
| 2-25LP | 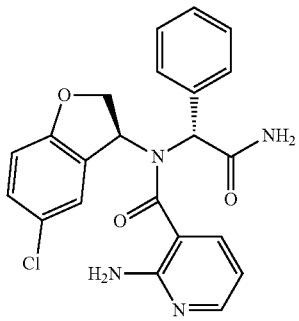 |
| 2-26LP | 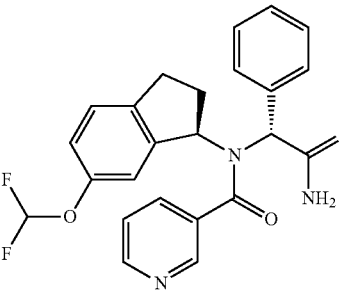 |
| 2-27LP | 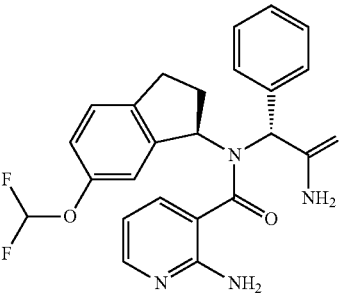 |
| 2-28LP | 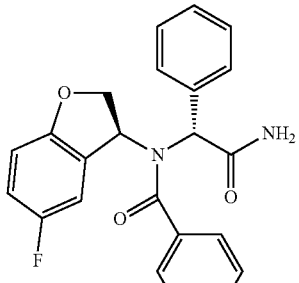 |
TABLE 7-continued
| Ex. No. | Strc. |
|---|---|
| 2-28HP | 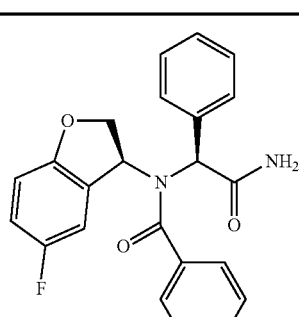 |
| 2-29LP | 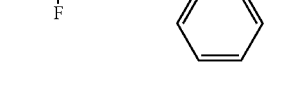 |
| 2-29HP | 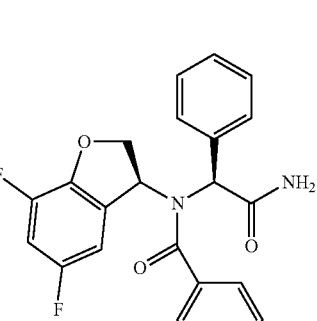 |
| 2-30LP | 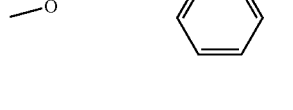 |

TABLE 7-continued
| Ex. No. | Strc. |
|---|---|
| 2-30HP | 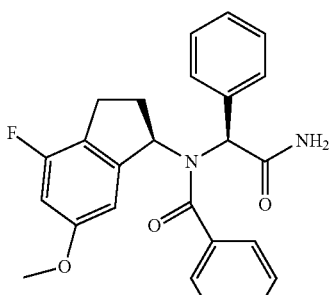 |
| 2-31LP | 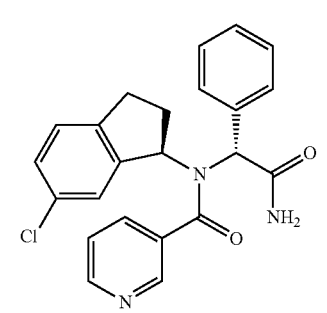 [SMILES: NC(=O)[C@@H](c1ccccc1)N(C(=O)c1cccnc1)[C@@H]1CCc2ccc(Cl)cc21] |
TABLE 8
| Ex. No. | Strc. |
|---|---|
| 2-31HP | 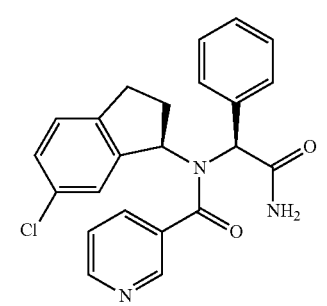 [SMILES: NC(=O)[C@H](c1ccccc1)N(C(=O)c1cccnc1)[C@@H]1CCc2ccc(Cl)cc21] |
| 2-32LP | 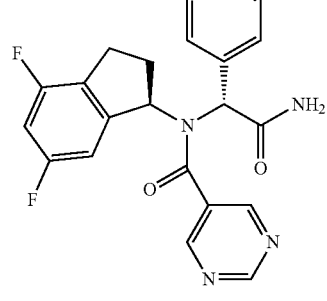 |
| 2-33LP | 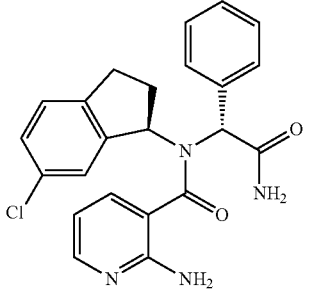 [SMILES: NC(=O)[C@@H](c1ccccc1)N(C(=O)c1cccnc1N)[C@@H]1CCc2ccc(Cl)cc21] |
| 2-34LP | 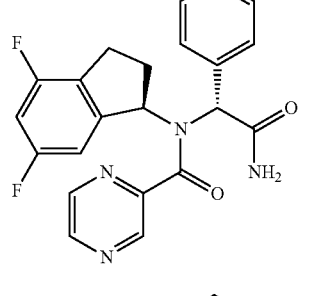 |
| 2-35LP | 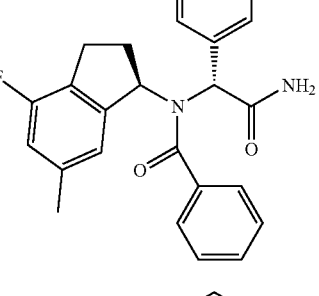 |
| 2-35HP | 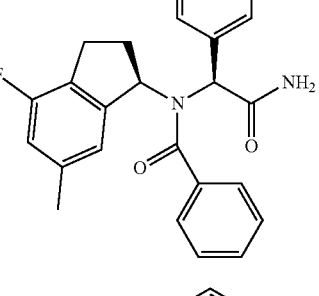 |
| 2-36LP | 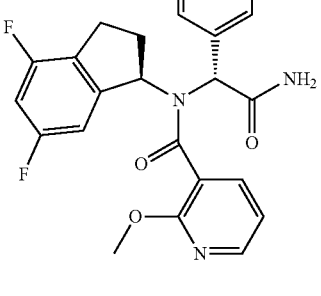 |

TABLE 8-continued
| Ex. No. | Strc. |
|---|---|
| 2-37LP | 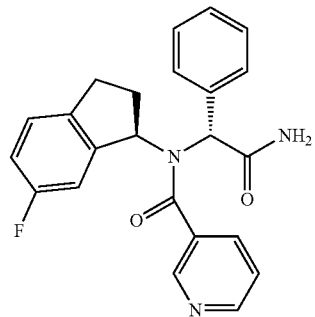 [SMILES: NC(=O)[C@@H](c1ccccc1)N(C(=O)c1cccnc1)[C@@H]1CCc2ccc(F)cc21] |
| 2-38LP | 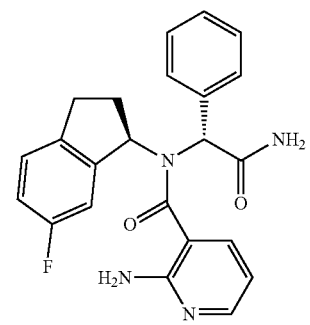 [SMILES: NC(=O)[C@@H](c1ccccc1)N(C(=O)c1cccnc1N)[C@@H]1CCc2ccc(F)cc21] |
| 2-39LP | 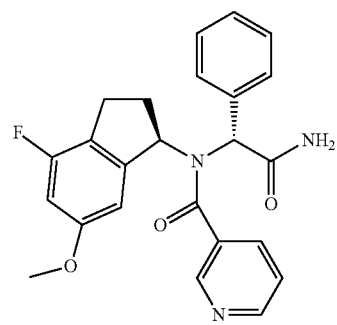 [SMILES: COc1cc(F)c2c(c1)[C@H](N(C(=O)c1cccnc1)[C@@H](C(N)=O)c1ccccc1)CC2] |
| 2-39HP | 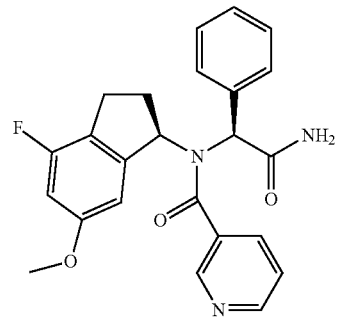 [SMILES: COc1cc(F)c2c(c1)[C@H](N(C(=O)c1cccnc1)[C@H](C(N)=O)c1ccccc1)CC2] |
TABLE 8-continued
| Ex. No. | Strc. |
|---|---|
| 2-40LP | 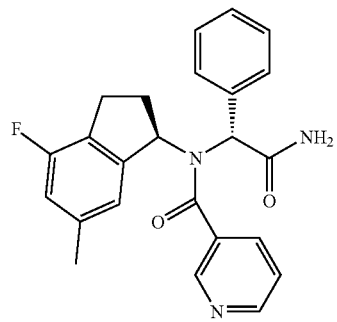 [SMILES: Cc1cc(F)c2c(c1)[C@H](N(C(=O)c1cccnc1)[C@@H](C(N)=O)c1ccccc1)CC2] |
TABLE 9
| Ex. No. | Strc. |
|---|---|
| 2-40HP | 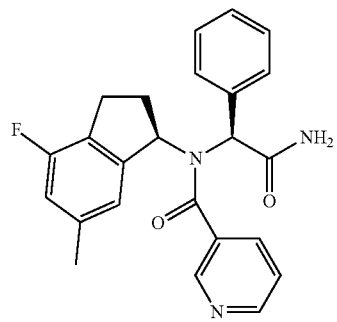 [SMILES: Cc1cc(F)c2c(c1)[C@H](N(C(=O)c1cccnc1)[C@H](C(N)=O)c1ccccc1)CC2] |
| 2-41LP | 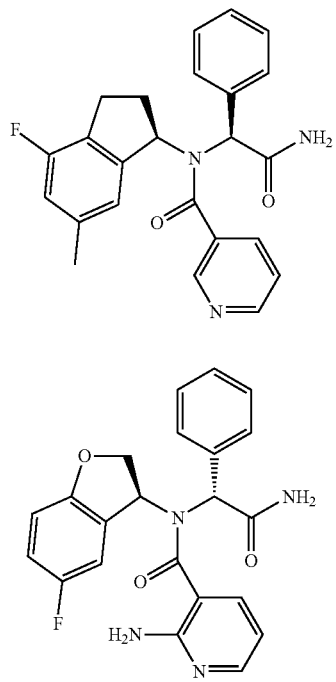 |
| 2-42LP | 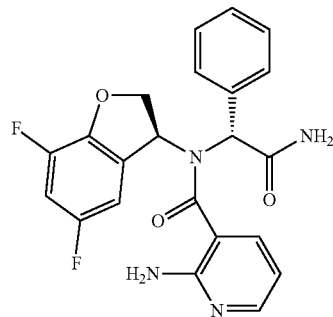 [SMILES: NC(=O)[C@@H](c1ccccc1)N(C(=O)c1cccnc1N)[C@@H]1COc2c(F)cc(F)cc21] |

TABLE 9-continued
| Ex. No. | Strc. |
|---|---|
| 2-43LP | 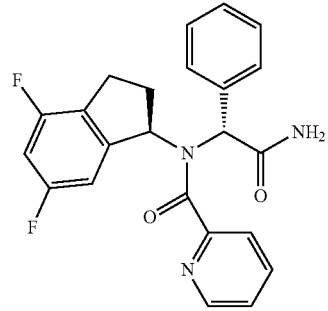 [SMILES: NC(=O)[C@@H](c1ccccc1)N(C(=O)c1ccccn1)[C@@H]1CCc2c(F)cc(F)cc21] |
| 2-44LP | 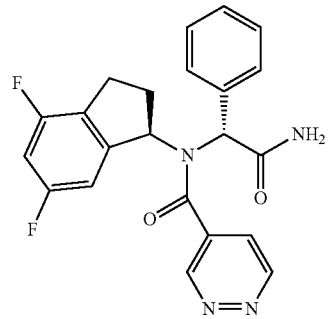 [SMILES: NC(=O)[C@@H](c1ccccc1)N(C(=O)c1ccnnc1)[C@@H]1CCc2c(F)cc(F)cc21] |
| 2-45LP | 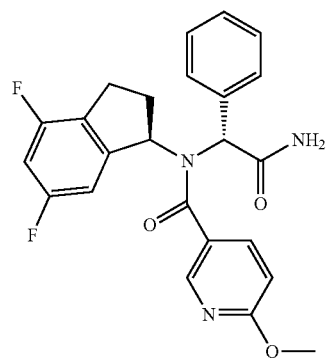 [SMILES: COc1ccc(C(=O)N([C@@H]2CCc3c(F)cc(F)cc32)[C@@H](C(N)=O)c2ccccc2)cn1] |
| 2-46LP | 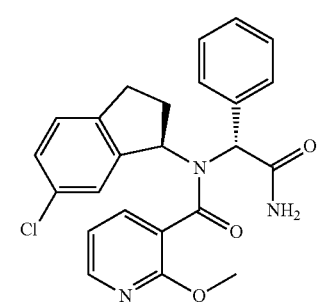 [SMILES: COc1ncccc1C(=O)N([C@@H]1CCc2ccc(Cl)cc21)[C@@H](C(N)=O)c1ccccc1] |
TABLE 9-continued
| Ex. No. | Strc. |
|---|---|
| 2-47LP | 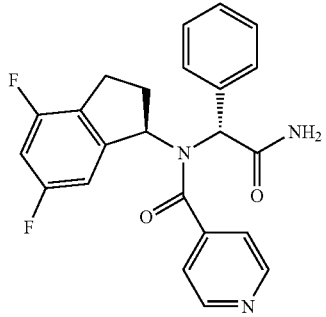 [SMILES: NC(=O)[C@@H](c1ccccc1)N(C(=O)c1ccncc1)[C@@H]1CCc2c(F)cc(F)cc21] |
| 2-48LP | 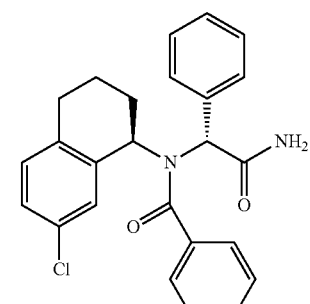 |
| 2-48HP | 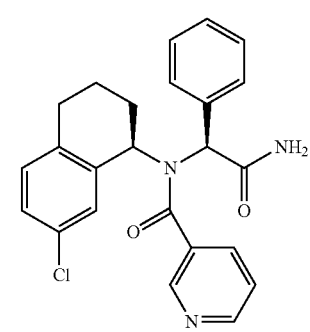 [SMILES: NC(=O)[C@H](c1ccccc1)N(C(=O)c1cccnc1)[C@@H]1CCCc2ccc(Cl)cc21] |
| 2-49LP | 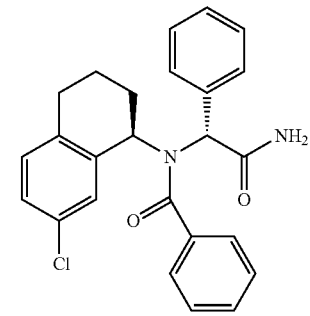 [SMILES: NC(=O)[C@@H](c1ccccc1)N(C(=O)c1ccccc1)[C@@H]1CCCc2ccc(Cl)cc21] |

TABLE 9-continued
| Ex. No. | Strc. |
|---|---|
| 2-49HP | 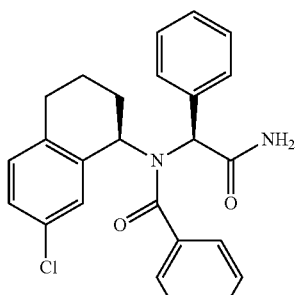 |
TABLE 10
| Ex. No. | Strc. |
|---|---|
| 2-50LP | |
| 2-51LP | |
| 2-52LP | 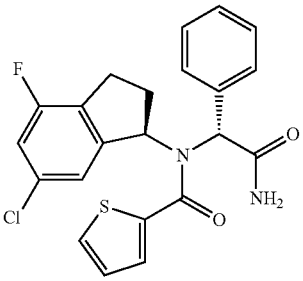 [SMILES: NC(=O)[C@@H](c1ccccc1)N(C(=O)c1cccs1)[C@@H]1CCc2c(F)cc(Cl)cc21] |
TABLE 10-continued
| Ex. No. | Strc. |
|---|---|
| 2-53LP | 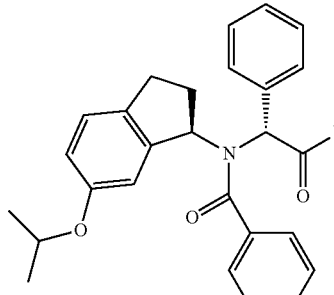 |
| 2-54LP | |
| 2-55LP | |
| 2-56LP | |

TABLE 10-continued

| Ex. No. | Strc. |
|---|---|
| 2-57LP | |
| 2-58LP | |
| 2-59LP | |
| 2-60LP | |
| 2-61LP | |

TABLE 11

| Ex. No. | Strc. |
|---|---|
| 2-62LP | |
| 2-63LP | |
| 2-64LP | |
| 2-64HP | |

TABLE 11-continued
| Ex. No. | Strc. |
|---|---|
| 2-65LP | 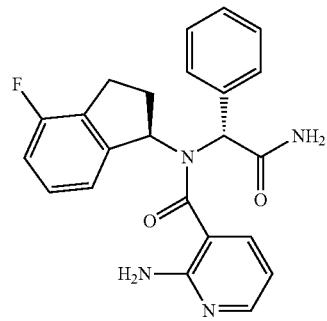 [SMILES: NC(=O)[C@@H](c1ccccc1)N(C(=O)c1cccnc1N)[C@@H]1CCc2c(F)cccc21] |
| 2-66LP | 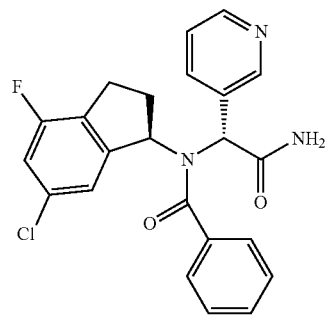 [SMILES: NC(=O)[C@@H](c1cccnc1)N(C(=O)c1ccccc1)[C@@H]1CCc2c(F)cc(Cl)cc21] |
| 2-66HP | 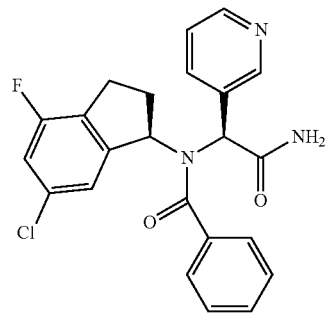 [SMILES: NC(=O)[C@H](c1cccnc1)N(C(=O)c1ccccc1)[C@@H]1CCc2c(F)cc(Cl)cc21] |
| 2-67LP | 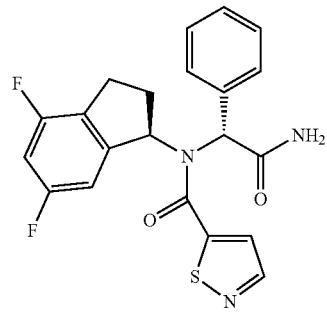 [SMILES: NC(=O)[C@@H](c1ccccc1)N(C(=O)c1ccns1)[C@@H]1CCc2c(F)cc(F)cc21] |
TABLE 11-continued
| Ex. No. | Strc. |
|---|---|
| 2-68LP | 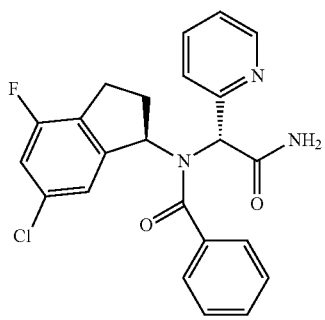 [SMILES: NC(=O)[C@@H](c1ccccn1)N(C(=O)c1ccccc1)[C@@H]1CCc2c(F)cc(Cl)cc21] |
| 2-69LP | 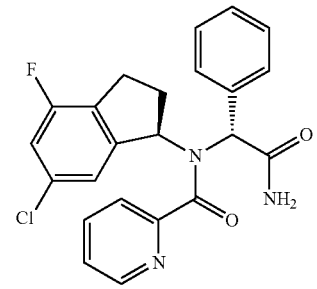 [SMILES: NC(=O)[C@@H](c1ccccc1)N(C(=O)c1ccccn1)[C@@H]1CCc2c(F)cc(Cl)cc21] |
| 2-70LP | 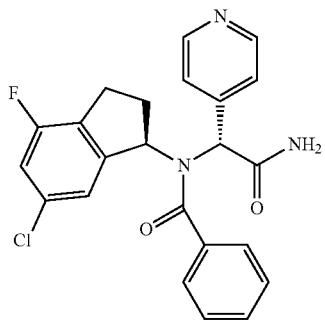 [SMILES: NC(=O)[C@@H](c1ccncc1)N(C(=O)c1ccccc1)[C@@H]1CCc2c(F)cc(Cl)cc21] |
| 2-71LP | 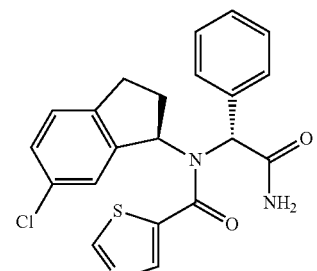 |

TABLE 12
| Ex. No. | Strc. |
|---|---|
| 2-72LP | 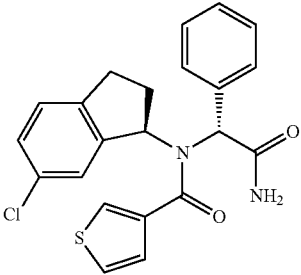 [SMILES: NC(=O)[C@@H](c1ccccc1)N(C(=O)c1ccsc1)[C@@H]1CCc2ccc(Cl)cc21] |
| 2-73LP | 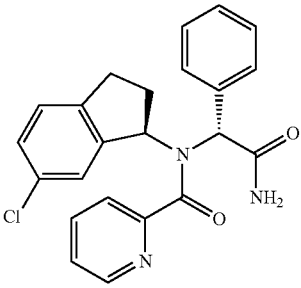 [SMILES: NC(=O)[C@@H](c1ccccc1)N(C(=O)c1ccccn1)[C@@H]1CCc2ccc(Cl)cc21] |
| 2-74LP | 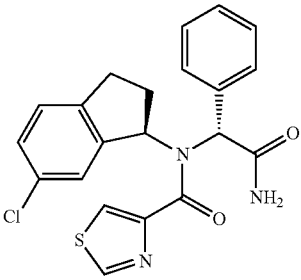 [SMILES: NC(=O)[C@@H](c1ccccc1)N(C(=O)c1cscn1)[C@@H]1CCc2ccc(Cl)cc21] |
| 2-75LP | 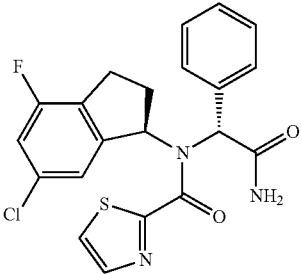 [SMILES: NC(=O)[C@@H](c1ccccc1)N(C(=O)c1nccs1)[C@@H]1CCc2c(F)cc(Cl)cc21] |
| 2-76LP | 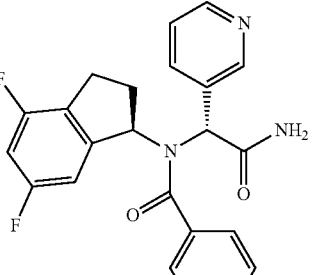 |
TABLE 12-continued
| Ex. No. | Strc. |
|---|---|
| 2-77LP | 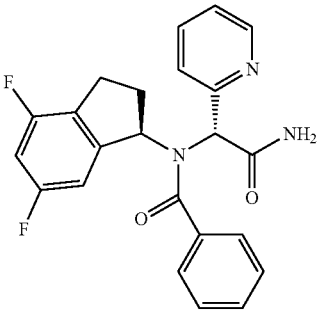 [SMILES: NC(=O)[C@@H](c1ccccn1)N(C(=O)c1ccccc1)[C@@H]1CCc2c(F)cc(F)cc21] |
| 2-77HP | 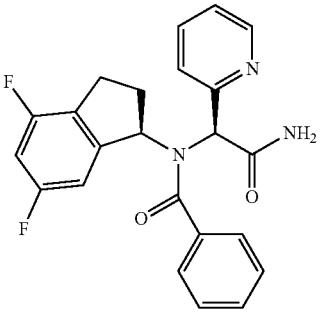 [SMILES: NC(=O)[C@H](c1ccccn1)N(C(=O)c1ccccc1)[C@@H]1CCc2c(F)cc(F)cc21] |
| 2-78LP | 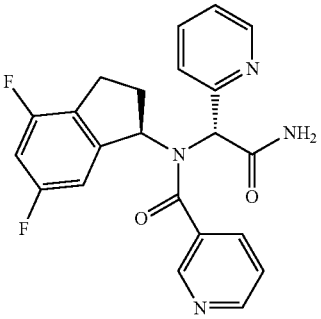 [SMILES: NC(=O)[C@@H](c1ccccn1)N(C(=O)c1cccnc1)[C@@H]1CCc2c(F)cc(F)cc21] |
| 2-79LP | 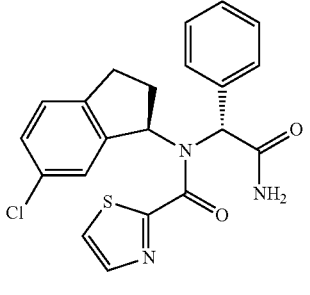 [SMILES: NC(=O)[C@@H](c1ccccc1)N(C(=O)c1nccs1)[C@@H]1CCc2ccc(Cl)cc21] |
| 2-80LP | 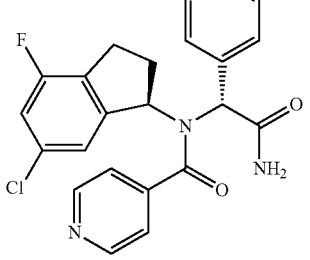 |

TABLE 12-continued

| Ex. No. | Strc. |
|---|---|
| 2-81LP | (structure) |
| 2-82LP | (structure) |

TABLE 13

| Ex. No. | Strc. |
|---|---|
| 2-83LP | (structure) |
| 2-84LP | (structure) |

TABLE 13-continued

| Ex. No. | Strc. |
|---|---|
| 2-85LP | (structure) |
| 2-86LP | (structure) |
| 2-87LP | (structure) |
| 2-88LP | (structure) |
| 2-89LP | (structure) |

TABLE 13-continued
| Ex. No. | Strc. |
|---|---|
| 2-90LP | 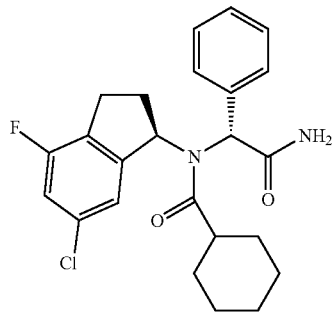 [SMILES: NC(=O)[C@@H](c1ccccc1)N(C(=O)C1CCCCC1)[C@@H]1CCc2c(F)cc(Cl)cc21] |
| 2-91LP | 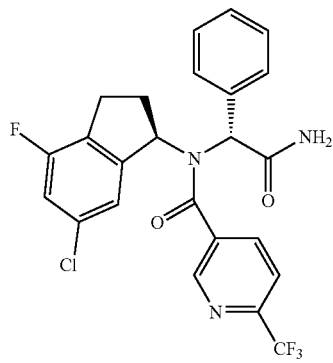 [SMILES: NC(=O)[C@@H](c1ccccc1)N(C(=O)c1ccc(C(F)(F)F)nc1)[C@@H]1CCc2c(F)cc(Cl)cc21] |
| 2-91HP | 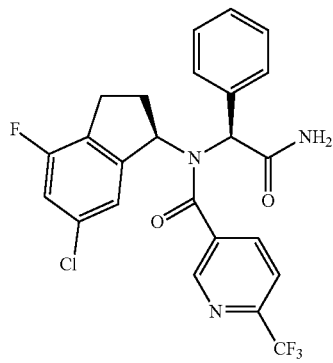 [SMILES: NC(=O)[C@H](c1ccccc1)N(C(=O)c1ccc(C(F)(F)F)nc1)[C@@H]1CCc2c(F)cc(Cl)cc21] |
| 2-92LP | 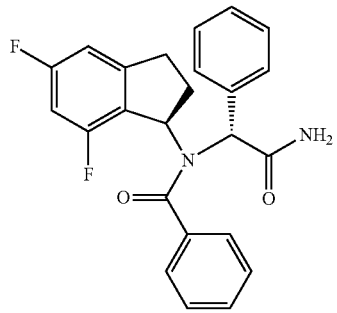 [SMILES: NC(=O)[C@@H](c1ccccc1)N(C(=O)c1ccccc1)[C@@H]1CCc2cc(F)cc(F)c21] |
TABLE 13-continued
| Ex. No. | Strc. |
|---|---|
| 2-92HP | 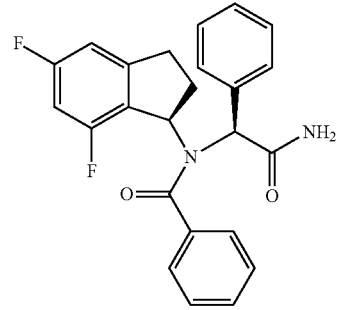 [SMILES: NC(=O)[C@H](c1ccccc1)N(C(=O)c1ccccc1)[C@@H]1CCc2cc(F)cc(F)c21] |
TABLE 14
| Ex. No. | Strc. |
|---|---|
| 2-93LP | 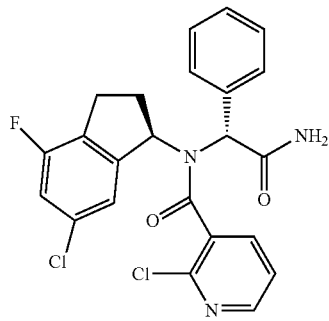 [SMILES: NC(=O)[C@@H](c1ccccc1)N(C(=O)c1cccnc1Cl)[C@@H]1CCc2c(F)cc(Cl)cc21] |
| 2-94LP | 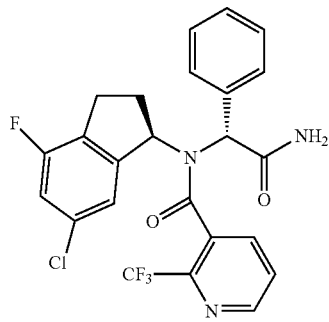 |
| 2-95LP | 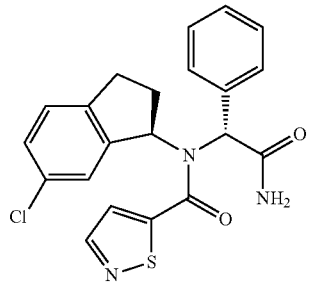 [SMILES: NC(=O)[C@@H](c1ccccc1)N(C(=O)c1ccns1)[C@@H]1CCc2ccc(Cl)cc21] |

TABLE 14-continued
| Ex. No. | Strc. |
|---|---|
| 2-96LP | 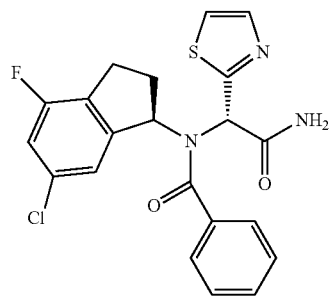 [SMILES: NC(=O)[C@@H](c1nccs1)N(C(=O)c1ccccc1)[C@@H]1CCc2c(F)cc(Cl)cc21] |
| 2-97LP | 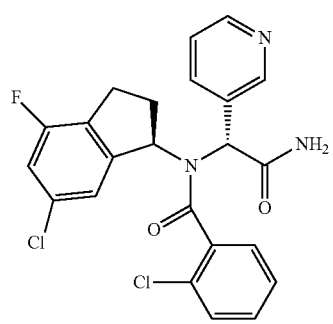 [SMILES: NC(=O)[C@@H](c1cccnc1)N(C(=O)c1ccccc1Cl)[C@@H]1CCc2c(F)cc(Cl)cc21] |
| 2-98LP | 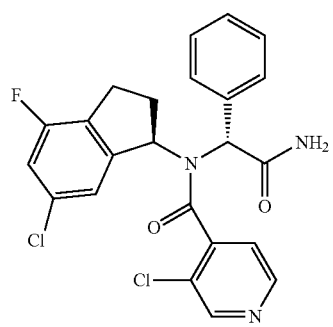 [SMILES: NC(=O)[C@@H](c1ccccc1)N(C(=O)c1ccncc1Cl)[C@@H]1CCc2c(F)cc(Cl)cc21] |
| 2-99LP | 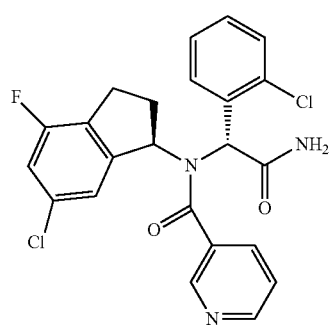 |
| 2-100LP | 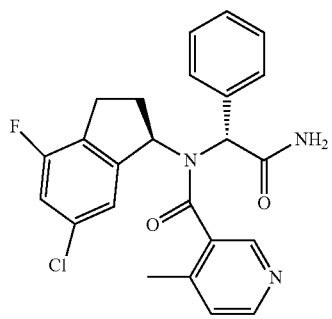 [SMILES: Cc1ccncc1C(=O)N([C@@H]1CCc2c(F)cc(Cl)cc21)[C@@H](C(N)=O)c1ccccc1] |
| 2-101LP | 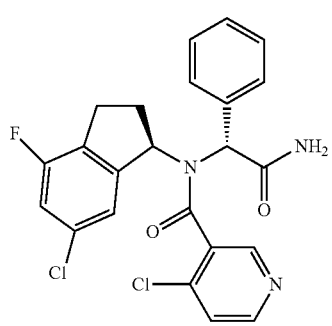 [SMILES: NC(=O)[C@@H](c1ccccc1)N(C(=O)c1cnccc1Cl)[C@@H]1CCc2c(F)cc(Cl)cc21] |
| 2-102LP | 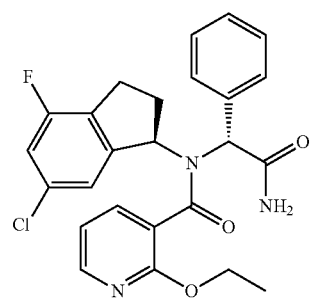 |
| 2-103LP | 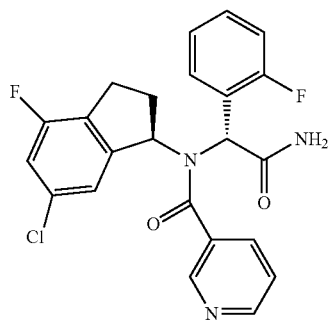 [SMILES: NC(=O)[C@@H](c1ccccc1F)N(C(=O)c1cccnc1)[C@@H]1CCc2c(F)cc(Cl)cc21] |

TABLE 14-continued
| Ex. No. | Strc. |
|---|---|
| 2-104LP | 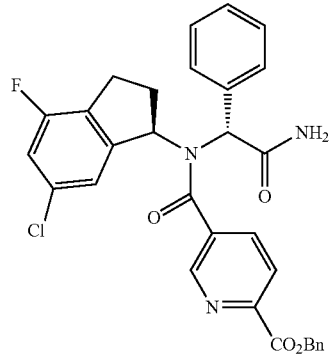 [SMILES: NC(=O)[C@@H](c1ccccc1)N(C(=O)c1ccc(C(=O)OCc2ccccc2)nc1)[C@@H]1CCc2c(F)cc(Cl)cc21] |
TABLE 15
| Ex. No. | Strc. |
|---|---|
| 2-105LP | 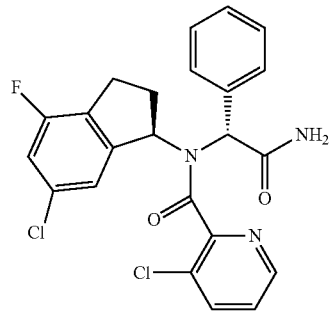 [SMILES: NC(=O)[C@@H](c1ccccc1)N(C(=O)c1ncccc1Cl)[C@@H]1CCc2c(F)cc(Cl)cc21] |
| 2-106LP | 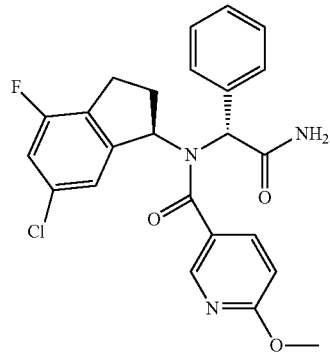 [SMILES: COc1ccc(C(=O)N([C@@H]2CCc3c(F)cc(Cl)cc32)[C@@H](C(N)=O)c2ccccc2)cn1] |
| 2-106HP | 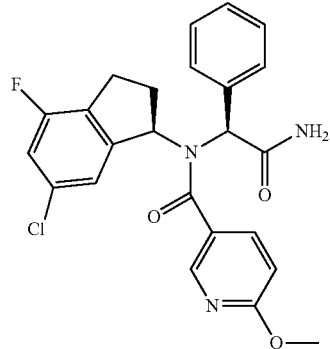 [SMILES: COc1ccc(C(=O)N([C@@H]2CCc3c(F)cc(Cl)cc32)[C@H](C(N)=O)c2ccccc2)cn1] |
TABLE 15-continued
| Ex. No. | Strc. |
|---|---|
| 2-107LP | 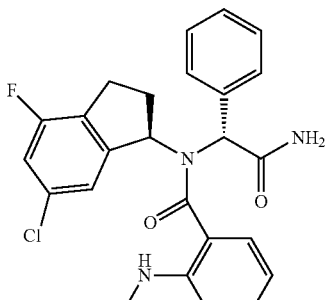 |
| 2-107HP | 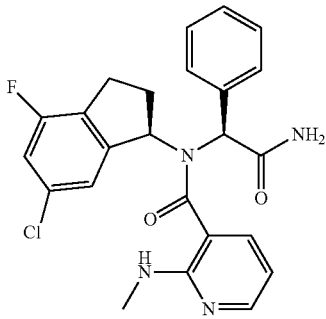 [SMILES: CNc1ncccc1C(=O)N([C@@H]1CCc2c(F)cc(Cl)cc21)[C@H](C(N)=O)c1ccccc1] |
| 2-108LP | 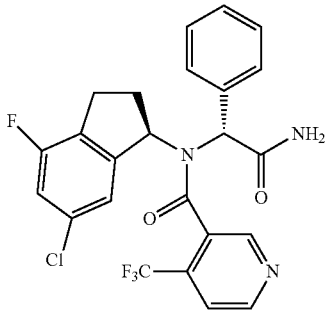 [SMILES: NC(=O)[C@@H](c1ccccc1)N(C(=O)c1cnccc1C(F)(F)F)[C@@H]1CCc2c(F)cc(Cl)cc21] |
| 2-109LP | 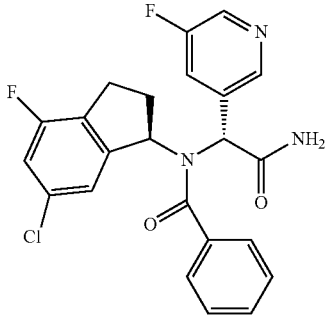 [SMILES: NC(=O)[C@@H](c1cncc(F)c1)N(C(=O)c1ccccc1)[C@@H]1CCc2c(F)cc(Cl)cc21] |

TABLE 15-continued
| Ex. No. | Strc. |
|---|---|
| 2-110LP | 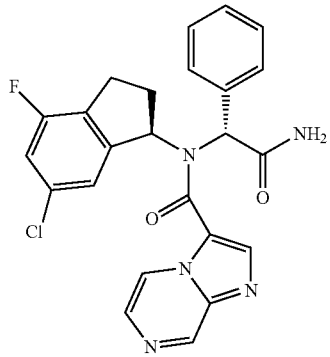 [SMILES: NC(=O)[C@@H](c1ccccc1)N(C(=O)c1cnc2cnccn12)[C@@H]1CCc2c(F)cc(Cl)cc21] |
| 2-111LP | 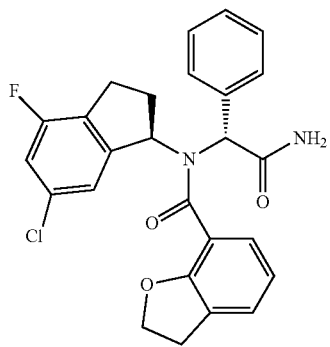 [SMILES: NC(=O)[C@@H](c1ccccc1)N(C(=O)c1cccc2c1OCC2)[C@@H]1CCc2c(F)cc(Cl)cc21] |
| 2-112LP | 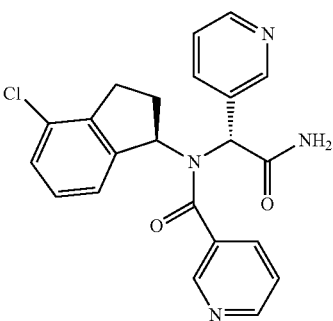 [SMILES: NC(=O)[C@@H](c1cccnc1)N(C(=O)c1cccnc1)[C@@H]1CCc2c(Cl)cccc21] |
| 2-113LP | 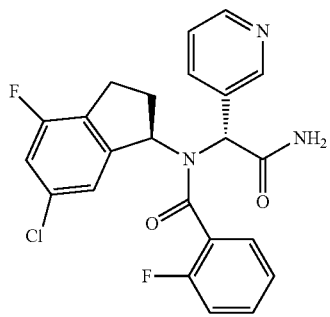 |
TABLE 15-continued
| Ex. No. | Strc. |
|---|---|
| 2-114LP | 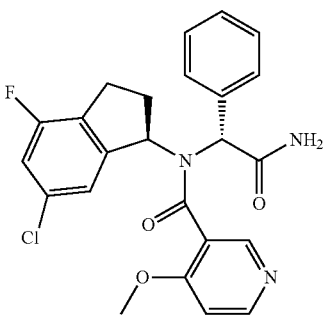 [SMILES: COc1ccncc1C(=O)N([C@@H]1CCc2c(F)cc(Cl)cc21)[C@@H](C(N)=O)c1ccccc1] |
TABLE 16
| Ex. No. | Strc. |
|---|---|
| 2-115LP | 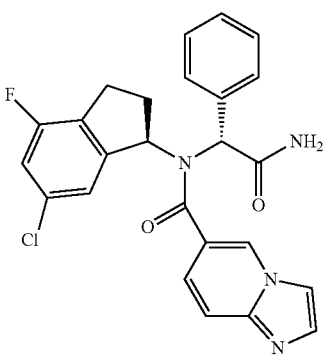 [SMILES: NC(=O)[C@@H](c1ccccc1)N(C(=O)c1ccc2nccn2c1)[C@@H]1CCc2c(F)cc(Cl)cc21] |
| 2-116LP | 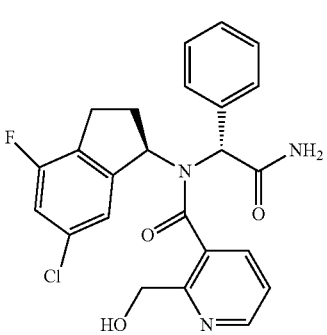 |
| 2-117LP | 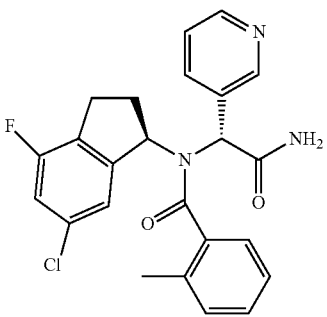 [SMILES: Cc1ccccc1C(=O)N([C@@H]1CCc2c(F)cc(Cl)cc21)[C@@H](C(N)=O)c1cccnc1] |

TABLE 16-continued
| Ex. No. | Strc. |
|---|---|
| 2-118LP | 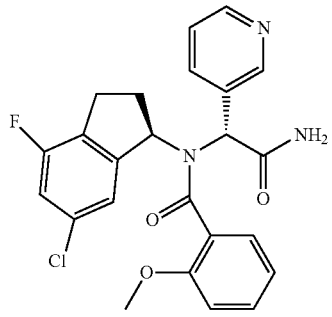 [SMILES: COc1ccccc1C(=O)N([C@@H]1CCc2c(F)cc(Cl)cc21)[C@@H](C(N)=O)c1cccnc1] |
| 2-119LP | 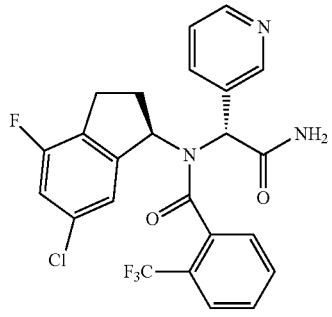 |
| 2-120LP | 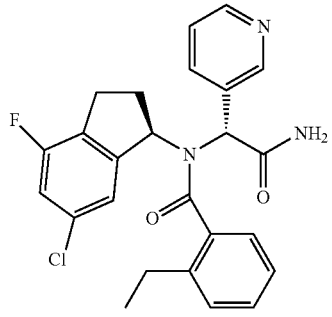 [SMILES: CCc1ccccc1C(=O)N([C@@H]1CCc2c(F)cc(Cl)cc21)[C@@H](C(N)=O)c1cccnc1] |
| 2-121LP | 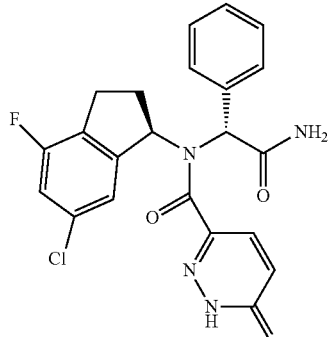 |
| 2-122LP | 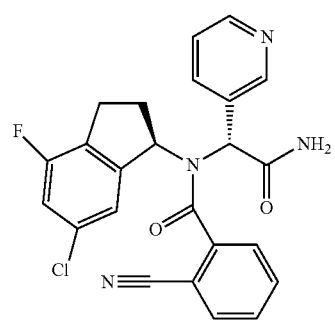 [SMILES: N#Cc1ccccc1C(=O)N([C@@H]1CCc2c(F)cc(Cl)cc21)[C@@H](C(N)=O)c1cccnc1] |
| 2-123LP | 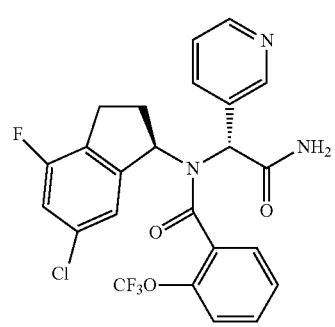 |
| 2-124LP | 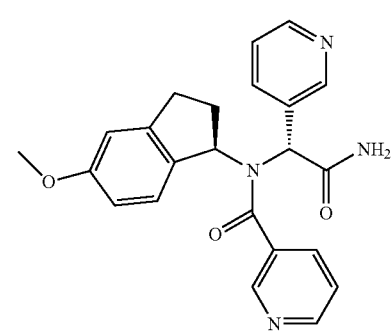 [SMILES: COc1ccc2c(c1)CC[C@H]2N(C(=O)c1cccnc1)[C@@H](C(N)=O)c1cccnc1] |
| 2-125LP | 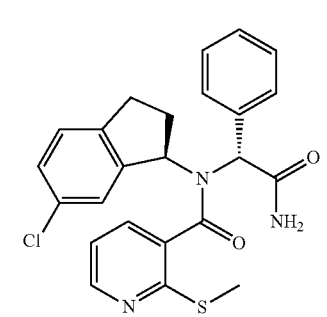 |

TABLE 16-continued
| Ex. No. | Strc. |
|---|---|
| 2-126LP | 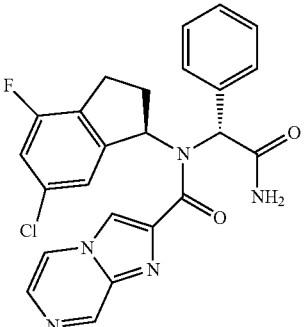 |
TABLE 17
| Ex. No. | Strc. |
|---|---|
| 2-127LP | 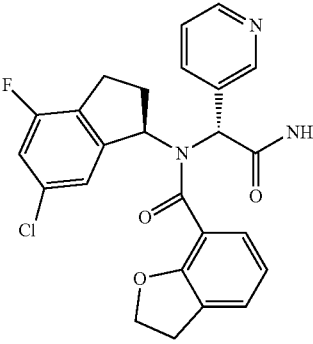 |
| 2-128LP | 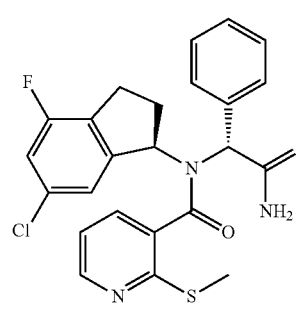 |
| 2-129LP | 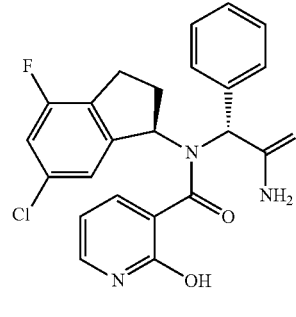 |
TABLE 17-continued
| Ex. No. | Strc. |
|---|---|
| 2-130LP | 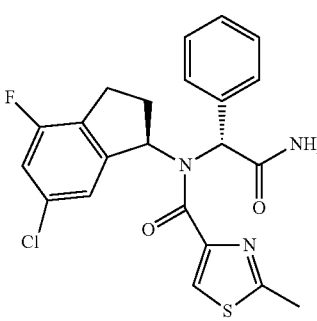 |
| 2-131LP | 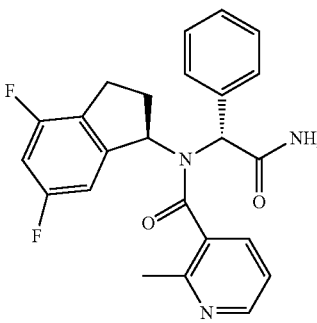 |
| 2-132LP | 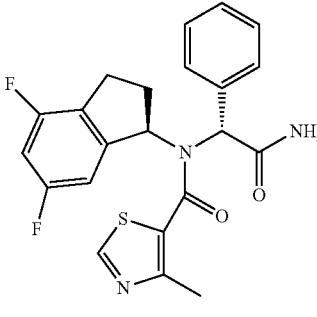 |
| 2-133LP | 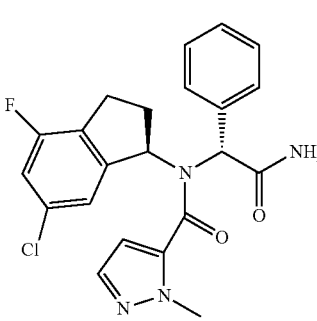 |

TABLE 17-continued
| Ex. No. | Strc. |
|---|---|
| 2-134LP | 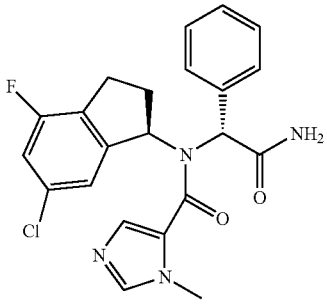 [SMILES: Cn1cncc1C(=O)N([C@@H]1CCc2c(F)cc(Cl)cc21)[C@@H](C(N)=O)c1ccccc1] |
| 2-135LP | 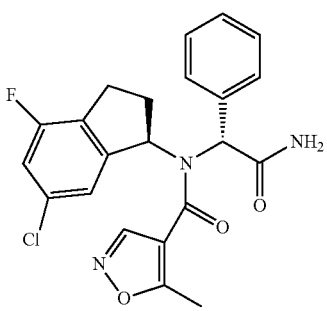 [SMILES: Cc1oncc1C(=O)N([C@@H]1CCc2c(F)cc(Cl)cc21)[C@@H](C(N)=O)c1ccccc1] |
| 2-136LP | 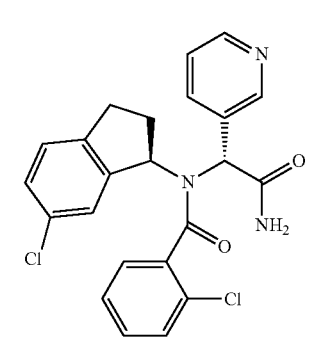 [SMILES: NC(=O)[C@@H](c1cccnc1)N(C(=O)c1ccccc1Cl)[C@@H]1CCc2ccc(Cl)cc21] |
| 2-137LP | 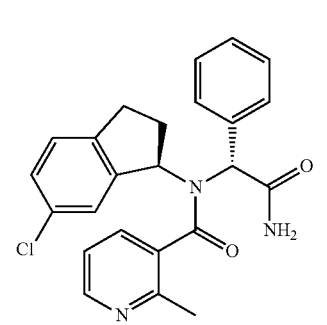 [SMILES: Cc1ncccc1C(=O)N([C@@H]1CCc2ccc(Cl)cc21)[C@@H](C(N)=O)c1ccccc1] |
| 2-138LP | 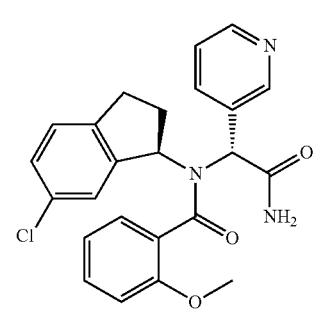 [SMILES: COc1ccccc1C(=O)N([C@@H]1CCc2ccc(Cl)cc21)[C@@H](C(N)=O)c1cccnc1] |
TABLE 18
| Ex. No. | Strc. |
|---|---|
| 2-139LP | 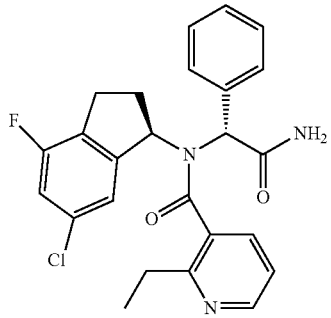 [SMILES: CCc1ncccc1C(=O)N([C@@H]1CCc2c(F)cc(Cl)cc21)[C@@H](C(N)=O)c1ccccc1] |
| 2-140LP | 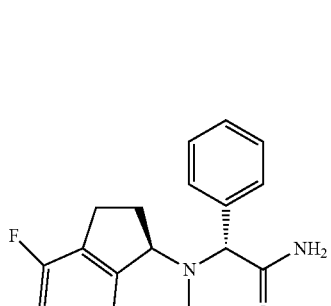 |
| 2-141LP | 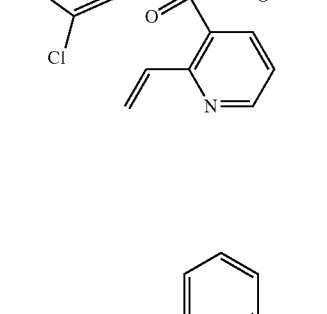 |
| 2-142LP | 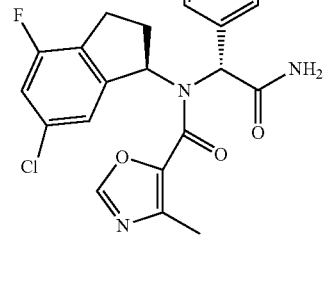 |

TABLE 18-continued

| Ex. No. | Strc. |
|---|---|
| 2-143LP | |
| 2-144LP | |
| 2-145LP | |
| 2-146LP | |
| 2-147LP | |
| 2-148LP | |
| 2-149LP | |
| 2-149HP | |

TABLE 19
| Ex. No. | Strc. |
|---|---|
| 2-150LP | 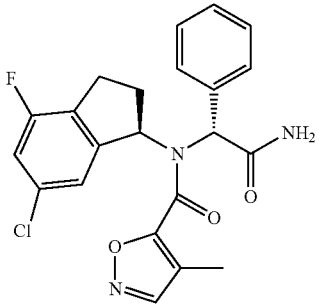 [SMILES: Cc1cnoc1C(=O)N([C@@H]1CCc2c(F)cc(Cl)cc21)[C@@H](C(N)=O)c1ccccc1] |
| 2-151LP | 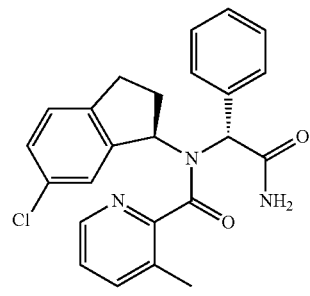 [SMILES: Cc1cccnc1C(=O)N([C@@H]1CCc2ccc(Cl)cc21)[C@@H](C(N)=O)c1ccccc1] |
| 2-152LP | 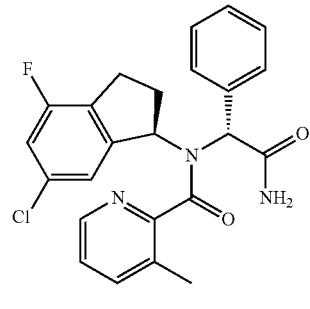 [SMILES: Cc1cccnc1C(=O)N([C@@H]1CCc2c(F)cc(Cl)cc21)[C@@H](C(N)=O)c1ccccc1] |
| 2-153LP | 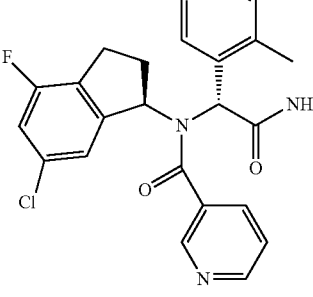 |
| 2-154LP | 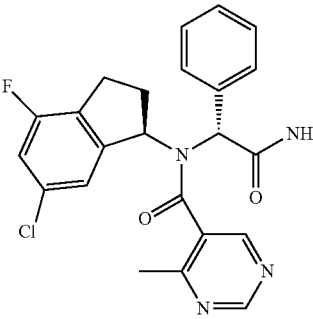 |
TABLE 19-continued
| Ex. No. | Strc. |
|---|---|
| 2-155LP | |
| 2-156LP | |
| 2-157LP | |
| 2-158LP | |
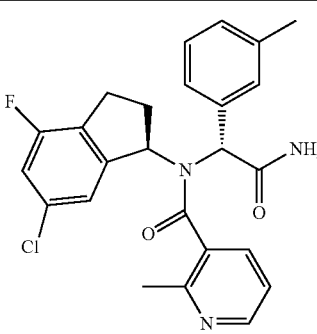

TABLE 19-continued
| Ex. No. | Strc. |
|---|---|
| 2-159LP | 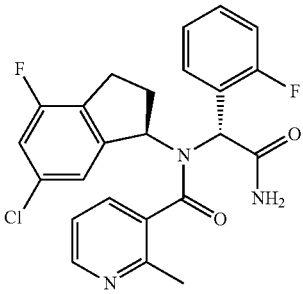 [SMILES: Cc1ncccc1C(=O)N([C@@H]1CCc2c(F)cc(Cl)cc21)[C@@H](C(N)=O)c1ccccc1F] |
| 2-160LP | 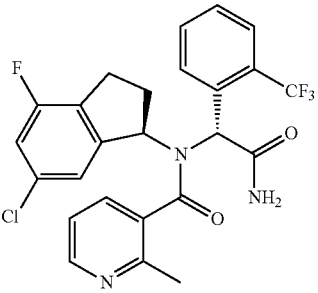 [SMILES: Cc1ncccc1C(=O)N([C@@H]1CCc2c(F)cc(Cl)cc21)[C@@H](C(N)=O)c1ccccc1C(F)(F)F] |
| 2-161LP | 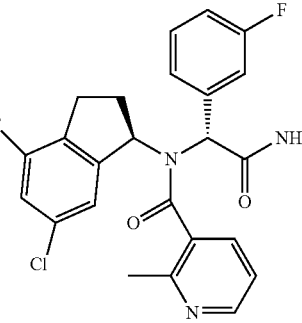 |
TABLE 20
| Ex. No. | Strc. |
|---|---|
| 2-162LP | 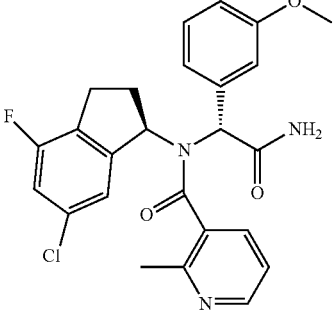 |
TABLE 20-continued
| Ex. No. | Strc. |
|---|---|
| 2-163LP | 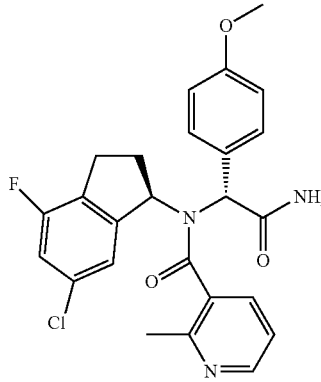 |
| 2-164LP | 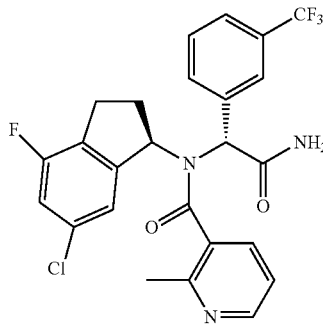 |
| 2-165LP | 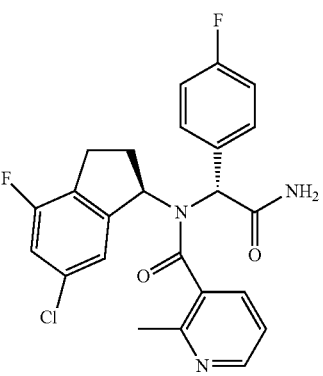 [SMILES: Cc1ncccc1C(=O)N([C@@H]1CCc2c(F)cc(Cl)cc21)[C@@H](C(N)=O)c1ccc(F)cc1] |
| 2-166LP | 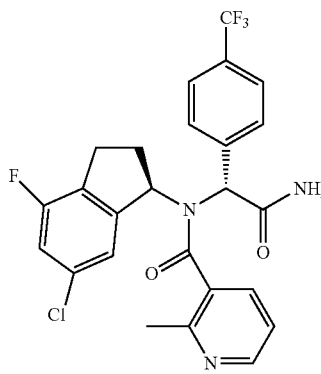 |

TABLE 20-continued
| Ex. No. | Strc. |
|---|---|
| 2-167LP | 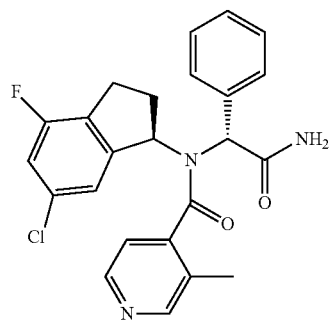 [SMILES: Cc1cnccc1C(=O)N([C@@H]1CCc2c(F)cc(Cl)cc21)[C@@H](C(N)=O)c1ccccc1] |
| 2-168LP | 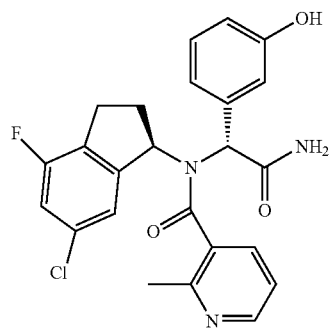 |
| 2-169LP | 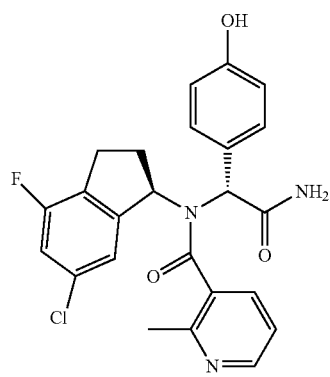 [SMILES: Cc1ncccc1C(=O)N([C@@H]1CCc2c(F)cc(Cl)cc21)[C@@H](C(N)=O)c1ccc(O)cc1] |
| 2-170LP | 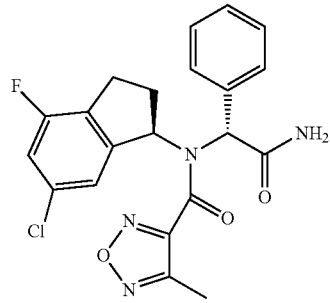 [SMILES: Cc1nonc1C(=O)N([C@@H]1CCc2c(F)cc(Cl)cc21)[C@@H](C(N)=O)c1ccccc1] |
TABLE 20-continued
| Ex. No. | Strc. |
|---|---|
| 2-171LP | 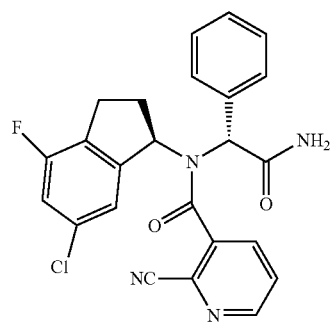 [SMILES: N#Cc1ncccc1C(=O)N([C@@H]1CCc2c(F)cc(Cl)cc21)[C@@H](C(N)=O)c1ccccc1] |
| 2-172LP | 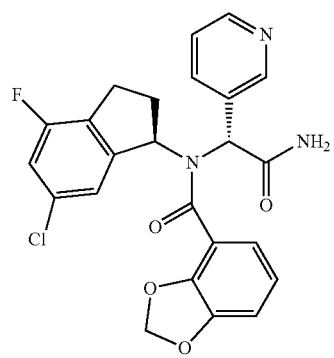 [SMILES: NC(=O)[C@@H](c1cccnc1)N(C(=O)c1cccc2c1OCO2)[C@@H]1CCc2c(F)cc(Cl)cc21] |
| 2-173LP | 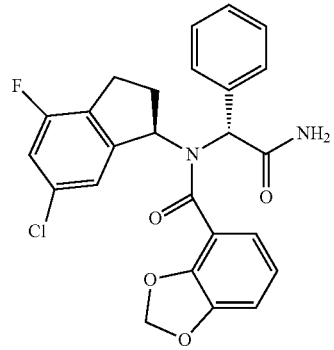 [SMILES: NC(=O)[C@@H](c1ccccc1)N(C(=O)c1cccc2c1OCO2)[C@@H]1CCc2c(F)cc(Cl)cc21] |
TABLE 21
| Ex. No. | Strc. |
|---|---|
| 2-174LP | 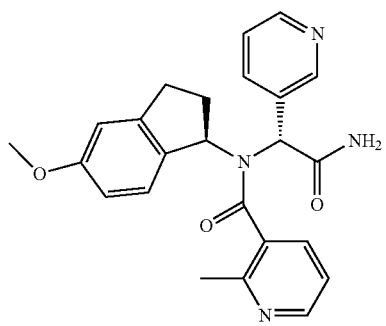 [SMILES: COc1ccc2c(c1)CC[C@H]2N(C(=O)c1cccnc1C)[C@@H](C(N)=O)c1cccnc1] |

TABLE 21-continued
| Ex. No. | Strc. |
|---|---|
| 2-175LP | 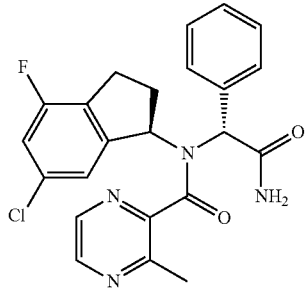 [SMILES: Cc1nccnc1C(=O)N([C@@H]1CCc2c(F)cc(Cl)cc21)[C@@H](C(N)=O)c1ccccc1] |
| 2-176LP | 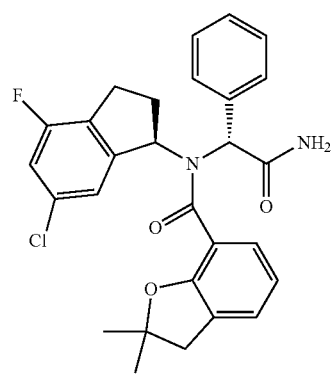 [SMILES: CC1(C)Cc2cccc(C(=O)N([C@@H]3CCc4c(F)cc(Cl)cc43)[C@@H](C(N)=O)c3ccccc3)c2O1] |
| 2-177LP | 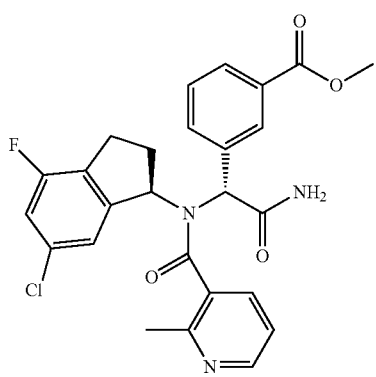 [SMILES: COC(=O)c1cccc([C@H](C(N)=O)N(C(=O)c2cccnc2C)[C@@H]2CCc3c(F)cc(Cl)cc32)c1] |
| 2-177HP | 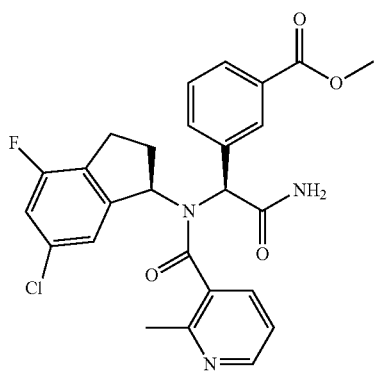 [SMILES: COC(=O)c1cccc([C@@H](C(N)=O)N(C(=O)c2cccnc2C)[C@@H]2CCc3c(F)cc(Cl)cc32)c1] |
TABLE 21-continued
| Ex. No. | Strc. |
|---|---|
| 2-178LP | 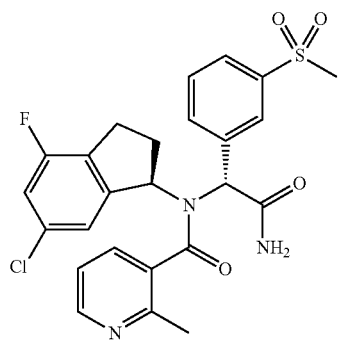 [SMILES: Cc1ncccc1C(=O)N([C@@H]1CCc2c(F)cc(Cl)cc21)[C@@H](C(N)=O)c1cccc(S(C)(=O)=O)c1] |
| 2-179LP | 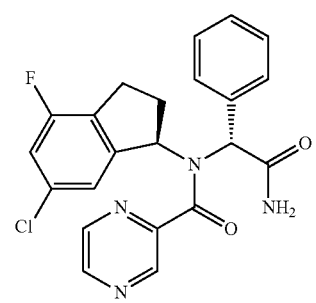 [SMILES: NC(=O)[C@@H](c1ccccc1)N(C(=O)c1cnccn1)[C@@H]1CCc2c(F)cc(Cl)cc21] |
| 2-180LP | 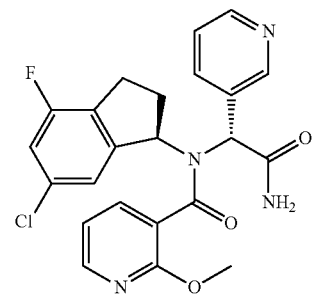 [SMILES: COc1ncccc1C(=O)N([C@@H]1CCc2c(F)cc(Cl)cc21)[C@@H](C(N)=O)c1cccnc1] |
| 2-181LP | 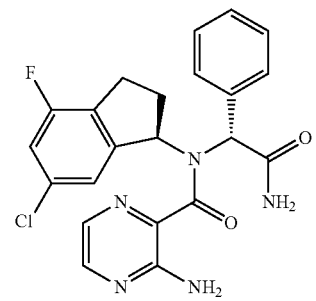 [SMILES: NC(=O)[C@@H](c1ccccc1)N(C(=O)c1nccnc1N)[C@@H]1CCc2c(F)cc(Cl)cc21] |

TABLE 21-continued

| Ex. No. | Strc. |
| --- | --- |
| 2-182LP | |
| 2-183LP | |
| 2-184LP | |

TABLE 22

| Ex. No. | Strc. |
| --- | --- |
| 2-185LP | |

TABLE 22-continued

| Ex. No. | Strc. |
| --- | --- |
| 2-186LP | |
| 2-187LP | |
| 2-187HP | |
| 2-188LP | |

TABLE 22-continued

| Ex. No. | Strc. |
|---|---|
| 2-189LP | |
| 2-190LP | |
| 2-191LP | |
| 2-192LP | |

TABLE 22-continued

| Ex. No. | Strc. |
|---|---|
| 2-192HP | |
| 2-193LP | |
| 2-193HP | |

TABLE 23

| Ex. No. | Strc. |
|---|---|
| 2-194LP | |

TABLE 23-continued
| Ex. No. | Strc. |
|---|---|
| 2-195LP | 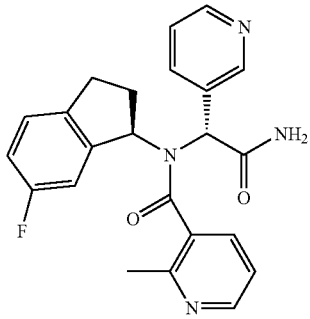 [SMILES: Cc1ncccc1C(=O)N([C@@H]1CCc2ccc(F)cc21)[C@@H](C(N)=O)c1cccnc1] |
| 2-196LP | 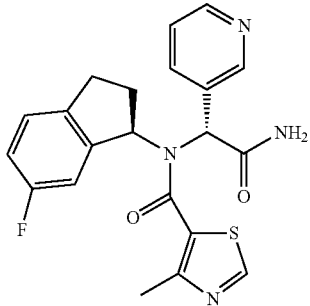 |
| 2-197LP | 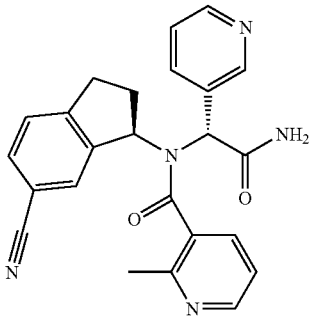 [SMILES: Cc1ncccc1C(=O)N([C@@H]1CCc2ccc(C#N)cc21)[C@@H](C(N)=O)c1cccnc1] |
| 2-198LP | 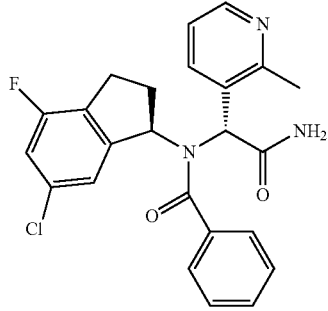 [SMILES: Cc1ncccc1[C@H](C(N)=O)N(C(=O)c1ccccc1)[C@@H]1CCc2c(F)cc(Cl)cc21] |
| 2-199LP | 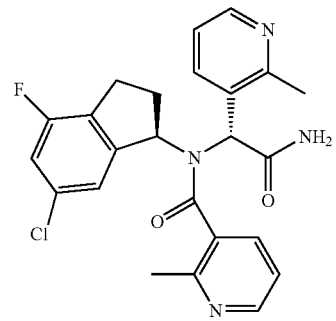 [SMILES: Cc1ncccc1C(=O)N([C@@H]1CCc2c(F)cc(Cl)cc21)[C@@H](C(N)=O)c1cccnc1C] |
| 2-200LP | 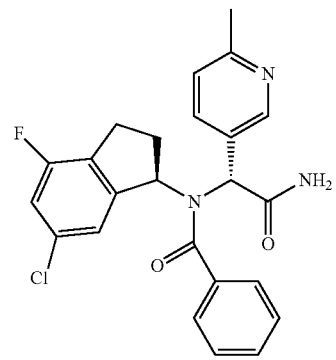 [SMILES: Cc1ccc([C@H](C(N)=O)N(C(=O)c2ccccc2)[C@@H]2CCc3c(F)cc(Cl)cc32)cn1] |
| 2-201LP | 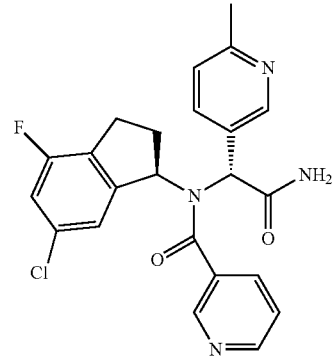 [SMILES: Cc1ccc([C@H](C(N)=O)N(C(=O)c2cccnc2)[C@@H]2CCc3c(F)cc(Cl)cc32)cn1] |
| 2-202LP | 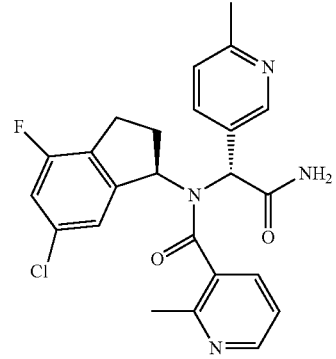 [SMILES: Cc1ccc([C@H](C(N)=O)N(C(=O)c2cccnc2C)[C@@H]2CCc3c(F)cc(Cl)cc32)cn1] |

TABLE 23-continued

| Ex. No. | Strc. |
| --- | --- |
| 2-203LP | |
| 2-204LP | |
| 2-205LP | |

TABLE 24

| Ex. No. | Strc. |
| --- | --- |
| 2-206LP | |

TABLE 24-continued

| Ex. No. | Strc. |
| --- | --- |
| 2-207LP | |
| 2-208LP | |
| 2-209LP | |
| 2-210LP | |

TABLE 24-continued
| Ex. No. | Strc. |
|---|---|
| 2-211LP | 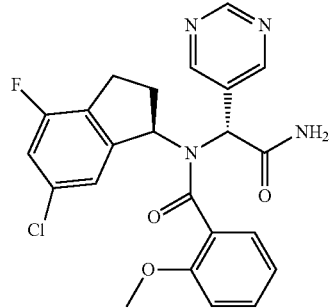 [SMILES: COc1ccccc1C(=O)N([C@@H]1CCc2c(F)cc(Cl)cc21)[C@@H](C(N)=O)c1cncnc1] |
| 2-212LP | 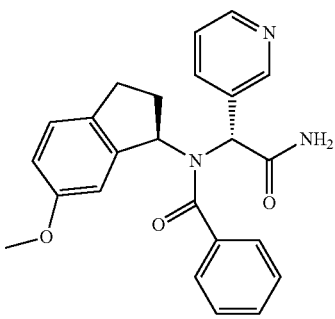 [SMILES: COc1ccc2c(c1)[C@H](N(C(=O)c1ccccc1)[C@@H](C(N)=O)c1cccnc1)CC2] |
| 2-213LP | 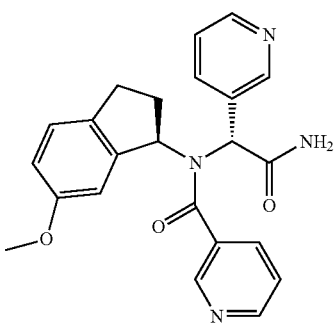 [SMILES: COc1ccc2c(c1)[C@H](N(C(=O)c1cccnc1)[C@@H](C(N)=O)c1cccnc1)CC2] |
| 2-214LP | 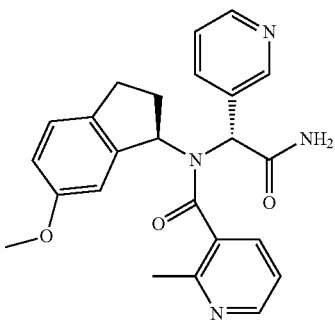 [SMILES: COc1ccc2c(c1)[C@H](N(C(=O)c1cccnc1C)[C@@H](C(N)=O)c1cccnc1)CC2] |
TABLE 24-continued
| Ex. No. | Strc. |
|---|---|
| 2-215LP | 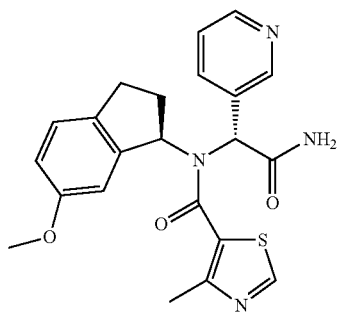 [SMILES: COc1ccc2c(c1)[C@H](N(C(=O)c1scnc1C)[C@@H](C(N)=O)c1cccnc1)CC2] |
| 2-216LP | 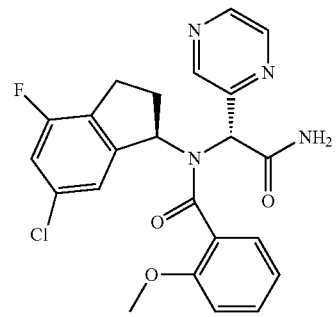 [SMILES: COc1ccccc1C(=O)N([C@@H]1CCc2c(F)cc(Cl)cc21)[C@@H](C(N)=O)c1cnccn1] |
| 2-217LP | 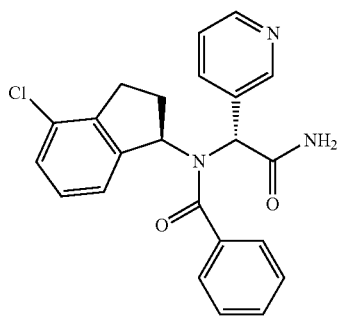 [SMILES: NC(=O)[C@@H](c1cccnc1)N(C(=O)c1ccccc1)[C@@H]1CCc2c(Cl)cccc21] |
TABLE 25
| Ex. No. | Strc. |
|---|---|
| 2-218LP | 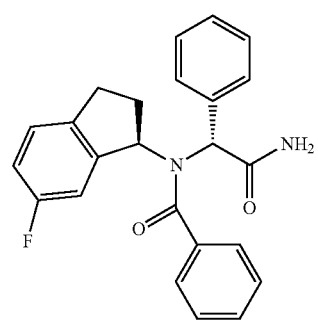 [SMILES: NC(=O)[C@@H](c1ccccc1)N(C(=O)c1ccccc1)[C@@H]1CCc2ccc(F)cc21] |

TABLE 25-continued
| Ex. No. | Strc. |
|---|---|
| 2-218HP | 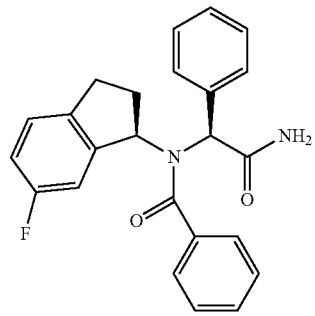 [SMILES: NC(=O)[C@H](c1ccccc1)N(C(=O)c1ccccc1)[C@@H]1CCc2ccc(F)cc21] |
| 2-219LP | 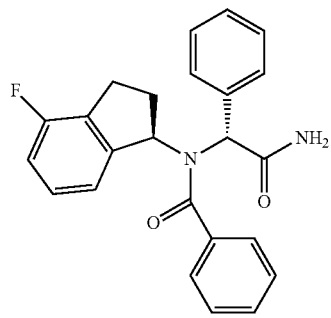 [SMILES: NC(=O)[C@@H](c1ccccc1)N(C(=O)c1ccccc1)[C@@H]1CCc2c(F)cccc21] |
| 2-219HP | 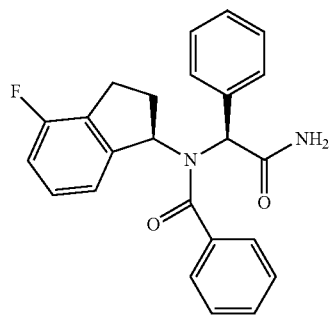 [SMILES: NC(=O)[C@H](c1ccccc1)N(C(=O)c1ccccc1)[C@@H]1CCc2c(F)cccc21] |
| 2-220LP | 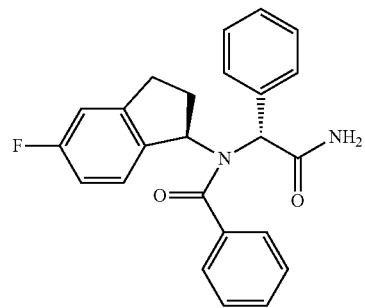 [SMILES: NC(=O)[C@@H](c1ccccc1)N(C(=O)c1ccccc1)[C@@H]1CCc2cc(F)ccc21] |
TABLE 25-continued
| Ex. No. | Strc. |
|---|---|
| 2-220HP | 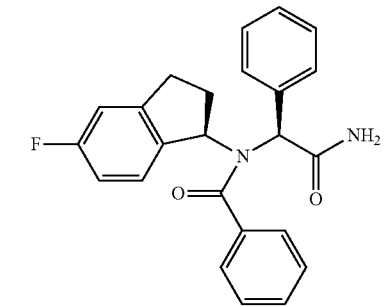 [SMILES: NC(=O)[C@H](c1ccccc1)N(C(=O)c1ccccc1)[C@@H]1CCc2cc(F)ccc21] |
| 2-221LP | 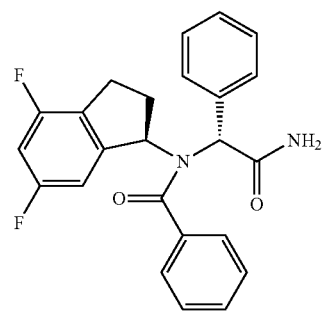 [SMILES: NC(=O)[C@@H](c1ccccc1)N(C(=O)c1ccccc1)[C@@H]1CCc2c(F)cc(F)cc21] |
| 2-221HP | 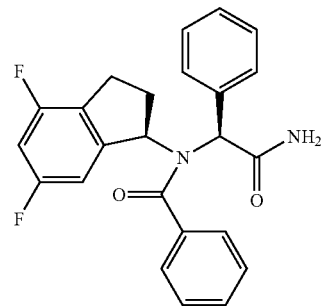 [SMILES: NC(=O)[C@H](c1ccccc1)N(C(=O)c1ccccc1)[C@@H]1CCc2c(F)cc(F)cc21] |
| 2-222LP | 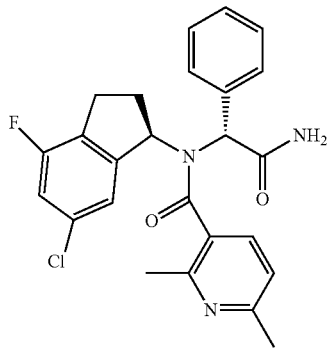 |

TABLE 25-continued
| Ex. No. | Strc. |
|---|---|
| 2-223LP | 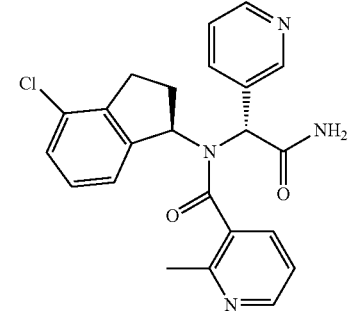 [SMILES: Cc1ncccc1C(=O)N([C@@H]1CCc2c(Cl)cccc21)[C@@H](C(N)=O)c1cccnc1] |
| 2-224LP | 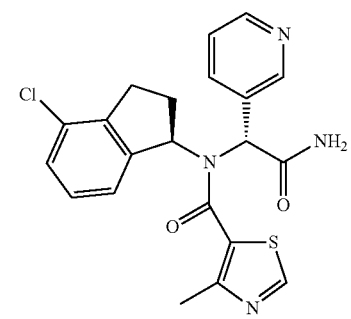 [SMILES: Cc1ncsc1C(=O)N([C@@H]1CCc2c(Cl)cccc21)[C@@H](C(N)=O)c1cccnc1] |
| 2-225LP | 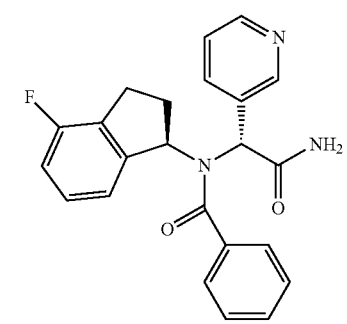 [SMILES: NC(=O)[C@@H](c1cccnc1)N(C(=O)c1ccccc1)[C@@H]1CCc2c(F)cccc21] |
TABLE 26
| Ex. No. | Strc. |
|---|---|
| 2-226LP | 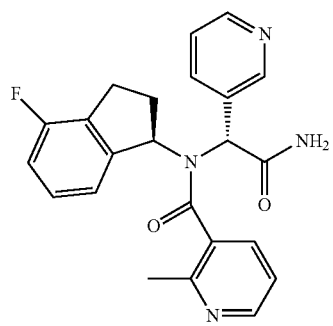 [SMILES: Cc1ncccc1C(=O)N([C@@H]1CCc2c(F)cccc21)[C@@H](C(N)=O)c1cccnc1] |
TABLE 26-continued
| Ex. No. | Strc. |
|---|---|
| 2-227LP | 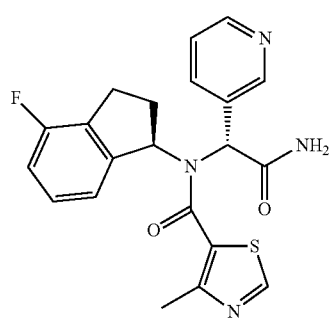 [SMILES: Cc1ncsc1C(=O)N([C@@H]1CCc2c(F)cccc21)[C@@H](C(N)=O)c1cccnc1] |
| 2-228LP | 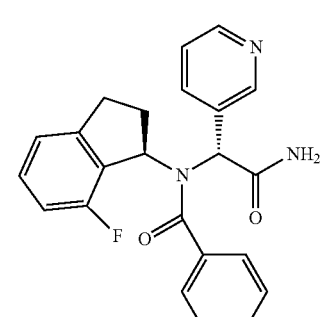 |
| 2-229LP | 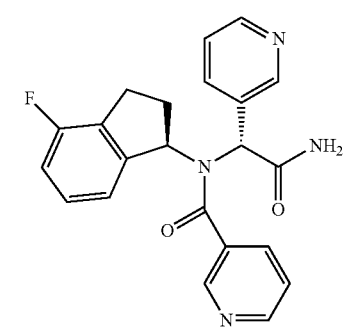 |
| 2-230LP | 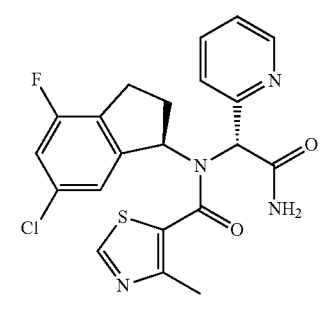 [SMILES: Cc1ncsc1C(=O)N([C@@H]1CCc2c(F)cc(Cl)cc21)[C@@H](C(N)=O)c1ccccn1] |

TABLE 26-continued
| Ex. No. | Strc. |
|---|---|
| 2-231LP | 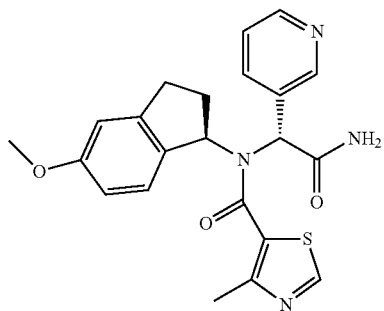 [SMILES: COc1ccc2c(c1)CC[C@H]2N(C(=O)c1scnc1C)[C@@H](C(N)=O)c1cccnc1] |
| 2-232LP | 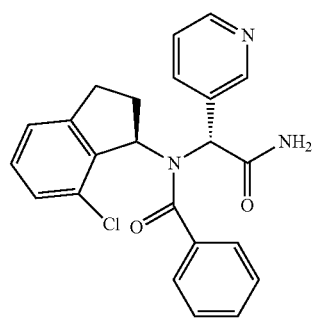 [SMILES: NC(=O)[C@@H](c1cccnc1)N(C(=O)c1ccccc1)[C@@H]1CCc2cccc(Cl)c21] |
| 2-233LP | 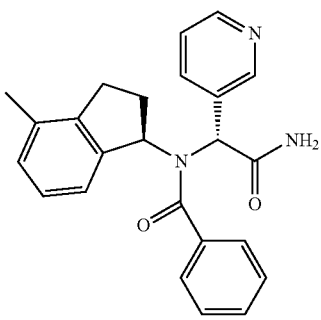 [SMILES: Cc1cccc2c1CC[C@H]2N(C(=O)c1ccccc1)[C@@H](C(N)=O)c1cccnc1] |
| 2-234LP | 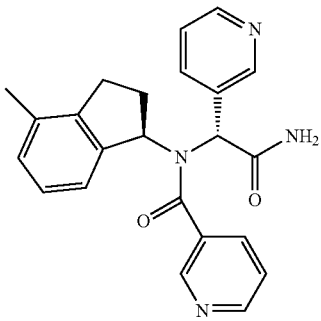 [SMILES: Cc1cccc2c1CC[C@H]2N(C(=O)c1cccnc1)[C@@H](C(N)=O)c1cccnc1] |
TABLE 26-continued
| Ex. No. | Strc. |
|---|---|
| 2-235LP | 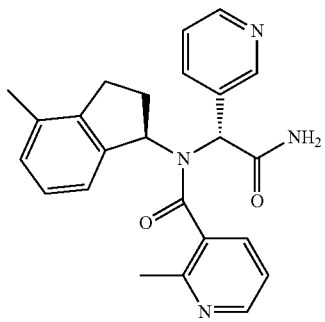 [SMILES: Cc1cccc2c1CC[C@H]2N(C(=O)c1cccnc1C)[C@@H](C(N)=O)c1cccnc1] |
| 2-236LP | 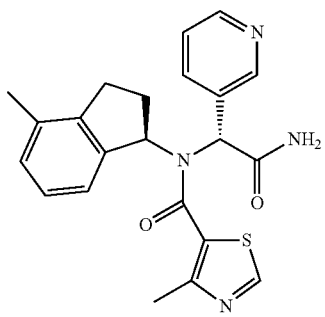 [SMILES: Cc1cccc2c1CC[C@H]2N(C(=O)c1scnc1C)[C@@H](C(N)=O)c1cccnc1] |
| 2-237LP | 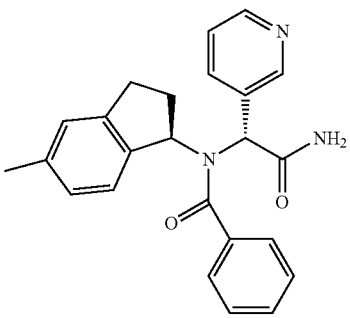 [SMILES: Cc1ccc2c(c1)CC[C@H]2N(C(=O)c1ccccc1)[C@@H](C(N)=O)c1cccnc1] |
TABLE 27
| Ex. No. | Strc. |
|---|---|
| 2-238LP | 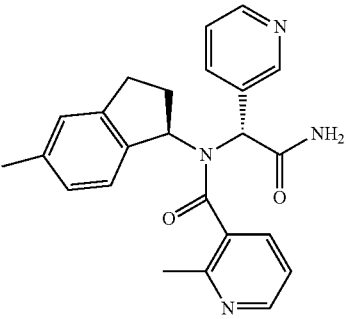 [SMILES: Cc1ccc2c(c1)CC[C@H]2N(C(=O)c1cccnc1C)[C@@H](C(N)=O)c1cccnc1] |

TABLE 27-continued
| Ex. No. | Strc. |
|---|---|
| 2-239LP | 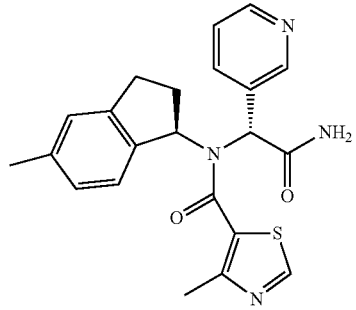 [SMILES: Cc1ccc2c(c1)CC[C@H]2N(C(=O)c1scnc1C)[C@@H](C(N)=O)c1cccnc1] |
| 2-240LP | 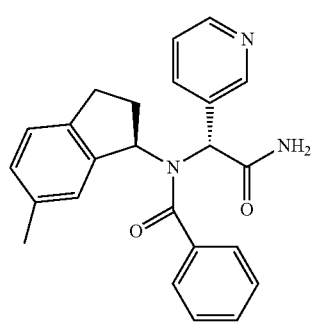 [SMILES: Cc1ccc2c(c1)[C@H](N(C(=O)c1ccccc1)[C@@H](C(N)=O)c1cccnc1)CC2] |
| 2-241LP | 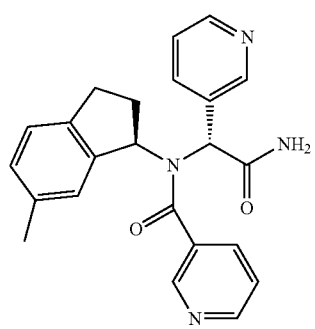 |
| 2-242LP | 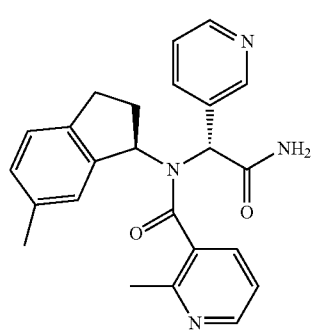 [SMILES: Cc1ccc2c(c1)[C@H](N(C(=O)c1cccnc1C)[C@@H](C(N)=O)c1cccnc1)CC2] |
| 2-243LP | 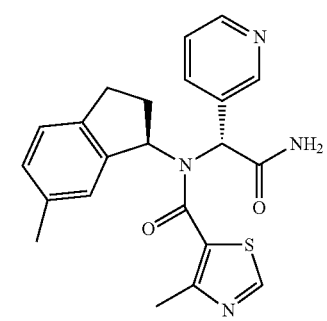 [SMILES: Cc1ccc2c(c1)[C@H](N(C(=O)c1scnc1C)[C@@H](C(N)=O)c1cccnc1)CC2] |
| 2-244LP | 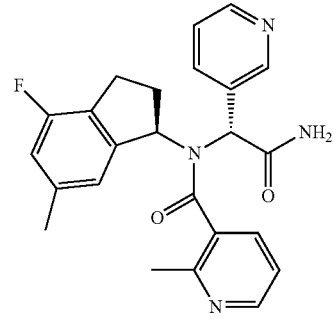 [SMILES: Cc1cc(F)c2c(c1)[C@H](N(C(=O)c1cccnc1C)[C@@H](C(N)=O)c1cccnc1)CC2] |
| 2-245LP | 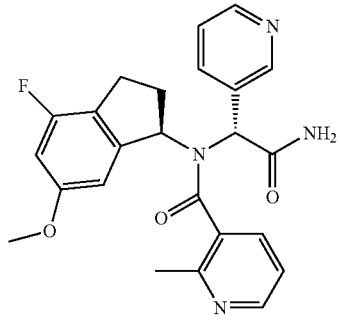 [SMILES: COc1cc(F)c2c(c1)[C@H](N(C(=O)c1cccnc1C)[C@@H](C(N)=O)c1cccnc1)CC2] |
| 2-246LP | 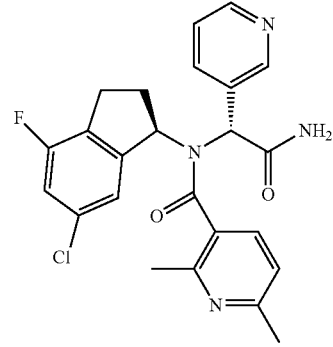 [SMILES: Cc1ccc(C(=O)N([C@@H]2CCc3c(F)cc(Cl)cc32)[C@@H](C(N)=O)c2cccnc2)c(C)n1] |

TABLE 27-continued
| Ex. No. | Strc. |
|---|---|
| 2-247LP | 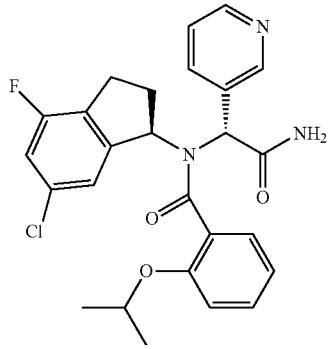 [SMILES: CC(C)Oc1ccccc1C(=O)N([C@@H]1CCc2c(F)cc(Cl)cc21)[C@@H](C(N)=O)c1cccnc1] |
| 2-248LP | 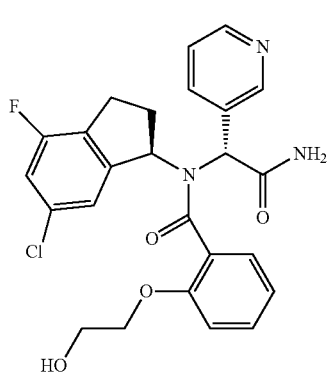 [SMILES: NC(=O)[C@@H](c1cccnc1)N(C(=O)c1ccccc1OCCO)[C@@H]1CCc2c(F)cc(Cl)cc21] |
| 2-249LP | 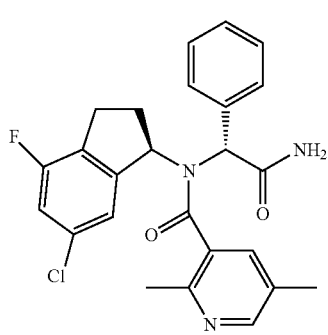 |
TABLE 28
| Ex. No. | Strc. |
|---|---|
| 2-250LP | 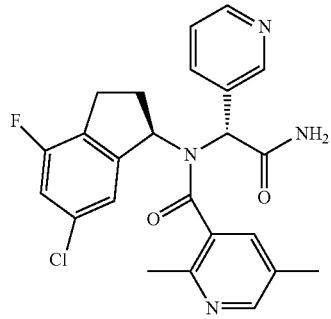 [SMILES: Cc1cnc(C)c(C(=O)N([C@@H]2CCc3c(F)cc(Cl)cc32)[C@@H](C(N)=O)c2ccccc2)c1] |
TABLE 28-continued
| Ex. No. | Strc. |
|---|---|
| 2-251LP | 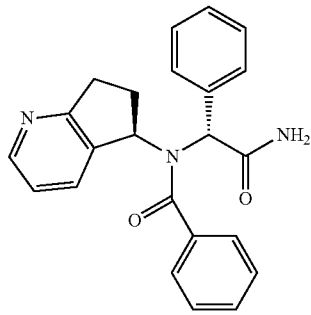 [SMILES: NC(=O)[C@@H](c1ccccc1)N(C(=O)c1ccccc1)[C@@H]1CCc2ncccc21] |
| 2-251HP | 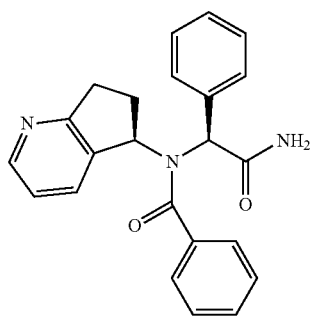 [SMILES: NC(=O)[C@H](c1ccccc1)N(C(=O)c1ccccc1)[C@@H]1CCc2ncccc21] |
| 2-252M | 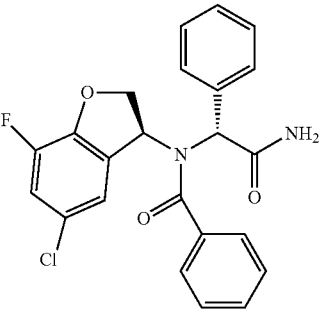 [SMILES: NC(=O)[C@@H](c1ccccc1)N(C(=O)c1ccccc1)[C@@H]1COc2c(F)cc(Cl)cc21] |
| 2-253M | 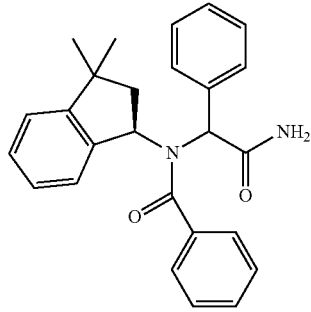 [SMILES: CC1(C)C[C@@H](N(C(=O)c2ccccc2)C(C(N)=O)c2ccccc2)c2ccccc21] |

TABLE 28-continued
| Ex. No. | Strc. |
|---|---|
| 2-254M | 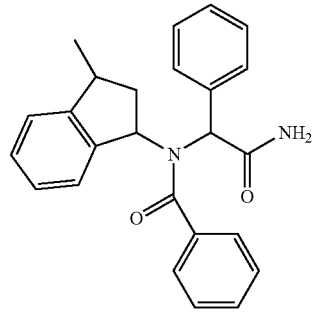 [SMILES: CC1CC(N(C(=O)c2ccccc2)C(C(N)=O)c2ccccc2)c2ccccc21] |
| 2-255M | 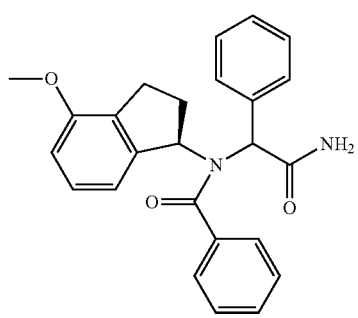 [SMILES: COc1cccc2c1CC[C@H]2N(C(=O)c1ccccc1)C(C(N)=O)c1ccccc1] |
| 2-256M | 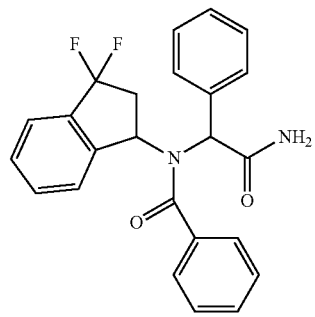 [SMILES: NC(=O)C(c1ccccc1)N(C(=O)c1ccccc1)C1CC(F)(F)c2ccccc21] |
| 2-257M | 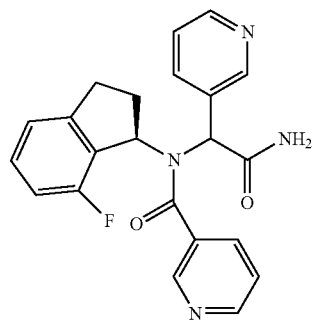 [SMILES: NC(=O)C(c1cccnc1)N(C(=O)c1cccnc1)[C@@H]1CCc2cccc(F)c21] |
TABLE 28-continued
| Ex. No. | Strc. |
|---|---|
| 2-258M | 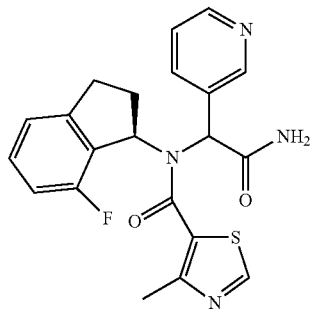 [SMILES: Cc1ncsc1C(=O)N(C(C(N)=O)c1cccnc1)[C@@H]1CCc2cccc(F)c21] |
| 2-259M | 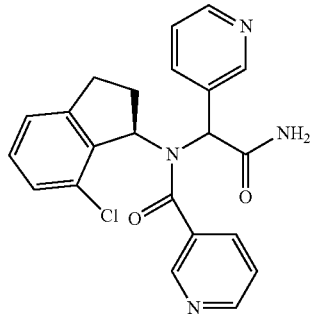 [SMILES: NC(=O)C(c1cccnc1)N(C(=O)c1cccnc1)[C@@H]1CCc2cccc(Cl)c21] |
| 2-260HP | 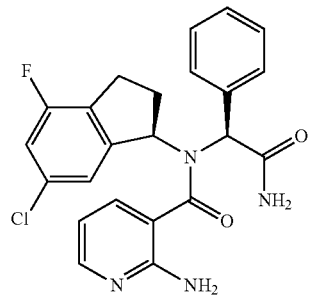 |
TABLE 29
| Ex. No. | Strc. |
|---|---|
| 3-1 | 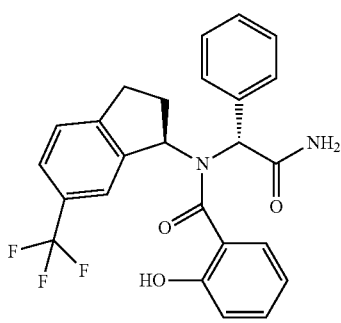 [SMILES: NC(=O)[C@@H](c1ccccc1)N(C(=O)c1ccccc1O)[C@@H]1CCc2ccc(C(F)(F)F)cc21] |

TABLE 29-continued
| Ex. No. | Strc. |
|---|---|
| 3-2 | 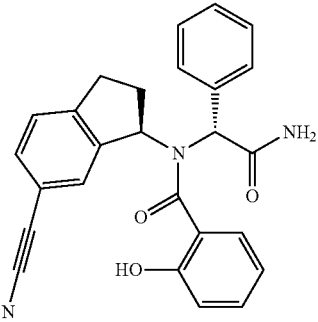 [SMILES: NC#Cc1ccc2c(c1)[C@H](N(C(=O)c1ccccc1O)[C@@H](C(N)=O)c1ccccc1)CC2] |
| 3-3 | 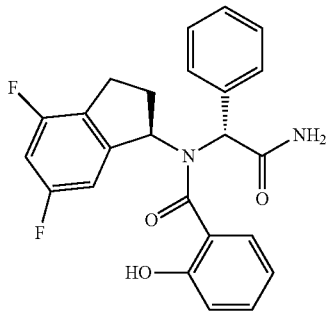 [SMILES: NC(=O)[C@@H](c1ccccc1)N(C(=O)c1ccccc1O)[C@@H]1CCc2c(F)cc(F)cc21] |
TABLE 30
| Ex. No. | Strc. |
|---|---|
| 4-1 | 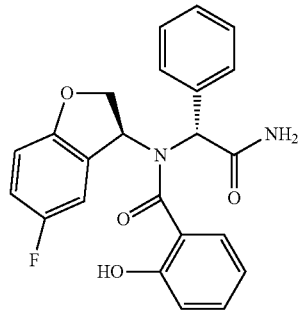 |
| 4-2 | 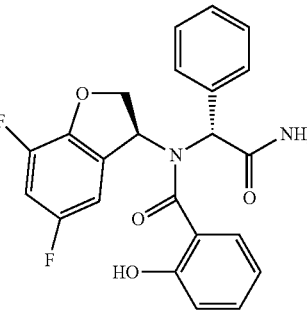 |
TABLE 30-continued
| Ex. No. | Strc. |
|---|---|
| 4-3 | |
| 4-4 | |
| 4-5 | 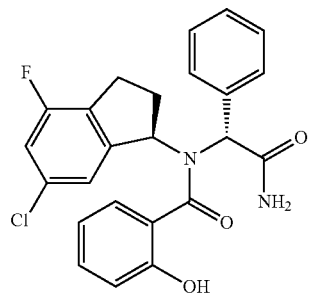 |
| 4-6 | 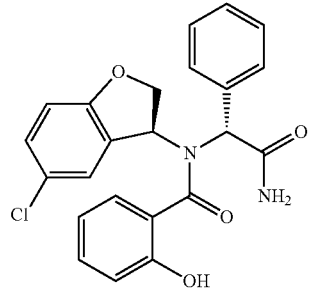 [SMILES: NC(=O)[C@@H](c1ccccc1)N(C(=O)c1ccccc1O)[C@@H]1COc2ccc(Cl)cc21] |

TABLE 31

| Ex. No. | Strc. |
|---|---|
| 4-7 | |
| 4-8 | |
| 4-9 | |

TABLE 32

| Ex. No. | Strc. |
|---|---|
| 5-1 | |

TABLE 32-continued

| Ex. No. | Strc. |
|---|---|
| 5-2 | |

TABLE 33

| Ex. No. | Strc. |
|---|---|
| 6-1 | |
| 6-2 | |

TABLE 34

| Ex. No. | Strc. |
|---|---|
| 6-3 | |

TABLE 34-continued
| Ex. No. | Strc. |
|---|---|
| 6-4 | 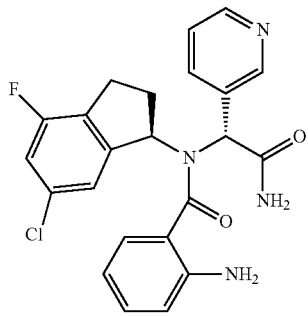 [SMILES: NC(=O)[C@@H](c1cccnc1)N(C(=O)c1ccccc1N)[C@@H]1CCc2c(F)cc(Cl)cc21] |
| 6-5 | 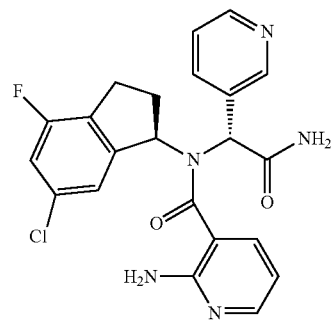 [SMILES: NC(=O)[C@@H](c1cccnc1)N(C(=O)c1cccnc1N)[C@@H]1CCc2c(F)cc(Cl)cc21] |
| 7 | 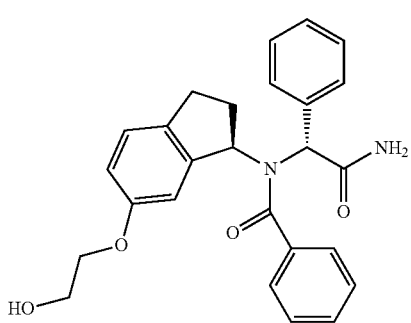 [SMILES: NC(=O)[C@@H](c1ccccc1)N(C(=O)c1ccccc1)[C@@H]1CCc2ccc(OCCO)cc21] |
| 8-1 | 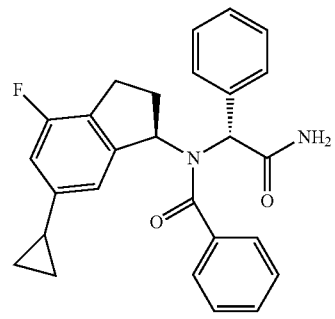 [SMILES: NC(=O)[C@@H](c1ccccc1)N(C(=O)c1ccccc1)[C@@H]1CCc2c(F)cc(C3CC3)cc21] |
TABLE 34-continued
| Ex. No. | Strc. |
|---|---|
| 8-2 | 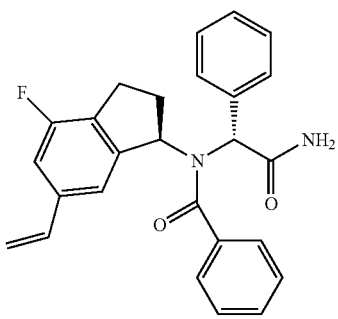 |
| 9 | 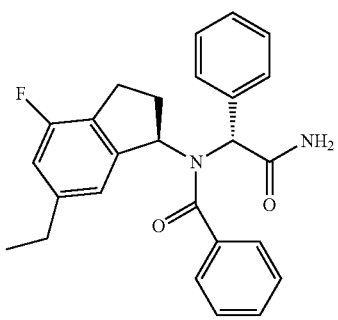 [SMILES: CCc1cc(F)c2c(c1)[C@H](N(C(=O)c1ccccc1)[C@@H](C(N)=O)c1ccccc1)CC2] |
| 10 | 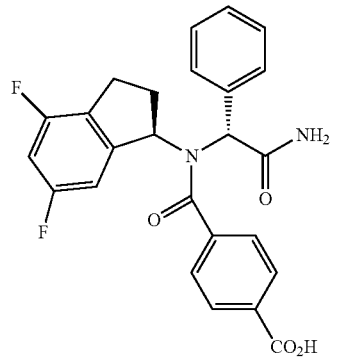 |
| 11 | 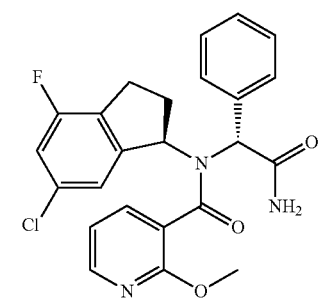 [SMILES: COc1ncccc1C(=O)N([C@@H]1CCc2c(F)cc(Cl)cc21)[C@@H](C(N)=O)c1ccccc1] |

TABLE 34-continued

| Ex. No. | Strc. |
|---|---|
| 12 | (structure) |
| 13 | (structure) |
| 14LP | (structure) |

TABLE 35

| Ex. No. | Strc. |
|---|---|
| 14HP | (structure) |
| 15LP | (structure) |
| 15HP | (structure) |
| 16 | (structure) |
| 17 | (structure) |

Reference Example 6-1

2-Acetyloxy-3-trifluoromethoxybenzoic acid

To a mixture of 3-trifluoromethoxysalicylic acid (0.5 g) and acetic anhydride (2 mL) was added sulfuric acid (2 drops), and the mixture was stirred for 1 hour at 80° C. The reaction mixture was allowed to cool to room temperature, and to the mixture was added ice. The insoluble compound was collected by filtration, and dried under reduced pressure to afford the title compound (0.519 g). The structural formula is shown in Table 36.

$^1$H-NMR (CDCl$_3$) δ ppm: 2.38 (3H, s), 7.36-7.42 (1H, m), 7.56-7.61 (1H, m), 8.05 (1H, dd, J=1.6, 8.0 Hz).

Reference Example 6-2

2-Acetyloxy-3-trifluoromethylbenzoic acid

The title compound was synthesized in a manner similar to that of Reference Example 6-1 by using the corresponding starting material. The spectrum data of the title compound is shown as follows, and the structural formula is shown in Table 36.

$^1$H-NMR (CDCl$_3$) δppm: 2.38 (3H, s), 7.44-7.50 (1H, m), 7.90-7.94 (1H, m), 8.29-8.34 (1H, m).

TABLE 36

| Ref. Ex. | Strc. |
|---|---|
| 6-1 | 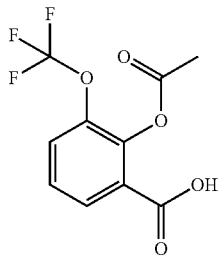 [SMILES: CC(=O)Oc1c(OC(F)(F)F)cccc1C(=O)O] |
| 6-2 | 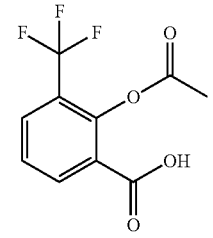 |

Example 18-1 to 18-16

Examples 18-1 to 18-16 were synthesized in a manner similar to that of Example 2-1 by using the corresponding starting materials. The spectrum data of Examples 18-1 to 18-16 are shown as follows, and the structural formulae are shown in Tables 37 and 38.

Example 18-1LP

N-[(R)-Carbamoylpyridin-3-ylmethyl]-N-[(R)-6-chloro-4-fluoroindan-1-yl]-2-difluoromethoxybenzamide RT (min.): 2.793
MS (ESI, m/z): 488.0998 (M−H)$^-$
$^1$H-NMR (DMSO-d$_6$) δppm: 1.22-1.37 (1H, m), 1.92-2.17 (1H, m), 2.50-2.70 (1H, m), 2.78-2.95 (1H, m), 4.78-5.45 (3H, m), 7.00-7.82 (10H, m), 8.43-8.67 (2H, m).

Example 18-2LP

N-[(R)-Carbamoylphenylmethyl]-N-[(R)-6-chloro-4-fluoroindan-1-yl]-6-hydroxy-2-methylnicotinamide RT (min.): 2.671
MS (ESI, m/z): 452.1191 (M−H)$^-$
$^1$H-NMR (DMSO-d$_6$) δppm: 1.05-1.35 (1H, m), 1.80-2.93 (6H, m), 4.88-5.19 (1H, m), 5.47-5.70 (1H, m), 6.23-6.31 (1H, m), 7.07-7.90 (10H, m), 11.70-12.04 (1H, m).

Example 18-3LP

N-[(R)-Carbamoyl-(3-cyanophenyl)methyl]-N-[(R)-6-chloro-4-fluoroindan-1-yl]-2-methoxybenzamide RT (min.): 3.565
MS (ESI, m/z): 476.1190 (M−H)$^-$
$^1$H-NMR (CDCl$_3$) δppm: 1.71-1.87 (1H, m), 2.26-2.40 (1H, m), 2.52-2.68 (1H, m), 2.79-2.93 (1H, m), 3.92 (1H, s), 4.04 (2H, m), 4.67-4.81 (1H, m), 5.33-6.81 (3H, m), 6.94-7.15 (3H, m), 7.37-7.57 (4H, m), 7.60-7.78 (2H, m), 8.03 (1H, br s).

Example 18-4LP

N-[(R)-Carbamoyl-(3-cyanophenyl)methyl]-N-[(R)-6-chloro-4-fluoroindan-1-yl]-2-methylnicotinamide RT (min.): 2.655
MS (ESI, m/z): 461.1196 (M−H)$^-$
$^1$H-NMR (CDCl$_3$) δppm: 1.56-1.78 (1H, m), 2.06-2.18 (1H, m), 2.47-2.89 (5H, m), 4.59-4.82 (1H, m), 5.19-5.80 (3H, m), 6.98-7.08 (1H, m), 7.19-7.29 (1H, m), 7.50-7.98 (6H, m), 8.53-8.68 (1H, br).

Example 18-5LP

N-[(R)-Carbamoylpyridin-3-ylmethyl]-N-[(R)-6-chloro-4-fluoroindan-1-yl]-3-cyanobenzamide RT (min.): 2.539
MS (ESI, m/z): 447.1042 (M−H)$^-$
$^1$H-NMR (CDCl$_3$) δppm: 1.70-1.90 (1H, m), 2.00-2.22 (1H, m), 2.50-2.94 (2H, m), 4.62-4.93 (1H, m), 5.25-5.77 (3H, m), 6.96-7.09 (1H, m), 7.37-7.45 (1H, m), 7.54-7.65 (1H, m), 7.70-8.06 (5H, m), 8.58-8.75 (2H, m).

Example 18-6LP

N-[(R)-Carbamoylphenylmethyl]-N-[(R)-6-chloro-4-fluoroindan-1-yl]-3-cyanobenzamide RT (min.): 3.598
MS (ESI, m/z): 446.1086 (M−H)$^-$
$^1$H-NMR (CDCl$_3$) δppm: 1.67-2.13 (2H, m), 2.45-2.88 (2H, m), 4.53-5.80 (4H, m), 6.88-7.08 (1H, m), 7.35-7.65 (6H, m), 7.67-7.89 (4H, m).

Example 18-7LP

N-[(R)-Carbamoylpyrazin-2-ylmethyl]-N-[(R)-6-chloro-4-fluoroindan-1-yl]-3-cyanobenzamide RT (min.): 2.931
MS (ESI, m/z): 448.0990 (M−H)$^-$
$^1$H-NMR (CDCl$_3$) δppm: 2.00-2.15 (1H, m), 2.32-2.53 (1H, m), 2.61-2.74 (1H, m), 2.84-3.04 (1H, m), 4.73-4.93

(1H, m), 5.36-5.77 (3H, m), 6.97-7.07 (1H, m), 7.50-7.68 (2H, m), 7.75-7.82 (1H, m), 7.83-7.95 (2H, m), 8.52-8.63 (2H, m), 8.81 (1 h, br s).

Example 18-8LP

N-[(R)-Carbamoyl-(3-hydroxymethylphenyl)methyl]-N-[(R)-6-chloro-4-fluoroindan-1-yl]-2-methylnicotinamide RT (min.): 2.195
MS (ESI, m/z): 512.1410 (M+HCO$_2$)$^-$
$^1$H-NMR (CDCl$_3$) δppm: 1.38-2.18 (3H, m), 2.38-3.13 (5H, m), 4.55-5.00 (3H, m), 5.15-5.24 (1H, m), 5.37-5.72 (2H, m), 6.83-7.03 (1H, m), 7.16-7.83 (7H, m), 8.52-8.60 (1H, m).

Example 18-9LP

N-[(R)-Carbamoyl-(3-carbamoylphenyl)methyl]-N-[(R)-6-chloro-4-fluoroindan-1-yl]-2-methylnicotinamide RT (min.): 1.969
MS (ESI, m/z): 525.1359 (M+HCO$_2$)
$^1$H-NMR (CDCl$_3$) δppm: 1.36-1.78 (1H, m), 2.00-2.12 (1H, m), 2.43-3.13 (5H, m), 4.62-4.98 (1H, m), 5.17-5.28 (1H, m), 5.32-6.50 (4H, m), 6.84-7.05 (1H, m), 7.17-7.32 (1H, m), 7.41-7.89 (5H, m), 7.94-8.11 (1H, m), 8.52-8.64 (1H, m).

Example 18-10LP

N-[(R)-Carbamoylpyridin-3-ylmethyl]-N-[(R)-6-chloro-4-fluoroindan-1-yl]-4-cyanothiophene-2-carboxamide RT (min.): 2.485
MS (ESI, m/z): 453.0600 (M−H)$^-$
$^1$H-NMR (CDCl$_3$) δppm: 1.80-1.93 (1H, m), 2.08-2.36 (1H, m), 2.64-2.79 (1H, m), 2.89-3.00 (1H, m), 4.57-4.98 (1H, m), 5.41-5.99 (3H, m), 7.00-7.12 (1H, m), 7.34-7.43 (1H, m), 7.57 (1H, s), 7.73 (1H, s), 7.85-7.95 (1H, m), 8.08-8.13 (1H, m), 8.61-8.70 (2H, m).

Example 18-11LP

{3-[(R)-Carbamoyl-{N-[(R)-6-chloro-4-fluoroindan-1-yl]-N-(2-methylpyridin-3-carbonyl)amino}methyl]benzyl}carbamic acid tert-butyl ester RT (min.): 3.089
MS (ESI, m/z): 611.2092 (M+HCO$_2$)$^-$
$^1$H-NMR (CDCl$_3$) δppm: 1.45 (9H, s), 1.63-1.82 (1H, m), 1.95-2.11 (1H, m), 2.41-3.13 (5H, m), 4.25-4.42 (2H, m), 4.55-5.05 (2H, m), 5.15-5.23 (1H, m), 5.38-5.65 (2H, m), 6.85-7.03 (1H, m), 7.15-7.53 (5H, m), 7.59-7.83 (2H, m), 8.53-8.61 (1H, m).

Example 18-12LP

N-[(R)-Carbamoyl-(3-nitrophenyl)methyl]-N-[(R)-6-chloro-4-fluoroindan-1-yl]-2-methylnicotinamide RT (min.): 2.836
MS (ESI, m/z): 481.1092 (M−H)$^-$
$^1$H-NMR (CDCl$_3$) δppm: 1.63-1.79 (1H, m), 2.09-2.22 (1H, m), 2.49-2.89 (5H, m), 4.72-4.89 (1H, m), 5.22-5.32 (1H, m), 5.38-6.00 (2H, m), 6.87-7.07 (1H, m), 7.56-7.97 (4H, m), 8.20-8.67 (3H, m).

Example 18-13LP

N-[(R)-Carbamoyl-(3-dimethylaminophenyl)methyl]-N-[(R)-6-chloro-4-fluoroindan-1-yl]-2-methylnicotinamide RT (min.): 2.572
MS (ESI, m/z): 479.1655 (M−H)$^-$
$^1$H-NMR (CDCl$_3$) δppm: 1.73-2.20 (2H, m), 2.41-2.55 (1H, m), 2.60-2.86 (4H, m), 2.92-3.02 (6H, m), 4.45-5.70 (4H, m), 6.44-7.05 (4H, m), 7.15-7.32 (2H, m), 7.48-7.84 (2H, m), 8.52-8.60 (1H, m).

Example 18-14LP

N-[(R)-Carbamoylphenylmethyl]-N-[(S)-5,7-difluoro-2,3-dihydrobenzofuran-3-yl]-2-methylnicotinamide RT (min.): 2.298
MS (ESI, m/z): 422.1331 (M−H)$^-$
$^1$H-NMR (CDCl$_3$) δppm: 2.35-2.83 (3H, m), 3.81-4.95 (3H, m), 5.22-5.81 (3H, m), 6.64-6.88 (1H, m), 7.09-7.73 (8H, m), 8.44-8.65 (1H, m).

Example 18-15M

N-(Carbamoylpyridin-3-ylmethyl)-N-[(S)-5,7-difluoro-2,3-dihydrobenzofuran-3-yl]-2-methylnicotinamide RT (min.): 0.838
MS (ESI, m/z): 423.1277 (M−H)$^-$
RT (min.): 0.937
MS (ESI, m/z): 423.1278 (M−H)$^-$
$^1$H-NMR (CDCl$_3$) δppm: 2.36-2.90 (3H, m), 4.08-4.88 (2H, m), 5.20-6.22 (4H, m), 6.68-6.91 (1H, m), 7.08-8.95 (8H, m).

Example 18-16LP

N-[(R)-Carbamoylphenyl-3-ylmethyl]-N-[(S)-5-chloro-7-fluoro-2,3-dihydrobenzofuran-3-yl]-2-methylnicotinamide RT (min.): 2.576
MS (ESI, m/z): 438.1034 (M−H)$^-$
$^1$H-NMR (CDCl$_3$) δppm: 2.38-2.83 (3H, m), 3.84-4.31 (2H, m), 5.20-5.63 (4H, m), 6.90-7.72 (9H, m), 8.43-8.63 (1H, m).

Example 19-1LP

N-[(R)-Carbamoylpyridin-3-ylmethyl]-N-[(R)-6-chloro-4-fluoroindan-1-yl]-2-hydroxybenzamide To a solution of (R)-6-chloro-4-fluoroindan-1-ylamine hydrochloride (6.66 g) in methanol (100 mL) were added triethylamine (4.80 mL) and 3-formylpyridine (3.24 g), and the mixture was stirred for 1 hour at 60° C. The reaction mixture was allowed to cool to room temperature, and to the mixture were added acetylsalicylic acid (5.41 g) and 4-phenylcyclohexen-1-ylisocyanide (5.50 g). The mixture was stirred overnight at 60° C., then allowed to cool to room temperature, and concentrated under reduced pressure. To the obtained residue were added 1,4-dioxane (150 mL), water (30 mL) and a solution of 4 mol/L hydrogen chloride in 1,4-dioxane (30 mL), and the mixture was stirred for 3 hours at room temperature. To the reaction mixture was added a saturated aqueous solution of sodium bicarbonate, and the crude product was extracted with ethyl acetate. The organic layer was washed with water and brine, and dried over anhydrous magnesium sulfate. The solvent was removed under reduced pressure, and the residue was purified by aminopropyl silica gel column chromatography (eluent: ethyl acetate/methanol=5/1) to afford a mixture of diastereomers. The mixture was purified by silica gel column chromatography (eluent: dichloromethane/diethyl ether/methanol=10/10/1) to afford the title compound (4.20 g) as low polarity product. The structural formula is shown in Table 39.

$^1$H-NMR (CDCl$_3$) δppm: 1.70-2.38 (2H, m), 2.53-2.94 (2H, m), 4.45-5.10 (1H, m), 5.27-6.41 (3H, m), 6.88-7.04 (3H, m), 7.27-7.35 (2H, m), 7.36-7.42 (1H, m), 7.51-7.54 (1H, m), 7.88-8.05 (1H, m), 8.62 (1H, dd, J=1.5, 4.8 Hz), 8.71-8.77 (1H, m), 9.10-9.75 (1H, m).

Example 19-2 to 19-41

Examples 19-2 to 19-41 were synthesized in a manner similar to that of Example 19-1 by using the corresponding starting materials. The spectrum data of Examples 19-2 to 19-41 are shown as follows, and the structural formulae are shown in Tables 39 to 42.

Example 19-2LP

N-[(R)-Carbamoyl-(3-cyanophenyl)methyl]-N-[(R)-6-chloro-4-fluoroindan-1-yl]-2-hydroxybenzamide RT (min.): 3.220
MS (ESI, m/z): 462.1035 (M−H)$^-$
$^1$H-NMR (CDCl$_3$) δppm: 1.67-1.83 (1H, m), 1.98-2.33 (1H, m), 2.55-2.92 (2H, m), 4.54-5.07 (1H, m), 5.31-6.00 (3H, m), 6.92-7.07 (3H, m), 7.31-7.40 (2H, m), 7.50-7.61 (2H, m), 7.65-7.76 (2H, m), 7.78-7.90 (1H, m), 8.23-8.60 (1H, br).

Example 19-3LP

N-[(R)-Carbamoyl-(3-carbamoylphenyl)methyl]-N-[(R)-6-chloro-4-fluoroindan-1-yl]-2-hydroxybenzamide RT (min.): 2.588
MS (ESI, m/z): 480.1143 (M−H)$^-$
$^1$H-NMR (DMSO-d$_6$) δppm: 1.09-1.21 (1H, m), 1.97-2.11 (1H, m), 2.46-2.59 (1H, m), 2.76-2.87 (1H, m), 5.01-5.11 (1H, m), 5.45 (1H, br s), 6.85-6.95 (2H, m), 7.06-7.30 (4H, m), 7.37-7.69 (5H, m), 7.82-7.93 (2H, m), 8.05 (1H, br s), 10.09 (1H, br s).

Example 19-4LP

N-[(R)-Carbamoyl-(3-hydroxymethylphenyl)methyl]-N-[(R)-6-chloro-4-fluoroindan-1-yl]-2-hydroxybenzamide RT (min.): 2.774
MS (ESI, m/z): 467.1188 (M−H)$^-$
$^1$H-NMR (DMSO-d$_6$) δppm: 1.10-1.27 (1H, m), 1.99-2.12 (1H, m), 2.46-2.58 (1H, m), 2.76-3.02 (1H, m), 4.51 (2H, d, J=5.6 Hz), 5.00-5.11 (1H, m), 5.26 (1H, t, J=5.6 Hz), 5.41 (1H, br s), 6.82-6.95 (2H, m), 6.98-7.63 (10H, m), 10.04 (1H, br s).

Example 19-5LP

N-[(R)-Carbamoyl-(3-nitrophenyl)methyl]-N-[(R)-6-chloro-4-fluoroindan-1-yl]-2-hydroxybenzamide RT (min.): 3.369
MS (ESI, m/z): 482.0940 (M−H)$^-$
$^1$H-NMR (DMSO-d$_6$) δppm: 1.14-1.33 (1H, m), 1.96-2.12 (1H, m), 2.46-2.62 (1H, m), 2.77-2.90 (1H, m), 4.97-5.58 (2H, m), 6.81-7.00 (2H, m), 7.06-8.45 (10H, m), 10.18-10.28 (1H, m).

Example 19-6LP

N-[(R)-Carbamoyl-(3-dimethylaminophenyl)methyl]-N-[(R)-6-chloro-4-fluoroindan-1-yl]-2-hydroxybenzamide RT (min.): 2.811
MS (ESI, m/z): 480.1507 (M−H)$^-$
$^1$H-NMR (DMSO-d$_6$) δppm: 1.21-1.35 (1H, m), 2.03-2.17 (1H, m), 2.47-2.61 (1H, m), 2.78-2.96 (7H, m), 5.02-5.13 (1H, m), 5.33 (1H, br s), 6.57-6.76 (3H, m), 6.83-6.95 (2H, m), 7.02-7.28 (5H, m), 7.42 (1H, br s), 7.58 (1H, br s), 10.02 (1H, br s).

Example 19-7LP

N-[(R)-Carbamoyl-(3-hydroxyphenyl)methyl]-N-[(R)-6-chloro-4-fluoroindan-1-yl]-2-hydroxybenzamide RT (min.): 2.916
MS (ESI, m/z): 453.1037 (M−H)$^-$
$^1$H-NMR (DMSO-d$_6$) δppm: 1.21-1.34 (1H, m), 2.05-2.18 (1H, m), 2.46-2.61 (1H, m), 2.79-2.91 (1H, m), 5.01-5.11 (1H, m), 5.32 (1H, br s), 6.70-6.80 (3H, m), 6.84-6.94 (2H, m), 7.05-7.30 (5H, m), 7.46 (1H, br s), 7.56 (1H, br s), 9.56 (1H, br s), 10.03 (1H, br s).

Example 19-8LP

{3-[(R)-Carbamoyl-{N-[(R)-6-chloro-4-fluoroindan-1-yl]-N-(2-hydroxybenzoyl)amino}methyl]benzyl}carbamic acid tert-butyl ester RT (min.): 3.584
MS (ESI, m/z): 566.1879 (M−H)$^-$
$^1$H-NMR (CDCl$_3$) δppm: 1.44 (9H, s), 1.71-1.89 (1H, m), 1.97-2.27 (1H, m), 2.49-2.93 (2H, m), 4.32 (2H, d, J=5.9 Hz), 4.45-5.95 (5H, m), 6.89-7.08 (3H, m), 7.25-7.47 (6H, m), 7.64 (1H, s), 8.45-8.89 (1H, m).

Example 19-9HP

N-[(S)-Carbamoylpyridin-3-ylmethyl]-N-[(R)-6-chloro-4-fluoroindan-1-yl]-2-hydroxybenzamide RT (min.): 2.021
MS (ESI, m/z): 438.1034 (M−H)$^-$ ¹H-NMR (CDCl₃) δppm: 2.47-2.68 (2H, m), 2.73-2.85 (1H, m), 3.08-3.19 (1H, m), 4.52 (1H, br s), 5.50-5.59 (1H, m), 5.84 (1H, br s), 6.04 (1H, br s), 6.46 (1H, br s), 6.83-7.02 (3H, m), 7.28-7.36 (3H, m), 7.92-7.97 (1H, m), 8.37-8.41 (1H, m), 8.54-8.58 (1H, m), 9.10 (1H, br).

Example 19-10M

N-(Carbamoylpyridin-3-ylmethyl)-N-[(S)-5,7-difluoro-2,3-dihydrobenzofuran-3-yl]-2-hydroxybenzamide RT (min.): 1.537
MS (ESI, m/z): 424.1128 (M−H)⁻
RT (min.): 1.614
MS (ESI, m/z): 424.1119 (M−H)⁻
¹H-NMR (CDCl₃) δppm: 4.30-5.15 (3H, m), 5.55-6.57 (3H, m), 6.66-6.88 (1H, m), 6.91-7.01 (2H, m), 7.04-7.44 (4H, m), 7.81-8.02 (1H, m), 8.25-8.86 (2H, m).

Example 19-11LP

N-[(R)-Carbamoylpyridin-3-ylmethyl]-N-[(R)-6-chloro-4-fluoroindan-1-yl]-2-hydroxy-5-methylbenzamide RT (min.): 2.416
MS (ESI, m/z): 452.1193 (M−H)⁻
¹H-NMR (CDCl₃) δppm: 1.75-1.92 (1H, m), 2.17-2.40 (4H, m), 2.56-2.67 (1H, m), 2.73-2.93 (1H, m), 4.60-4.97 (1H, m), 5.46-5.95 (2H, m), 6.20-6.55 (1H, m), 6.81 (1H, d, J=8.1 Hz), 6.94-7.03 (1H, m), 7.05-7.13 (2H, m), 7.35-7.41 (1H, m), 7.49 (1H, s), 7.96 (1H, br s), 8.58-8.63 (1H, m), 8.73 (1H, s), 9.20 (1H, br).

Example 19-12LP

N-[(R)-Carbamoylpyridin-3-ylmethyl]-N-[(R)-6-chloro-4-fluoroindan-1-yl]-2-hydroxy-4-methylbenzamide RT (min.): 2.416
MS (ESI, m/z): 452.1195 (M−H)⁻
¹H-NMR (CDCl₃) δppm: 1.75-1.92 (1H, m), 2.00-2.41 (4H, m), 2.55-2.68 (1H, m), 2.78-2.94 (1H, m), 4.60-5.02 (1H, m), 5.46-6.31 (3H, m), 6.71-6.76 (1H, m), 6.79 (1H, s), 6.96-7.03 (1H, m), 7.23 (1H, d, J=7.9 Hz), 7.35-7.40 (1H, m), 7.54 (1H, s), 7.94 (1H, br s), 8.59-8.64 (1H, m), 8.69 (1H, s), 9.22 (1H, br).

Example 19-13LP

N-[(R)-Carbamoylpyridin-3-ylmethyl]-N-[(R)-6-chloro-4-fluoroindan-1-yl]-2-hydroxy-3-methoxybenzamide RT (min.): 2.295
MS (ESI, m/z): 468.1145 (M−H)⁻
¹H-NMR (CDCl₃) δppm: 1.77-1.94 (1H, m), 2.22-2.42 (1H, m), 2.54-2.66 (1H, m), 2.77-2.95 (1H, m), 3.92 (3H, s), 4.66-4.83 (1H, m), 5.42-6.82 (3H, m), 6.90-7.03 (4H, m), 7.30-7.37 (1H, m), 7.53 (1H, s), 7.98 (1H, br s), 8.56-8.61 (1H, m), 8.67 (1H, s).

Example 19-14LP

N-[(R)-Carbamoylpyridin-3-ylmethyl]-N-[(R)-6-chloro-4-fluoroindan-1-yl]-2-hydroxy-3-isopropylbenzamide RT (min.): 3.092
MS (ESI, m/z): 480.1507 (M−H)⁻
¹H-NMR (CDCl₃) δppm: 1.25 (6H, t, J=6.9 Hz), 1.69-2.38 (2H, m), 2.55-2.68 (1H, m), 2.75-2.94 (1H, m), 3.38 (1H, septet, J=6.9 Hz), 4.59-4.92 (1H, m), 5.47-5.90 (3H, m), 6.80-6.92 (1H, m), 6.97-7.04 (1H, m), 7.18 (1H, dd, J=1.6, 7.7 Hz), 7.30 (1H, dd, J=1.4, 7.7 Hz), 7.36-7.40 (1H, m), 7.63 (1H, s), 7.99 (1H, br s), 8.60-8.83 (3H, m).

Example 19-15LP

N-[(R)-Carbamoylpyridin-3-ylmethyl]-N-[(R)-6-chloro-4-fluoroindan-1-yl]-2-fluoro-6-hydroxybenzamide RT (min.): 2.311
MS (ESI, m/z): 456.0944 (M−H)⁻
¹H-NMR (CDCl₃) δppm: 1.50-2.00 (1H, m), 2.24-2.94 (3H, m), 4.60-4.88 (1H, m), 5.45-5.94 (3H, m), 6.58-6.84 (2H, m), 6.96-7.07 (1H, m), 7.12-7.56 (3H, m), 7.77-8.17 (1H, m), 8.51-9.07 (2H, m).

Example 19-16LP

N-[(R)-Carbamoylpyridin-3-ylmethyl]-N-[(R)-6-chloro-4-fluoroindan-1-yl]-4-fluoro-2-hydroxybenzamide RT (min.): 2.361
MS (ESI, m/z): 456.0941 (M−H)⁻
¹H-NMR (CDCl₃) δppm: 1.70-1.90 (1H, m), 1.98-2.39 (1H, m), 2.56-2.69 (1H, m), 2.78-2.93 (1H, m), 4.64-5.05 (1H, m), 5.43-6.33 (3H, m), 6.60-6.71 (2H, m), 6.97-7.05 (1H, m), 7.31 (1H, dd, J=6.4, 8.4 Hz), 7.38-7.44 (1H, m), 7.51 (1H, s), 7.92-7.99 (1H, m), 8.63 (1H, dd, J=1.4, 4.9 Hz), 8.72-8.76 (1H, m).

Example 19-17LP

N-[(R)-Carbamoylpyridin-3-ylmethyl]-4-chloro-N-[(R)-6-chloro-4-fluoroindan-1-yl]-2-hydroxybenzamide RT (min.): 2.589
MS (ESI, m/z): 472.0653 (M−H)⁻
¹H-NMR (CDCl₃) δppm: 1.70-1.90 (1H, m), 2.12-2.39 (1H, m), 2.56-2.69 (1H, m), 2.78-2.93 (1H, m), 4.64-5.00 (1H, m), 5.38-6.41 (3H, m), 6.87-7.06 (3H, m), 7.22-7.28 (1H, m), 7.42 (1H, dd, J=4.9, 8.0 Hz), 7.48 (1H, s), 7.91-8.00 (1H, m), 8.62 (1H, dd, J=1.4, 4.8 Hz), 8.76 (1H, s).

Example 19-18LP

N-[(R)-Carbamoylpyridin-3-ylmethyl]-N-[(R)-6-chloro-4-fluoroindan-1-yl]-2-hydroxy-4-nitrobenzamide RT (min.): 2.510
MS (ESI, m/z): 483.0887 (M−H)⁻

¹H-NMR (CDCl₃) δppm: 1.70-1.90 (1H, m), 2.25-2.42 (1H, m), 2.56-2.68 (1H, m), 2.75-2.89 (1H, m), 4.73-4.86 (1H, m), 5.33-5.47 (1H, m), 5.79-6.21 (2H, m), 6.97-7.06 (1H, m), 7.43-7.54 (3H, m), 7.75-7.83 (2H, m), 7.97-8.06 (1H, m), 8.66-8.70 (1H, m), 8.86 (1H, br s).

Example 19-19LP

N-[(R)-Carbamoylpyridin-3-ylmethyl]-N-[(R)-6-chloro-4-fluoroindan-1-yl]-2-hydroxy-4-methoxybenzamide RT (min.): 2.297
MS (ESI, m/z): 468.1145 (M−H)⁻
¹H-NMR (CDCl₃) δppm: 1.78-1.92 (1H, m), 1.97-2.33 (1H, m), 2.59-2.71 (1H, m), 2.84-2.96 (1H, m), 3.81 (3H, s), 4.67-5.07 (1H, m), 5.50-6.18 (3H, m), 6.47 (1H, dd, J=2.5, 8.7 Hz), 6.53 (1H, d, J=2.5 Hz), 6.99-7.04 (1H, m), 7.32 (1H, d, J=8.7 Hz), 7.37 (1H, dd, J=4.8, 7.9 Hz), 7.60 (1H, s), 7.85-7.96 (1H, m), 8.60-8.67 (2H, m), 9.69 (1H, br s).

Example 19-20LP

N-[(R)-Carbamoylpyridin-3-ylmethyl]-3-chloro-N-[(R)-6-chloro-4-fluoroindan-1-yl]-2-hydroxybenzamide RT (min.): 2.523
MS (ESI, m/z): 472.0646 (M−H)⁻
¹H-NMR (CDCl₃) δppm: 1.50-2.40 (2H, m), 2.54-2.65 (1H, m), 2.76-2.90 (1H, m), 4.65-4.90 (1H, m), 5.30-5.52 (1H, m), 5.76-6.23 (2H, m), 6.90-7.03 (2H, m), 7.24-7.28 (1H, m), 7.36 (1H, dd, J=4.8, 7.9 Hz), 7.40 (1H, dd, J=1.5, 8.0 Hz), 7.56 (1H, s), 7.91-8.01 (1H, m), 8.56-8.61 (1H, m), 8.66-8.69 (1H, m).

Example 19-21LP

N-[(R)-Carbamoylpyridin-3-ylmethyl]-N-[(R)-6-chloro-4-fluoroindan-1-yl]-2-hydroxy-4-trifluoromethylbenzamide RT (min.): 2.813
MS (ESI, m/z): 506.0924 (M−H)⁻
¹H-NMR (CDCl₃) δppm: 1.65-1.90 (1H, m), 2.22-2.42 (1H, m), 2.55-2.67 (1H, m), 2.73-2.89 (1H, m), 4.71-4.88 (1H, m), 5.37-5.51 (1H, m), 5.94-6.52 (2H, m), 6.95-7.05 (1H, m), 7.12-7.21 (2H, m), 7.37-7.46 (2H, m), 7.48 (1H, s), 7.91-8.02 (1H, m), 8.58-8.62 (1H, m), 8.82 (1H, br s).

Example 19-22LP

N-[(R)-Carbamoylpyridin-3-ylmethyl]-N-[(R)-6-chloro-4-fluoroindan-1-yl]-5-fluoro-2-hydroxybenzamide RT (min.): 2.341
MS (ESI, m/z): 456.0941 (M−H)⁻
¹H-NMR (CDCl₃) δppm: 1.65-1.91 (1H, m), 2.15-2.45 (1H, m), 2.56-2.69 (1H, m), 2.74-2.91 (1H, m), 4.65-4.86 (1H, m), 5.40-5.61 (1H, m), 5.83-6.46 (2H, m), 6.86 (1H, dd, J=4.3, 8.9 Hz), 6.94-7.04 (3H, m), 7.40 (1H, dd, J=4.9, 8.0 Hz), 7.48 (1H, s), 7.90-8.01 (1H, m), 8.57-8.63 (1H, m), 8.75 (1H, br s).

Example 19-23LP

N-[(R)-Carbamoylpyridin-3-ylmethyl]-N-[(R)-6-chloro-4-fluoroindan-1-yl]-2-hydroxy-3-trifluoromethoxybenzamide RT (min.): 2.789
MS (ESI, m/z): 522.0866 (M−H)⁻
¹H-NMR (CDCl₃) δppm: 1.65-1.93 (1H, m), 2.15-2.39 (1H, m), 2.55-2.67 (1H, m), 2.74-2.91 (1H, m), 4.66-4.90 (1H, m), 5.35-5.53 (1H, m), 5.70-6.21 (2H, m), 6.92-7.04 (2H, m), 7.25-7.33 (2H, m), 7.38 (1H, dd, J=4.9, 8.1 Hz), 7.52 (1H, s), 7.93-8.04 (1H, m), 8.59-8.63 (1H, m), 8.69-8.73 (1H, m).

Example 19-24LP

N-[(R)-Carbamoylpyridin-3-ylmethyl]-N-[(R)-6-chloro-4-fluoroindan-1-yl]-3-hydroxyisonicotinamide RT (min.): 1.394
MS (ESI, m/z): 439.0989 (M−H)⁻
¹H-NMR (DMSO-d₆) δppm: 1.21-2.13 (2H, m), 2.47-3.01 (2H, m), 5.01-5.45 (2H, m), 7.08-7.61 (6H, m), 7.68-7.92 (1H, m), 8.11-8.33 (2H, m), 8.47-8.67 (2H, m), 10.2-11.1 (1H, m).

Example 19-25LP

N-[(R)-Carbamoylpyridin-3-ylmethyl]-N-[(R)-6-chloro-4-fluoroindan-1-yl]-3-fluoro-2-hydroxybenzamide RT (min.): 2.252
MS (ESI, m/z): 456.0941 (M−H)⁻
¹H-NMR (CDCl₃) δppm: 1.86-3.06 (4H, m), 4.06-5.36 (2H, m), 5.50 (1H, br s), 6.56 (1H, br s), 6.75-7.44 (6H, m), 7.80-8.08 (1H, m), 8.58-8.66 (1H, m), 8.69-8.76 (1H, m).

Example 19-26LP

N-[(R)-Carbamoylpyridin-3-ylmethyl]-N-[(R)-6-chloro-4-fluoroindan-1-yl]-2-hydroxy-5-methoxybenzamide RT (min.): 2.240
MS (ESI, m/z): 468.1144 (M−H)⁻
¹H-NMR (CDCl₃) δppm: 1.72-1.88 (1H, m), 2.00-2.39 (1H, m), 2.55-2.67 (1H, m), 2.74-2.92 (1H, m), 3.74 (3H, s), 4.60-4.95 (1H, m), 5.40-6.32 (3H, m), 6.82-6.89 (3H, m), 6.96-7.02 (1H, m), 7.35-7.41 (1H, m), 7.54 (1H, s), 7.92-8.01 (1H, m), 8.50-8.98 (3H, m).

Example 19-27LP

N-[(R)-Carbamoylpyridin-3-ylmethyl]-5-chloro-N-[(R)-6-chloro-4-fluoroindan-1-yl]-2-hydroxybenzamide RT (min.): 2.525
MS (ESI, m/z): 472.0644 (M−H)⁻

¹H-NMR (CDCl₃) δppm: 1.70-1.90 (1H, m), 2.15-2.45 (1H, m), 2.57-2.70 (1H, m), 2.75-2.91 (1H, m), 4.60-4.97 (1H, m), 5.39-5.60 (1H, m), 5.70-6.38 (2H, m), 6.87 (1H, d, J=8.6 Hz), 6.97-7.04 (1H, m), 7.21-7.28 (2H, m), 7.41 (1H, dd, J=4.9, 8.0 Hz), 7.46 (1H, br s), 7.93-8.05 (1H, m), 8.60-8.66 (1H, m), 8.72-8.76 (1H, m).

Example 19-28LP

5-Acetyl-N-[(R)-carbamoylpyridin-3-ylmethyl]-N-[(R)-6-chloro-4-fluoroindan-1-yl]-2-hydroxybenzamide RT (min.): 2.083
MS (ESI, m/z): 480.1145 (M−H)⁻
¹H-NMR (CDCl₃) δppm: 1.75-1.92 (1H, m), 2.15-2.45 (1H, m), 2.52 (3H, s), 2.56-2.70 (1H, m), 2.75-2.91 (1H, m), 4.65-4.99 (1H, m), 5.39-5.58 (1H, m), 5.70-6.30 (2H, m), 6.96-7.03 (2H, m), 7.44 (1H, dd, J=4.9, 8.0 Hz), 7.50 (1H, br s), 7.86-8.08 (3H, m), 8.65 (1H, d, J=4.5 Hz), 8.75 (1H, br s).

Example 19-29LP

N-[(R)-Carbamoylpyridin-3-ylmethyl]-N-[(R)-6-chloro-4-fluoroindan-1-yl]-4-ethoxy-2-hydroxybenzamide RT (min.): 2.485
MS (ESI, m/z): 482.1299 (M−H)⁻
¹H-NMR (CDCl₃) δppm: 1.41 (3H, t, J=7.0 Hz), 1.79-2.36 (2H, m), 2.59-2.72 (1H, m), 2.84-2.97 (1H, m), 4.03 (2H, q, J=7.0 Hz), 4.65-5.14 (1H, m), 5.50-6.20 (3H, m), 6.45 (1H, dd, J=2.4, 8.7 Hz), 6.51 (1H, d, J=2.4 Hz), 6.98-7.04 (1H, m), 7.30 (1H, d, J=8.7 Hz), 7.36 (1H, dd, J=4.8, 8.0 Hz), 7.59 (1H, s), 7.85-7.94 (1H, m), 8.60-8.67 (2H, m), 9.67 (1H, br).

Example 19-30LP

5-Acetylamino-N-[(R)-carbamoylpyridin-3-ylmethyl]-N-[(R)-6-chloro-4-fluoroindan-1-yl]-2-hydroxybenzamide RT (min.): 1.746
MS (ESI, m/z): 495.1254 (M−H)⁻
¹H-NMR (CD₃OD) δppm: 1.33-2.36 (5H, m), 2.55-3.06 (2H, m), 4.85-5.78 (2H, m), 6.83-7.61 (5H, m), 7.64 (1H, s), 7.91-8.09 (1H, m), 8.48-8.71 (2H, m).

Example 19-31LP

N-[(R)-Carbamoyl(5-fluoropyridin-3-yl)methyl]-N-[(R)-6-chloro-4-fluoroindan-1-yl]-2-hydroxybenzamide RT (min.): 2.881
MS (ESI, m/z): 456.0943 (M−H)⁻
¹H-NMR (CDCl₃) δppm: 1.70-1.89 (1H, m), 2.14-2.38 (1H, m), 2.58-2.70 (1H, m), 2.79-2.92 (1H, m), 4.67-4.95 (1H, m), 5.49-6.34 (3H, m), 6.91-6.97 (2H, m), 6.99-7.04 (1H, m), 7.28-7.35 (2H, m), 7.50 (1H, s), 7.76-7.86 (1H, m), 8.46-8.51 (2H, m), 8.90 (1H, br).

Example 19-32LP

N-[(R)-Carbamoyl(5-methoxypyridin-3-yl)methyl]-N-[(R)-6-chloro-4-fluoroindan-1-yl]-2-hydroxybenzamide RT (min.): 2.520
MS (ESI, m/z): 468.1147 (M−H)⁻
¹H-NMR (CDCl₃) δppm: 1.73-1.91 (1H, m), 2.01-2.36 (1H, m), 2.55-2.68 (1H, m), 2.77-2.93 (1H, m), 3.88 (3H, s), 4.64-4.94 (1H, m), 5.47-6.10 (3H, m), 6.89-6.95 (1H, m), 6.96-7.05 (2H, m), 7.29-7.36 (2H, m), 7.53-7.63 (2H, m), 8.24 (1H, d, J=1.8 Hz), 8.32 (1H, d, J=2.8 Hz), 8.94 (1H, br).

Example 19-33LP

N-[(R)-Carbamoyl(5-methylpyridin-3-yl)methyl]-N-[(R)-6-chloro-4-fluoroindan-1-yl]-2-hydroxybenzamide RT (min.): 2.185
MS (ESI, m/z): 452.1190 (M−H)⁻
¹H-NMR (CDCl₃) δppm: 1.77-1.93 (1H, m), 2.12-2.46 (4H, m), 2.55-2.68 (1H, m), 2.76-2.93 (1H, m), 4.60-4.98 (1H, m), 5.40-6.43 (3H, m), 6.88-7.04 (3H, m), 7.24-7.37 (2H, m), 7.51 (1H, s), 7.76 (1H, br s), 8.44 (1H, s), 8.54 (1H, br s), 9.57 (1H, br).

Example 19-34LP

N-[(R)-Carbamoyl(5-trifluoromethylpyridin-3-yl)methyl]-N-[(R)-6-chloro-4-fluoroindan-1-yl]-2-hydroxybenzamide RT (min.): 3.266
MS (ESI, m/z): 506.0909 (M−H)⁻
¹H-NMR (CDCl₃) δppm: 1.71-1.87 (1H, m), 2.10-2.43 (1H, m), 2.59-2.72 (1H, m), 2.81-2.94 (1H, m), 4.79-5.00 (1H, m), 5.51-6.58 (3H, m), 6.89-6.98 (2H, m), 6.99-7.04 (1H, m), 7.27-7.35 (2H, m), 7.45 (1H, s), 8.20 (1H, s), 8.75-8.98 (3H, m).

Example 19-35LP

N-[(R)-Carbamoyl(6-trifluoromethylpyridin-3-yl)methyl]-N-[(R)-6-chloro-4-fluoroindan-1-yl]-2-hydroxybenzamide RT (min.): 3.395
MS (ESI, m/z): 506.0911 (M−H)⁻
¹H-NMR (DMSO-d₆) δppm: 1.21-1.79 (1H, m), 2.00-2.17 (1H, m), 2.45-2.92 (2H, m), 4.89-5.62 (2H, m), 6.69-8.22 (10H, m), 8.65-8.87 (1H, m), 10.14-10.43 (1H, m).

Example 19-36LP

N-[(R)-Carbamoyl(5-chloropyridin-3-yl)methyl]-N-[(R)-6-chloro-4-fluoroindan-1-yl]-2-hydroxybenzamide RT (min.): 3.077
MS (ESI, m/z): 472.0647 (M−H)⁻
¹H-NMR (CDCl₃) δppm: 1.72-1.89 (1H, m), 2.16-2.38 (1H, m), 2.58-2.70 (1H, m), 2.81-2.94 (1H, m), 4.65-4.96

(1H, m), 5.47-6.45 (3H, m), 6.91-6.96 (2H, m), 6.98-7.03 (1H, m), 7.28-7.35 (2H, m), 7.48 (1H, s), 8.00 (1H, br s), 8.55-8.59 (2H, m), 9.00 (1H, br).

Example 19-37LP

N-[(R)-Carbamoylpyridin-3-ylmethyl]-N-[(S)-5-chloro-7-fluoro-2,3-dihydrobenzofuran-3-yl]-2-hydroxybenzamide RT (min.): 1.942
MS (ESI, m/z): 440.0827 (M−H)⁻
$^1$H-NMR (CDCl$_3$) δppm: 4.32-5.01 (3H, m), 5.56-6.60 (3H, m), 6.92-7.00 (2H, m), 7.04-7.11 (1H, m), 7.26-7.37 (3H, m), 7.43 (1H, dd, J=4.8, 8.0 Hz), 7.89-8.02 (1H, m), 8.61-8.65 (1H, m), 8.84 (1H, br s), 10.25 (1H, br).

Example 19-38LP

N-[(R)-Carbamoyl(5-hydroxypyridin-3-yl)methyl]-N-[(R)-6-chloro-4-fluoroindan-1-yl]-2-hydroxybenzamide RT (min.): 2.133
MS (ESI, m/z): 454.0983 (M−H)⁻
$^1$H-NMR (DMSO-d$_6$) δppm: 1.21-1.39 (1H, m), 2.02-2.17 (1H, m), 2.42-2.93 (2H, m), 4.97-5.44 (2H, m), 6.83-6.96 (2H, m), 7.05-7.70 (7H, m), 7.96-8.15 (2H, m), 10.12 (1H, br).

Example 19-39LP

N-[(R)-Carbamoyl(5-cyanopyridin-3-yl)methyl]-N-[(R)-6-chloro-4-fluoroindan-1-yl]-2-hydroxybenzamide RT (min.): 2.915
MS (ESI, m/z): 463.0988 (M−H)⁻
$^1$H-NMR (CDCl$_3$) δppm: 1.70-1.86 (1H, m), 2.21-2.45 (1H, m), 2.61-2.73 (1H, m), 2.81-2.94 (1H, m), 4.71-4.90 (1H, m), 5.47-5.64 (1H, m), 5.71-6.70 (2H, m), 6.88 (1H, d, J=8.2 Hz), 6.94-7.06 (2H, m), 7.27-7.35 (2H, m), 7.41 (1H, s), 8.28 (1H, br s), 8.52-8.96 (3H, m).

Example 19-40LP

N-[(S)-Carbamoylpyridin-3-ylmethyl]-N-[(S)-6-chloro-4-fluoroindan-1-yl]-2-hydroxybenzamide RT (min.): 2.176
MS (ESI, m/z): 438.1033 (M−H)⁻
$^1$H-NMR (CDCl$_3$) δ: 1.70-2.40 (2H, m), 2.54-2.94 (2H, m), 4.48-5.03 (1H, m), 5.40-6.53 (3H, m), 6.88-7.04 (3H, m), 7.28-7.35 (2H, m), 7.39 (1H, dd, J=4.8, 7.9 Hz), 7.50-7.55 (1H, m), 7.88-8.05 (1H, m), 8.62 (1H, dd, J=1.5, 4.8 Hz), 8.69-8.78 (1H, m), 9.38 (1H, br).

Example 19-41LP

N-[(R)-Carbamoylpyridin-3-ylmethyl]-N-[(R)-6-chloro-4-fluoroindan-1-yl]-2-hydroxy-3-methylbenzamide RT (min.): 2.536
MS (ESI, m/z): 452.1197 (M−H)⁻
$^1$H-NMR (CDCl$_3$) δppm: 1.69-1.87 (1H, m), 1.98-2.36 (4H, m), 2.54-2.66 (1H, m), 2.73-2.93 (1H, m), 4.58-4.97 (1H, m), 5.46-5.98 (3H, m), 6.80-6.87 (1H, m), 6.97-7.04 (1H, m), 7.15-7.24 (2H, m), 7.34-7.40 (1H, m), 7.61 (1H, br s), 7.98 (1H, br s), 8.59-8.75 (3H, m).

Example 20-1

N-[(R)-Carbamoylpyridin-3-ylmethyl]-N-[(R)-6-chloro-4-fluoroindan-1-yl]-2,4-dihydroxybenzamide 4-{N-[(R)-Carbamoylpyridin-3-ylmethyl]-N-[(R)-6-chloro-4-fluoroindan-1-yl]carbamoy}-3-hydroxyphenyl acetate To a solution of (R)-6-chloro-4-fluoroindan-1-ylamine hydrochloride (0.11 g) in methanol (4 mL) were added triethylamine (68 µL) and 3-formylpyridine (0.054 g), and the mixture was stirred for 2 hours at 60° C. The reaction mixture was allowed to cool to room temperature, and to the mixture were added 2,4-diacetoxybenzoic acid (0.097 g) and 4-phenylcyclohexen-1-ylisocyanide (0.092 g). The mixture was stirred overnight at 60° C., then allowed to cool to room temperature, and concentrated under reduced pressure. To the obtained residue were added 1,4-dioxane (5 mL), water (0.5 mL) and a solution of 4 mol/L hydrogen chloride in 1,4-dioxane (0.5 mL), and the mixture was stirred for 3 hours at room temperature. To the reaction mixture was added a saturated aqueous solution of sodium bicarbonate, and the mixture was purified by preparative reverse phase liquid chromatography (Capcell Pak C18 UG80, eluent: acetonitrile/water=1/9 to 7/3) to afford N-[(R)-carbamoylpyridin-3-ylmethyl]-N-[(R)-6-chloro-4-fluoroindan-1-yl]-2,4-dihydroxybenzamide (Example 20-1-1LP, 3 mg) and 4-{N-[(R)-carbamoylpyridin-3-ylmethyl]-N-[(R)-6-chloro-4-fluoroindan-1-yl]carbamoyl}-3-hydroxyphenyl acetate (Example 20-1-2LP, 17 mg). The structural formulae are shown in Table 43.

Example 20-1-1LP

N-[(R)-Carbamoylpyridin-3-ylmethyl]-N-[(R)-6-chloro-4-fluoroindan-1-yl]-2,4-dihydroxybenzamide RT (min.): 1.798
MS (ESI, m/z): 454.0987 (M−H)⁻
$^1$H-NMR (CD$_3$OD) δppm: 1.10-2.10 (2H, m), 2.54-2.69 (1H, m), 2.80-3.00 (1H, m), 5.12-5.90 (2H, m), 6.37-6.42 (2H, m), 6.89-7.00 (1H, m), 7.06-7.14 (1H, m), 7.45-7.52 (1H, m), 7.60 (1H, s), 7.89-7.97 (1H, m), 8.50-8.56 (1H, m), 8.60 (1H, br s).

Example 20-1-2LP

4-{N-[(R)-Carbamoylpyridin-3-ylmethyl]-N-[(R)-6-chloro-4-fluoroindan-1-yl]carbamoy}-3-hydroxyphenyl acetate RT (min.): 2.215
MS (ESI, m/z): 496.1094 (M−H)⁻
$^1$H-NMR (CD$_3$OD) δppm: 1.30-2.36 (5H, m), 2.55-3.08 (2H, m), 5.14-5.80 (2H, m), 6.67-6.77 (2H, m), 6.85-7.11 (1H, m), 7.21-7.56 (2H, m), 7.61 (1H, s), 7.87-8.08 (1H, m), 8.48-8.72 (2H, m).

Example 20-2LP

N-[(R)-Carbamoylpyridin-3-ylmethyl]-N-[(R)-6-chloro-4-fluoroindan-1-yl]-2,3-dihydroxybenzamide The title compound was synthesized in a manner similar to that of Example 20-1 by using the corresponding starting material. The spectrum data of the title compound is shown as follows, and the structural formula is shown in Table 43.

RT (min.): 1.885

MS (ESI, m/z): 454.0985 (M−H)⁻

¹H-NMR (CD₃OD) δppm: 1.22-3.08 (4H, m), 5.06-5.80 (2H, m), 6.59-7.14 (4H, m), 7.40-7.55 (1H, m), 7.64 (1H, s), 7.90-8.13 (1H, m), 8.45-8.72 (2H, m).

Example 21-1

N-[(R)-(3-Aminophenyl)carbamoylmethyl]-N-[(R)-6-chloro-4-fluoroindan-1-yl]-2-methylnicotinamide A suspension of Raney catalyst was prepared as follows. A mixture of Raney (registered trademark) 2800 nickel, slurry in water, active catalyst (Sigma-Aldrich) (200 µL) and ethanol was stirred, and the solvent was removed by decantation. The catalyst was washed 3 times with ethanol, and ethanol (1 mL) was added to form a suspension. To a solution of N-[(R)-carbamoyl-(3-nitrophenyl)methyl]-N-[(R)-6-chloro-4-fluoroindan-1-yl]-2-methylnicotinamide (Example 18-12LP, 55 mg) in ethanol (5 mL) was added the suspension of Raney catalyst at room temperature, and the mixture was stirred for 2 hours under hydrogen atmosphere. The catalyst was removed by filtration, and the filtrate was concentrated under reduced pressure to afford the title compound (36 mg). The structural formula is shown in Table 43.

RT (min.): 1.959

MS (ESI, m/z): 451.1350 (M−H)⁻

¹H-NMR (DMSO-d₆) δppm: 1.40-1.58 (1H, m), 2.03-2.16 (1H, m), 2.29-2.95 (5H, m), 4.93-5.34 (4H, m), 6.34-6.60 (3H, m), 7.00-7.85 (7H, m), 8.48-8.56 (1H, m).

Example 21-2 to 21-3

Examples 21-2 to 21-3 were synthesized in a manner similar to that of Example 21-1 by using the corresponding starting materials. The spectrum data of examples 21-2 to 21-3 are shown as follows, and the structural formulae are shown in Table 43.

Example 21-2

N-[(R)-(3-Aminophenyl)carbamoylmethyl]-N-[(R)-6-chloro-4-fluoroindan-1-yl]-2-hydroxybenzamide RT (min.): 2.395

MS (ESI, m/z): 452.1190 (M−H)⁻

¹H-NMR (DMSO-d₆) δppm: 1.27-1.41 (1H, m), 2.07-2.21 (1H, m), 2.46-2.61 (1H, m), 2.79-2.91 (1H, m), 5.03-5.13 (1H, m), 5.18 (2H, br s), 5.25 (1H, br s), 6.45-6.57 (3H, m), 6.81-6.93 (2H, m), 6.99-7.29 (5H, m), 7.41 (1H, br s), 7.58 (1H, br s), 10.00 (1H, br s).

Example 21-3

4-Amino-N-[(R)-carbamoylpyridin-3-ylmethyl]-N-[(R)-6-chloro-4-fluoroindan-1-yl]-2-hydroxybenzamide RT (min.): 1.611

MS (ESI, m/z): 453.1149 (M−H)⁻

¹H-NMR (CD₃OD) δppm: 1.45-2.09 (2H, m), 2.54-2.67 (1H, m), 2.83-2.97 (1H, m), 5.22-5.84 (2H, m), 6.23 (1H, d, J=2.0 Hz), 6.28 (1H, dd, J=2.0, 8.3 Hz), 6.91-6.97 (1H, m), 7.02 (1H, d, J=8.3 Hz), 7.48 (1H, dd, J=5.0, 7.8 Hz), 7.57 (1H, s), 7.88-7.94 (1H, m), 8.50-8.54 (1H, m), 8.56-8.60 (1H, m).

Example 22

N-[(R)-(3-Acetylaminophenyl)carbamoylmethyl]-N-[(R)-6-chloro-4-fluoroindan-1-yl]-2-methylnicotinamide To a mixture of N-[(R)-(3-aminophenyl)carbamoylmethyl]-N-[(R)-6-chloro-4-fluoroindan-1-yl]-2-methylnicotinamide (Example 21-1, 80 mg), N,N-diisopropylethylamine (0.03 mL) and dichloromethane (3 mL) was added acetyl chloride (14 mg) at room temperature, and the mixture was stirred for 2 hours. To the reaction mixture was added water, and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane=5/1 to ethyl acetate/methanol=10/1) to afford the title compound (75 mg). The structural formula is shown in Table 43.

RT (min.): 2.267

MS (ESI, m/z): 539.1513 (M+HCO₂)

¹H-NMR (DMSO-d₆) δppm: 1.29-1.53 (1H, m), 1.99-2.15 (4H, m), 2.34-2.70 (4H, m), 2.84-2.97 (1H, m), 4.90-5.38 (2H, m), 6.88-7.94 (10H, m), 8.51-8.59 (1H, m), 10.07 (1H, s).

Example 23

N-[(R)-Carbamoyl-(3-methanesulfonylaminophenyl)methyl]-N-[(R)-6-chloro-4-fluoroindan-1-yl]-2-methylnicotinamide To a mixture of N-[(R)-(3-aminophenyl)carbamoylmethyl]-N-[(R)-6-chloro-4-fluoroindan-1-yl]-2-methylnicotinamide (Example 21-1, 80 mg), N,N-diisopropylethylamine (0.03 mL) and dichloromethane (3 mL) was added methanesulfonyl chloride (18 mg) at room temperature, and the mixture was stirred for 2 hours. To the reaction mixture was added water, and the crude product was extracted with ethyl acetate. The organic layer was washed with water and brine, and dried over anhydrous magnesium sulfate. The solvent was removed under reduced pressure, and the residue was purified by silica gel column chromatography (eluent: ethyl acetate/n-hexane=5/1 to ethyl acetate/methanol=10/1) to afford the title compound (34 mg). The structural formula is shown in Table 43.

RT (min.): 2.397

MS (ESI, m/z): 529.1127 (M−H)⁻

¹H-NMR (DMSO-d₆) δppm: 1.28-1.53 (1H, m), 1.98-2.15 (1H, m), 2.35-2.70 (4H, m), 2.84-3.05 (4H, m), 4.93-5.37 (2H, m), 6.97-7.87 (10H, m), 8.51-8.60 (1H, m), 9.93 (1H, br s).

TABLE 37
| Ex. No. | Strc. |
|---|---|
| 18-1LP | 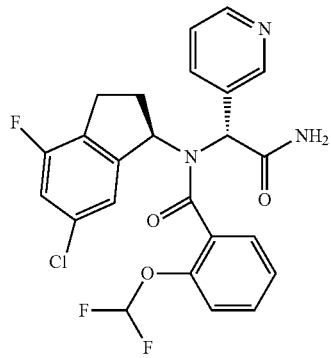 [SMILES: NC(=O)[C@@H](c1cccnc1)N(C(=O)c1ccccc1OC(F)F)[C@@H]1CCc2c(F)cc(Cl)cc21] |
| 18-2LP | 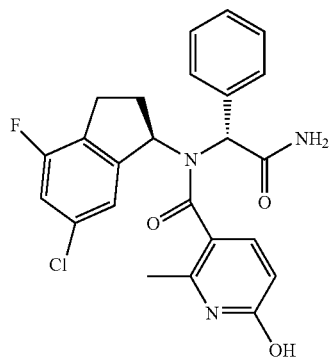 [SMILES: Cc1nc(O)ccc1C(=O)N([C@@H]1CCc2c(F)cc(Cl)cc21)[C@@H](C(N)=O)c1ccccc1] |
| 18-3LP | 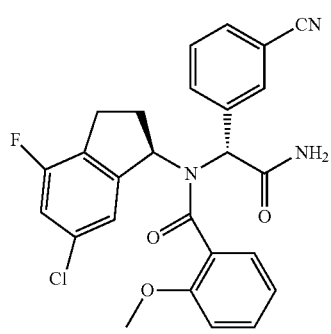 [SMILES: COc1ccccc1C(=O)N([C@@H]1CCc2c(F)cc(Cl)cc21)[C@@H](C(N)=O)c1cccc(C#N)c1] |
| 18-4LP | 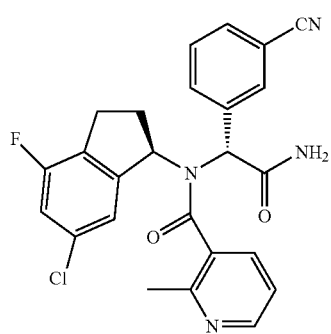 [SMILES: Cc1ncccc1C(=O)N([C@@H]1CCc2c(F)cc(Cl)cc21)[C@@H](C(N)=O)c1cccc(C#N)c1] |
TABLE 37-continued
| Ex. No. | Strc. |
|---|---|
| 18-5LP | 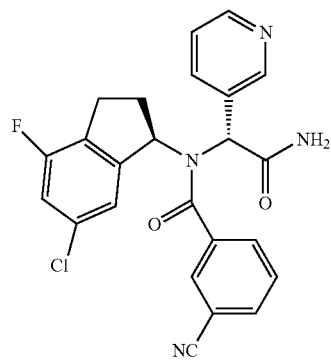 [SMILES: N#Cc1cccc(C(=O)N([C@@H]2CCc3c(F)cc(Cl)cc32)[C@@H](C(N)=O)c2cccnc2)c1] |
| 18-6LP | 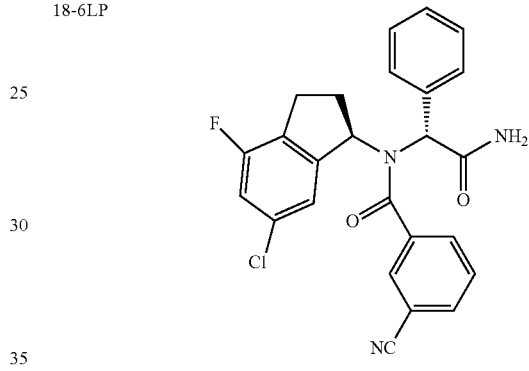 |
| 18-7LP | 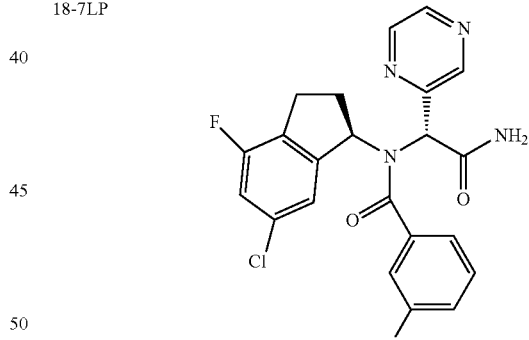 |
| 18-8LP | 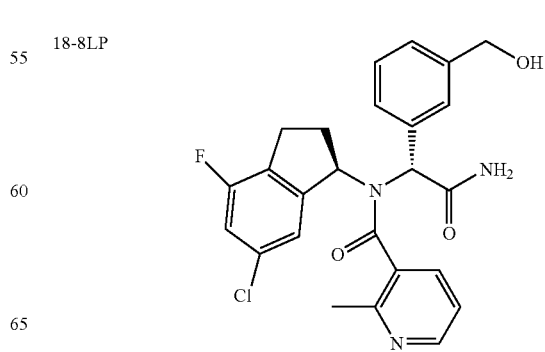 |

TABLE 37-continued

| Ex. No. | Strc. |
|---|---|
| 18-9LP | |
| 18-10LP | |
| 18-11LP | |
| 18-12LP | |

TABLE 38

| Ex. No. | Strc. |
|---|---|
| 18-13LP | |
| 18-14LP | |
| 18-15M | |
| 18-16LP | |

TABLE 39
| Ex. No. | Strc. |
|---|---|
| 19-1LP | 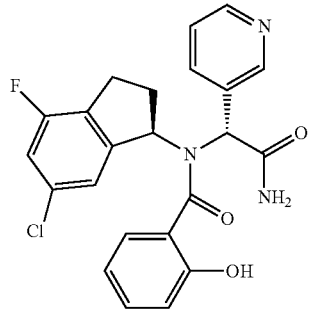 |
| 19-2LP | 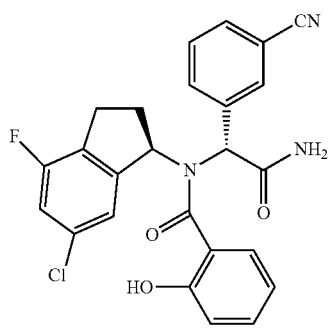 [SMILES: N#Cc1cccc([C@H](C(N)=O)N(C(=O)c2ccccc2O)[C@@H]2CCc3c(F)cc(Cl)cc32)c1] |
| 19-3LP | 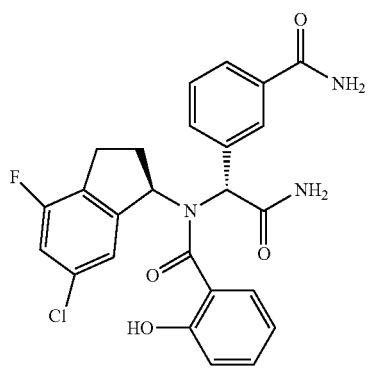 [SMILES: NC(=O)c1cccc([C@H](C(N)=O)N(C(=O)c2ccccc2O)[C@@H]2CCc3c(F)cc(Cl)cc32)c1] |
| 19-4LP | 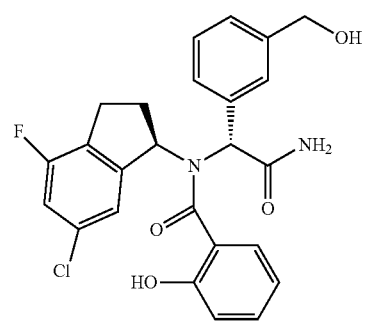 [SMILES: NC(=O)[C@@H](c1cccc(CO)c1)N(C(=O)c1ccccc1O)[C@@H]1CCc2c(F)cc(Cl)cc21] |
TABLE 39-continued
| Ex. No. | Strc. |
|---|---|
| 19-5LP | 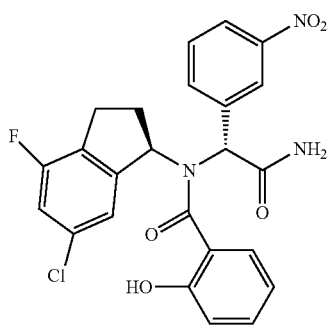 [SMILES: NC(=O)[C@@H](c1cccc([N+](=O)[O-])c1)N(C(=O)c1ccccc1O)[C@@H]1CCc2c(F)cc(Cl)cc21] |
| 19-6LP | 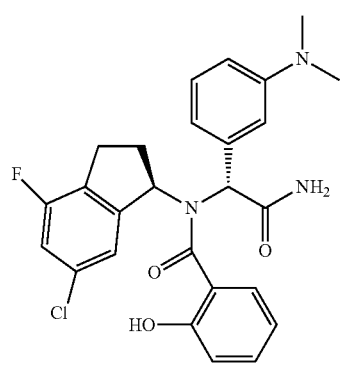 [SMILES: CN(C)c1cccc([C@H](C(N)=O)N(C(=O)c2ccccc2O)[C@@H]2CCc3c(F)cc(Cl)cc32)c1] |
| 19-7LP | 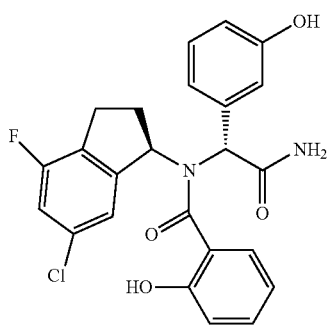 |
| 19-8LP | 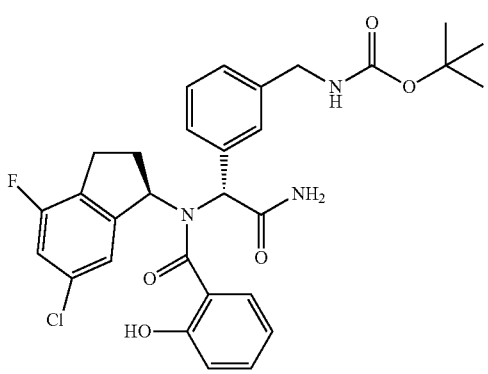 [SMILES: CC(C)(C)OC(=O)NCc1cccc([C@H](C(N)=O)N(C(=O)c2ccccc2O)[C@@H]2CCc3c(F)cc(Cl)cc32)c1] |

TABLE 39-continued
| Ex. No. | Strc. |
|---|---|
| 19-9HP | 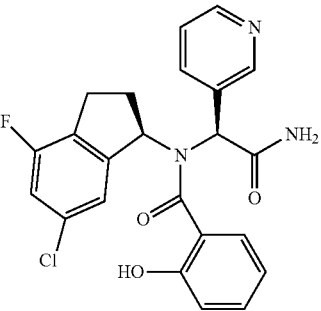 [SMILES: NC(=O)[C@H](c1cccnc1)N(C(=O)c1ccccc1O)[C@@H]1CCc2c(F)cc(Cl)cc21] |
| 19-10M | 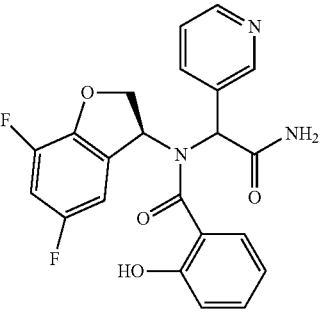 [SMILES: NC(=O)C(c1cccnc1)N(C(=O)c1ccccc1O)[C@@H]1COc2c(F)cc(F)cc21] |
| 19-11LP | 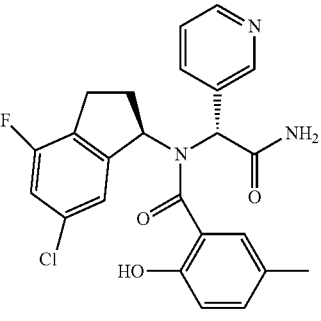 |
| 19-12LP | 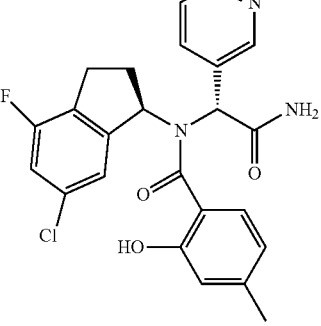 |
TABLE 40
| Ex. No. | Strc. |
|---|---|
| 19-13LP | 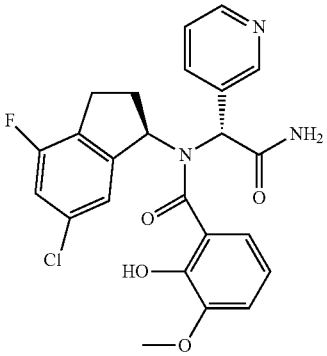 [SMILES: COc1cccc(C(=O)N([C@@H]2CCc3c(F)cc(Cl)cc32)[C@@H](C(N)=O)c2cccnc2)c1O] |
| 19-14LP | 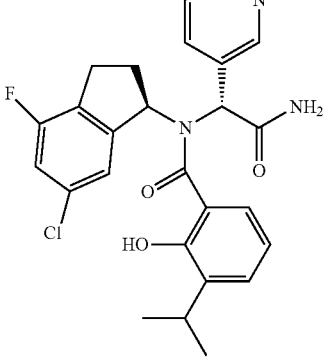 |
| 19-15LP | 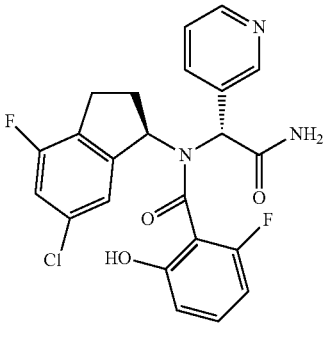 [SMILES: NC(=O)[C@@H](c1cccnc1)N(C(=O)c1c(O)cccc1F)[C@@H]1CCc2c(F)cc(Cl)cc21] |
| 19-16LP | 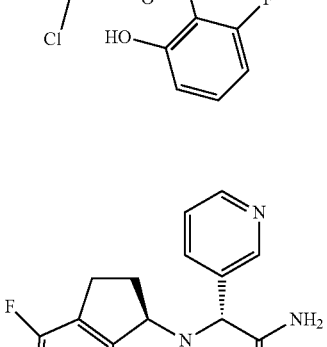 |

TABLE 40-continued
| Ex. No. | Strc. |
|---|---|
| 19-17LP | 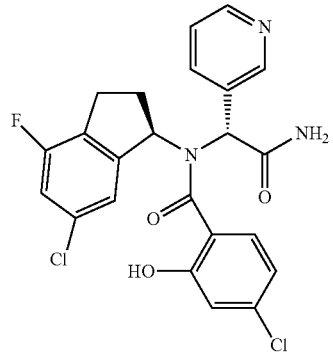 [SMILES: NC(=O)[C@@H](c1cccnc1)N(C(=O)c1ccc(Cl)cc1O)[C@@H]1CCc2c(F)cc(Cl)cc21] |
| 19-18LP | 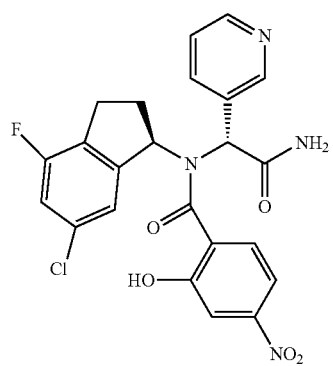 [SMILES: NC(=O)[C@@H](c1cccnc1)N(C(=O)c1ccc([N+](=O)[O-])cc1O)[C@@H]1CCc2c(F)cc(Cl)cc21] |
| 19-19LP | 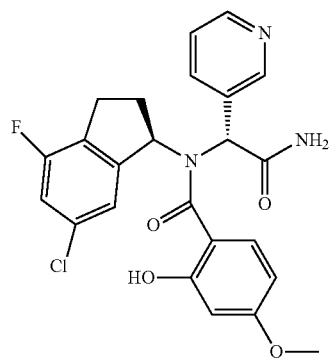 [SMILES: COc1ccc(C(=O)N([C@@H]2CCc3c(F)cc(Cl)cc32)[C@@H](C(N)=O)c2cccnc2)c(O)c1] |
| 19-20LP | 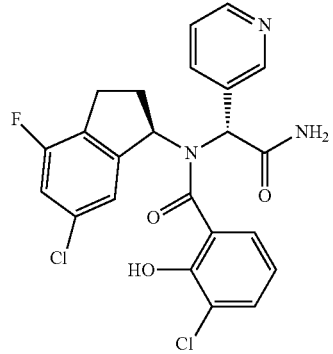 [SMILES: NC(=O)[C@@H](c1cccnc1)N(C(=O)c1cccc(Cl)c1O)[C@@H]1CCc2c(F)cc(Cl)cc21] |♦
TABLE 40-continued
| Ex. No. | Strc. |
|---|---|
| 19-21LP | 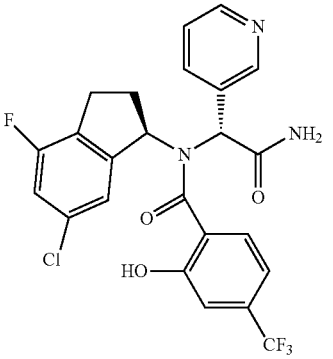 [SMILES: NC(=O)[C@@H](c1cccnc1)N(C(=O)c1ccc(C(F)(F)F)cc1O)[C@@H]1CCc2c(F)cc(Cl)cc21] |
| 19-22LP | 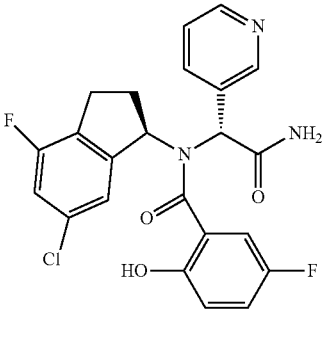 |
| 19-23LP | 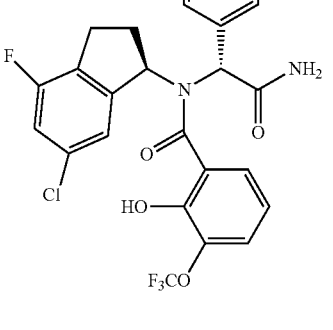 |
| 19-24LP | 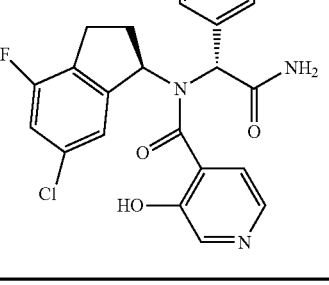 |

TABLE 41
| Ex. No. | Strc. |
|---|---|
| 19-25LP | 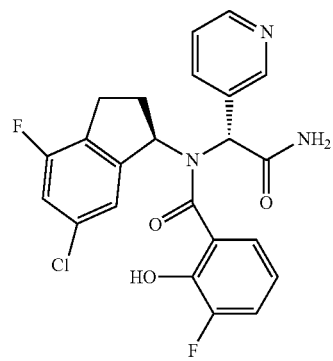 |
| 19-26LP | 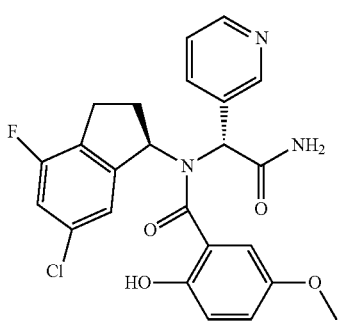 [SMILES: COc1ccc(O)c(C(=O)N([C@@H]2CCc3c(F)cc(Cl)cc32)[C@@H](C(N)=O)c2cccnc2)c1] |
| 19-27LP | 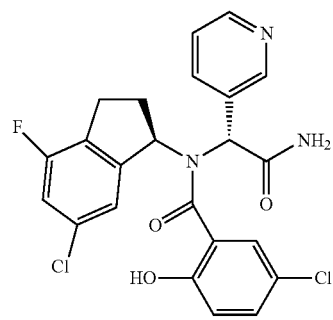 [SMILES: NC(=O)[C@@H](c1cccnc1)N(C(=O)c1cc(Cl)ccc1O)[C@@H]1CCc2c(F)cc(Cl)cc21] |
| 19-28LP | 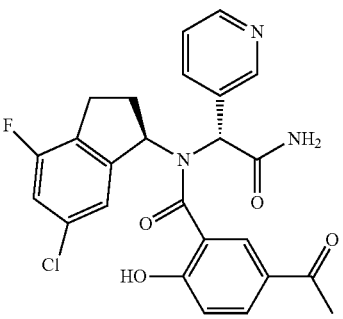 [SMILES: CC(=O)c1ccc(O)c(C(=O)N([C@@H]2CCc3c(F)cc(Cl)cc32)[C@@H](C(N)=O)c2cccnc2)c1] |
TABLE 41-continued
| Ex. No. | Strc. |
|---|---|
| 19-29LP | 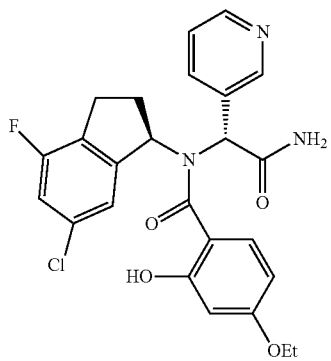 [SMILES: CCOc1ccc(C(=O)N([C@@H]2CCc3c(F)cc(Cl)cc32)[C@@H](C(N)=O)c2cccnc2)c(O)c1] |
| 19-30LP | 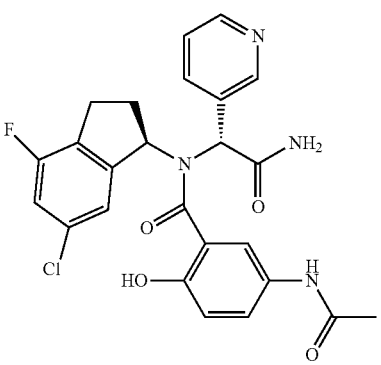 [SMILES: CC(=O)Nc1ccc(O)c(C(=O)N([C@@H]2CCc3c(F)cc(Cl)cc32)[C@@H](C(N)=O)c2cccnc2)c1] |
| 19-31LP | 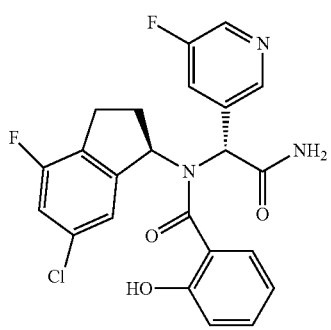 [SMILES: NC(=O)[C@@H](c1cncc(F)c1)N(C(=O)c1ccccc1O)[C@@H]1CCc2c(F)cc(Cl)cc21] |
| 19-32LP | 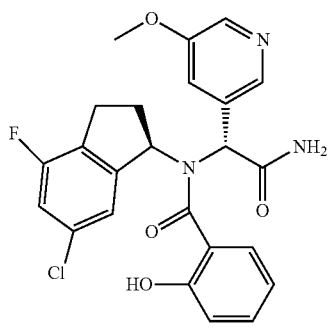 |

TABLE 41-continued

| Ex. No. | Strc. |
|---|---|
| 19-33LP | |
| 19-34LP | |
| 19-35LP | |
| 19-36LP | |

TABLE 42

| Ex. No. | Strc. |
|---|---|
| 19-37LP | |
| 19-38LP | |
| 19-39LP | |
| 19-40LP | |

TABLE 42-continued
| Ex. No. | Strc. |
|---|---|
| 19-41LP | 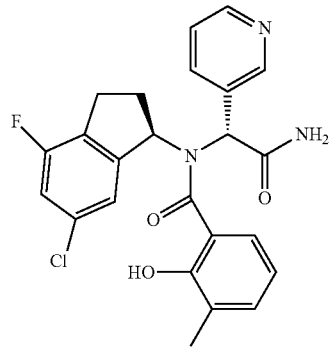 [SMILES: Cc1cccc(C(=O)N([C@@H]2CCc3c(F)cc(Cl)cc32)[C@@H](C(N)=O)c2cccnc2)c1O] |
TABLE 43
| Ex. No. | Strc. |
|---|---|
| 20-1-1 LP | 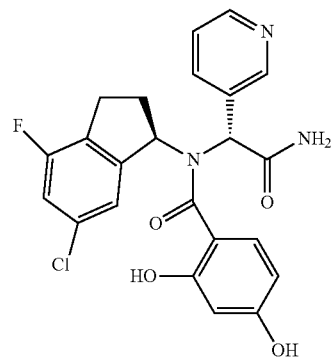 [SMILES: NC(=O)[C@@H](c1cccnc1)N(C(=O)c1ccc(O)cc1O)[C@@H]1CCc2c(F)cc(Cl)cc21] |
| 20-1-2 LP | 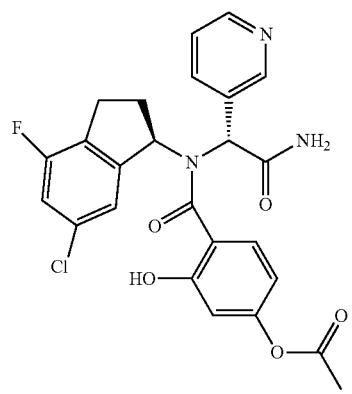 [SMILES: CC(=O)Oc1ccc(C(=O)N([C@@H]2CCc3c(F)cc(Cl)cc32)[C@@H](C(N)=O)c2cccnc2)c(O)c1] |
| 20-2 LP | 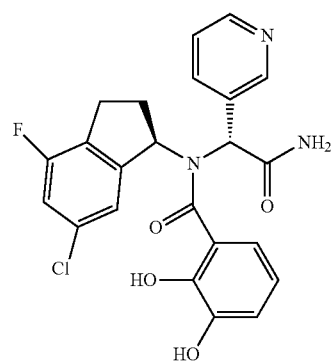 [SMILES: NC(=O)[C@@H](c1cccnc1)N(C(=O)c1cccc(O)c1O)[C@@H]1CCc2c(F)cc(Cl)cc21] |
TABLE 43-continued
| Ex. No. | Strc. |
|---|---|
| 21-1 | 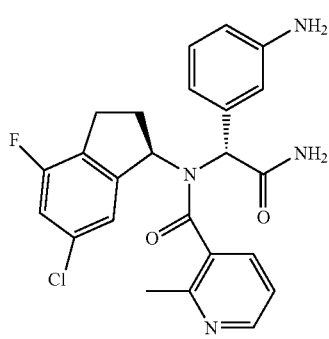 |
| 21-2 | 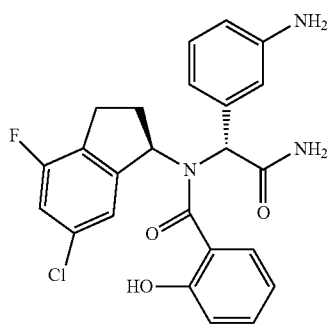 |
| 21-3 | 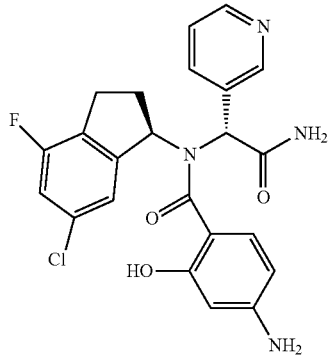 [SMILES: NC(=O)[C@@H](c1cccnc1)N(C(=O)c1ccc(N)cc1O)[C@@H]1CCc2c(F)cc(Cl)cc21] |
| 22 | 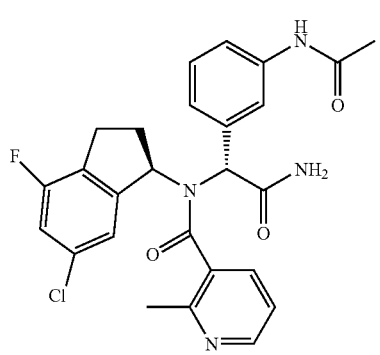 [SMILES: CC(=O)Nc1cccc([C@H](C(N)=O)N(C(=O)c2cccnc2C)[C@@H]2CCc3c(F)cc(Cl)cc32)c1] |

TABLE 43-continued

| Ex. No. | Strc. |
|---|---|
| 23 | (structure: fluoro-chloro-indanyl with N-methanesulfonamido-phenyl acetamide and 2-methylpyridine-3-carbonyl group) |

Test Example 1

Confirmation Test of Inhibitory Effects on Icilin-Induced Wet-Dog Shakes

Test compounds were dissolved in dimethylacetamide (wako), and 0.5% methylcellulose solution (wako) was added to make the solution or suspension containing 5% of dimethylacetamide. At a dose of 3 or 10 mg/kg/5 mL of test compounds were orally administered to female SD rats. After 1 hour, wet-dog shakes were induced by the intraperitoneal injection of icilin (1 mg/kg) which was dissolved in polyethylene glycol 400 (wako). From 5 minutes after the administration of icilin, wet-dog shakes were counted for 5 minutes. For control example, vehicle (a mixture of dimethylacetamide (wako): 0.5% methylcellulose (wako)=5:95) was administrated similarly, and the number of wet-dog shakes was counted in the same manner. A percent inhibition of wet-dog shakes by test compound was calculated from the following formula: [1−(test compound wet-dog shake count/vehicle wet-dog shake count)]×100. Results are shown in Tables 44 and 45.

TABLE 44

| Ex. No. | Dose (mg/kg) | % inhibition of Wet-Dog Shake |
|---|---|---|
| 1-1 | 10 | 95 |
| 1-6 | 10 | 64 |
| 2-2LP | 10 | 100 |
| 2-4LP | 10 | 79 |
| 2-5LP | 10 | 89 |
| 2-11LP | 10 | 85 |
| 2-26LP | 10 | 83 |
| 2-27LP | 10 | 95 |
| 2-31LP | 10 | 87 |
| 2-33LP | 10 | 98 |
| 2-39LP | 10 | 98 |
| 2-40LP | 10 | 95 |
| 2-56LP | 10 | 50 |
| 2-66LP | 10 | 100 |
| 2-71LP | 10 | 83 |
| 2-76LP | 10 | 95 |
| 2-86LP | 10 | 73 |
| 2-221LP | 10 | 100 |
| 3-2 | 10 | 73 |
| 4-2 | 10 | 86 |
| 6-1 | 10 | 89 |
| 12 | 10 | 93 |
| 1-3 | 3 | 69 |
| 2-6LP | 3 | 69 |
| 2-23LP | 3 | 56 |
| 2-36LP | 3 | 74 |
| 2-46LP | 3 | 79 |
| 2-87LP | 3 | 36 |
| 2-88LP | 3 | 46 |
| 2-89LP | 3 | 100 |
| 2-93LP | 3 | 100 |
| 2-97LP | 3 | 35 |
| 2-100LP | 3 | 47 |
| 2-107LP | 3 | 68 |
| 2-111LP | 3 | 91 |
| 2-118LP | 3 | 62 |
| 2-125LP | 3 | 37 |
| 2-128LP | 3 | 65 |
| 2-131LP | 3 | 100 |
| 2-132LP | 3 | 49 |
| 2-133LP | 3 | 55 |
| 2-137LP | 3 | 53 |
| 2-147LP | 3 | 91 |
| 2-150LP | 3 | 49 |
| 2-152LP | 3 | 44 |
| 2-154LP | 3 | 36 |
| 2-161LP | 3 | 42 |
| 2-167LP | 3 | 64 |
| 2-168LP | 3 | 36 |
| 2-172LP | 3 | 43 |
| 2-173LP | 3 | 99 |
| 2-175LP | 3 | 40 |
| 2-179LP | 3 | 32 |
| 2-180LP | 3 | 32 |
| 2-252M | 3 | 31 |
| 4-5 | 3 | 76 |
| 4-8 | 3 | 37 |
| 4-9 | 3 | 36 |
| 11 | 3 | 100 |
| 13 | 3 | 93 |
| 14LP | 3 | 100 |
| 15LP | 3 | 100 |

TABLE 45

| Ex. No. | Dose (mg/kg) | % inhibition of Wet-Dog Shake |
|---|---|---|
| 18-13LP | 10 | 86 |
| 19-6LP | 10 | 99 |
| 19-12LP | 10 | 82 |
| 19-15LP | 10 | 72 |
| 19-16LP | 10 | 63 |
| 19-17LP | 10 | 66 |
| 19-25LP | 10 | 86 |
| 19-41LP | 10 | 92 |
| 21-1 | 10 | 99 |
| 21-2 | 10 | 94 |
| 19-31LP | 3 | 71 |

Test Example 2

Confirmation Test of Elongation Action of Micturition Interval of Overactive Bladder Induced by Acetic Acid Urethane (sigma) was dissolved into pure water by 25% w/v, and female SD rats were anesthetized with 1.25 g/kg urethane by subcutaneous administration. Cannulae were placed in femoral vein and bladder, and the bladder cannula was connected to both a syringe pump and a pressure transducer. Detrusor overactivity was induced by intravesical infusion of 0.25% acetic acid in saline at a rate of 3.6 mL/h, and intravesical pressure was monitored via pressure transducer concurrently. Test compounds were dissolved into a mixture of dimethylacetamide and saline (20:80), and were administered via the femoral vein. When an average of the three micturition interval before administration was taken as 100%, an average of the three micturition interval after administration was calculated as Elongation of micturition interval (%) Dose and results are shown in tables 46 and 47.

TABLE 46

| Ex. No | Dose/Volume | Elongation of micturition interval (%) |
|---|---|---|
| 1-1 | 1 mg/kg/ml | 209 |
| 1-3 | 1 mg/kg/ml | 200 |
| 2-2LP | 1 mg/kg/2 ml | 221 |
| 2-4LP | 1 mg/kg/2 ml | 156 |
| 2-5LP | 1 mg/kg/2 ml | 177 |
| 2-6LP | 0.3 mg/kg/ml | 184 |
| 2-23LP | 1 mg/kg/ml | 205 |
| 2-31LP | 1 mg/kg/ml | 176 |
| 2-46LP | 1 mg/kg/ml | 186 |
| 2-66LP | 1 mg/kg/ml | 175 |
| 2-86LP | 1 mg/kg/2 ml | 145 |
| 2-89LP | 1 mg/kg/2 ml | 196 |
| 2-111LP | 0.3 mg/kg/2 ml | 135 |
| 2-131LP | 1 mg/kg/ml | 162 |
| 2-147LP | 1 mg/kg/2 ml | 146 |
| 2-221LP | 1 mg/kg/2 ml | 154 |
| 6-1 | 1 mg/kg/2 ml | 194 |
| 11 | 1 mg/kg/ml | 162 |
| 12 | 1 mg/kg/ml | 142 |
| 13 | 1 mg/kg/ml | 184 |
| 14LP | 1 mg/kg/ml | 181 |
| 15LP | 1 mg/kg/ml | 188 |

TABLE 47

| Ex. No. | Dose/Volume | Elongation of micturition interval (%) |
|---|---|---|
| 19-1LP | 1 mg/kg/ml | 178 |

As shown in Tables 44 and 45, the compounds of the present invention exhibited potent TRPM8 inhibitory effects. Further, as shown in Tables 46 and 47, the compounds of the present invention have the elongation action against micturition interval and were proved to be effective for suppression of detrusor overactivity.

Industrial Applicability

The compounds of the present invention exhibit potent TRPM8 inhibitory activity and thus are useful as an agent for treating or preventing of diseases or symptoms caused by the activation of TRPM8, in particular the symptoms of lower urinary tract symptoms (LUTS), especially, overactive bladder syndrome (OAB).

The invention claimed is:

1. A compound of formula (I) or a pharmaceutically acceptable salt thereof:

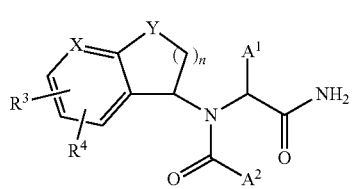
(I)

(wherein
$A^1$ is a group selected from the group consisting of the following a) to c):
a) $C_{6-10}$ aryl, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, $C_{1-6}$ alkoxycarbonyl, cyano, hydroxy-$C_{1-6}$ alkyl, carbamoyl, nitro, amino, $C_{1-6}$ alkoxycarbonylamino-$C_{1-6}$ alkyl, mono(di)$C_{1-6}$ alkylamino, ($C_{1-6}$ alkyl)carbonylamino, $C_{1-6}$ alkylsulfonylamino and $C_{1-6}$ alkylsulfonyl,
b) 5-membered heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, cyano and halo-$C_{1-6}$ alkoxy, and
c) 6-membered heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, cyano and halo-$C_{1-6}$ alkoxy;
$A^2$ is a group selected from the group consisting of the following d) to f):
d) $C_{6-10}$ aryl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano, amino, nitro, carboxy, ($C_{1-6}$ alkyl)carbonylamino, ($C_{1-6}$ alkyl)carbonyloxy, ($C_{1-6}$ alkyl)carbonyl and ($C_{7-10}$ aralkyloxy)carbonyl,
e) heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, cyano, mono(di)$C_{1-6}$ alkylamino, $C_{1-6}$ alkylsulfanyl, amino, ($C_{7-10}$ aralkyloxy)carbonyl, hydroxy-$C_{1-6}$ alkyl, hydroxy-$C_{1-6}$ alkoxy, $C_{2-6}$ alkenyl, morpholino and ($C_{1-6}$ alkyl)carbonyl , and
f) $C_{3-6}$ cycloalkyl;
X is CH or N;
Y is —$CR^1R^2$— or an oxygen atom;
$R^1$ and $R^2$ independently represent a hydrogen atom, a halogen atom or $C_{1-6}$ alkyl;
$R^3$ and $R^4$ independently represent a hydrogen atom, a halogen atom, $C_{1-6}$ alkyl, $C_{1-6}$ alkoxy, halo-$C_{1-6}$ alkyl, halo-$C_{1-6}$ alkoxy, hydroxy-$C_{1-6}$ alkoxy, $C_{3-6}$ cycloalkyl, $C_{3-6}$ cycloalkoxy, $C_{2-6}$ alkenyl or cyano with the proviso that when X is CH, and $R^1$ and $R^2$ are hydrogen atoms, $R^3$ and $R^4$ are not hydrogen atoms at the same time; and
n is 1 or 2).

2. The compound according to claim 1 or a pharmaceutically acceptable salt thereof, wherein X is CH; and n is 1.

3. The compound according to claim 2 or a pharmaceutically acceptable salt thereof, wherein a group of formula (II):

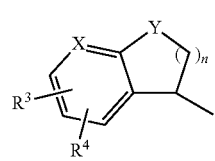
(II)

is a group of the following formula (III):

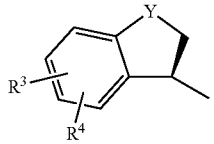

(wherein R³ and R⁴ independently represent a hydrogen atom, a halogen atom, $C_{1-6}$ alkyl, $C_{1-6}$ alkoxy, halo-$C_{1-6}$ alkyl, halo-$C_{1-6}$ alkoxy, hydroxy-$C_{1-6}$ alkoxy, $C_{3-6}$ cycloalkyl, $C_{3-6}$ cycloalkoxy, $C_{2-6}$ alkenyl or cyano with the proviso that R³ and R⁴ are not hydrogen atoms at the same time).

4. The compound according to claim 3 or a pharmaceutically acceptable salt thereof, wherein Y is —CR¹R²—.

5. The compound according to claim 4 or a pharmaceutically acceptable salt thereof, wherein a group of formula (IV):

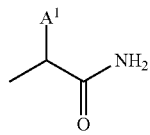

is a group of the following formula (V):

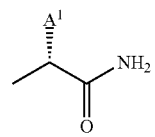

(wherein A¹ is a group selected from the group consisting of the following a1), b) and c):
a1) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, $C_{1-6}$alkoxycarbonyl, cyano, hydroxy-$C_{1-6}$ alkyl, carbamoyl, nitro, amino, $C_{1-6}$ alkoxycarbonylamino-$C_{1-6}$ alkyl, mono(di)$C_{1-6}$ alkylamino, ($C_{1-6}$ alkyl)carbonylamino, $C_{1-6}$ alkylsulfonylamino and $C_{1-6}$ alkylsulfonyl,
b) 5-membered heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, cyano and halo-$C_{1-6}$ alkoxy, and
c) 6-membered heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, cyano and halo-$C_{1-6}$ alkoxy).

6. The compound according to claim 5 or a pharmaceutically acceptable salt thereof, wherein a group of formula (II):

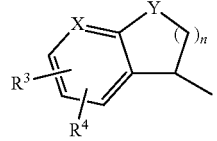

is a group of the following formula (VI):

(VI)

(wherein R³ and R⁴ independently represent a hydrogen atom, a halogen atom, $C_{1-6}$ alkyl, $C_{1-6}$ alkoxy, halo-$C_{1-6}$ alkyl, halo-$C_{1-6}$ alkoxy, hydroxy-$C_{1-6}$ alkoxy, $C_{3-6}$ cycloalkyl, $C_{2-6}$ alkenyl or cyano with the proviso that R³ and R⁴ are not hydrogen atoms at the same time).

7. The compound according to claim 6 or a pharmaceutically acceptable salt thereof, wherein A² is a group selected from the group consisting of the following d1) and e):
d1) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano, amino, nitro, carboxy, ($C_{1-6}$ alkyl)carbonylamino, ($C_{1-6}$ alkyl)carbonyloxy, ($C_{1-6}$ alkyl)carbonyl and ($C_{7-10}$ aralkyloxy)carbonyl, and
e) heterocycle, wherein the ring is unsubstituted or substituted with 1 to 2 substituents independently selected from the group consisting of the following: a halogen atom, hydroxy, $C_{1-6}$ alkyl, $C_{1-6}$ alkoxy, halo-$C_{1-6}$ alkyl, halo-$C_{1-6}$ alkoxy, cyano, mono(di)$C_{1-6}$ alkylamino, $C_{1-6}$ alkylsulfanyl, amino, ($C_{7-10}$ aralkyloxy)carbonyl, hydroxy-$C_{1-6}$ alkyl, hydroxy-$C_{1-6}$ alkoxy, $C_{2-6}$ alkenyl, morpholino and ($C_{1-6}$ alkyl)carbonyl.

8. The compound according to claim 7 or a pharmaceutically acceptable salt thereof, wherein A¹ is a group selected from the group consisting of the following a2), b1) and c1):
a2) phenyl, wherein the ring is unsubstituted or substituted with 1 to 2 substituents independently selected from the group consisting of the following: a halogen atom, hydroxy, hydroxy-$C_{1-6}$ alkyl, cyano, amino, mono(di)$C_{1-6}$ alkylamino and $C_{1-6}$ alkoxy,
b1) thiazolyl, and
c1) a group selected from the group consisting of pyridyl, pyrimidinyl and pyrazinyl, wherein the each ring is unsubstituted or substituted with 1 to 2 substituents independently selected from the group consisting of the following: a halogen atom, $C_{1-6}$ alkyl, $C_{1-6}$ alkoxy and cyano;
A² is a group selected from the group consisting of the following d2) and e1):
d2) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano, ($C_{1-6}$ alkyl)carbonyloxy and amino, and e1) heterocycle, wherein the ring is unsubstituted or substituted with 1 to 2 substituents independently selected from the group consisting of the following: a halogen atom, $C_{1-6}$ alkyl, $C_{1-6}$ alkoxy, cyano, mono(di)$C_{1-6}$ alkylamino, $C_{1-6}$ alkylsulfanyl, amino, hydroxy-$C_{1-6}$ alkyl and $C_{2-6}$ alkenyl; and $R^3$ and $R^4$ independently represent a hydrogen atom, a halogen atom, $C_{1-6}$ alkyl, $C_{1-6}$ alkoxy, halo-$C_{1-6}$ alkyl, halo-$C_{1-6}$ alkoxy, $C_{3-6}$ cycloalkyl or cyano with the proviso that $R^3$ and $R^4$ are not hydrogen atoms at the same time.

9. The compound according to claim 8 or a pharmaceutically acceptable salt thereof, wherein $A^2$ is a group selected from the group consisting of the following d2) and e2):
   d2) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy, hydroxy-$C_{1-6}$ alkoxy, halo-$C_{1-6}$ alkyl, halo-$C_{1-6}$ alkoxy, cyano, ($C_{1-6}$ alkyl)carbonyloxy and amino, and
   e2) a group selected from the group consisting of pyridyl, pyrimidinyl, pyrazinyl, thienyl, thiazolyl, isothiazolyl, 2,3-dihydrobenzofuranyl, pyrazolyl, imidazolyl, isoxazolyl, oxazolyl, furazanyl and benzo[1,3]dioxolyl, wherein the each ring is unsubstituted or substituted with 1 to 2 substituents independently selected from the group consisting of the following: a halogen atom, $C_{1-6}$ alkyl, $C_{1-6}$ alkoxy, cyano, mono(di)$C_{1-6}$ alkylamino, $C_{1-6}$ alkylsulfanyl, amino, hydroxy-$C_{1-6}$ alkyl and $C_{2-6}$ alkenyl.

10. The compound according to claim 9 or a pharmaceutically acceptable salt thereof,
    wherein $A^1$ is phenyl, pyridyl or pyrazinyl, in which the each ring is unsubstituted or substituted with selected from the group consisting of the following: a halogen atom, amino, mono(di)$C_{1-6}$ alkylamino or hydroxy;
    $A^2$ is a group selected from the group consisting of the following d3) and e3):
    d3) phenyl, wherein the ring is unsubstituted or substituted with 1 to 2 substituents independently selected from the group consisting of the following: a halogen atom, hydroxy, $C_{1-6}$ alkyl, $C_{1-6}$ alkoxy and amino, and
    e3) a group selected from the group consisting of pyridyl, pyrimidinyl, pyrazinyl, thiazolyl, 2,3-dihydrobenzofuranyl, pyrazolyl, isoxazolyl and benzo[1,3]dioxolyl, wherein the each ring is unsubstituted or substituted with 1 to 2 substituents independently selected from the group consisting of the following: a halogen atom, $C_{1-6}$ alkyl, $C_{1-6}$ alkoxy, mono(di)$C_{1-6}$ alkylamino, $C_{1-6}$ alkylsulfanyl, and amino, and
    $R^3$ and $R^4$ independently represent a hydrogen atom, a halogen atom, $C_{1-6}$ alkyl, $C_{1-6}$ alkoxy, halo-$C_{1-6}$ alkoxy, $C_{3-6}$ cycloalkyl or cyano with the proviso that $R^3$ and $R^4$ are not hydrogen atoms at the same time.

11. The compound according to claim 10 or a pharmaceutically acceptable salt thereof, wherein $A^1$ is phenyl, pyridyl or pyrazinyl, in which the each ring is unsubstituted or substituted with selected from the group consisting of the following: a halogen atom or hydroxy;
    $A^2$ is a group selected from the group consisting of the following d4) and e3):
    d4) phenyl, wherein the ring is unsubstituted or substituted with 1 to 2 substituents independently selected from the group consisting of the following: a halogen atom, hydroxy, $C_{1-6}$ alkoxy and amino, and
    e3) a group selected from the group consisting of pyridyl, pyrimidinyl, pyrazinyl, thiazolyl, 2,3-dihydrobenzofuranyl, pyrazolyl, isoxazolyl and benzo[1,3]dioxolyl, wherein the each ring is unsubstituted or substituted with 1 to 2 substituents independently selected from the group consisting of the following: a halogen atom, $C_{1-6}$ alkyl, $C_{1-6}$ alkoxy, mono(di)$C_{1-6}$ alkylamino, $C_{1-6}$ alkylsulfanyl, and amino, and
    $R^3$ and $R^4$ independently represent a hydrogen atom, a halogen atom, $C_{1-6}$ alkyl, $C_{1-6}$ alkoxy, halo-$C_{1-6}$ alkoxy, $C_{3-6}$ cycloalkyl or cyano with the proviso that $R^3$ and $R^4$ are not hydrogen atoms at the same time.

12. The compound according to claim 1 selected from the following group consisting of:
    N-[(R)-carbamoylphenylmethyl]-N-[(R)-4,6-difluoroindan-1-yl]nicotinamide;
    N-[(R)-carbamoylphenylmethyl]-N-[(R)-6-methoxyindan-1-yl]nicotinamide;
    N-[(R)-carbamoylphenylmethyl]-N-[(R)-6-chloroindan-1-yl]benzamide;
    N-[(R)-carbamoylphenylmethyl]-N-[(R)-6-methoxyindan-1-yl]benzamide;
    N-[(R)-carbamoylphenylmethyl]-N-[(R)-6-cyclopropylindan-1-yl]benzamide;
    N-[(R)-carbamoylphenylmethyl]-N-[(R)-6-difluoromethoxyindan-1-yl]benzamide;
    N-[(R)-carbamoylphenylmethyl]-N-[(R)-6-difluoromethoxyindan-1-yl]nicotinamide;
    2-amino-N-[(R)-carbamoylphenylmethyl]-N-[(R)-6-difluoromethoxyindan-1-yl]nicotinamide;
    N-[(R)-carbamoylphenylmethyl]-N-[(R)-6-chloroindan-1-yl]nicotinamide;
    2-amino-N-[(R)-carbamoylphenylmethyl]-N-[(R)-6-chloroindan-1-yl]nicotinamide;
    N-[(R)-carbamoylphenylmethyl]-N-[(R)-4-fluoro-6-methoxyindan-1-yl]nicotinamide;
    N-[(R)-carbamoylphenylmethyl]-N-[(R)-4-fluoro-6-methylindan-1-yl]nicotinamide;
    N-[(R)-carbamoylphenylmethyl]-N-[(R)-4-fluoroindan-1-yl]nicotinamide;
    N-[(R)-carbamoylpyridin-3-ylmethyl]-N-[(R)-6-chloro-4-fluoroindan-1-yl]benzamide;
    N-[(R)-carbamoylphenylmethyl]-N-[(R)-6-chloroindan-1-yl]thiazole-5-carboxamide;
    N-[(R)-carbamoylpyridin-3-ylmethyl]-N-[(R)-4,6-difluoroindan-1-yl]benzamide;
    N-[(R)-carbamoylphenylmethyl]-N-[(R)-6-chloro-4-fluoroindan-1-yl]-5-fluoronicotinamide;
    N-[(R)-carbamoylphenylmethyl]-N-[(R)-4,6-difluoroindan-1-yl]benzamide;
    N-[(R)-carbamoylphenylmethyl]-N-[(R)-6-cyanoindan-1-yl]-2-hydroxybenzamide;
    N-[(R)-carbamoylphenylmethyl]-N-[(S)-5-chloro-2,3-dihydrobenzofuran-3-yl]-2-hydroxybenzamide;
    2-amino-N-[(R)-carbamoylphenylmethyl]-N-[(R)-4,6-difluoroindan-1-yl]benzamide;
    N-[(R)-carbamoylpyridin-3-ylmethyl]-N-[(R)-6-chloro-4-fluoroindan- 1-yl]-2-methylnicotinamide;
    2-amino-N-[(R)-carbamoylphenylmethyl]-N-[(R)-4,6-difluoroindan-1-yl]nicotinamide;
    N-[(R)-carbamoylphenylmethyl]-N-[(R)-6-chloro-4-fluoroindan-1-yl]benzamide;
    N-[(R)-carbamoylphenylmethyl]-N-[(R)-6-chloro-4-fluoroindan-1-yl]nicotinamide;
    N-[(R)-carbamoylphenylmethyl]-N-[(R)-4,6-difluoroindan-1-yl]-2-methoxynicotinamide;

N-[(R)-carbamoylphenylmethyl]-N-[(R)-6-chloroindan-1-yl]-2-methoxynicotinamide \;
N-[(R)-carbamoylpyridin-3-ylmethyl]-N-[(R)-6-chloroindan-1-yl]benzamide;
N-[(R)-carbamoylphenylmethyl]-N-[(R)-6-chloroindan-1-yl]-4-methylthiazole-5-carboxamide;
N-[(R)-carbamoylphenylmethyl]-N-[(R)-6-chloro-4-fluoroindan-1-yl]-2-methoxybenzamide;
N-[(R)-carbamoylphenylmethyl]-2-chloro-N-[(R)-6-chloro-4-fluoroindan-1-yl]nicotinamide;
N-[(R)-carbamoylpyridin-3-ylmethyl]-2-chloro-N-[(R)-6-chloro-4-fluoroindan-1-yl]benzamide;
N-[(R)-carbamoylphenylmethyl]-N-[(R)-6-chloro-4-fluoroindan-1-yl]-4-methylnicotinamide;
N-[(R)-carbamoylphenylmethyl]-N-[(R)-6-chloro-4-fluoroindan-1-yl]-2-(methylamino)nicotinamide;
N-[(R)-carbamoylphenylmethyl]-N-[(R)-6-chloro-4-fluoroindan-1-yl]-2,3-dihydrobenzofuran-7-carboxamide;
N-[(R)-carbamoylpyridin-3-ylmethyl]-N-[(R)-6-chloro-4-fluoroindan-1-yl]-2-methoxybenzamide;
N-[(R)-carbamoylphenylmethyl]-N-[(R)-6-chloroindan-1-yl]-2-(methylsulfanyl)nicotinamide;
N-[(R)-carbamoylphenylmethyl]-N-[(R)-6-chloro-4-fluoroindan-1-yl]-2-(methylsulfanyl)nicotinamide;
N-[(R)-carbamoylphenylmethyl]-N-[(R)-4,6-difluoroindan-1-yl]-2-methylnicotinamide;
N-[(R)-carbamoylphenylmethyl]-N-[(R)-4,6-difluoroindan-1-yl]-4-methylthiazole-5-carboxamide;
N-[(R)-carbamoylphenylmethyl]-N-[(R)-6-chloro-4-fluoroindan-1-yl]-2-methyl-2H-pyrazole-3-carboxamide (Example 2-133LP);
N-[(R)-carbamoylphenylmethyl]-N-[(R)-6-chloroindan-1-yl]-2-methylnicotinamide;
N-[(R)-carbamoylphenylmethyl]-N-[(R)-6-chloro-4-fluoroindan-1-yl]-5-methylthiazole-4-carboxamide;
N-[(R)-carbamoylphenylmethyl]-N-[(R)-6-chloro-4-fluoroindan-1-yl]-4-methylisoxazole-5-carboxamide;
N-[(R)-carbamoylphenylmethyl]-N-[(R)-6-chloro-4-fluoroindan- 1-yl]-3-methylpyridine-2-carboxamide;
N-[(R)-carbamoylphenylmethyl]-N-[(R)-6-chloro-4-fluoroindan-1-yl]-4-methylpyrimidine-5-carboxamide;
N-[(R)-carbamoyl-(3-fluorophenyl)methyl]-N-[(R)-6-chloro-4-fluoroindan-1-yl]-2-methylnicotinamide;
N-[(R)-carbamoylphenylmethyl]-N-[(R)-6-chloro-4-fluoroindan-1-yl]-3-methylisonicotinamide;
N-[(R)-carbamoyl-(3-hydroxyphenyl)methyl]-N-[(R)-6-chloro-4-fluoroindan-1-yl]-2-methylnicotinamide;
N-[(R)-carbamoylpyridin-3-ylmethyl]-N-[(R)-6-chloro-4-fluoroindan-1-yl]benzo [1,3]dioxole-4-carboxamide;
N-[(R)-carbamoylphenylmethyl]-N-[(R)-6-chloro-4-fluoroindan-1-yl]benzo [1,3]dioxole-4-carboxamide;
N-[(R)-carbamoylphenylmethyl]-N-[(R)-6-chloro-4-fluoroindan-1-yl]3-methylpyrazine-2-carboxamide;
N-[(R)-carbamoylphenylmethyl]-N-[(R)-6-chloro-4-fluoroindan-1-yl]pyrazine-2-carboxamide;
N-[(R)-carbamoylpyridin-3-ylmethyl]-N-[(R)-6-chloro-4-fluoroindan-1-yl]-2-methoxynicotinamide;
N-[(RS)-carbamoylphenylmethyl]-N-[(SR)-5-chloro-7-fluoro-2,3-dihydrobenzofuran-3-yl]benzamide;
N-[(R)-carbamoylpyridin-3-ylmethyl]-N-[(R)-6-chloro-4-fluoroindan-1-yl]-2-hydroxybenzamide;
N-[(R)-carbamoylpyrazin-2-ylmethyl]-N-[(R)-6-chloro-4-fluoroindan-1-yl]-2-hydroxybenzamide;
N-[(R)-carbamoylphenylmethyl]-N-[(R)-6-chloro-4-fluoroindan-1-yl]-2-hydroxy-3-methylbenzamide;
N-[(R)-carbamoylphenylmethyl]-N-[(R)-6-chloro-4-fluoroindan-1-yl]-2-methoxynicotinamide;
2-amino-N-[(R)-carbamoylphenylmethyl]-N-[(R)-6-chloro-4-fluoroindan-1-yl]nicotinamide;
N-[(R)-carbamoylphenylmethyl]-N-[(R)-6-chloro-4-fluoroindan-1-yl]-2-methylnicotinamide;
N-[(R)-carbamoylphenylmethyl]-N-[(R)-6-chloro-4-fluoroindan-1-yl]-4-methylthiazole-5-carboxamide;
N-[(R)-carbamoyl-(3-dimethylaminophenyl)methyl]-N-[(R)-6-chloro-4-fluoroindan-1-yl]-2-methylnicotinamide;
N-[(R)-carbamoyl-(3-dimethylaminophenyl)methyl]-N-[(R)-6-chloro-4-fluoroindan-1-yl]-2-hydroxybenzamide;
N-[(R)-carbamoylpyridin-3-ylmethyl]-N-[(R)-6-chloro-4-fluoroindan-1-yl]-2-hydroxy-4-methylbenzamide;
N-[(R)-carbamoylpyridin-3-ylmethyl]-N-[(R)-6-chloro-4-fluoroindan-1-yl]-2-fluoro-6-hydroxybenzamide;
N-[(R)-carbamoylpyridin-3-ylmethyl]-N-[(R)-6-chloro-4-fluoroindan-1-yl]-4-fluoro-2-hydroxybenzamide;
N-[(R)-carbamoylpyridin-3-ylmethyl]-4-chloro-N-[(R)-6-chloro-4-fluoroindan-1-yl]-2-hydroxybenzamide;
N-[(R)-carbamoylpyridin-3-ylmethyl]-N-[(R)-6-chloro-4-fluoroindan-1-yl]-3-fluoro-2-hydroxybenzamide;
N-[(R)-(3-aminophenyl)carbamoylmethyl]-N-[(R)-6-chloro-4-fluoroindan-1-yl]-2-methylnicotinamide;
N-[(R)-(3-aminophenyl)carbamoylmethyl]-N-[(R)-6-chloro-4-fluoroindan-1-yl]-2-hydroxybenzamide;
N-[(R)-carbamoyl(5-fluoropyridin-3-yl)methyl]-N-[(R)-6-chloro-4-fluoroindan-1-yl]-2-hydroxybenzamide; and
N-[(R)-carbamoylpyridin-3-ylmethyl]-N-[(R)-6-chloro-4-fluoroindan-1-yl]-2-hydroxy-3-methylbenzamide; or a pharmaceutically acceptable salt thereof.

13. A pharmaceutical composition comprising the compound according to claim 1 or a pharmaceutically acceptable salt thereof.

14. The pharmaceutical composition according to claim 13, which is an agent for the treatment or prevention of a disease or a symptom caused by hyperexcitability or a disorder of afferent neurons.

* * * * *